United States Patent
Alam et al.

(10) Patent No.: US 9,765,322 B2
(45) Date of Patent: Sep. 19, 2017

(54) PECTIN DEGRADING ENZYMES FROM MACROPHOMINA PHASEOLINA AND USES THEREOF

(71) Applicants: Bangladesh Jute Research Institute, Dhaka (BD); Rafia Hasina, Honolulu, HI (US)

(72) Inventors: Maqsudul Alam, Honolulu, HI (US); Mohammed S. Islam, Dhaka (BD); Mohammed M. Hossen, Dhaka (BD); Mohammed S. Haque, Dhaka (BD); Mohammed M. Alam, Dhaka (BD)

(73) Assignee: Bangladesh Jute Research Institute, Dhaka (BD)

( * ) Notice: Subject to any disclaimer, the term of this patent is extended or adjusted under 35 U.S.C. 154(b) by 0 days.

(21) Appl. No.: 14/421,729

(22) PCT Filed: Aug. 15, 2013

(86) PCT No.: PCT/US2013/055198
§ 371 (c)(1),
(2) Date: Feb. 13, 2015

(87) PCT Pub. No.: WO2014/028772
PCT Pub. Date: Feb. 20, 2014

(65) Prior Publication Data
US 2015/0259667 A1    Sep. 17, 2015

Related U.S. Application Data

(60) Provisional application No. 61/683,914, filed on Aug. 16, 2012.

(51) Int. Cl.
| | |
|---|---|
| *C12N 15/60* | (2006.01) |
| *C12N 9/88* | (2006.01) |
| *C12N 9/18* | (2006.01) |
| *C12N 9/24* | (2006.01) |

(52) U.S. Cl.
CPC ............... *C12N 9/88* (2013.01); *C12N 9/18* (2013.01); *C12N 9/2405* (2013.01); *C12Y 301/01011* (2013.01); *C12Y 402/02002* (2013.01); *C12Y 402/02023* (2013.01)

(58) Field of Classification Search
None
See application file for complete search history.

(56) References Cited

FOREIGN PATENT DOCUMENTS

| WO | WO-2004/074468 A1 | 9/2004 |
|---|---|---|
| WO | WO-2010/101158 A1 | 9/2010 |

OTHER PUBLICATIONS

H,C. Dube et al. "Extra-cellular Pectic Enzymes of Macrophomina phaseolina. The Incitant of Root-Rot of Sesamun indicum", Proc. Nat. Acad. Sci 41(6): 576-579. (1975).*
GenBank: AHHD01000048 (Oct. 2013).*
Islam, M.S. et al., "UNIPROT:K2SGE4", Nov. 28, 2012 (Nov. 28, 2012), XP055229130, Retrieved from the Internet: URL: http://ibis.internal.epo.org/exam/dbfetch.jsp?id=UNIPROT:K2SGE4 [retrieved on Nov. 18, 2015].
Supplemental Partial European Search Report, dated Dec. 11, 2015, from related European Application No. 13829902.9.
"UPI00032CD420", May 5, 2013 (May 5, 2013), XP055229132, Retrieved from the Internet: URL: http://www.uniprot.org/uniparc/UPI00032cd420 [retrieved on Nov. 18, 2015].
Wang, G. et al., "EM_EST:EX519280", Oct. 11, 2007 (Oct. 11, 2007), XP055229129, Retrieved from the Internet: URL: http://ibis.internal.epo.org/exam/dbfetch.jsp?id=EM_EST:EX519280 [retrieved on Nov. 18, 2015].
Accession No. xp_0030000083, "pectate lyase [Verticillium alfalfae VsMs.102]", Ma L.J.J. et al., Aug. 11, 2010.
Accession No. XM_003000037.1, "pectate lyase mRNA [Verticillium alfalfae VaMs.102]", Ma L.J.J. et al., Aug. 11, 2010.

* cited by examiner

*Primary Examiner* — Rebecca Prouty
(74) *Attorney, Agent, or Firm* — Foley Hoag LLP

(57) ABSTRACT

The present invention discloses isolated polynucleotide encoding enzymes, derived from the fungus *Macrophomina phaseolina* ("*M. phaseolina*"), responsible for degrading pectin, and it comprises and/or consists of nucleotide sequences set forth in SEQ ID Nos. 2, 5, 8, 11, 14, 17, 20, 23, 26, 29, 32, 35, 38, 41, 44, 47, 50, 53, 56, 59, 62, 1, 4, 7, 10, 13, 16, 19, 22, 25, 28, 31, 34, 37, 40, 43, 46, 49, 52, 55, 58 and 61, or the complement of such sequences. The present invention also relates to isolated polypeptide encoded by the polynucleotide sequences set forth in SEQ ID Nos. 3, 6, 9, 12, 15, 18, 21, 24, 27, 30, 33, 36, 39, 42, 45, 48, 51, 54, 57, 60 and 63; a recombinant gene construct comprising the polynucleotide; a transformant and a transgenic fungus comprising the recombinant gene construct, with or having enhanced production of pectin degrading enzyme. The polypeptide of the invention can be used for, amongst other things, manufactured fruit juice, textile products, pulp and paper, coffee, tea and oil extraction and pectic waste water treatment.

7 Claims, 7 Drawing Sheets

PECTIN DEGRADING ENZYMES FROM MACROPHOMINA PHASEOLINA AND USES THEREOF

RELATED APPLICATIONS

This application is a National Stage application of PCT/US2013/055198, field Aug. 15, 2013, which claims the benefit of priority to U.S. Provisional Patent Application Ser. No. 61/683,914, filed Aug. 16, 2012.

SEQUENCE LISTING

The instant application contains a Sequence Listing which has been submitted via EFS-Web and is hereby incorporated by reference in its entirety. Said ASCII copy is named JGX_501_ST25.txt and is 171 kilobytes in size.

FIELD OF INVENTION

The present invention relates to isolated polypeptides from *M. phaseolina* having pectate lyase activity and isolated polynucleotides encoding the polypeptides, and methods for making and using these polynucleotides and polypeptides. The invention also relates to nucleic acid constructs, vectors, and host cells comprising the polynucleotides as well as methods for producing and using the polypeptides. The polypeptides of the invention can be used in, amongst other things, the textile industry for the retting and degumming of fibre and fabrics; in food industry for the extraction of fruit and vegetable juice; in paper industry for the production of good quality paper; and also for fermentation of coffee and tea, oil extraction and pectic waste water treatment.

BACKGROUND OF THE INVENTION

Pectin is a group of complex heteropolymers, present in the middle lamella of the primary plant-cell wall and act as intercellular cement. They also have an important function in the water-regulation of plants due to their colloidal nature. The middle lamellas which are situated between the cell walls are mainly built up from protopectin (an insoluble form of pectin).

Pectin is composed of two different definite regions: "smooth" and "hairy" regions. The "smooth" region consists of a backbone of α-1, 4-linked D-galacturonic acid, forming a polygalactouronic acid with some of the carboxyl groups esterified with methanol (Rouse A. Pectin: distribution, significance. In: Nagy S, Shaw P, Veldhuis Meds. Citrus Science and Technology, Vol I. Westport Conn.: AVI publishing Inc. 1977). In the "hairy" region, the galacturonic acid backbone is broken down by α-1, 2-linked L-rhamnose unit.

Pectin/pectate lyases depolymerize pectin in smooth region, which cleaves glycosidic bonds via β-elimination to yield oligomers that are 4, 5-unsaturated non-reducing end (Lombard V, Bernard T, Rancurel C, Brumer H, Coutinho P M, Henrissat B. A hierarchical classification of polysaccharide lyases for glycogenomics. Biochem J. 2010; 432(3): 437-444). Whereas rhamnogalacturonase cleave within the hairy regions of pectin (Jensen M H, Otten H, Christensen U, Borchert T V, Christensen L L, Larsen S, Leggio L L. Structural and biochemical studies elucidate the mechanism of rhamnogalacturonan lyase from *Aspergillus aculeatus*. J Mol Biol. 2010; 404(1):100-111).

Pectin esterase hydrolyses the pectin to methanol and polygalacturonic acid. This enzyme can be produced by several fungi including *Aspergillus* sp, *Botrytis cinerea*, *Fusarium moniliforme, Rhizopus stolonifer, Trichoderma* sp. etc (Polizeli M L, Jorge J A, Terenzi H F. Pectinase production by *Neurospora crassa*: purification and biochemical characterization of extracellular polygalacturonase activity, J. Gen. Microbiol. 1991; 137: 1815-1823). But *Aspergillus* is the major source for the commercial production of pectin esterase (Torres E F, Aguilar C, Esquivel J C C, Gonzales G V. Pectinase. In: Enzyme Technology, Pandey, A., Webb, C., Soccol, C. R., Larroche, C (Eds), Asiatech Publishiers Inc., New Delhi, India, 2005. pp. 273-296).

Pectin-degrading enzymes are important tools in the food industry, primarily for fruit and vegetable processing such as fruit juice production or wine making. Other areas of applications include the pulp and paper industry (Reid I, Ricard M. Pectinase in papermaking: solving retention problems in mechanical pulps bleached with hydrogen peroxide. Enz. Microbiol. Technol. 2000; 26:115-123), animal feed (Barreto de Menezes T J, Salva J G, Baldini V L, Papini R S, Sales A M. Protein enrichment of citrus wastes by solid substrate fermentation. Proc. Biochem. 1989; 23:167-171), retting of flax and other vegetable fibers (Hoondal G S, Tiwari R P, Tiwari R, Dahiya N, Beg Q K. Microbial alkaline pectinases and their applications: a review. Appl. Microbiol. Biotechnol. 2000; 9:409-418), coffee and tea fermentation (Gar J G. Tea, coffee and cocoa. In: wood BJB, editor. Microbiology of fermented foods. 1985; vol 2. London: Elsevier Sci. Ltd. pp: 133-154), oil extraction (Scott D. Enzymes, industrial. In: Encyclopedia of Chemical Technology. Grayson M, Ekarth D and Othmer K (eds), 1978; Wiley, N.Y. pp: 173-224), bio-scouring of cotton fibers (Singh R, Saxena S, Gupta R. Microbial pectinolytic enzymes: A review. Proc. Biochem. 2005; 40:2931-2944), degumming of plant bast fibers (Kapoor M, Beg Q K, Bhushan B, Singh K, Dadich K S, Hoondal G S. Application of alkaline and thermostable polygalacturonase from *Bacillus* sp. MGcp-2 in degumming of ramie (*Boehmeria nivea*) and sunn hemp (*Crotolaria juncia*) bast fibers. Proc. Biochem. 2001; 36:803-817), textile industry (Karmakar S R. Chemical technology in the pretreatment processes of textiles. In: Textile science and technology series 1st ed., Amsterdam: Elsevier Science B. V. 1999; p. 12) and waste management (Kashyap D R, Vohra P K, Chopra S, Tewari R. Applications of pectinases in the commercial sector: a review. Biores. Technol. 2001; 77:215-227). WO 98/45393 discloses detergent compositions containing protopectinase with remarkable detergency against muddy soiling.

These enzymes are used either individually or in a cocktail (mixed) form in the industry. For example, in the food industry it is used as individual enzyme such as pectin esterase required for gellification as well as combination of different enzymes such as pectin esterase with polygalacturonase required for liquefaction of plant material (Heldt-Hansen H P, Kofod L V, Budolfsen G, Nielsen P M, Hüttel S, Bladt T. Application of tailor made pectinases. In: Visser I and Voragen A J G (eds), Pectin and Peactnases. Progress in Biotechnology. 1996; 14:463-474).

The cloning and expression of several of these enzymes obtained from *Aspergillus niger* has been reported. EP 0 278 355 describes the cloning of the pectin lyase gene, the sequence thereof and the expression. EP 0 353 188 adds some other pectin lyases. EO 0 421 919 discloses two polygalacturonases and another endo-polygalacturonase has been disclosed in EP 0 388 593. Both of these patent applications used *Aspergillus niger* as the source of the gene.

WO 94/14952 describes three enzymes with endo-polygalacturonase activity which is obtainable from *Aspergillus aculeatus*. However, no publication was reported on cloning of genes encoding pectin degrading enzymes from *M. phaseolina.*

The present invention takes a genomics approach to disclose the genes and their encoded proteins of the pectin degrading enzymes derived from *M. phaseolina* that can be used in, among other things, industrial processes or purposes.

SUMMARY OF THE INVENTION

Among other things, the present invention relates to at least twenty-one pectin degrading enzymes which are derivable from *M. phaseolina*. The current invention also relates to the use of fungus *M. phaseolina* in the degradation of pectin.

The primary object of the present invention is to disclose the sets of nucleotides sequences encoding pectate lyase (SEQ ID Nos. 1, 2, 4, 5, 7, 8, 10, 11, 13, 14, 16, 17, 19, 20, 22, 23, 25 and 26), Pectate lyase C (SEQ ID No. 28, 29, 31, 32, 34, 35, 37, 38, 40, 41, 43 and 44), pectinesterase (SEQ ID No. 46, 47, 49, 50, 52, 53, 55 and 56) and rhamnogalacturonase (SEQ ID Nos. 58, 59, 61 and 62) of the fungus *M. phaseolina*. For each gene of the invention, an open reading frame (ORF) sequence was derived manually from the respective genomic sequence by deleting predicted intron sequences and splicing together exon sequences. Vectors, expression vectors, and host cells comprising the enzyme genes are also included.

Further, the invention provides deduced polypeptide sequences from the ORF sequences of the genes. The polypeptide sequences of the invention correspond to those of pectate lyase (SEQ ID Nos. 3, 6, 9, 12, 15, 18, 21, 24 and 27), Pectate lyase C (SEQ ID Nos. 30, 33, 36, 39, 42 and 45), pectinesterase (SEQ ID Nos. 48, 51, 54 and 57) and rhamnogalacturonase (SEQ ID Nos. 60 and 63). The present invention also relates to an isolated polynucleotide comprising the complement of the nucleotide sequences described above.

Another object of the present invention is to provide the molecular biology and genetic information of the genes and enzymes set forth in the primary object to be exploited/utilized for the regulation, conversion of pectin degradation for the production of valuable industrial products.

Moreover, the object of present invention is to facilitate in vitro production of the pectin degrading polypeptide, and the present invention also includes an expression construct capable of expressing polypeptide containing at least 70% sequential amino acids as set forth in SEQ ID Nos. 3, 6, 9, 12, 15, 18, 21, 24, 27, 30, 33, 36, 39, 42, 45, 48, 51, 54, 57, 60 and 63. Preferably, the expression construct has inserted DNA or cDNA with sequential nucleotide as set forth in SEQ ID Nos. 2, 5, 8, 11, 14, 17, 20, 23, 26, 29, 32, 35, 38, 41, 44, 47, 50, 53, 56, 59, 62, 1, 4, 7, 10, 13, 16, 19, 22, 25, 28, 31, 34, 37, 40, 43, 46, 49, 52, 55, 58 and 61.

Another object of the present invention discloses a recombinant gene construct comprising a polynucleotide template having nucleotide sequence set forth in SEQ ID Nos. 2, 5, 8, 11, 14, 17, 20, 23, 26, 29, 32, 35, 38, 41, 44, 47, 50, 53, 56, 59, 62, 1, 4, 7, 10, 13, 16, 19, 22, 25, 28, 31, 34, 37, 40, 43, 46, 49, 52, 55, 58 and 61, wherein the polynucleotide template is expressible in a host cell to produce an enzyme which degrade pectin. Preferably, the recombinant gene construct further comprises a promoter region operably-linked to enhance expression of the polynucleotide template.

One of the preferred embodiments of the present invention is the ms6 strain of *M. phaseolina* isolated from an infected jute plant. The isolated polypeptide is also preferably derived from this strain.

Furthermore, the object of the present invention is to provide a potential commercially feasible way to isolate pectin degrading enzyme from *M. phaseolina* in order to keep up with the increasing global demand for, amongst other things, the production of fruit juice, textile products, pulp and paper, coffee, tea and oil extraction.

Further object of the invention is directed to utilize the pectin degrading substances in processing of animal feeds, fruit juice, textile products, pulp and paper, coffee, tea and oil extraction, retting/degumming of bast fibres.

Any or all of these utilities are capable of being developed into a kit for commercialization either as research products or as supplies for industrial and other uses. The kits may comprise polynucleotides and/or polypeptides corresponding to one or more *M. phaseolina* genes of the invention, antibodies, and/or other reagents.

One skilled in the art will readily appreciate that the present invention is well adapted to carry out the objects and obtain the ends and advantages mentioned, as well as those inherent therein. The embodiments described herein are not intended as limitations or restriction on the scope of the invention.

These and other features, aspects, and advantages of the present invention will become better understood with reference to the following description and claims.

BRIEF DESCRIPTION OF THE DRAWINGS

The accompanying drawings, which are incorporated in and form a part of the specification, illustrate the embodiments of the present invention and together with the description, serve to explain the principles of the invention.

FIG. 1 is the electrophoresed agarose gel image showing the PCR amplification result in which lane 1 is polynucleotides of pectate lyase of SEQ ID NO. 1 and lane M is DNA molecular weight ladder.

FIG. 2 is the electrophoresed agarose gel image showing the PCR amplification result in which lane 1 is polynucleotides of pectate lyase of SEQ ID NO. 4 and lane M is DNA molecular weight ladder.

FIG. 3 is the electrophoresed agarose gel image showing the PCR amplification result in which lane 1 is polynucleotides of pectate lyase of SEQ ID NO. 7 and lane M is DNA molecular weight ladder.

FIG. 4 is the electrophoresed agarose gel image showing the PCR amplification result in which lane 1 is polynucleotides of pectate lyase of SEQ ID NO. 10 and lane M is DNA molecular weight ladder.

FIG. 5 is the electrophoresed agarose gel image showing the PCR amplification result in which lane 1 is polynucleotides of pectate lyase of SEQ ID NO. 13 and lane M is DNA molecular weight ladder.

FIG. 6 is the electrophoresed agarose gel image showing the PCR amplification result in which lane 1 is polynucleotides of pectate lyase of SEQ ID NO. 16 and lane M is DNA molecular weight ladder.

FIG. 7 is the electrophoresed agarose gel image showing the PCR amplification result in which lane 1 is polynucleotides of pectate lyase of SEQ ID NO. 19 and lane M is DNA molecular weight ladder.

FIG. 8 is the electrophoresed agarose gel image showing the PCR amplification result in which lane 1 is polynucleotides of pectate lyase of SEQ ID NO. 22 and lane M is DNA molecular weight ladder.

DETAILED DESCRIPTION OF THE INVENTION

Figure 1:
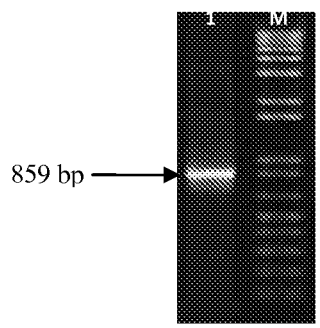
Figure 2:
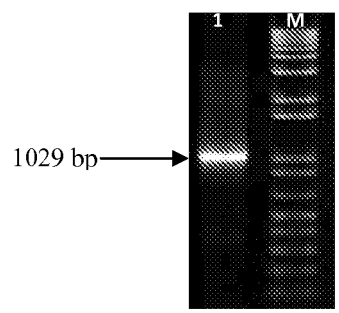
Figure 3:
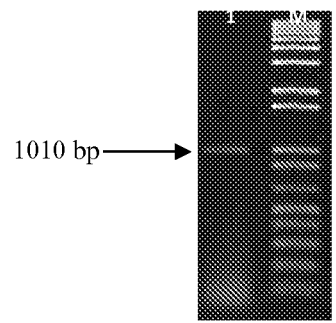
Figure 4:
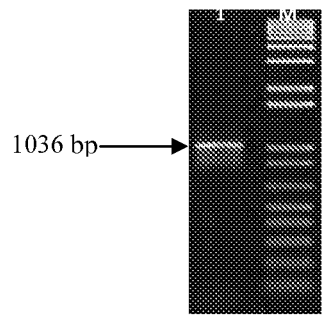
Figure 5:
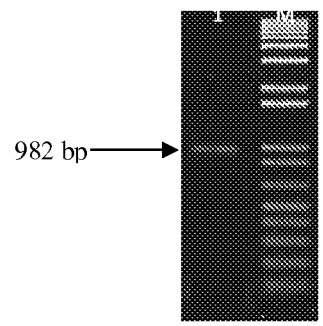
Figure 6:
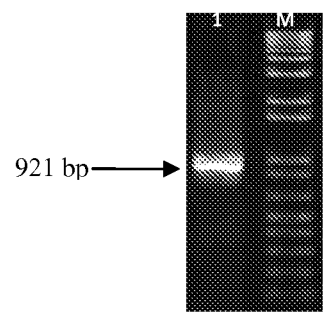
Figure 7:
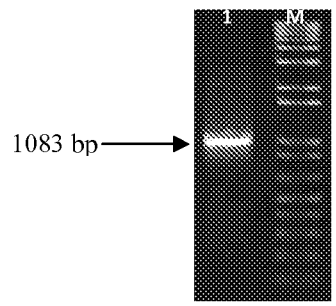
Figure 8:
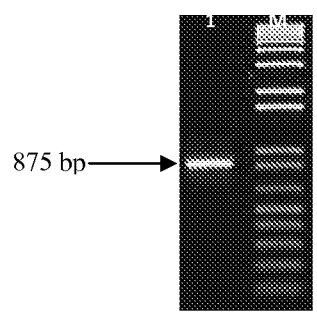
Figure 9:
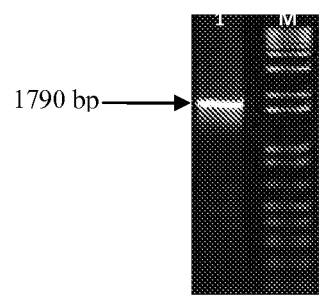
FIG. 9 is the electrophoresed agarose gel image showing the PCR amplification result in which lane 1 is polynucleotides of pectate lyase C of SEQ ID NO. 28 and lane M is DNA molecular weight ladder.
Figure 10:
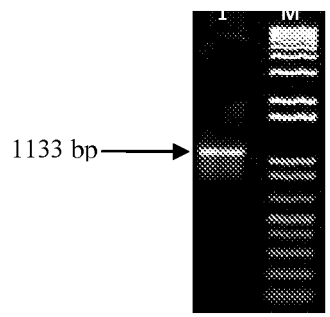
FIG. 10 is the electrophoresed agarose gel image showing the PCR amplification result in which lane 1 is polynucleotides of pectate lyase C of SEQ ID NO. 31 and lane M is DNA molecular weight ladder.
Figure 11:
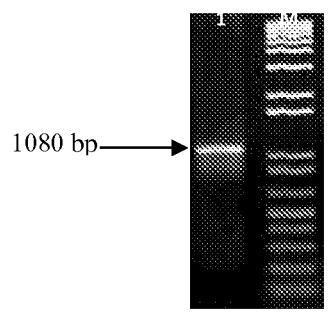
FIG. 11 is the electrophoresed agarose gel image showing the PCR amplification result in which lane 1 is polynucleotides of pectate lyase C of SEQ ID NO. 34 and lane M is DNA molecular weight ladder.
Figure 12:
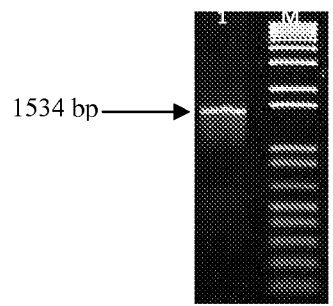
FIG. 12 is the electrophoresed agarose gel image showing the PCR amplification result in which lane 1 is polynucleotides of pectate lyase C of SEQ ID NO. 37 and lane M is DNA molecular weight ladder.
Figure 13:
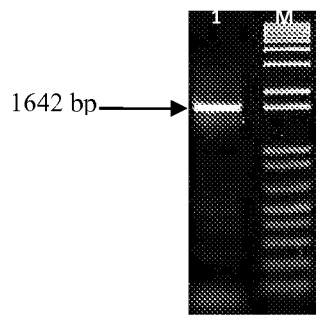
FIG. 13 is the electrophoresed agarose gel image showing the PCR amplification result in which lane 1 is polynucleotides of pectate lyase C of SEQ ID NO. 40 and lane M is DNA molecular weight ladder.
Figure 14:
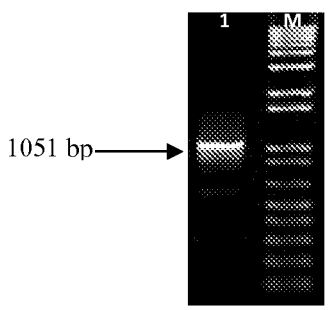
FIG. 14 is the electrophoresed agarose gel image showing the PCR amplification result in which lane 1 is polynucleotides of pectate lyase C of SEQ ID NO. 43 and lane M is DNA molecular weight ladder.
Figure 15:
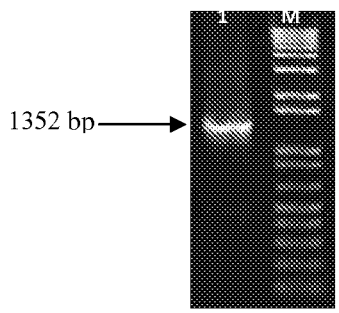
FIG. 15 is the electrophoresed agarose gel image showing the PCR amplification result in which lane 1 is polynucleotides of pectinesterase of SEQ ID NO. 46 and lane M is DNA molecular weight ladder.
Figure 16:
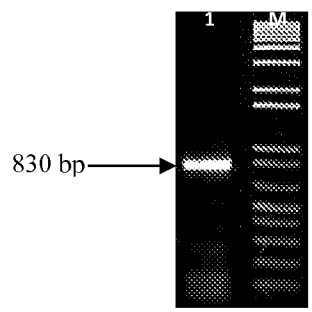
FIG. 16 is the electrophoresed agarose gel image showing the PCR amplification result in which lane 1 is polynucleotides of pectinesterase of SEQ ID NO. 49 and lane M is DNA molecular weight ladder.
Figure 17:
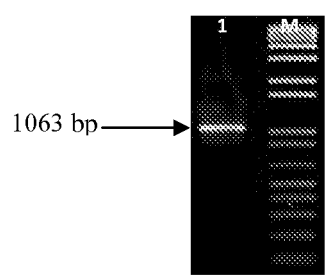
FIG. 17 is the electrophoresed agarose gel image showing the PCR amplification result in which lane 1 is polynucleotides of pectinesterase of SEQ ID NO. 55 and lane M is DNA molecular weight ladder.
Figure 18:
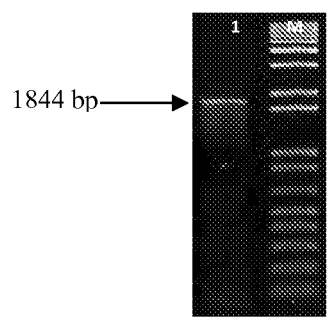
FIG. 18 is the electrophoresed agarose gel image showing the PCR amplification result in which lane 1 is polynucleotides of rhamnogalacturonase of SEQ ID NO. 58 and lane M is DNA molecular weight ladder.
Figure 19:
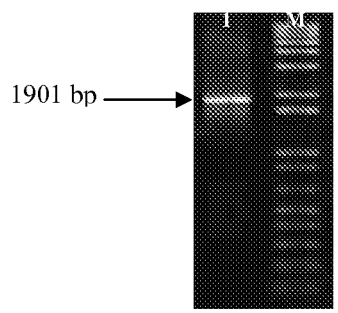
FIG. 19 is the electrophoresed agarose gel image showing the PCR amplification result in which lane 1 is polynucleotides of rhamnogalacturonase of SEQ ID NO. 61 and lane M is DNA molecular weight ladder.

The definitions and/or methods provided herein define the present invention and guide those of ordinary skill in the art in the practice of the present invention. Except where otherwise stated, terms are to be understood according to conventional usage by those of ordinary skill in the relevant art. To the extent to which any of the definitions and/or methods is found to be inconsistent with any of the definitions and/or methods provided in any patent or non-patent reference incorporated herein or in any reference found elsewhere, it is understood that the said definition and/or method which has been expressly provided/adopted in this application will be used herein. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below.

The present invention provides the nucleotide sequences of *M. phaseolina* genes involved in pectin degradation. The genes encode proteins with pectin degrading enzyme activity that is either in use in an industry including food, animal feed, paper, oil extraction, textile, waste water or of interest to an industry. Described herein below are the genes of the invention, their identification, characterization, modification, and methods of usage in various industrial processes.

The nucleotide sequences of *M. phaseolina* genomic DNA was obtained by a whole-genome random shotgun DNA sequencing effort. The genomic DNA was prepared from an isolate of *M. phaseolina* ms6 which was isolated from the infected jute (*Corchorus* spp.) plant. The generated nucleotide sequences were assembled to form contigs and scaffolds by the Newbler assembler. The nucleotide sequences were initially annotated by software programs, such as Augustus, Glimmer M (The Institute of Genome Research, Rockville, Md.) and Evidence Modeler (EVM), which can identify putative coding regions, introns, and splice junctions. Further automated and manual curation of the nucleotide sequences were performed to refine and establish precise characterization of the coding regions and other gene features.

The genomic sequences of the invention that encode the pectin degrading enzymes are identified primarily by comparison of nucleotide sequences of *M. phaseolina* genomic DNA and the nucleotide sequences of known enzyme genes of other microorganisms. The nucleotide sequences of these *M. phaseolina* genes, the reading frames, the positions of exons and introns, the structure of the enzymes, and their potential usefulness in various industries, such as those involved in the making of food and feed, beverages, textiles and detergents, were not known.

Over 14000 cDNAs from *M. phaseolina* were partially or fully sequenced. Among them twenty-one cDNAs encoding new enzymes with putative roles in pectin degradation were discovered.

Open reading frames (ORFs) are analyzed by following full or partial sequencing of clones of cDNA libraries derived from *M. phaseolina* mRNA and are further analyzed by using sequence analysis software, and by determining homology to known sequences in databases (public/private).

In the context of this disclosure, a number of terms used throughout the specification have the indicated meanings unless expressly indicated to have a different meaning.

The term "gene", as used herein, is defined as the genomic sequences of the fungus *M. phaseolina*, particularly polynucleotide sequence encoding polypeptide of the series of enzymes. The term can further include nucleic acid molecules comprising upstream, downstream, and/or intron nucleotide sequences.

The term "open reading frame (ORF)," means a series of nucleotide triplets coding for amino acids without any termination codons and the triplet sequence is translatable into protein using the codon usage information appropriate for a particular organism.

A "coding sequence" or "coding region" refers to a nucleic acid molecule having sequence information necessary to produce a gene product, such as an amino acid or polypeptide, when the sequence is expressed. The coding sequence may comprise untranslated sequences (e.g., introns or 5' or 3' untranslated regions) within translated regions, or may lack such intervening untranslated sequences (e.g., as in cDNA).

As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may also be derived from SEQ ID Nos. 1, 4, 7, 10, 13, 16, 19, 22, 25, 28, 31, 34, 37, 40, 43, 46, 49, 52, 55, 58, 61, 2, 5, 8, 11, 14, 17, 20, 23, 26, 29, 32, 35, 38, 41, 44, 47, 50, 53, 56, 59 and 62, or the complement of such sequences.

"Isolated" means altered "by the hand of man" from the natural state. If a composition or substance occurs in nature, it has been "isolated" if it has been changed or removed from its original environment, or both. For example, a polynucleotide or a polypeptide naturally present in a living plant or animal is not "isolated," but the same polynucleotide or polypeptide separated from the coexisting materials of its natural state is "isolated", as the term is employed herein.

The term "recombinant," when used herein to refer to a polypeptide or protein, means that a polypeptide or protein is derived from recombinant (e.g., microbial or mammalian) expression systems. "Microbial" refers to recombinant polypeptides or proteins made in bacterial or fungal expression systems. Polypeptides or proteins expressed in most bacterial systems, e.g., *Escherichia coli*, will be free of glycosylation modifications; polypeptides or proteins expressed in fungi will be glycosylated.

The term "vector" refers to a plasmid, phage, cosmid, yeast, or virus, an artificial replicating sequence (ARS) or an artificial chromosome for expressing a polypeptide from a nucleotide sequence. The term "vector" is also intended to refer to a nucleic acid molecule capable of transporting another nucleic acid to which it has been linked. One type of vector is a "plasmid," which refers to a circular double-stranded DNA loop into which additional DNA segments may be ligated. Another type of vector is a viral vector, where additional DNA segments may be ligated into the viral genome. Certain vectors are capable of autonomous replication in a host cell into which they are introduced (e.g., bacterial vectors having a bacterial origin of replication and episomal mammalian vectors). Other vectors can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "expression vector" is defined herein as a linear or circular DNA molecule that comprises a polynucleotide encoding a polypeptide of the invention, which is operably linked to additional nucleotides that provide for its expression.

The term "expression construct" can comprise an assembly of a genetic element(s) having a regulatory role in gene expression, for example, promoters or enhancers, or a coding sequence which is transcribed into RNA, mRNA and translated into protein, and which is operably linked to promoter or appropriate transcription initiation and termination sequences.

The term "operably linked" denotes herein a configuration in which a control sequence is placed at an appropriate position relative to the coding sequence of the polynucleotide sequence such that the control sequence directs the expression of the coding sequence of a polypeptide.

The term "host cell", as used herein, includes any cell type which is susceptible to transformation, transfection, transduction, and the like with a nucleic acid construct or expression vector comprising a polynucleotide of the present invention.

The term "recombinant host cells" generally means cultured cells which comprises a recombinant transcriptional unit, and will express heterologous polypeptides or proteins, and RNA encoded by the DNA segment or synthetic gene in the recombinant transcriptional unit. The cells can be prokaryotic or eukaryotic.

"Polypeptide" as used herein, is a single linear chain of amino acids bonded together by peptide bonds, and having a sequence greater than 100 amino acids in length.

The term "promoter" as used herein, refers to a nucleic acid sequence that functions to direct transcription of a downstream gene. The promoter will generally be appropriate to the host cell in which the target gene is being expressed. The promoter together with other transcriptional and translational regulatory nucleic acid sequences (also termed "control sequences") is necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

The term "in-vitro" as used herein, generally refers to a biological reaction which occurs in an artificial environment outside a living organism, which is usually conducted in a laboratory using components of an organism that have been isolated from their usual biological context in order to permit a more detailed or more convenient analysis to be performed.

The term "% homology" is used interchangeably herein with the term "% identity" herein and normally refers to the level of nucleic acid or amino acid sequence identity between the nucleic acid sequence that encodes any one of the inventive polypeptides or the inventive polypeptide's amino acid sequence, when aligned using a sequence alignment program.

For example, as used herein, 80% homology means the same thing as 80% sequence identity determined by a defined algorithm, and accordingly a homologue of a given sequence has greater than 80% sequence identity over a length of the given sequence. Exemplary levels of sequence identity include, but are not limited to, 80, 85, 90, 95, 98% or more sequence identity to a given sequence, e.g., the coding sequence for any one of the inventive polypeptides, as described herein.

Exemplary computer programs which can be used to determine identity between two sequences include, but are not limited to, the suite of BLAST programs, e.g., BLASTN, BLASTX, and TBLASTX, BLASTP and TBLASTN, publicly accessible at www.ncbi.nlm.nih.gov/BLAST.

Sequence searches are typically carried out using the BLASTN program when evaluating a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases.

A preferred alignment of selected sequences in order to determine "% identity" between two or more sequences is performed using for example, the CLUSTAL-W program.

The term "primer" as used herein, is an oligonucleotide capable of binding to a target nucleic acid sequence and priming the nucleic acid synthesis. An amplification oligonucleotide as defined herein will preferably be 10 to 50, most preferably 15 to 25 nucletides in length. The amplification oligonucleotides of the present invention may be chemically synthesized.

The abbreviation used throughout the specification to refer to nucleic acids comprising nucleotide sequences are the conventional one-letter abbreviations. Thus when included in a nucleic acid, the naturally occurring encoding nucleotides are abbreviated as follows: adenine (A), guanine (G), cytosine (C), thymine (T) and uracil (U). Also, unless otherwise specified, the nucleic acid sequences presented herein is the 5'→3'direction.

As used herein, the term "complementary" and derivatives thereof are used in reference to pairing of nucleic acids by the well-known rules that A pairs with T or U and C pairs with G. Complement can be "partial" or "complete". In partial complement, only some of the nucleic acid bases are matched according to the base pairing rules; while in complete or total complement, all the bases are matched according to the pairing rule. The degree of complement between the nucleic acid strands may have significant effects on the efficiency and strength of hybridization between nucleic acid strands as well known in the art. This may be of particular in detection method that depends upon binding between nucleic acids.

The DNA sequences of the invention were generated by sequencing reactions and may contain minor errors which may exist as misidentified nucleotides, insertions, and/or deletions. However, such minor errors, if present, should not disturb the identification of the sequences as a gene of *M. phaseolina* that encodes an enzyme of industrial interest, and are specifically included within the scope of the invention.

Encompassed by the present invention are genomic nucleotide sequences and coding sequences of genes that encode enzymes of *M. phaseolina* of industrial interest. Accordingly, in one embodiment, SEQ ID Nos. 2, 5, 8, 11, 14, 17, 20, 23, 26, 29, 32, 35, 38, 41, 44, 47, 50, 53, 56, 59 and 62, and/or any mixtures/combinations thereof, are provided each of which identifies a nucleotide sequence of the opening reading frame (ORF) of an identified gene. In another embodiment, the genomic sequences of the genes identified by SEQ ID Nos. 1, 4, 7, 10, 13, 16, 19, 22, 25, 28, 31, 34, 37, 40, 43, 46, 49, 52, 55, 58 and 61, and/or any mixtures/combinations thereof, are provided.

As used herein, "gene" refers to (i) a gene comprising and/or consisting at least one of the nucleotide sequences and/or fragments thereof that are set forth in SEQ ID Nos. 2, 5, 8, 11, 14, 17, 20, 23, 26, 29, 32, 35, 38, 41, 44, 47, 50, 53, 56, 59, 62, 1, 4, 7, 10, 13, 16, 19, 22, 25, 28, 31, 34, 37, 40, 43, 46, 49, 52, 55, 58 and 61; (ii) any nucleotide sequence or fragment thereof that encodes the amino acid sequence that are set forth in SEQ ID Nos. 3, 6, 9, 12, 15, 18, 21, 24, 27, 30, 33, 36, 39, 42, 45, 48, 51, 54, 57, 60 and 63; (iii) any nucleotide sequence that hybridizes to the complement of the nucleotide sequences set forth in SEQ ID Nos. 2, 5, 8, 11, 14, 17, 20, 23, 26, 29, 32, 35, 38, 41, 44, 47, 50, 53, 56, 59, 62, 1, 4, 7, 10, 13, 16, 19, 22, 25, 28, 31, 34, 37, 40, 43, 46, 49, 52, 55, 58 and 61 under medium stringency conditions, e.g., hybridization to filter-bound DNA in an appropriate/effective amount of 6× sodium chloride/sodium citrate (SSC) at an appropriate/effective level of temperature, such as 45° C. (approximately) followed by one or more washes in an appropriate/effective amount of SDS, such as 0.2×SSC/0.1% SDS, at an appropriate/effective level of temperature, such as 50 to 65° C. (approximately), or under highly stringent conditions, e.g., hybridization to filter-bound nucleic acid in an appropriate/effective amount of SSC, such as 6×SSC, at an appropriate/effective level of temperature, such as 45° C. (approximately), followed by one or more washes in an appropriate/effective amount of SDS, such as 0.1×SSC/0.2% SDS, at an appropriate/effective level of temperature, such as 68° C. (approximately), or under other hybridization conditions which are apparent to those of skill in the art (see, for example, Ausubel F M, Brent R, Kingston R E, Moore D D, Seidman J G, Smith J A, Struhl K. Current Protocols in Molecular Biology, 1994; Green Publishing Associates, Inc. and John Wiley & Sons, Inc., New York). Preferably, the polynucleotides that hybridize to the complements of the DNA sequences disclosed herein encode gene products, e.g., gene products that are functionally equivalent to a gene product encoded by one of the enzyme genes or fragments thereof.

As described above, gene sequences include not only degenerate nucleotide sequences that encode the amino acid sequences of SEQ ID Nos. 3, 6, 9, 12, 15, 18, 21, 24, 27, 30, 33, 36, 39, 42, 45, 48, 51, 54, 57, 60 and 63, but also degenerate nucleotide sequences that when translated in organisms other than *M. phaseolina*, would yield a polypeptide comprising one of the amino acid sequences of SEQ ID Nos. 3, 6, 9, 12, 15, 18, 21, 24, 27, 30, 33, 36, 39, 42, 45, 48, 51, 54, 57, 60 and 63, or a fragment thereof. One of skill in the art would know how to select the appropriate codons or modify the nucleotide sequences of SEQ ID Nos. 2, 5, 8, 11, 14, 17, 20, 23, 26, 29, 32, 35, 38, 41, 44, 47, 50, 53, 56, 59, 62, 1, 4, 7, 10, 13, 16, 19, 22, 25, 28, 31, 34, 37, 40, 43, 46, 49, 52, 55, 58 and 61, when using the gene sequences in *M. phaseolina* or in other organisms. For example, in *Candida albicans*, the codon CTG encodes a serine residue instead of leucine residue.

The nucleotide sequences of the invention can be used as genetic markers and/or sequence markers to aid the development of a genetic, physical, or sequence map of the *M. phaseolina* genome. The nucleotide sequences and corresponding gene products of the invention can also be used to detect the presence of *M. phaseolina*. Hybridization and antibody-based methods well known in the art can be used to determine the presence and concentration of the nucleotide sequences and corresponding gene products of the invention.

The nucleotide sequences can also be used for identifying inhibitors of the enzymes which may have therapeutic effects, given the fact that the enzymes may play a role in the invasion of a host during an infection.

In another embodiment, in addition to the nucleotide sequences of *M. phaseolina* described above, homologs or orthologs of the genes of the invention which can be present in *M. phaseolina* and other fungal species are also included. Particularly preferred are homologs or orthologs in filamentous fungi. These enzyme genes can be identified and isolated by molecular biological techniques well known in the art.

The term "Fungi" as used herein includes the phyla Ascomycota, Basidiomycota, Chytridiomycota, and Zygomycota (Hawksworth D L, Kirk P M, Sutton B C, Pegler D N. Ainsworth and Bisby's Dictionary of the Fungi (8th Ed.). 1995; CAB International, Wallingford, United Kingdom. 616p) and yeast. Representative groups of Ascomycota include, e.g., *Neurospora, Penicillium, Aspergillus*. Representative groups of Basidiomycota include mushrooms, rusts, and smuts. Representative groups of Chytridiomycota include Allomyces, Blastocladiella, Coelomomyces. Representative groups of Zygomycota include, e.g., *Rhizopus* and *Mucor*.

The term "Filamentous fungi" include all filamentous forms of fungi. The filamentous fungi are characterized by a vegetative mycelium composed of chitin, cellulose, glucan, chitosan, mannan, and other complex polysaccharides. Vegetative growth is done by hyphal elongation and carbon catabolism is obligately aerobic.

Accordingly, the present invention also provides fungal nucleotide sequences that are hybridizable to the polynucleotides of the genes. In one embodiment, the present invention includes an isolated nucleic acid comprising and/or consisting of a nucleotide sequence that is at least 50% identical to a nucleotide sequence selected from the group comprising and/or consisting of: SEQ ID Nos. 2, 5, 8, 11, 14, 17, 20, 23, 26, 29, 32, 35, 38, 41, 44, 47, 50, 53, 56, 59, 62, 1, 4, 7, 10, 13, 16, 19, 22, 25, 28, 31, 34, 37, 40, 43, 46, 49, 52, 55, 58 and 61, and/or any mixtures/combinations thereof.

In another embodiment, the present invention includes an isolated nucleic acid comprising a fungal nucleotide sequence that hybridizes under medium stringency conditions to a second nucleic acid that consists and/or comprises of a nucleotide sequence selected from the group comprising and/or consisting of SEQ ID No. 2, 5, 8, 11, 14, 17, 20, 23, 26, 29, 32, 35, 38, 41, 44, 47, 50, 53, 56, 59, 62, 1, 4, 7, 10, 13, 16, 19, 22, 25, 28, 31, 34, 37, 40, 43, 46, 49, 52, 55, 58 and 61, and/or any mixtures/combinations thereof.

In yet another embodiment, the present invention includes an isolated nucleic acid comprising a fungal nucleotide sequence that encodes a polypeptide the amino acid sequence of which is at least 50% identical to an amino acid sequence selected from the group comprising and/or consisting of SEQ ID Nos. 3, 6, 9, 12, 15, 18, 21, 24, 27, 30, 33, 36, 39, 42, 45, 48, 51, 54, 57, 60 and 63.

The nucleotide sequences of the invention still further include fungal nucleotide sequences which are at least 40% identical to the nucleotide sequences set forth in SEQ ID Nos. 2, 5, 8, 11, 14, 17, 20, 23, 26, 29, 32, 35, 38, 41, 44, 47, 50, 53, 56, 59, 62, 1, 4, 7, 10, 13, 16, 19, 22, 25, 28, 31, 34, 37, 40, 43, 46, 49, 52, 55, 58 and 61.

To isolate homologous genes, the *M. phaseolina* gene sequence described above can be labeled and used to screen a cDNA library constructed from mRNA obtained from the organism of interest, including but not limited to *M. phaseolina*. Accordingly, nucleic acid probes, preferably detectably labeled, consisting of any one of the nucleotide sequences of SEQ ID No. 2, 5, 8, 11, 14, 17, 20, 23, 26, 29, 32, 35, 38, 41, 44, 47, 50, 53, 56, 59, 62, 1, 4, 7, 10, 13, 16, 19, 22, 25, 28, 31, 34, 37, 40, 43, 46, 49, 52, 55, 58 and 61 are included. Hybridization conditions can be preferably of a lower stringency when the cDNA library was derived from an organism different from the type of organism from which the labeled sequence was derived. cDNA screening can also identify clones derived from alternatively spliced transcripts in the same species. Alternatively, the labeled probe can be used to screen a genomic library derived from the organism of interest, again, using appropriately stringent conditions. Low stringency conditions will be well known to those of skill in the art, and will vary predictably depending on the specific organisms from which the library and the labeled sequences are derived. (Details in Sambrook J, Russell D W. Molecular Cloning, A Laboratory Manual, Third edition, 2001, Cold Spring Harbor Press, N.Y.; and Ausubel F M, Brent R, Kingston R E, Moore D D, Seidman J G, Smith J A, Struhl K. Current Protocols in Molecular Biology, 1994; Green Publishing Associates, Inc. and John Wiley & Sons, Inc., New York).

Further, a homologous gene sequence can be isolated by performing a polymerase chain reaction (PCR) using two degenerate oligonucleotide primer pools designed on the basis of amino acid sequences within the gene of interest. The template for the reaction can be cDNA obtained by reverse transcription of mRNA prepared from the organism of interest. The PCR product can be sub-cloned and sequenced to ensure that the amplified sequences represent the sequences of a homologous enzyme gene sequence.

The PCR fragment can then be used to isolate a full length cDNA clone by a variety of methods well known to those of ordinary skill in the art. Alternatively, the labeled fragment can be used to screen a genomic library.

In another embodiment of the invention, the *M. phaseolina* gene sequences can be used in developing modified or novel enzymes that exhibit particularly desirable chemical and/or physical characteristics. Because of the apparent relatedness/similarity of the amino acid sequences among the enzymes of *M. phaseolina* and other filamentous fungi, the structure of an enzyme of another fungus can be used to predict the structure of the *M. phaseolina* enzyme, and aid in the rational modification of the *M. phaseolina* enzyme for useful and superior properties. The sequences provided by the present invention can also be used as preparatory materials for the rational modification or design of novel enzymes with characteristics that enable the enzymes to perform better in demanding processes.

The gene nucleotide sequences can be altered by random and site-directed mutagenesis techniques or directed molecular evolution techniques, such as but not limited to the methods described in (Arnold F H. Protein engineering for unusal environments. Curr. Opinion Biotechnol. 1993; 4:450-455), oligonucleotide-directed mutagenesis (Reidhaar-Olson J F, Sauer R T. Combinatorial cassette mutagenesis as a probe of the informational content of protein sequences. Science, 1988; 241:53-57), chemical mutagenesis (Eckert K A, Drinkwater N R. recA-dependent and recA-independent N-ethyl-N-nitrosourea mutagenesis at a plasmid-encoded herpes simplex virus thymidine kinase gene in E. coll. Mutat Res. 1987; 178:1-10), site-directed mutagenesis (Kunkel T A. Rapid and efficient site-specific mutagenesis without phenotypic selection. Proc. Natl. Acad. Sci. USA, 1985; 82:488-492; Oliphant A, Nussbaum A L, Struhl K. Cloning of random-sequence oligodeoxynucleotides. Gene 1986; 44 177-183), error prone PCR (Cadwell R C, Joyce G F. Randomization of genes by PCR mutagenesis. PCR Methods Appl. 1992; 2:28-33), cassette mutagenesis (Stauss H j, Davies H, Sadovnikova E, Chain B, Horowitz N, Sinclair C. Induction of cytotoxic T lymphocytes with peptides in vitro: identification of candidate T-cell epitopes in human papilloma virus. PNAS 1992; 89(17):

7871-7875) DNA shuffling methods as described in Stemmer W P. DNA shuffling by random fragmentation and reassembly: in vitro recombination for molecular evolution. PNAS 1994; 91(22):10747-10751 and in U.S. Pat. Nos. 5,605,793; 6,117,679; and 6,132,970, and the methods as described in U.S. Pat. Nos. 5,939,250, 5,965,408, 6,171,820. The mutations in the nucleotide sequence can be determined by sequencing the gene in the clones.

In one embodiment, the 747 bp long polynucleotide illustrated in SEQ ID No. 2 is the full length cDNA clone encoded pectate lyase protein exhibiting an open reading frame encoding 248 amino acid polypeptide, as in SEQ ID No. 3, with a calculated molecular mass about 26 kD. Through SMART analysis of SEQ ID No. 2, it reveals presence of Pfam pectate lyase domain in the sequence. Pectate lyase is an extracellular enzyme that catalyzes the eliminative cleavage of pectate to produce oligosaccharides with 4-deoxy-alpha-D-gluc-4-enuronosyl groups at their non-reducing ends. This enzyme is involved in the degradation of pectin.

Preferably, the 735 bp long polynucleotide illustrated in SEQ ID No. 5 is the full length cDNA clone encoded pectate lyase protein exhibiting an open reading frame encoding 244 amino acid polypeptide, as in SEQ ID No. 6, with a calculated molecular mass about 25 kD. Through SMART analysis of SEQ ID No. 5, it reveals presence of Pfam pectate lyase domain in the sequence. Pectate lyase is an extracellular enzyme that catalyzes the eliminative cleavage of pectate to produce oligosaccharides with 4-deoxy-alpha-D-gluc-4-enuronosyl groups at their non-reducing ends. This enzyme is involved in the degradation of pectin.

Similarly, another aspect, the 756 bp long long polynucleotide illustrated in SEQ ID No. 8 is the full length cDNA clone encoded pectate lyase protein exhibiting an open reading frame encoding 251 amino acid polypeptide, as in SEQ ID No. 9, with a calculated molecular mass about 26 kD. Through SMART analysis of SEQ ID No. 8, it reveals presence of Pfam pectate lyase domain in the sequence. Pectate lyase is an extracellular enzyme that catalyzes the eliminative cleavage of pectate to produce oligosaccharides with 4-deoxy-alpha-D-gluc-4-enuronosyl groups at their non-reducing ends. This enzyme is involved in the degradation of pectin.

In another aspect, the 771 bp long long polynucleotide illustrated in SEQ ID No. 11 is the full length cDNA clone encoded pectate lyase protein exhibiting an open reading frame encoding 256 amino acid polypeptide, as in SEQ ID No. 12, with a calculated molecular mass about 27 kD. Through SMART analysis of SEQ ID No. 11, it reveals presence of Pfam pectate lyase domain in the sequence. Pectate lyase is an extracellular enzyme that catalyzes the eliminative cleavage of pectate to produce oligosaccharides with 4-deoxy-alpha-D-gluc-4-enuronosyl groups at their non-reducing ends. This enzyme is involved in the degradation of pectin.

Further in another aspect, the 750 bp long long polynucleotide illustrated in SEQ ID No. 14 is the full length cDNA clone encoded pectate lyase protein exhibiting an open reading frame encoding 249 amino acid polypeptide, as in SEQ ID No. 15, with a calculated molecular mass about 26 kD. Through SMART analysis of SEQ ID No. 14, it reveals presence of Pfam pectate lyase domain in the sequence. Pectate lyase is an extracellular enzyme that catalyzes the eliminative cleavage of pectate to produce oligosaccharides with 4-deoxy-alpha-D-gluc-4-enuronosyl groups at their non-reducing ends. This enzyme is involved in the degradation of pectin.

Yet another aspect, the 756 bp long long polynucleotide illustrated in SEQ ID No. 17 is the full length cDNA clone encoded pectate lyase protein exhibiting an open reading frame encoding 251 amino acid polypeptide, as in SEQ ID No. 18, with a calculated molecular mass about 26 kD. Through SMART analysis of SEQ ID No. 17, it reveals presence of Pfam pectate lyase domain in the sequence. Pectate lyase is an extracellular enzyme that catalyzes the eliminative cleavage of pectate to produce oligosaccharides with 4-deoxy-alpha-D-gluc-4-enuronosyl groups at their non-reducing ends. This enzyme is involved in the degradation of pectin.

Yet another aspect, the 894 bp long long polynucleotide illustrated in SEQ ID No. 20 is the full length cDNA clone encoded pectate lyase protein exhibiting an open reading frame encoding 297 amino acid polypeptide, as in SEQ ID No. 21, with a calculated molecular mass about 30 kD. Through SMART analysis of SEQ ID No. 20, it reveals presence of Pfam pectate lyase domain in the sequence. Pectate lyase is an extracellular enzyme that catalyzes the eliminative cleavage of pectate to produce oligosaccharides with 4-deoxy-alpha-D-gluc-4-enuronosyl groups at their non-reducing ends. This enzyme is involved in the degradation of pectin.

Yet another aspect, the 747 bp long long polynucleotide illustrated in SEQ ID No. 23 is the full length cDNA clone encoded pectate lyase protein exhibiting an open reading frame encoding 248 amino acid polypeptide, as in SEQ ID No. 24, with a calculated molecular mass about 26 kD. Through SMART analysis of SEQ ID No. 23, it reveals presence of Pfam pectate lyase domain in the sequence. Pectate lyase is an extracellular enzyme that catalyzes the eliminative cleavage of pectate to produce oligosaccharides with 4-deoxy-alpha-D-gluc-4-enuronosyl groups at their non-reducing ends. This enzyme is involved in the degradation of pectin.

Yet another aspect, the 1707 bp long long polynucleotide illustrated in SEQ ID No. 26 is the full length cDNA clone encoded pectate lyase protein exhibiting an open reading frame encoding 568 amino acid polypeptide, as in SEQ ID No. 27, with a calculated molecular mass about 64 kD. Through SMART analysis of SEQ ID No. 26, it reveals presence of Pfam pectate lyase domain in the sequence. Pectate lyase is an extracellular enzyme that catalyzes the eliminative cleavage of pectate to produce oligosaccharides with 4-deoxy-alpha-D-gluc-4-enuronosyl groups at their non-reducing ends. This enzyme is involved in the degradation of pectin.

In another aspect, the 1314 bp long long polynucleotide illustrated in SEQ ID No. 29 is the full length cDNA clone encoded pectate lyase C protein exhibiting an open reading frame encoding 437 amino acid polypeptide, as in SEQ ID No. 30, with a calculated molecular mass about 46 kD. Through sequence analysis of SEQ ID No. 29, it reveals presence of pectate lyase C domain motif in the sequence. Pectate lyase C is an extracellular enzyme that cleaves polygalacturonate, a major component of plant cell wall. This enzyme is involved in the degradation of pectin.

In another aspect, the 972 bp long long polynucleotide illustrated in SEQ ID No. 32 is the full length cDNA clone encoded pectate lyase C protein exhibiting an open reading frame encoding 323 amino acid polypeptide, as in SEQ ID No. 33, with a calculated molecular mass about 34 kD. Through sequence analysis of SEQ ID No. 32, it reveals presence of pectate lyase C domain motif in the sequence. Pectate lyase C is an extracellular enzyme that cleaves polygalacturonate, a major component of plant cell wall. This enzyme is involved in the degradation of pectin.

In another aspect, the 966 bp long long polynucleotide illustrated in SEQ ID No. 35 is the full length cDNA clone encoded pectate lyase C protein exhibiting an open reading frame encoding 321 amino acid polypeptide, as in SEQ ID No. 36, with a calculated molecular mass about 33 kD. Through sequence analysis of SEQ ID No. 35, it reveals presence of pectate lyase C domain motif in the sequence. Pectate lyase C is an extracellular enzyme that cleaves polygalacturonate, a major component of plant cell wall. This enzyme is involved in the degradation of pectin.

In another aspect, the 1536 bp long long polynucleotide illustrated in SEQ ID No. 38 is the full length cDNA clone encoded pectate lyase C protein exhibiting an open reading frame encoding 511 amino acid polypeptide, as in SEQ ID No. 39, with a calculated molecular mass about 56 kD. Through sequence analysis of SEQ ID No. 38, it reveals presence of pectate lyase C domain motif in the sequence. Pectate lyase C is an extracellular enzyme that cleaves polygalacturonate, a major component of plant cell wall. This enzyme is involved in the degradation of pectin.

In another aspect, the 1137 bp long long polynucleotide illustrated in SEQ ID No. 41 is the full length cDNA clone encoded pectate lyase C protein exhibiting an open reading frame encoding 378 amino acid polypeptide, as in SEQ ID No. 42, with a calculated molecular mass about 39 kD. Through sequence analysis of SEQ ID No. 41, it reveals presence of pectate lyase C domain motif in the sequence. Pectate lyase C is an extracellular enzyme that cleaves polygalacturonate, a major component of plant cell wall. This enzyme is involved in the degradation of pectin.

In another aspect, the 1137 bp long long polynucleotide illustrated in SEQ ID No. 44 is the full length cDNA clone encoded pectate lyase C protein exhibiting an open reading frame encoding 378 amino acid polypeptide, as in SEQ ID No. 45, with a calculated molecular mass about 39 kD. Through sequence analysis of SEQ ID No. 44, it reveals presence of pectate lyase C domain motif in the sequence. Pectate lyase C is an extracellular enzyme that cleaves polygalacturonate, a major component of plant cell wall. This enzyme is involved in the degradation of pectin.

In another aspect, the 1182 bp long long polynucleotide illustrated in SEQ ID No. 47 is the full length cDNA clone encoded pectinesterase protein exhibiting an open reading frame encoding 393 amino acid polypeptide, as in SEQ ID No. 48, with a calculated molecular mass about 42 kD. Through SMART sequence analysis of SEQ ID No. 47, it reveals presence of pectinesterase domain in the sequence. Pectinesterase is an extracellular enzyme that catalyzes the de-esterification of methyl ester linkages of galacturonan backbone of pectic substances to release acidic pectins and methanol. The resulting pectin is then acted upon by polygalacturonases and lyases.

In another aspect, the 975 bp long long polynucleotide illustrated in SEQ ID No. 50 is the full length cDNA clone encoded pectinesterase protein exhibiting an open reading frame encoding 324 amino acid polypeptide, as in SEQ ID No. 51, with a calculated molecular mass about 35 kD. Through SMART sequence analysis of SEQ ID No. 50, it reveals presence of pectinesterase domain in the sequence. Pectinesterase is an extracellular enzyme that catalyzes the de-esterification of methyl ester linkages of galacturonan backbone of pectic substances to release acidic pectins and methanol. The resulting pectin is then acted upon by polygalacturonases and lyases.

In another aspect, the 5895 bp long long polynucleotide illustrated in SEQ ID No. 53 is the full length cDNA clone encoded pectinesterase protein exhibiting an open reading frame encoding 1964 amino acid polypeptide, as in SEQ ID No. 54, with a calculated molecular mass about 206 kD. Through SMART sequence analysis of SEQ ID No. 53, it reveals presence of multiple pectinesterase domains in the sequence. Pectinesterase is an extracellular enzyme that catalyzes the de-esterification of methyl ester linkages of galacturonan backbone of pectic substances to release acidic pectins and methanol. The resulting pectin is then acted upon by polygalacturonases and lyases.

In another aspect, the 981 bp long long polynucleotide illustrated in SEQ ID No. 56 is the full length cDNA clone encoded pectinesterase protein exhibiting an open reading frame encoding 326 amino acid polypeptide, as in SEQ ID No. 57, with a calculated molecular mass about 34 kD. Through SMART sequence analysis of SEQ ID No. 56, it reveals presence of pectinesterase domains in the sequence. Pectinesterase is an extracellular enzyme that catalyzes the de-esterification of methyl ester linkages of galacturonan backbone of pectic substances to release acidic pectins and methanol. The resulting pectin is then acted upon by polygalacturonases and lyases.

In another aspect, the 1593 bp long long polynucleotide illustrated in SEQ ID No. 59 is the full length cDNA clone encoded rhamnogalacturonase protein exhibiting an open reading frame encoding 530 amino acid polypeptide, as in SEQ ID No. 60, with a calculated molecular mass about 57 kD. Through SMART sequence analysis of SEQ ID No. 59, it reveals presence of rhamnogalacturonase domains in the sequence.

Rhamnogalacturonase cleaves alpha-1, 4 glycosidic bonds between L-rhamnose and D-galacturonic acids in the backbone of rhamnogalacturonan-I, a major component of the plant cell wall polysaccharide, pectin.

Still in another aspect, the 1605 bp long long polynucleotide illustrated in SEQ ID No. 62 is the full length cDNA clone encoded rhamnogalacturonase protein exhibiting an open reading frame encoding 534 amino acid polypeptide, as in SEQ ID No. 63, with a calculated molecular mass about 57 kD. Through SMART sequence analysis of SEQ ID No. 62, it reveals presence of rhamnogalacturonase domains in the sequence.

Rhamnogalacturonase cleaves alpha-1, 4 glycosidic bonds between L-rhamnose and D-galacturonic acids in the backbone of rhamnogalacturonan-1, a major component of the plant cell wall polysaccharide, pectin.

The present invention also relates to (a) nucleic acid vectors that comprise and/or consist a nucleotide sequence comprising any of the foregoing sequences of the genes and/or their complements; (b) expression constructs that comprise a nucleotide sequence consisting and/or comprising any of the foregoing coding sequences of the genes operably linked with a regulatory element that directs the expression of the coding sequences; and (c) recombinant host cells that comprise and/or consist any of the foregoing sequences of the gene, including coding regions operably linked with a regulatory element that directs the expression of the coding sequences in the host cells.

The techniques for modifying polynucleotide sequences utilizing recombinant DNA methods are well known in the art. The various sequences may be joined in accordance with known techniques, such as restriction, joining complementary restriction sites and ligating, blunt ending by filling in overhangs and blunt ligation or the like. Poly linkers and adapters may be employed, when appropriate, and introduced or removed by known techniques to allow for ease of assembly of the DNA vectors and expression constructs. A large number of vectors are available for cloning and genetic manipulation. Normally, cloning can be performed in *E. coli*.

In another embodiment of the invention, vectors that comprise an enzyme gene sequence of the invention may further comprise replication functions that enable the transfer, maintenance and propagation of the vectors in one or more species of host cells, including but not limited to *E. coli* cells, filamentous fungal cells, yeast cells, and *Bacillus* cells. The vector may contain any means for assuring self-replication. Alternatively, the vector may be one which, when introduced into the host cell, is integrated into the genome and replicated together with the chromosome(s) into which it has been integrated. The choice of the vector will typically depend on the compatibility of the vector with the host cell into which the vector is to be introduced.

Expression construct of the invention comprises and/or consists of a promoter, a nucleotide sequence encoding for a gene sequence of the invention, a transcription termination sequence and selectable marker (optional). Any method known in the art for introducing this expression construct into a host cell can be used. Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton M M, Hames J E, Timberlake W E. Transformation of *Aspergillus nidulans* by using a trpC plasmid. PNAS, 1984; 81(5):1470-1474. Suitable methods for transforming *Fusarium* species are described by Malardier L, Daboussi M J, Julien J, Roussel F, Scazzocchio C, Brygoo Y. Cloning of the nitrate reductase gene (niaD) of *Aspergillus nidulans* and its use for transformation of *Fusarium oxysporum*. Gene 1989; 78:147-156, and WO 96/00787. Yeast may be transformed using the procedures described by Becker D M, Guarente L. High-efficiency transformation of yeast by electroporation. In: Abelson J N and Simon M I (eds), Guide to Yeast Genetics and Molecular Biology, Methods in Enzymology, 1991; 194:182-187, Academic Press, Inc., New York; Ito H, Fukuda Y, Murata K, Kimura A. Transformation of intact yeast cells treated with alkali cations. Journal of Bacteriology, 1983; 153: 163-168 and Hinnen A, Hicks J B, Fink G R. Transformation of yeast. PNAS, 1978; 75 (4): 1929-1933.

For industrial applications, the enzymes of the present invention are produced by a fungal cell. Preferably, the expression host cell is a filamentous fungal cell which has been used in large scale industrial fermentation. Appropriate cell lines or host systems can be chosen to ensure the correct modification and processing of the foreign protein expressed. Preferably, an expression host is selected which is capable of the efficient secretion of their endogenous proteins. A host cell may also be chosen for deficiencies in extracellular protease activities since the secreted enzyme may be degraded in the culture medium.

The present invention also relates to methods for producing a polypeptide of the present invention, comprising: (i) cultivating a cell, which in its wild-type form is capable of producing the polypeptide, under conditions conducive for production of the polypeptide; and (ii) recovering the polypeptide. In a preferred aspect, the cell is *M. phaseolina*.

Another embodiment of the invention also relates to methods for producing a polypeptide of the present invention, comprising: (i) cultivating a host cell under conditions conducive for production of the polypeptide, wherein the host cell comprises a nucleotide sequence of SEQ ID Nos. 2, 5, 8, 11, 14, 17, 20, 23, 26, 29, 32, 35, 38, 41, 44, 47, 50, 53, 56, 59, 62, 1, 4, 7, 10, 13, 16, 19, 22, 25, 28, 31, 34, 37, 40, 43, 46, 49, 52, 55, 58 or 61, wherein the nucleotide sequence encodes a polypeptide which comprises or consists of the mature polypeptide of SEQ ID Nos. 3, 6, 9, 12, 15, 18, 21, 24, 27, 30, 33, 36, 39, 42, 45, 48, 51, 54, 57, 60 or 63, and (ii) recovering the polypeptide.

In another embodiment of the present invention, the expression host cells or transformants are cultivated in a suitable nutrient medium for growth and expression of proteins using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art (see In: More Gene Manipulations in Fungi. Bennett J W, Lasure L., (eds). 1991; Academic Press, San Diego, Calif.). If the polypeptide is secreted into the nutrient medium, the polypeptide can be recovered directly from the medium. If the polypeptide is not secreted into the medium, it can be recovered from cell lysates.

The polypeptides may be detected using methods known in the art that are specific for the polypeptides. These detection methods may include use of specific antibodies, formation of an enzyme product, or disappearance of an enzyme substrate. An enzyme assay may be used to determine the activity of the polypeptide.

The produced polypeptide may be recovered using methods known in the art. The polypeptide may be recovered in various methods from the nutrient medium by conventional procedures including, but not limited to, filtration, centrifugation, extraction, spray-drying, evaporation and precipitation or combination thereof.

The polypeptides of the present invention may be purified by a variety of procedures that are well known in the art including, but not limited to, chromatography method (such as ion exchange, affinity, hydrophobic, chromatofocusing, and size exclusion), electrophoretic procedures (such as isoelectric focusing), differential solubility (such as ammonium sulfate precipitation), SDS-PAGE, or extraction to obtain substantially pure polypeptides (see details in Protein Purification, Principles, High Resolution Methods and Applications. Janson J C, Rydén L. (eds( ) 1989; VCH Publishers Inc., New York).

The present invention also relates those gene products (e.g., RNA or proteins) that are encoded by the gene sequences set forth in SEQ ID Nos. 2, 5, 8, 11, 14, 17, 20, 23, 26, 29, 32, 35, 38, 41, 44, 47, 50, 53, 56, 59 and 62. The enzyme gene products of the invention also includes those RNA or proteins that are encoded by the genomic sequences of the genes as set forth in SEQ ID Nos. 1, 4, 7, 10, 13, 16, 19, 22, 25, 28, 31, 34, 37, 40, 43, 46, 49, 52, 55, 58 and 61. The enzymes of the invention comprise an amino acid sequence selected from the group comprising and/or consisting of SEQ ID Nos. 3, 6, 9, 12, 15, 18, 21, 24, 27, 30, 33, 36, 39, 42, 45, 48, 51, 54, 57, 60 and 63.

The enzymes of the present invention display at least one of the activities of an enzyme selected from the group comprising and/or consisting of pectate lyase, pectate lyase C, pectinesterase and rhamnogalacturonase. The enzyme gene products of the invention can be readily produced, e.g., by synthetic techniques or by methods of recombinant DNA technology using techniques that are well known in the art (See, Creighton T E. Proteins: Structures and Molecular Principles, 1983; W. H. Freeman and Co., N.Y.)

In another embodiment, the methods and compositions of the invention also include proteins and polypeptides that represent functionally equivalent gene products. Such functionally equivalent gene products include, but are not limited to, natural variants of the polypeptides having an amino acid sequence set forth in SEQ ID Nos. 3, 6, 9, 12, 15, 18, 21, 24, 27, 30, 33, 36, 39, 42, 45, 48, 51, 54, 57, 60 and 63.

Such equivalent gene products can contain, e.g. deletions, additions or substitutions of amino acid residues within the amino acid sequences encoded by the enzyme gene sequences described above, but which result in a silent change, thus producing a functionally equivalent product. Amino acid substitutions can be made on the basis of similarity in polarity, charge, solubility, hydrophobicity, hydrophilicity and/or the amphipathic nature of the residues involved.

Other modifications of the gene product coding sequences described above can be made to generate polypeptides that are better suited, e.g., for expression, for scale up, etc. in a chosen host cell. For example, cysteine residues can be deleted or substituted with another amino acid in order to eliminate disulfide bridges.

Another embodiment of the present invention further includes enzymes of the present invention in solid form. Enzymes in solid form or enzyme granulate can be used, for example, in solid detergent and in animal feed. Methods of making solid forms of enzymes are well known in the art, such as but not limited to prilling (spray-cooling in a waxy material), extrusion, agglomeration, or granulation (dilution with an inert material and binders). Solid enzymatic compositions comprising a solid form of an enzyme of the invention, in the form of mixed powder, tablets, and the like, is contemplated.

The present disclosure includes as contained in the appended claims, as well as that of the foregoing description. Although this invention has been described in its preferred form with a degree of distinctiveness, it is understood that the present disclosure of the preferred form has been made only by way of example and that numerous changes in the details of construction and the combination and arrangements of parts may be resorted to without departing from the scope of the invention and claims.

Various references are cited herein, the disclosures of which are incorporated by reference in their entireties.

EXAMPLE

The following example is intended to further illustrate the invention, without any intent for the invention to be limited to the specific embodiments described therein.

Example 1 Isolation of Genomic DNA from M. phaseolina

Genomic DNA was isolated from M. phaseolina strain ms6 using the procedures described by Kieser T, Bibb M J, Buttner M J, Chater K F, Hopwood D A. Practical Streptomyces Genetics, 2000; John Innes Foundation, Norwich, UK, pp. 162-208. Briefly, mycelia were scraped from a stock Petri plate using inoculating loop and inoculated into a liquid potato-dextrose media in a conical flask. The conical flask was incubated without shaking for about 72 hours at 30° C. The mycelia grow on the surface at the air-medium interface. The mycelia were harvested using a sterile toothpick and placed between sterile paper towels and several were washed with physiological solution (Sodium phosphate buffer pH 7.0). The mycelia were squeezed to remove excess liquid and the harvested mycelia were allowed to air dry for 30 minutes. The semi-dry mycelia were placed in liquid nitrogen and ground to generate fine powder and finally isolate the DNA following the protocol describe in Kieser T, Bibb N A Buttner M J, Chater K F, Hopwood D A. Practical *Streptomyces* Genetics, 2000; John Innes Foundation, Norwich, UK, pp. 162-208.

Example 2 Designing and Synthesis of Primers

The primers used in the study were either designed from the manually curated transcriptome and the "gene models" predicted from the genomic sequences of *M. phaseolina* ms6, by choosing the sequences manually with complete ORFs or using databases where similar genes have been successfully isolated from other plants. Comparative bioinformatic analysis of the nucleotide sequences obtained from transcriptome were carried out using NCBI BLAST, BLASTP, RPS-BLAST, BLASTX and PSI-BLAST to identify homologues of the related genes and for the proper identification of gene. Nucleotide sequence alignments were performed using clustalW version 1.82 whenever multiple sequences were found from the "gene pool". The alignment was then edited. Gene specific primers (both forward and reverse) were selected manually or through Primer 3 plus tool and the primers were custom synthesized.

All oligonucleotides used in this study were synthesized and HPLC purified by the supplier and procured from Integrated DNA Technologies (IDT). Stock solution of 100 pmol were prepared in autoclaved $ddH_2O$ and stored at −20° C., in aliquots for use.

| Gene name | SEQ ID No. | Sequence identifier | Primer Sequence | Amplified product (bp) |
|---|---|---|---|---|
| Pectate lyase | 1 | 64 | Forward TCATCACCGACCCACAATCGC | 859 |
| | | 65 | Reverse CTTAGCAAGCGGGAGCCGTC | |
| Pectate lyase | 4 | 66 | Forward CAGACAACGGCGTCGACAGT | 1029 |
| | | 67 | Reverse ACGGACCACATCCAACGCGA | |
| Pectate lyase | 7 | 68 | Forward ATGCCCTGGTACCCTGCCCC | 1010 |
| | | 69 | Reverse GAAAGGTCCCGGGCTCACGC | |
| Pectate lyase | 10 | 70 | Forward CCGCTCCTCTGTGCGTTGTTGAA | 1036 |
| | | 71 | Reverse ACAGCGATAGAGCCGCAACACG | |

-continued

| Gene name | SEQ ID No. | Sequence identifier | Primer | Sequence | Amplified product (bp) |
|---|---|---|---|---|---|
| Pectate lyase | 13 | 72 | Forward | TTTCCTCACCACCACTTCCCCTCT | 982 |
|  |  | 73 | Reverse | CGAAAGCCAGCCCAAGCGAC |  |
| Pectate lyase | 16 | 74 | Forward | GGCAAGCATCCTCTCTCCGGC | 921 |
|  |  | 75 | Reverse | CCTGAGGCCCATCGTCCGAGT |  |
| Pectate lyase | 19 | 76 | Forward | TCCCTGCCTCTCCATCCTACCCT | 1083 |
|  |  | 77 | Reverse | CCAACCGTGTGGCCGTCGAA |  |
| Pectate lyase | 22 | 78 | Forward | ACATGCAGTTCAAGTACGCCGCT | 875 |
|  |  | 79 | Reverse | GCAGGGGCCCACACCTCTTG |  |
| Pectate lyase | 25 | 80 | Forward | TCCAAGGCAGAGCCTCCGAAACA | 2382 |
|  |  | 81 | Reverse | GCTCCCTGCGGGCGTGTTTTA |  |
| Pectate lyase C | 28 | 82 | Forward | ACAGACCCCATCACATCCGCCA | 1790 |
|  |  | 83 | Reverse | TTGCATTGAGCCCTCTTGGGCTGT |  |
| Pectate lyase C | 31 | 84 | Forward | CTGTCCTCCAGCAGCAGCCTC | 1133 |
|  |  | 85 | Reverse | CGAGCAACCCGTCGAGGTCAA |  |
| Pectate lyase C | 34 | 86 | Forward | CATGAAGGCCACCACCCTCGC | 1080 |
|  |  | 87 | Reverse | CCGAACCCTGGCTCGGGCAT |  |
| Pectate lyase C | 37 | 88 | Forward | ACCCCCACGCCGAACAATACC | 1534 |
|  |  | 89 | Reverse | CCGCCAAGTCTATCCGCTCGC |  |
| Pectate lyase C | 40 | 90 | Forward | GGCTTCGGTGGACCGTCCTAT | 1642 |
|  |  | 91 | Reverse | CCACCCGCTCCGCCCTTAAA |  |
| Pectate lyase C | 43 | 92 | Forward | AGGAGATGGGCTGCCGTCCT | 1051 |
|  |  | 93 | Reverse | GCTCAGCAAGCGTCCAACCCA |  |
| Pectinesterase | 46 | 94 | Forward | TCCCGTGCCATGGTAGCCTTT | 1352 |
|  |  | 95 | Reverse | GCTGGCCACCACAATCCACA |  |
| Pectinesterase | 49 | 96 | Forward | TGGCCTCTTGATCAGGCTCGT | 830 |
|  |  | 97 | Reverse | GCGGTGACCCATCCCTGCTT |  |
| Pectinesterase | 52 | 98 | Forward | TCGTCCACCGGTACCACGTT | 7503 |
|  |  | 99 | Reverse | TGCTACGCAAGTGTGCAAAGTGT |  |
| Pectinesterase | 55 | 100 | Forward | ATCACAGCATGCCTCGCCTCG | 1063 |
|  |  | 101 | Reverse | CAGTCCTGCCGGTTCCTTGCAT |  |
| Rhamnogalacturonase | 58 | 102 | Forward | CGGAGGATTGCTGCGGGACTT | 1844 |
|  |  | 103 | Reverse | CCGCGAAACCATCCACAACACG |  |
| Rhamnogalacturonase | 61 | 104 | Forward | ACGGGCCAAGGTGCCAGAAC | 1901 |
|  |  | 105 | Reverse | CACCCTTCTCCTGACCCTCGCT |  |

Example 3 Amplification, Cloning and Sequencing of Pectate Lyase, Pectate Lyase C, Pectinesterase and Rhamnogalacturonase from *M. phaseolina* ms6

Total RNA was isolated from three days old mycelium grown on liquid medium as previously described by Chomczynski P and Sacchi N, Single-step method of RNA isolation by acid guanidinium thiocyanate-phenol-chloroform extraction (Anal Biochem 1987, 162: 156-159). The quality or the integrity of the RNA was checked by agarose gel electrophoresis and was quantified using Thermo Scientific Nano Drop 2000 as per standard procedures. cDNA first strand was synthesised using SuperScript III reverse transcriptase (Invitrogen) following the manufacturer's instructions. The gene was amplified from the cDNA by PCR using the gene specific primers. The PCR reaction (50 μL) contained 1 μL of cDNA, 20 pmoles of each primers, 5 μL of 10×PCR Buffer, 5 μL of 2.5 mM dNTP mix and 1.0 unit of PfuTaq DNA polymerase. PCR was carried out in Thermal Cycler (Applied Biosystems) using the following conditions: initial denaturation for 5 minutes ("min") at 95° C. followed by 35 cycles of denaturation at 95° C. for 30 seconds ("sec"), annealing at 59-61° C. for 30 sec and extension at 72° C. for 1 to 2.0 min depending on the length of the targeted gene, with a final extension at 72° C. for 7 min. The PCR product was analyzed by 1% agarose gel using 1×TAE buffer and the amplicon was eluted from the gel using QIAGEN gel extraction kit following the manufacturer's instructions. The purified PCR product was ligated into pCR®8/GW/TOPO® TA cloning kit (Invitrogen) and transformed into competent *E. coli* cells (Invitrogen). Plasmids were isolated from putative colonies using QIAprip Spin Miniprep Kit (QIAGEN) following the manufacturer's instructions. The presence of the insert was checked by using the gene specific primers and positive plasmids were subjected to Sequencing.

Example 3 Analysis of the Sequence

The nucleotide sequence and the amino acid sequence were analyzed by BLASTN and BLASTP programs respectively. The sequences reported from other plants were aligned with ClustalW. Phylogenetic analysis was carried out using the Neighbour Joining (NJ).

```
SEQ ID NO:          1
LENGTH:             1047 (including 150 bp 5' UTR and 150 bp 3' UTR)
TYPE:               DNA
ORGANISM:           M. phaseolina
GAAGAGTATATAGAGGTGGCCACGACTGCACTGTTGAACTCATCACCGACCCACAATCGCTTTCTTTCTGCCC

ACTCTCGTTCACAACACAGATCTCTGATCTACCACATTCGTTCTTACCGAGGATCAAAAATTCCTCCCATCTC

CACAATGCAGTACAAGTACACCGTCCTTGCCGCCACTATGGCCGCCGTTGCCTTCGCCCAGCAGAACTTGATT

GGCATTCCTACCGGTACTAAAGCTAAGCCTTTCACCCAGCCCGAGACCATTACCTTCTTCGACGGTAAAATGA

TGGAATACGGCCGCGGCAAGCCCTGTGGCACCGACGATGACAAGGGTGACCTTGAGGCCGTCTTCATCATCAA

GCCCGGCGGCACGCTGCAGAACGCCATCATCGGCGCCGACTCCCTTGAGGGCGTGCACTGCGAGGGCGCCTGC

ACCATCAAGAACGTCTGGTTCAAGGACGTGTGCGAAGACGCCATCACCCTCAAGGGCAACGGCCCGTACCTGA

TCACCGGTGGCGGTGCGCAGCACGCCAAGGACAAGGTCGTCCAGCACAACGGCAAGGGCACCGTGACCATCTC

CGATTACAAGATCGGCGCCGTCGGTAAGCTGTACCGCAGCTGTGGCAACTGCAGCAACAACGGCGGCCCCCGC

AACGTCGTCCTCGACCGCATCTCTTCCTTCGGCCCCGGCACCACGTCCGACCTTGTCGGCATCAACTCCAACT

ACAACGACGTCGCCACCATCAGTGGCGTCTGCGGCCCTGTCAAGAACATGTGTCAGGAGTTCACCGGCATCGA

GAAGGACGGCAACAAGGAGAGCCCCCACAGGGAGCCCCCGATTGGTGCTTGCAAGGGCCCCCAGGGCCAGCTC

AAGACGGCTCCCGCTTGCTAAGCGCCTCACGGAATTATCATGGGTGTGCAGTTACGGGAAAGGAAATCGATAT

CGACCTCCCTATTGGTAACATCAATCTGGCTCCAAATTGCATCATCCGCCACTGGTCGGCCATGACAGGACAG

AGCGAAGTCAAAAGTTTCGGTGTAC

SEQ ID NO:          2
LENGTH:             747
TYPE:               DNA
ORGANISM:           M. phaseolina
FEATURE NAME/KEY:   CDS
LOCATION:           (1) ... (747)
atgcagtacaagtacaccgtccttgccgccactatggccgccgttgccttcgcccagcag
 M  Q  Y  K  Y  T  V  L  A  A  T  M  A  A  V  A  F  A  Q  Q aacttgattggcattcctaccggtactaaagctaagcctttcacccagcccgagaccatt
 N  L  I  G  I  P  T  G  T  K  A  K  P  F  T  Q  P  E  T  I accttcttcgacggtaaaatgatggaatacggccgcggcaagccctgtggcaccgacgat
 T  F  F  D  G  K  M  M  E  Y  G  R  G  K  P  C  G  T  D  D gacaagggtgaccttgaggccgtcttcatcatcaagcccggcggcacgctgcagaacgcc
 D  K  G  D  L  E  A  V  F  I  I  K  P  G  G  T  L  Q  N  A atcatcggcgccgactcccttgagggcgtgcactgcgagggcgcctgcaccatcaagaac
 I  I  G  A  D  S  L  E  G  V  H  C  E  G  A  C  T  I  K  N gtctggttcaaggacgtgtgcgaagacgccatcaccctcaagggcaacggcccgtacctg
 V  W  F  K  D  V  C  E  D  A  I  T  L  K  G  N  G  P  Y  L atcaccggtggcggtgcgcagcacgccaaggacaaggtcgtccagcacaacggcaagggc
 I  T  G  G  G  A  Q  H  A  K  D  K  V  V  Q  H  N  G  K  G accgtgaccatctccgattacaagatcggcgccgtcggtaagctgtaccgcagctgtggc
 T  V  T  I  S  D  Y  K  I  G  A  V  G  K  L  Y  R  S  C  G aactgcagcaacaacggcggcccccgcaacgtcgtcctcgaccgcatctcttccttcggc
 N  C  S  N  N  G  G  P  R  N  V  V  L  D  R  I  S  S  F  G cccggcaccacgtccgaccttgtcggcatcaactccaactacaacgacgtcgccaccatc
 P  G  T  T  S  D  L  V  G  I  N  S  N  Y  N  D  V  A  T  I agtggcgtctgcggccctgtcaagaacatgtgtcaggagttcaccggcatcgagaaggac
 S  G  V  C  G  P  V  K  N  M  C  Q  E  F  T  G  I  E  K  D ggcaacaaggagagcccccacagggagcccccgattggtgcttgcaagggcccccagggc
 G  N  K  E  S  P  H  R  E  P  P  I  G  A  C  K  G  P  Q  G
```

```
cagctcaagacggctcccgcttgctaa
 Q   L   K   T   A   P   A   C   -

SEQ ID NO:           3
LENGTH:              248
TYPE:                PRT
ORGANISM:            M. phaseolina
MQYKYTVLAATMAAVAFAQQNLIGIPTGTKAKPFTQPETITFFDGKMMEYGRGKPCGTDDDKGDLEAVFIIKP

GGTLQNAIIGADSLEGVHCEGACTIKNVWFKDVCEDAITLKGNGPYLITGGGAQHAKDKVVQHNGKGTVTISD

YKIGAVGKLYRSCGNCSNNGGPRNVVLDRISSFGPGTTSDLVGINSNYNDVATISGVCGPVKNMCQEFTGIEK

DGNKESPHREPPIGACKGPQGQLKTAPAC*

SEQ ID NO:           4
LENGTH:              1167 (including 150 bp 5' UTR and 150 bp 3' UTR)
TYPE:                DNA
ORGANISM:            M. phaseolina
CTACCACGAATCGGAATTAAACGACGAATCTCCTGGTGAAGACTATAAAAGGCAGACAACGGCGTCGACAGTA

AAGACCATCGCAATCCAACAGTCCAGTTCCTCCTCAAGTCTCTCACTCCCATCCTCCACTTTCCAATCACTTC

CAACATGAAGTTCATCTACGCCGCTATCACCGCCACCGTGGCTGGCCTTGCCTCTGCGCAGTCCCTGACCATC

CCCACCCGCTCCGGCAGCAAGGTCGTCCTCTCCGCGCCCAGTACCATCTCCGGCTCGCAAGACTTTGGTAACA

AGGAGTTCGACCGCGGAATCCCCTGCGACTCGGACGATGACACTGGCAGCTCCAGCGCCGTCTTCATCCTCAA

GAACGGCGCCAGCATCTCCAACGTCATCATTGGTACCGACGCGCTCGAGGGCGTCCACTGCGAGGGTGCCTGC

ACCCTGACCAACGTCTGGTTCCGTGACGTCTGCGAGGGTGAGCTAAATCCACAACATACCATCAAACACTCAA

GTAGTGCACACGAATGCTAATGGGAAAATCCAGACGCCATCTCCGCGCTCGGCACCGGCAATGTCCTCATCCA

GGGCGGCGGTGCGCAGAACGCCAAGGACAAGGTCGTCCAGCACAACGGCCGCGGCACCGTCACCATCAAGAAC

TACACCGTCGTCAACGCCGGCAAGCTGTACCGCAGCTGCGGCGACTGCACCAACAACGGCGGCCCCCGCAACG

TCGTCGTGGACAACGTCCGCGTCAACGGCATGACCTCTGACCTCGTCGGCATCAACTCCAACTACGGTGACAG

TAAGTCGGCAAAAGATACTTCAAATCGTTGGAGGAACACTCAATACTGACTGTCGATTCCAGCTGCTACCATC

AGCAACTCTTGCGCGTCTCCAAGAAGGTCTGCCAGGAGTACAAGGGCGTCACCAAGGGCAACGGCGACAGCG

AGAAGGTCTCCACCACTGCCAACTGCAAGGGTGCTCAGGGTACTCTGTCTAAGCTTCCCACTTGCTAGACAAC

CTAAAAGCAAAACCAAACTAGAGCTTGGGCACGGATCACTCGCGTTGGATGTGGTCCGTGGAATCCTTGGTCA

GTGCTCAATCGCCTGCTTCGAGTGGGAAACGGCCGTCTCAATTGATACCGGGCGAGTGTCTGCGCATGGATG

SEQ ID NO:           5
LENGTH:              735
TYPE:                DNA
ORGANISM:            M. phaseolina
FEATURE NAME/KEY:    CDS
LOCATION:            (1) ... (735)
atgaagttcatctacgccgctatcaccgccaccgtggctggccttgcctctgcgcagtcc
 M   K   F   I   Y   A   A   I   T   A   T   V   A   G   L   A   S   A   Q   S ctgaccatccccacccgctccggcagcaaggtcgtcctctccgcgcccagtaccatctcc
 L   T   I   P   T   R   S   G   S   K   V   V   L   S   A   P   S   T   I   S ggctcgcaagactttggtaacaaggagttcgaccgcggaatcccctgcgactcggacgat
 G   S   Q   D   F   G   N   K   E   F   D   R   G   I   P   C   D   S   D   D gacactggcagctccagcgccgtcttcatcctcaagaacggcgccagcatctccaacgtc
 D   T   G   S   S   S   A   V   F   I   L   K   N   G   A   S   I   S   N   V atcattggtaccgacgcgctcgagggcgtccactgcgaggtgcctgcaccctgaccaac
 I   I   G   T   D   A   L   E   G   V   H   C   E   G   A   C   T   L   T   N gtctggttccgtgacgtctgcgaggacgccatctccgcgctcggcaccggcaatgtcctc
 V   W   F   R   D   V   C   E   D   A   I   S   A   L   G   T   G   N   V   L atccagggcggcggtgcgcagaacgccaaggacaaggtcgtccagcacaacggccgcggc
 I   Q   G   G   G   A   Q   N   A   K   D   K   V   V   Q   H   N   G   R   G accgtcaccatcaagaactacaccgtcgtcaacgccggcaagctgtaccgcagctgcggc
 T   V   T   I   K   N   Y   T   V   V   N   A   G   K   L   Y   R   S   C   G
```

```
gactgcaccaacaacggcggcccccgcaacgtcgtcgtggacaacgtccgcgtcaacggc
 D   C   T   N   N   G   G   P   R   N   V   V   V   D   N   V   R   V   N   G atgacctctgacctcgtcggcatcaactccaactacggtgacactgctaccatcagcaac
 M   T   S   D   L   V   G   I   N   S   N   Y   G   D   T   A   T   I   S   N tcttgcggcgtctccaagaaggtctgccaggagtacaagggcgtcaccaagggcaacggc
 S   C   G   V   S   K   K   V   C   Q   E   Y   K   G   V   T   K   G   N gacagcgagaaggtctccaccactgccaactgcaagggtgctcagggtactctgtctaag
 D   S   E   K   V   S   T   T   A   N   C   K   G   A   Q   G   T   L   S   K cttcccacttgctag
 L   P   T   C   -
```

```
SEQ ID NO:       6
LENGTH:          244
TYPE:            PRT
ORGANISM:        M. phaseolina
```
MKFIYAAITATVAGLASAQSLTIPTRSGSKVVLSAPSTISGSQDFGNKEFDRGIPCDSDDDTGSSSAVFILKN

GASISNVIIGTDALEGVHCEGACTLTNVWFRDVCEDAISALGTGNVLIQGGGAQNAKDKVVQHNGRGTVTIKN

YTVVNAGKLYRSCGDCTNNGGPRNVVVDNVRVNGMTSDLVGINSNYGDTATISNSCGVSKKVCQEYKGVTKGN

GDSEKVSTTANCKGAQGTLSKLPTC*

```
SEQ ID NO:       7
LENGTH:          1110 (including 150 bp 5' UTR and 150 bp 3' UTR)
TYPE:            DNA
ORGANISM:        M. phaseolina
```
CAGCGGTATATAAATGCCCTGGTACCCTGCCCCAAAATGCCTTCTTCACCACCACAGTCCTTCGTTTCAATCG

TTCAGCACATTCACTCTTTCATTCACACTCACTAACCGATCTGCGATCGTGTTCTTTGCCTTCCACTACCAGA

CACAATGTTCTCCAAGCTTTTCCTGCTTCCCCTCCTGGCGGCTTCCGCCCTGGCTGCTCCTGCCGACGACACT

TTCGGCTACGAGCTCGTTCGCCGCGCGAACTTCCCCATTCCTGCCTCCAAGGGCAACGTCAAGCTCAGCGCTG

CCAAGTCCGTGTCCGGCACCTTCGATGGTGGCATGAAGACCTACGGCCGTGGTGTCAAGTGCACCGGTCAGGC

CGAGGGTGGTGACAAGGACGCCGTCTTCATCCTCGAGAACGGTGCTACCCTCAAGAACGCCATCATTGGTACC

GACCAGATCGAGGGCGTCCACTGCAAGGGCTCCTGCACCATCGAAAACGTCTGGTGGGCCGGTGTCTGCGAGG

ACGCGCTCTCCCTGAAGGGTGACGGTTCCGCCAAGGTCATCGGCGGCGGCGCTACTGGCGCTGAAGACAAGGT

ACGTACGCCTCTGATACGCCTTCGCTCAGATTGCTGACCAGATCTGGTACAGGTCATCCAGCACAACGGCGTT

GGCTCCGTCTCGATTGATGGCTTCACTGTTGCCGACTTCGGCAAGCTCTACCGCTCGTGCGGAAACTGCAAGA

AGATGGGCAAGAGAACCGTCACCATCAAGAACGTGAAGGCTAGCAACGGAAAGCTTTTGGCTGGCATCAACTC

CAACTACGGCGACACTGCTACCATCACCGGCACCTGCGCTACCTCCGTCAAGAAGGTCTGCACCGAGTTCAAG

GGCAACAACAGCGGCAAGGAGCCCACCGAGATCAGCTCCGGCCCCAGCAACGCCTGCAAGTACTCCTCCCTCA

AGGCCTGCTAGGGCCTGCTAGACGGTTGCTCAACAAACAAACATGGCATTTGCCGCGTGAGCCCGGGACCTTT

CCGGGCTCGGGAGAAGAAAGTGGATGGCATTCTATTCTTGTATCGACTTCTAGTACTAGAGCATCTTCTATAC

CTCTAATTTACTGTG

```
SEQ ID NO:       8
LENGTH:          756
TYPE:            DNA
ORGANISM:        M. phaseolina
FEATURE NAME/KEY: CDS
LOCATION:        (1) ... (756)
atgttctccaagcttttcctgcttcccctcctggcggcttccgccctggctgctcctgcc
 M   F   S   K   L   F   L   L   P   L   L   A   A   S   A   L   A   A   P   A gacgacactttcggctacgagctcgttcgccgcgcgaacttccccattcctgcctccaag
 D   D   T   F   G   Y   E   L   V   R   R   A   N   F   P   I   P   A   S   K ggcaacgtcaagctcagcgctgccaagtccgtgtccggcaccttcgatggtggcatgaag
 G   N   V   K   L   S   A   A   K   S   V   S   G   T   F   D   G   G   M   K acctacggccgtggtgtcaagtgcaccggtcaggccgagggtggtgacaaggacgccgtc
 T   Y   G   R   G   V   K   C   T   G   Q   A   E   G   G   D   K   D   A   V
```

```
ttcatcctcgagaacggtgctaccctcaagaacgccatcattggtaccgaccagatcgag
 F  I  L  E  N  G  A  T  L  K  N  A  I  I  G  T  D  Q  I  E ggcgtccactgcaagggctcctgcaccatcgaaaacgtctggtgggccggtgtctgcgag
 G  V  H  C  K  G  S  C  T  I  E  N  V  W  W  A  G  V  C  E gacgcgctctccctgaagggtgacggttccgccaaggtcatcggcggcggcgctactggc
 D  A  L  S  L  K  G  D  G  S  A  K  V  I  G  G  G  A  T  G gctgaagacaaggtcatccagcacaacggcgttggctccgtctcgattgatggcttcact
 A  E  D  K  V  I  Q  H  N  G  V  G  S  V  S  I  D  G  F  T gttgccgacttcggcaagctctaccgctcgtgcggaaactgcaagaagatgggcaagaga
 V  A  D  F  G  K  L  Y  R  S  C  G  N  C  K  K  M  G  K  R accgtcaccatcaagaacgtgaaggctagcaacggaaagcttttggctggcatcaactcc
 T  V  T  I  K  N  V  K  A  S  N  G  K  L  L  A  G  I  N  S aactacggcgacactgctaccatcaccggcacctgcgctacctccgtcaagaaggtctgc
 N  Y  G  D  T  A  T  I  T  G  T  C  A  T  S  V  K  K  V  C accgagttcaagggcaacaacagcggcaaggagcccaccgagatcagctccggccccagc
 T  E  F  K  G  N  N  S  G  K  E  P  T  E  I  S  S  G  P  S aacgcctgcaagtactcctccctcaaggcctgctag
 N  A  C  K  Y  S  S  L  K  A  C  -

SEQ ID NO:          9
LENGTH:             251
TYPE:               PRT
ORGANISM:           M. phaseolina
MFSKLFLLPLLAASALAAPADDTFGYELVRRANFPIPASKGNVKLSAAKSVSGTFDGGMKTYGRGVKCTGQAE

GGDKDAVFILENGATLKNAIIGTDQIEGVHCKGSCTIENVWWAGVCEDALSLKGDGSAKVIGGGATGAEDKVI

QHNGVGSVSIDGFTVADFGKLYRSCGNCKKMGKRTVTIKNVKASNGKLLAGINSNYGDTATITGTCATSVKKV

CTEFKGNNSGKEPTEISSGPSNACKYSSLKAC*

SEQ ID NO:          10
LENGTH:             1127 (including 150 bp 5' UTR and 150 bp 3' UTR)
TYPE:               DNA
ORGANISM:           M. phaseolina
CCGCTCCTCTGTGCGTTGTTGAACCTTGCTGTTTGTAGGTATAAAGCCCCCCGTCATTGCTGAGGACGTGTA

TGGACAGGATCCCTCAAACAGATTGTCTTCTACATCTCAGCGCATTAAGAACCCCATAAATACCAAGAGTTAC

AAACATGCGTTCTACAAATCTGCTCGTCCTCCTCGCAACCTCCCTCAGCCTGGTCGCAGCGAGCCCGTTGGAT

GCGCCGACCAAAGTGATGGGCAAGCGGTTCGCCACCAATGTTCTACCCGCATCATCTGGACATGTTGTCCTCC

CCTCAGCAACCACTGTGAGCACTTTTTGACGGCGGAATGAAGAAGTACGACCGTGGTACCTCTTGCACTGGTCA

GTCCGAAGGGGGGGATGCGGACGCTGTCTTCCTCGTTCAGTCCGGAGGCACCCTCAAGAATGTCATCATTGGT

GCGGACCAATCTGAAGGTGTCCACTGTCTCGGCCCGTGCACGATCCAGAACGTGTGGTGGGAGGCCGTCTGCG

AGGGTGAGAGCCAGACGCTTCGCGTTGTAAAGGGGCGAAATGCTGACCTCAAGACCCAGACGCCTTGACCATC

AAACAAACTTCTGGGACCTCCTACGTCGTTGGCGGCGGTGCTTTTGGCGCGTCAGACAAAATTATCCAGCACA

ACGGAGGCGGTACCGTCTCGATCAAGGACTTCTACGCCCAAGATTTCGGCAAAGTTTACCGCAGCTGCGGCAA

TTGCGGCACTCAGTACAAACGCACCGTCACCATGTCTGGGATTTGGGCCGTTAATGGTGATCTCCTTGCCGGC

GTTAACTCCAATTACGGTGATACCGCGACCATTTCCGGCACTTGTGCAGACAACGTGGACAACATCTGCGCCT

GGTACGAAGGAAACGATGATGGCGATGAGCCCACCAAGTTGGGCACTGGCATCAGCTCTTACTGTGTCTATAC

CGCCAATGGTGTCGATGACTGCCCTTGAGTTGAACATTGGCTTCTATTTGCCACGACACTATGATCGTGTTGC

GGCTCTATCGCTGTTGTGTCCGGTTGGTGAGGGCACCCGTACATATGTGGAATGGAGGTCACGTGGTGGATAG

CATGTACATATTCTTGCCTGTTATGCCTACAC

SEQ ID NO:          11
LENGTH:             771
TYPE:               DNA
ORGANISM:           M. phaseolina
FEATURE NAME/KEY:   CDS
LOCATION:           (1) ... (771)
```

```
atgcgttctacaaatctgctcgtcctcctcgcaacctccctcagcctggtcgcagcgagc
 M  R  S  T  N  L  L  V  L  L  A  T  S  L  S  L  V  A  A  S ccgttggatgcgccgaccaaagtgatgggcaagcggttcgccaccaatgttctacccgca
 P  L  D  A  P  T  K  V  M  G  K  R  F  A  T  N  V  L  P  A tcatctggacatgttgtcctcccctcagcaaccactgtgagcacttttgacggcggaatg
 S  S  G  H  V  V  L  P  S  A  T  T  V  S  T  F  D  G  G  M aagaagtacgaccgtggtacctcttgcactggtcagtccgaaggggggatgcggacgct
 K  K  Y  D  R  G  T  S  C  T  G  Q  S  E  G  G  D  A  D  A gtcttcctcgttcagtccggaggcaccctcaagaatgtcatcattggtgcggaccaatct
 V  F  L  V  Q  S  G  G  T  L  K  N  V  I  I  G  A  D  Q  S gaaggtgtccactgtctcggcccgtgcacgatccagaacgtgtggtgggaggccgtctgc
 E  G  V  H  C  L  G  P  C  T  I  Q  N  V  W  W  E  A  V  C gaggacgcccttgaccatcaaacaaacttctgggacctcctacgtcgttggcggcggtgct
 E  D  A  L  T  I  K  Q  T  S  G  T  S  Y  V  V  G  G  G  A tttggcgcgtcagacaaaattatccagcacaacggaggcggtaccgtctcgatcaaggac
 F  G  A  S  D  K  I  I  Q  H  N  G  G  G  T  V  S  I  K  D ttctacgcccaagatttcggcaaagtttaccgcagctgcggcaattgcggcactcagtac
 F  Y  A  Q  D  F  G  K  V  Y  R  S  C  G  N  C  G  T  Q  Y aaacgcaccgtcaccatgtctgggatttgggccgttaatggtgatctccttgccggcgtt
 K  R  T  V  T  M  S  G  I  W  A  V  N  G  D  L  L  A  G  V aactccaattacggtgataccgcgaccatttccggcacttgtgcagacaacgtggacaac
 N  S  N  Y  G  D  T  A  T  I  S  G  T  C  A  D  N  V  D  N atctgcgcctggtacgaaggaaacgatgatggcgatgagcccaccaagttgggcactggc
 I  C  A  W  Y  E  G  N  D  D  G  D  E  P  T  K  L  G  T  G atcagctcttactgtgtctataccgccaatggtgtcgatgactgcccttga
 I  S  S  Y  C  V  Y  T  A  N  G  V  D  D  C  P  -
```

SEQ ID NO:       12
LENGTH:          256
TYPE:            PRT
ORGANISM:        M. phaseolina

MRSTNLLVLLATSLSLVAASPLDAPTKVMGKRFATNVLPASSGHVVLPSATTVSTFDGGMKKYDRGTSCTGQS

EGGDADAVFLVQSGGTLKNVIIGADQSEGVHCLGPCTIQNVWWEAVCEDALTIKQTSGTSYVVGGGAFGASDK

IIQHNGGGTVSIKDFYAQDFGKVYRSCGNCGTQYKRTVTMSGIWAVNGDLLAGVNSNYGDTATISGTCADNVD

NICAWYEGNDDGDEPTKLGTGISSYCVYTANGVDDCP*

SEQ ID NO:       13
LENGTH:          1164 (including 150 bp 5' UTR and 150 bp 3' UTR)
TYPE:            DNA
ORGANISM:        M. phaseolina

AGTGACATATAAGTCCTCTGTTCTGCCATCGGAAAATGCTTCTCATCACCAACATTCTCTTCCTTCTTTCCTC

ACCACCACTTCCCCTCTTTCAAACAATTACCGGATAGATCTGTGATCATCCCCTACTTTCGTTTAACAACATA

CAAAATGCAGTCCAAGATCGTTCTCGGCCTTTCTCTCCTCGCCGCCACCGGCATGGCGGCTCCCTCCGAGCCC

CTCCGCGTCCGCGCCACCCTCCCCATCCCCTCCTCCAAGGGCTCTGTCACCTACGATGAGGTCAAGTCCATCA

CCGGCACTTTCGACGGTGGCATGAAGACCTACGGCCGTGGTGTTTCCTGCACTGGCCAGAAGGAGGGTGGCAA

CAAGGACGCCGTCTTCCAGCTTGAGGACGGTGCTACCCTCAAGAACGTCATCATTGGCGAGGACCAGATCGAG

GGTATCCACTGCATGGGCAGCTGCACCCTGGAGAACGTCTGGTGGAGCGCCGTCTGCGAGGGTTTGTCTTCTT

CCATCCACTGAAGCACTTCACAGCTAACGTCATCTCAGACGCTCTTACCTTCAAGGGTGACGGTGACGCCAAG

GTCATCGGCGGCGGTGCCCAGGGCGCCGACGACAAGGTCCTCCAGCACAACGGTGTCGGCGATGTGACCATCG

ACGGCTTCACCGTTGTCGATTTCGGCAAGCTGTATCGCTCTTGCGGCAGTAAGTTCCCCCCGGCTTCTGCCCA

CCTCCATCCCTCATTCACCTGCTCACACACGTGTTCCAGACTGCAAGCAGAACGGCGGCACCCGCAACGTCAA

CATCTCCAACGTCAAGGCCTACAACGGCAAGGTCCTCACCGGCATCAACTCCAACTACGGCGACGTCGCCACC

TTCAAGGACACCTGCGCCTCTTCCGTCAAGGACATCTGCGTCGAGTACAAGGGTACCAACAACAACGACGAGG

```
AGCCCTCCAAGATCGGCTCCGGTCCTTCCGACAACTGCGTCTACTCCGACATCCCCTCTTGCTAGACGGCTCG

CCAACGGTCGCTTGGGCTGGCTTTCGCGGATGCCCATTGTGAATAATCCGCTTGTTTCTTGTATGTAATTATT

TTAAAGGCAAGAAGACCATTTAAATCAATAAATAGAGACGGGGCTAGACCTCGCTTGTACTACGCACAC
```

SEQ ID NO:          14
LENGTH:             750
TYPE:               DNA
ORGANISM:           M. phaseolina
FEATURE NAME/KEY:   CDS
LOCATION:           (1) ... (750)

```
atgcagtccaagatcgttctcggcctttctcctcgccgccaccggcatggcggctccc
 M  Q  S  K  I  V  L  G  L  S  L  L  A  A  T  G  M  A  A  P tccgagcccctccgcgtccgcgccacccteccatccctcctccaagggctctgtcacc
 S  E  P  L  R  V  R  A  T  L  P  I  P  S  S  K  G  S  V  T tacgatgaggtcaagtccatcaccggcactttcgacggtggcatgaagacctacggccgt
 Y  D  E  V  K  S  I  T  G  T  F  D  G  G  M  K  T  Y  G  R ggtgtttcctgcactggccagaaggagggtggcaacaaggacgccgtcttccagcttgag
 G  V  S  C  T  G  Q  K  E  G  G  N  K  D  A  V  F  Q  L  E gacggtgctacccctcaagaacgtcatcattggcgaggaccagatcgagggtatccactgc
 D  G  A  T  L  K  N  V  I  I  G  E  D  Q  I  E  G  I  H  C atgggcagctgcaccctggagaacgtctggtggagcgccgtctgcgaggacgctcttacc
 M  G  S  C  T  L  E  N  V  W  W  S  A  V  C  E  D  A  L  T ttcaagggtgacggtgacgccaaggtcatcggcggcggtgcccagggcgccgacgacaag
 F  K  G  D  G  D  A  K  V  I  G  G  G  A  Q  G  A  D  D  K gtcctccagcacaacggtgtcggcgatgtgaccatcgacggcttcaccgttgtcgatttc
 V  L  Q  H  N  G  V  G  D  V  T  I  D  G  F  T  V  V  D  F ggcaagctgtatcgctcttgcggcaactgcaagcagaacggcggcacccgcaacgtcaac
 G  K  L  Y  R  S  C  G  N  C  K  Q  N  G  G  T  R  N  V  N atctccaacgtcaaggcctacaacggcaaggtcctcaccggcatcaactccaactacggc
 I  S  N  V  K  A  Y  N  G  K  V  L  T  G  I  N  S  N  Y  G gacgtcgccaccttcaaggacaccctgcgcctcttccgtcaaggacatctgcgtcgagtac
 D  V  A  T  F  K  D  T  C  A  S  S  V  K  D  I  C  V  E  Y aagggtaccaacaacaacgacgaggagcccctccaagatcggctccggtccttccgacaac
 K  G  T  N  N  N  D  E  E  P  S  K  I  G  S  G  P  S  D  N tgcgtctactccgacatcccctcttgctag
 C  V  Y  S  D  I  P  S  C  -
```

SEQ ID NO:    15
LENGTH:       249
TYPE:         PRT
ORGANISM:     M. phaseolina

MQSKIVLGLSLLAATGMAAPSEPLRVRATLPIPSSKGSVTYDEVKSITGTFDGGMKTYGRGVSCTGQKEGGNK

DAVFQLEDGATLKNVIIGEDQIEGIHCMGSCTLENVWWSAVCEDALTFKGDGDAKVIGGGAQGADDKVLQHNG

VGDVTIDGFTVVDFGKLYRSCGNCKQNGGTRNVNISNVKAYNGKVLTGINSNYGDVATFKDTCASSVKDICVE

YKGTNNNDEEPSKIGSGPSDNCVYSDIPSC*

SEQ ID NO:    16
LENGTH:       1238 (including 150 bp 5' UTR and 150 bp 3' UTR)
TYPE:         DNA
ORGANISM:     M. phaseolina

```
CTATAAAGATGGAGACCAGCCAGCTTCTAGAGGCTTTTCCCTCCAGGCAAGCATCCTCTCTCCGGCCATCACT

TTCATTCTTTCGCATTCTTCCACTCTTTTGTCCAACTCCGACCCGAACAGATCTGTGATCGTTCACTACACTA

CACAATGTTGACCAAGACTCTTCTTCCCCTCCTCGCCATCTCTGGCGCCGTCTCTGCCGTCAAGACCAAGACC

TTCGGCAAGAACCTCGTCCGCCGTGCGGACTTCCCTATCCCTGAATCCCAGGGTTCCGTCACCTTTGACGCCG

CCGAGGAGGTCGATGGCGAGTACGACGGTGGCTACAAGACGTACGGCCGTGGTGTTTCTTGCACTGGCCAGGA

GGAGGGTGGCGACTCTGACGCCGTCTTCATCCTGAAGGACGGTGCTTCCCTCAAGAACGCCATCATCGGCTCT

GACCAGATTGAGGGTGTCCACTGCGAGGGCTCCTGCACTCTTGAGAACGTTTGGTGGGAGGCCGTCTGCGAGG
```

```
ACGCTCTGTCCTTCAAGGGTGACGGTGATGCCACCGTCACTGGCGGTGGTGCAACTGGTGCTGAGGACAAAGT

CCTCCAGCAAAACGGTATTGGCTCCATCACCGTCGATGGCTTCACCGTTGTGGACTTCGGCAAGCTGTACCGC

TCTTGCGGTAACTGCGACGAGATGGGCCAGCGCACTGTACGTCAATGCTATCGCTCATTCTGTAGGGCAGAGA

GTGCTGACATGGCTGTGCGACTTAGATCACCCTCAAGAACGTCAAGGCCTACTCCGGCAAGAAGCTTGTCGGC

ATCAACTCCAACTACGGTGACAGTGCGTCATGTTCCTTTAGGCTTTCAACCCTTGAGCCATGTGCTAATAGCA

TCCTCAGCTGCCACCATCACCGACACTTGCGCGACCGACGTCTCTGACATTTGCACGGAGTACGTAGTCACTC

GGACGATGGGCCTCAGGAACGAAGACACTAACATAATTATCTTTACAGGTACGAAGGAAACGATACCGGAGAC

GAACCTGAAGAGATCAGCTCCGGCCCCTCTGATGCCTGCATTTACAGCGACGTTCCGGAGTGCTAGACGCACA

GCTCGAACATGCCGCCTCAAAGCAAGCATTCTGATGGAGGGCCAGGGGGTGGGAAGGGATTTAGAGCCTCCGA

AAAGGTGGAAGTGGGTTTAGGACTTCGTTGTATAATATAAACTTGTTTCCGAAAATAAGAACCATCCTGC
```

```
SEQ ID NO:            17
LENGTH:               756
TYPE:                 DNA
ORGANISM:             M. phaseolina
FEATURE NAME/KEY:     CDS
LOCATION:             (1) ... (756)

atgttgaccaagactcttcttcccctcctcgccatctctggcgccgtctctgccgtcaag
 M   L   T   K   T   L   L   P   L   L   A   I   S   G   A   V   S   A   V   K accaagaccttcggcaagaacctcgtccgccgtgcggacttccctatccctgaatcccag
 T   K   T   F   G   K   N   L   V   R   R   A   D   F   P   I   P   E   S   Q ggttccgtcacctttgacgccgccgaggaggtcgatggcgagtacgacggtggctacaag
 G   S   V   T   F   D   A   A   E   E   V   D   G   E   Y   D   G   G   Y   K acgtacggccgtggtgtttcttgcactggccaggaggagggtggcgactctgacgccgtc
 T   Y   G   R   G   V   S   C   T   G   Q   E   E   G   G   D   S   D   A   V ttcatcctgaaggacggtgcttccctcaagaacgccatcatcggctctgaccagattgag
 F   I   L   K   D   G   A   S   L   K   N   A   I   I   G   S   D   Q   I   E ggtgtccactgcgagggctcctgcactcttgagaacgtttggtgggaggccgtctgcgag
 G   V   H   C   E   G   S   C   T   L   E   N   V   W   W   E   A   V   C   E gacgctctgtccttcaagggtgacggtgatgccaccgtcactggcggtggtgcaactggt
 D   A   L   S   F   K   G   D   G   D   A   T   V   T   G   G   G   A   T   G gctgaggacaaagtcctccagcaaaacggtattggctccatcaccgtcgatggcttcacc
 A   E   D   K   V   L   Q   Q   N   G   I   G   S   I   T   V   D   G   F   T gttgtggacttcggcaagctgtaccgctcttgcggtaactgcgacgagatgggccagcgc
 V   V   D   F   G   K   L   Y   R   S   C   G   N   C   D   E   M   G   Q   R actatcacccttcaagaacgtcaaggcctactccggcaagaagcttgtcggcatcaactcc
 T   I   T   L   K   N   V   K   A   Y   S   G   K   K   L   V   G   I   N   S aactacggtgacactgccaccatcaccgacacttgcgcgaccgacgtctctgacatttgc
 N   Y   G   D   T   A   T   I   T   D   T   C   A   T   D   V   S   D   I   C acggagtacgaaggaaacgataccggagacgaacctgaagagatcagctccggcccctct
 T   E   Y   E   G   N   D   T   G   D   E   P   E   E   I   S   S   G   P   S gatgcctgcatttacagcgacgttccggagtgctag
 D   A   C   I   Y   S   D   V   P   E   C   -

SEQ ID NO:            18
LENGTH:               251
TYPE:                 PRT
ORGANISM:             M. phaseolina
MLTKTLLPLLAISGAVSAVKTKTFGKNLVRRADFPIPESQGSVTFDAAEEVDGEYDGGYKTYGRGVSCTGQEE

GGDSDAVFILKDGASLKNAIIGSDQIEGVHCEGSCTLENVWWEAVCEDALSFKGDGDATVTGGGATGAEDKVL

QQNGIGSITVDGFTVVDFGKLYRSCGNCDEMGQRTITLKNVKAYSGKKLVGINSNYGDTATITDTCATDVSDI

CTEYEGNDTGDEPEEISSGPSDACIYSDVPEC*

SEQ ID NO:            19
LENGTH:               1245 (including 150 bp 5' UTR and 150 bp 3' UTR)
TYPE:                 DNA
ORGANISM:             M. phaseolina
```

-continued

```
GGTTCACCTCATCAACTCGCTTCTTCATTCGTTCCTTGCTGTGCAAGACACCATCCAGACGGACATTCCATTA

CAACGGTCTTTGATAGCCAATCCAACTTTGTCTACTCCCTGCCTCTCCATCCTACCCTACCAATAAGCCCATC

CAAAATGCAGTACAGCATCCGCTCGCTCGCCTTCGGCCTCGCCGCCCTGGCCGTCTCCACCGACGCTTTCATG

GTTCCCCGTGACCCTAGCAAGGGCTGGGGCTTCCCCAACGCCAACAACGCTCGCGTTGCTGCTGCCGCCGCCT

CCACTCCTGTCCAGACCCCCGGCAACACCCCTACCACTCCCGTGGCCACCCCTGGTGTCACTGGCGGCGCCAC

TGCCGCCGCTGGCTTCCCCGCCTCGTCCGGCACCAGCCAGCTCAGCGCCCCCATGACCGTCACCGGCAGCTTC

GACGGTGGCATGAAGGCCTTCGGCCGCGGTGTCTCCTGCACTGGCCAGGCTGAGGGTGGCGACAGCGACGCTG

TCTTCATGATCGAGGAGGGCGGTACTCTCTCCAACGTCATCATCGCCGCCGATCAGATCGAGGGTGTCCACTG

CTTCGGTTCCTGCACTCTCAAGAACGTCTGGTGGGTCGCCGTCTGCGAGGACGCTTTCACCATCAAGGAGCAG

GGCGCCTCTGGCACTACCCACATCATCGGCGGTGGTGCTCAGGGCGCCGAAGACAAGGTTCTCCAGCACAACG

GCGGCGGCACTCTCGCTGTCTCTGGCTTCCTCGCCAAGGACTTCGGTAAGCTCTACCGCAGCTGCGGCAACTG

CGACGAGATGCCCGAGCGCCACGTTACCATCGACGGCGTTACCGCTGAGTCTGGTGACATCCTGGTCGGCATC

AACTCCAACATGGGCGACAGTAAGTAACTCCTGATTTTGCAAGCGATGAGGCAATGCTAACAATGCGCAGCTG

CTACCATCACCAACACCTGCGCCACCGGCGTCGAGACCATCTGCCAGGAGTTCAACGGTGTCACGGACGGCAG

CGAGCCCGAGGCTGCCGGCAGCGGCCCTAGCACTGCTTGCAAGTACACTGCCGCTGACGCCCAGGCCTGCTAA

GCACATCCCTTTCTTGATTGACCAGTAAAAGTTCGACGGCCACACGGTTGGGTAATGCAGGGATTGGCAAAAT

GTCCGTCCGGCATAATTAGCACTTCTTTGATGTAGATATTGGGCCGGGTGTCCACAATGTATAACTCTGACAT

GTCA
```

```
SEQ ID NO:         20
LENGTH:            894
TYPE:              DNA
ORGANISM:          M. phaseolina
FEATURE NAME/KEY:  CDS
LOCATION:          (1) ... (894)
```

```
atgcagtacagcatccgctcgctcgccttcggcctcgccgccctggccgtctccaccgac
 M  Q  Y  S  I  R  S  L  A  F  G  L  A  A  L  A  V  S  T  D gctttcatggttccccgtgaccctagcaagggctggggcttccccaacgccaacaacgct
 A  F  M  V  P  R  D  P  S  K  G  W  G  F  P  N  A  N  N  A cgcgttgctgctgccgccgcctccactcctgtccagacccccggcaacacccctaccact
 R  V  A  A  A  A  A  S  T  P  V  Q  T  P  G  N  T  P  T  T cccgtggccacccctggtgtcactggcggcgccactgccgccgctggcttccccgcctcg
 P  V  A  T  P  G  V  T  G  G  A  T  A  A  A  G  F  P  A  S tccggcaccagccagctcagcgcccccatgaccgtcaccggcagcttcgacggtggcatg
 S  G  T  S  Q  L  S  A  P  M  T  V  T  G  S  F  D  G  G  M aaggccttcggccgcggtgtctcctgcactggccaggctgagggtggcgacagcgacgct
 K  A  F  G  R  G  V  S  C  T  G  Q  A  E  G  G  D  S  D  A gtcttcatgatcgaggagggcggtactctctccaacgtcatcatcgccgccgatcagatc
 V  F  M  I  E  E  G  G  T  L  S  N  V  I  I  A  A  D  Q  I gagggtgtccactgcttcggttcctgcactctcaagaacgtctggtgggtcgccgtctgc
 E  G  V  H  C  F  G  S  C  T  L  K  N  V  W  W  V  A  V  C gaggacgctttcaccatcaaggagcagggcgcctctggcactacccacatcatcggcggt
 E  D  A  F  T  I  K  E  Q  G  A  S  G  T  T  H  I  I  G  G ggtgctcagggcgccgaagacaaggttctccagcacaacggcggcggcactctcgctgtc
 G  A  Q  G  A  E  D  K  V  L  Q  H  N  G  G  G  T  L  A  V tctggcttcctcgccaaggacttcggtaagctctaccgcagctgcggcaactgcgacgag
 S  G  F  L  A  K  D  F  G  K  L  Y  R  S  C  G  N  C  D  E atgcccgagcgccacgttaccatcgacggcgttaccgctgagtctggtgacatcctggtc
 M  P  E  R  H  V  T  I  D  G  V  T  A  E  S  G  D  I  L  V ggcatcaactccaacatgggcgacactgctaccatcaccaacacctgcgccaccggcgtc
 G  I  N  S  N  M  G  D  T  A  T  I  T  N  T  C  A  T  G  V
```

```
gagaccatctgccaggagttcaacggtgtcacggacggcagcgagcccgaggctgccggc
 E  T  I  C  Q  E  F  N  G  V  T  D  G  S  E  P  E  A  A  G agcggccctagcactgcttgcaagtacactgccgctgacgcccaggcctgctaa
 S  G  P  S  T  A  C  K  Y  T  A  A  D  A  Q  A  C  -
```

```
SEQ ID NO:        21
LENGTH:           297
TYPE:             PRT
ORGANISM:         M. phaseolina
MQYSIRSLAFGLAALAVSTDAFMVPRDPSKGWGFPNANNARVAAAAASTPVQTPGNTPTTPVATPGVTGGATA

AAGFPASSGTSQLSAPMTVTGSFDGGMKAFGRGVSCTGQAEGGDSDAVFMIEEGGTLSNVIIAADQIEGVHCF

GSCTLKNVWWVAVCEDAFTIKEQGASGTTHIIGGGAQGAEDKVLQHNGGGTLAVSGFLAKDFGKLYRSCGNCD

EMPERHVTIDGVTAESGDILVGINSNMGDTATITNTCATGVETICQEFNGVTDGSEPEAAGSGPSTACKYTAA

DAQAC*
```

```
SEQ ID NO:        22
LENGTH:           1047 (including 150 bp 5' UTR and 150 bp 3' UTR)
TYPE:             DNA
ORGANISM:         M. phaseolina
GAATGGTATAAAGAGCGGTGGGATATCCATCATTGAGCTCATCACCAACCCACAATTACTTTCGTTCTACACT

CCTCTCGTTTACACAACGGATCACTGATCTACCACATTCGCTCTTACCAAAGATCCTGTCTACCAACCATCTA

CAACATGCAGTTCAAGTACGCCGCTCTCGCTGCCGCCCTGGCCGCCGTCGGCTCCACGCAGAGCCTCCCCATC

CCCGCCTCCCGCGGAGTTGATCCCAACAAGGGCCAAAGGATCGTCAAGCCCGGCAATCCTTTCGACGGCGGGA

TGAAGGAGTTTGGCCGTGGTGTCGTCTGCAACGACAAGGCCGACACTGGCGTCAGGAACGCCGTCTTCGTCAT

CGAGGACGGCGGTGTTCTGCGCAACGCCATCATCGGCGCCGACGCCGTCGAGGGCATCCACTGCGAGGGCAAG

TGCACCATCGAGAACGTCTGGTTCCGCGACGTGTGCGAGGACGCCATCACGCTGAAGGGCAACGGCCCTTACA

CCATCACTGGCGGCGGCGCCCAGAACGCCGGCGACAAGGTCATCCAGCACAACGGCAAGGGCGAGCTGCGCAT

CTCAAACTACCAGGTCAACAACGTCGGCAAGCTGTTCCGCACCTGCGGCAACTGCAGCAACAACGGCGGCCCG

CGCAGCATCGTCGCCACCGGCATCAGGGCCTTCGGCGTCACCAGCGACCTCATCGGCATCAACTCCAACTACG

GCGACAAGGCCTCCATCACCGGCTCCTGCGGCAACACCAAGACGGTCTGCCAGGAATATGTCGGCATCGAGAA

GGGCGCCAACGGCGGGAAGGACAGCGAGAAGAGGGTCCCGCCGGTCGGCGCTTGCACCGGCCAGGGCGGTCTC

GCCAGGCTCCCTTCCTGCTAGACGCCTCGCGGAATCTTGCGCTGAGTATGGGATGGGAGGAATGGATTGACCG

CCTCAGTTTGGGATCCGTGCGAACAGTCGGGAACTTCGCAACTGCCTCATCCGTCAAGAGGTGTGGGCCCCTG

CCGGACAGGATGAAACGCGTTTATG
```

```
SEQ ID NO:        23
LENGTH:           747
TYPE:             DNA
ORGANISM:         M. phaseolina
FEATURE NAME/KEY: CDS
LOCATION:         (1)...(747)
atgcagttcaagtacgccgctctcgctgccgccctggccgccgtcggctccacgcagagc
 M  Q  F  K  Y  A  A  L  A  A  A  L  A  A  V  G  S  T  Q  S ctccccatccccgcctcccgcggagttgatcccaacaagggccaaaggatcgtcaagccc
 L  P  I  P  A  S  R  G  V  D  P  N  K  G  Q  R  I  V  K  P ggcaatccttcgacggcgggatgaaggagtttggccgtggtgtcgtctgcaacgacaag
 G  N  P  F  D  G  G  M  K  E  F  G  R  G  V  V  C  N  D  K gccgacactggcgtcaggaacgccgtcttcgtcatcgaggacggcggtgttctgcgcaac
 A  D  T  G  V  R  N  A  V  F  V  I  E  D  G  G  V  L  R  N gccatcatcggcgccgacgccgtcgagggcatccactgcgagggcaagtgcaccatcgag
 A  I  I  G  A  D  A  V  E  G  I  H  C  E  G  K  C  T  I  E aacgtctggttccgcgacgtgtgcgaggacgccatcacgctgaagggcaacggcccttac
 N  V  W  F  R  D  V  C  E  D  A  I  T  L  K  G  N  G  P  Y accatcactggcggcggcgcccagaacgccggcgacaaggtcatccagcacaacggcaag
 T  I  T  G  G  G  A  Q  N  A  G  D  K  V  I  Q  H  N  G  K
```

```
ggcgagctgcgcatctcaaactaccaggtcaacaacgtcggcaagctgttccgcacctgc
 G  E  L  R  I  S  N  Y  Q  V  N  N  V  G  K  L  F  R  T  C ggcaactgcagcaacaacggcggcccgcgcagcatcgtcgccaccggcatcagggccttc
 G  N  C  S  N  N  G  G  P  R  S  I  V  A  T  G  I  R  A  F ggcgtcaccagcgacctcatcggcatcaactccaactacggcgacaaggcctccatcacc
 G  V  T  S  D  L  I  G  I  N  S  N  Y  G  D  K  A  S  I  T ggctcctgcggcaacaccaagacggtctgccaggaatatgtcggcatcgagaagggcgcc
 G  S  C  G  N  T  K  T  V  C  Q  E  Y  V  G  I  E  K  G  A aacggcgggaaggacagcgagaagagggtcccgccggtcggcgcttgcaccggccagggc
 N  G  G  K  D  S  E  K  R  V  P  P  V  G  A  C  T  G  Q  G ggtctcgccaggctcccttcctgctag
 G  L  A  R  L  P  S  C  -
```

SEQ ID NO: 24
LENGTH: 248
TYPE: PRT
ORGANISM: M. phaseolina

MQFKYAALAAALAAVGSTQSLPIPASRGVDPNKGQRIVKPGNPFDGGMKEFGRGVVCNDKADTGVRNAVFVIE

DGGVLRNAIIGADAVEGIHCEGKCTIENVWFRDVCEDAITLKGNGPYTITGGGAQNAGDKVIQHNGKGELRIS

NYQVNNVGKLFRTCGNCSNNGGPRSIVATGIRAFGVTSDLIGINSNYGDKASITGSCGNTKTVCQEYVGIEKG

ANGGKDSEKRVPPVGACTGQGGLARLPSC*

SEQ ID NO: 25
LENGTH: 2495 (including 150 bp 5' UTR and 150 bp 3' UTR)
TYPE: DNA
ORGANISM: M. phaseolina

GTTTGGTGCGTGGGAACGCATTTAACGGTGGATGAATCGATCCAAGGCTTCCAAGGCAGAGCCTCCGAAACAG

TCAATATTCCATCCAAACCAACGCCTATTGGATTCAAGATTTGGGCACTTTGTAACGAGGCTTTTTTGGTTGA

TTGGATGTTCCATTCAAATGGCGAAGGACCGTGGGATCTTGACGAGTATTACACCGACGAACAGTACGAAATT

AACCTCACACAGACGGCTGCAGTGGTGCCCGATTTGGTGGCTCAGTTATGCCCACATGAGCTGCCATTTGACA

GCCCAAAATACATCGTTTGGATAGACAATCTGCTTACTTCTGCGCGGCTTATGACAACGCTCCGGAACGAGAA

TATTGGCGCTGCAGGGACTGTTCGAATGGGCAAGACACAGCGTGAGAAGAATGAAGAGAAGGCAGCTAGCAAA

AAGAAGCAAGCCACCAAAGAAGATAACCGTGGTTTACACCAAAGGCTTCGAGATTTGAGGTCAAAAAATGAAG

GACAGATCGAATGGGGCACGCAGTATTGCTGTCTATCACAGGACGAGCAGTCAATGCAATTTGGCTGGCAGGA

TGCAAGAATTGTGCTATTCATGAGCACTGTTCATGACGGTAAACAATGGGTGATTCGACGACGACGGCGGCCC

ACAAAGACCTCCACCAATTCGAAGATCACTCAGAAGCCATTTGGTGATAACGTGGAACAAGATATGGAGATTC

CGAGGTGGGCAGACGAGTACAATCACAACAAGAATGCGGTTGACCGTTTTGACCAATTCAAAGCCGAACGCCA

AATCAATCGACTTTGTTATCGAACATGGAAGCCTCTTTGGAACTTCCTCTTCCAATCATCGATCATCAGTGCA

TATCTGCTCACTTGTAGAGGCTTGGATGACGATGAGAAACCTCCATTCGCGTCCCTGAACGCATTCCGCCAGA

GGCTTTGGGAGCAGCTCTTTGAACGCTCAGAACGCGTTGACGGACGCCGTGGACGAGCAGAGCCTCGTTATCG

TGAGATTCCACGCGAAGAACATCAATATGAGAGGCTTAAGGTCCAAGGGAACTGCAGTGAATGTATGGCTAAC

ATGCGCAAATCAACGCGTATTCGAAGGCCACTTGCAGAGCGTTCCACCAACATTCGGCCACCAAGGCCAAGGT

GGGGCTGTGGGCTATGTAATCTGAATCTTTGTGAAGGCATTTGCTTCAAAAATCACTTGAATCGGGTGATAGG

AAGCAGTTGAATTTGATGTGGAAGTTGGGCTCGATTTGGTCGCGAATTCGTCGCGATTTAGATCTAAAACACC

AAGATTTGGGCCGTAAATCGAATATATATAAATGCAAATAGACTCATTTGAATTTGACAGCTTATGCGACCTC

AAAACACTACGTTTTAGTTGAATTATTGCGATTATTGGGCTGCGAAAAGCCCCTGATGACTTTGGTGTTCTGA

CCCCTGTCACCACCCCTGTCGCTCTCAAGCTCTCCATAGATTGAGAGCATATCCAGCCTACGAAGGGATACCA

CTGCCCCCTCCTGGCGGCTTCCGCCCTGGCTGCTCCTGCCGACGACACTTTCGGCTACGAGCTCGTTCGCCGT

GCGAACTTCCCTATTCCTGCCTCCAAGGGCACCGTCAAGTACAGCGCTGCCAAGTCCATCTCCGGCACTTTCG

ATGGTGGCCTGAAGACCCTACAGCCGTGGTGTCAAGTGCATCGGTCAGGCTGAGGGCGGTGACAAAAAAGCCG

```
TCTTCATCCCTGAGGACGGTGCTAGCCTCAAGAGCGCCATCACTGGCACCGAGCAGATCGAGGGCGTCCACTG

CAAGGGGCTCCTGCACTATCGAGAACGTCTGGTGGGCTGGTGTCTGCGAGGATGCTCTCTCCCTCAAGGGCAA

CGGCAACGCCAAGATCATTGGTGGCGGTGCCACTGGTGCCGAAGACAAGGGTAAGCTCTCTTCTGCAAGAGCG

TTGCGATCGGATTTCTAACACTCTCTGGTGCAGGTCATCCAGCACCGGTTTTGGATCCGTCTCTATTGACGGC

TTCACTGTTGCCGATTTCGGCAAGCTCTACCGCTCTTGCGGAAACTGCAAGAAGCAGGGCAAGAGAACTGTCA

CCATCAAGAATGTCAAGGCATCATCCGGCAAGCTGCTCGCTGGTATCAACTCCAACTACGGCGACACTGCTAC

CATCACCGGCACCTGCGCTGCCTCCGTCAAGAAGATCTGCACCGAGTTCATGGGCAACAACAGCGGCAAGGAG

CCCAGTGTGGTTTTCAATCTCGATCTTATCAATCTTATCAATCGATCCCTATCAATCGATATCAAGTCCATCA

TGGAATTGAATTGACGATTGATAAGGATCGACAGCCTCCTGGTTGCCCTGCCAAACGCCACCAAACAAACGCC

ATAAAACACGCCCGCAGGGAGCCGCAGGACCCGAAATGCATCAAACAGTCCTCTTCTATTGCATTATCAATTA

TCGGGCATGGATG
```

```
SEQ ID NO:         26
LENGTH:            1707
TYPE:              DNA
ORGANISM:          M. phaseolina
FEATURE NAME/KEY:  CDS
LOCATION:          (1) ... (1707)
```

```
atgttccattcaaatggcgaaggaccgtgggatcttgacgagtattacaccgacgaacag
 M   F   H   S   N   G   E   G   P   W   D   L   D   E   Y   Y   T   D   E   Q tacgaaattaacctcacacagacggctgcagtggtgcccgatttggtggctcagttatgc
 Y   E   I   N   L   T   Q   T   A   A   V   V   P   D   L   V   A   Q   L   C ccacatgagctgccatttgacagcccaaaatacatcgtttggatagacaatctgcttact
 P   H   E   L   P   F   D   S   P   K   Y   I   V   W   I   D   N   L   L   T tctgcgcggcttatgacaacgctccggaacgagaatattggcgctgcagggactgttcga
 S   A   R   L   M   T   T   L   R   N   E   N   I   G   A   A   G   T   V   R atgggcaagacacagcgtgagaagaatgaagagaaggcagctagcaaaaagaagcaagcc
 M   G   K   T   Q   R   E   K   N   E   E   K   A   A   S   K   K   K   Q   A accaaagaagataaccgtggtttacaccaaaggcttcgagatttgaggtcaaaaaatgaa
 T   K   E   D   N   R   G   L   H   Q   R   L   R   D   L   R   S   K   N   E ggacagatcgaatggggcacgcagtattgctgtctatcacaggacgagcagtcaatgcaa
 G   Q   I   E   W   G   T   Q   Y   C   C   L   S   Q   D   E   Q   S   M   Q tttggctggcaggatgcaagaattgtgctattcatgagcactgttcatgacggtaaacaa
 F   G   W   Q   D   A   R   I   V   L   F   M   S   T   V   H   D   G   K   Q tgggtgattcgacgacgacggcggcccacaaagacctccaccaattcgaagatcactcag
 W   V   I   R   R   R   R   R   P   T   K   T   S   T   N   S   K   I   T   Q aagccatttggtgataacgtggaacaagatatggagattccgaggtgggcagacgagtac
 K   P   F   G   D   N   V   E   Q   D   M   E   I   P   R   W   A   D   E   Y aatcacaacaagaatgcggttgaccgttttgaccaattcaaagccgaacgccaaatcaat
 N   H   N   K   N   A   V   D   R   F   D   Q   F   K   A   E   R   Q   I   N cgactttgttatcgaacatggaagcctctttggaacttcctcttccaatcatcgatcatc
 R   L   C   Y   R   T   W   K   P   L   W   N   F   L   F   Q   S   S   I   I agtgcatatctgctcacttgtagaggcttggatgacgatgagaaacctccattcgcgtcc
 S   A   Y   L   L   T   C   R   G   L   D   D   D   E   K   P   P   F   A   S ctgaacgcattccgccagaggctttgggagcagctctttgaacgctcagaacgcgttgac
 L   N   A   F   R   Q   R   L   W   E   Q   L   F   E   R   S   E   R   V   D ggacgccgtggacgagcagagcctcgttatcgtgagattccacgcgaagaacatcaatat
 G   R   R   G   R   A   E   P   R   Y   R   E   I   P   R   E   E   H   Q   Y gagaggcttaaggtccaagggaactgcagtgaatcctacgaagggataccactgccccct
 E   R   L   K   V   Q   G   N   C   S   E   S   Y   E   G   I   P   L   P   P cctggcggcttccgccctggctgctcctgccgacgacactttcggctacgagctcgttcg
 P   G   G   F   R   P   G   C   S   C   R   R   H   F   R   L   R   A   R   S
```

```
ccgtgcgaacttccctattcctgcctccaagggcaccgtcaagtacagcgctgccaagtc
 P  C  E  L  P  Y  S  C  L  Q  G  H  R  Q  V  Q  R  C  Q  V catctccggcactttcgatggtggcctgaagaccctacagccgtggtgtcaagtgcatcg
 H  L  R  H  F  R  W  W  P  E  D  P  T  A  V  V  S  S  A  S gtcaggctgagggcggtgacaaaaaagccgtcttcatccctgaggacggtgctagcctca
 V  R  L  R  A  V  T  K  K  P  S  S  S  L  R  T  V  L  A  S agagcgccatcactggcaccgagcagatcgagggcgtccactgcaaggggctcctgcact
 R  A  P  S  L  A  P  S  R  S  R  A  S  T  A  R  G  S  C  T atcgagaacgtctggtgggctggtgtctgcgaggatgctctctcccctcaagggcaacggc
 I  E  N  V  W  W  A  G  V  C  E  D  A  L  S  L  K  G  N  G aacgccaagatcattggtggcggtgccactggtgccgaagacaagggtcatccagcaccg
 N  A  K  I  I  G  G  G  A  T  G  A  E  D  K  G  H  P  A  P gttttggatccgtctctattgacggcttcactgttgccgatttcggcaagctctaccgct
 V  L  D  P  S  L  L  T  A  S  L  L  P  I  S  A  S  S  T  A cttgcggaaactgcaagaagcagggcaagagaactgtcaccatcaagaatgtcaaggcat
 L  A  E  T  A  R  S  R  A  R  E  L  S  P  S  R  M  S  R  H catccggcaagctgctcgctggtatcaactccaactacggcgacactgctaccatcaccg
 H  P  A  S  C  S  L  V  S  T  P  T  T  A  T  L  L  P  S  P gcacctgcgctgcctccgtcaagaagatctgcaccgagttcatgggcaacaacagcggca
 A  P  A  L  P  P  S  R  R  S  A  P  S  S  W  A  T  T  A  A aggagcccagtgtggttttcaatctcgatcttatcaatcttatcaatcgatccctatcaa
 R  S  P  V  W  F  S  I  S  I  L  S  I  L  S  I  D  P  Y  Q tcgatatcaagtccatcatggaattga
 S  I  S  S  P  S  W  N  -

SEQ ID NO:             27
LENGTH:                568
TYPE:                  PRT
ORGANISM:              M. phaseolina
MFHSNGEGPWDLDEYYTDEQYEINLTQTAAVVPDLVAQLCPHELPFDSPKYIVWIDNLLTSARLMTTLRNENI

GAAGTVRMGKTQREKNEEKAASKKKQATKEDNRGLHQRLRDLRSKNEGQIEWGTQYCCLSQDEQSMQFGWQDA

RIVLFMSTVHDGKQWVIRRRRRPTKTSTNSKITQKPFGDNVEQDMEIPRWADEYNHNKNAVDRFDQFKAERQI

NRLCYRTWKPLWNFLFQSSIISAYLLTCRGLDDDEKPPFASLNAFRQRLWEQLFERSERVDGRRGRAEPRYRE

IPREEHQYERLKVQGNCSESYEGIPLPPPGGFRPGCSCRRHFRLRARSPCELPYSCLQGHRQVQRCQVHLRHF

RWWPEDPTAVVSSASVRLRAVTKKPSSSLRTVLASRAPSLAPSRSRASTARGSCTIENVWWAGVCEDALSLKG

NGNAKIIGGGATGAEDKGHPAPVLDPSLLTASLLPISASSTALAETARSRARELSPSRMSRHHPASCSLVSTP

TTATLLPSPAPALPPSRRSAPSSWATTAARSPVWFSISILSILSIDPYQSISSPSWN*

SEQ ID NO:             28
LENGTH:                1922 (including 150 bp 5' UTR and 150 bp 3' UTR)
TYPE:                  DNA
ORGANISM:              M. phaseolina
CAAGATGTGCTTTTGCTCTCCAGGACATTCCTCTCCATCCCTCGTTTCCAATCACTTTCAGTCTTTGCCACTC

CTTCGCTGTCCACTGTAGTCCGGAACTACATCAGTAAACCACCTTCTTTTCCAACAGACCCCATCACATCCGC

CAAAATGGTCAACATTGCTGCCGTCTGCCGCGCTGCGGCTTTCTTTCTTCCTGTCCTCGCCGCCGCCCAGAGC

GGTGTCGTTGGTACCCCTTCCGGTTTCGCCGCCGGCACCACTGGTGGTGGTGACGCTGCCGCCGCCGCTCCCT

CCGACGTTGCTGAGCTCATCTCTTGGCTTGAGGATGAGACTCCCCGTGTCATCCTCATCGACAAGGAGTTCAA

CTTCCTCGGCACGGAGGGCACCAAGAGCGATCAGGGCTGCCGTCCCGACAGCAACAAGTGCCCTGGCAAGGGT

GGCCAGGATGCCATCAACCAGGCCAACTGGTGCGACAACGGCAACGCTGGCGAGGGTGTCTCGGCCGTCACCG

TCAAGTACGACCAGGCTGCGCTCAAGGGCATCGCTGTCAAGAGCAACAAGTCCATCGTCGGTGTTGGCGACAA

GGGTGTCCTCAAGGGCAAGGGCCTCAGCCTGACTGGTGGCGTTGAGAACGTTATCATCCAGAACATCCACATC

ACCGACCTGAACCCCGAGTACATCTGGGGTGGTGATGCCATCACGCTCGCTGGTTCCGACAAGGTCTGGAGTA
```

```
AGTACTTCCGAACTGTTTCGATCCCATACGGTTGGCCTTGAAACCCAAATCGGGAAACGCACTATACCCAATA

TGGCAATTTTCTACGAACATCGAGACACCGCAGCAGAACACGAGTTTCACGCCATTGCTTGTTTCTGTGGCTG

TCAATGCTGTCTCGAAGTCCCTGTATGCTGTTTGGCTTGATGCGCTAGTGCGTTTCCTGAGAGAGGTGCCCAC

CACACCATCATGCCCCAAGCTCCCTTACCCCTTTCCCAGCATCCCACATCATGCTATATCCTTTACTATGCTT

TCAACAGTAAAACTAACGCCCGAAACGTCGATCATGTCAAAATTTCTCTCGTCGGTCGCCAGATGATCGTTAC

CGGCTACGACAAGGCCGGTAGGGTCACGATCTCCAACTCCGAGTTCGACGGCCAGACCGACTGGTCCGCCTCC

TGCAACGGCGAACACTACTGGACCGTCCTCGTGTACGGTGCCGACGACCAGATCACCTTCGCAAACAACTACA

TGCACGACACCTCGGGCCGTTCGCCCAAGATCGGTGGTGCCGACGGCGCTGGCATCACCTTCCACGCGGTCAA

CAACGTCTTCCAGACCAACAAGGGCCATAACTTCGACATCGGCTCCGGTGCCGAGGTTTTGCTCGAGGGTAAC

ACCTTCAACGAGTGCAACCAGCCCATCACCTCCAAGTCGGCCAACGAGGGCGGCGCCATCTTCAACACCCCCT

CCGGCTCCGAGAGCTCCTGCTCCAGCTACCTCAAGCGCGCCTGCCAGGCCAACACTCTCACCAGCTCCGGTGA

CTTCGGCACTTACAAGGACACCTCGGTTCTCGAGGGCTTCAACGGCGCCACCTCCATCTGGGAGGCCGTCAGC

GCTGAGGAGGCTGCTGCGTCCGTCATCGCCAACGCCGGTATTGGCAAGCTCCAGGGCGGTGCTAGCAACTCCA

CTGCCAAGTTCAGTATGTCTTCTCCCTTCAACCCTGTATCACAGGAGACATGTACTAATAATTCTCTCCTCTG

CAGGGCGCTTCCAATCCTAGATTAATAAGCACGATCGACCGAATACTAGCATCAGTACGGTTTTTAGATAAAA

AGGGATCTGTCTGGTTTACTGTAGATATTTAGCCTTCCTTTCTTTGGCTTCACATATTTTTAACTTTACAGCC

CAAGAGGGCTCAATGCAAATACTT
```

```
SEQ ID NO:        29
LENGTH:           1314
TYPE:             DNA
ORGANISM:         M. phaseolina
FEATURE NAME/KEY: CDS
LOCATION:         (1) ... (1314)
```

```
atggtcaacattgctgccgtctgccgcgctgcggctttcttcttcctgtcctcgccgcc
 M   V   N   I   A   A   V   C   R   A   A   A   F   F   L   P   V   L   A   A gcccagagcggtgtcgttggtaccccttccggtttcgccgccggcaccactggtggtggt
 A   Q   S   G   V   V   G   T   P   S   G   F   A   A   G   T   T   G   G   G gacgctgccgccgccgctcccctccgacgttgctgagctcatctcttggcttgaggatgag
 D   A   A   A   A   A   P   S   D   V   A   E   L   I   S   W   L   E   D   E actccccgtgtcatcctcatcgacaaggagttcaacttcctcggcacggagggcaccaag
 T   P   R   V   I   L   I   D   K   E   F   N   F   L   G   T   E   G   T   K agcgatcagggctgccgtcccgacagcaacaagtgccctggcaagggtggccaggatgcc
 S   D   Q   G   C   R   P   D   S   N   K   C   P   G   K   G   G   Q   D   A atcaaccaggccaactggtgcgacaacggcaacgctggcgagggtgtctcggccgtcacc
 I   N   Q   A   N   W   C   D   N   G   N   A   G   E   G   V   S   A   V   T gtcaagtacgaccaggctgcgctcaagggcatcgctgtcaagagcaacaagtccatcgtc
 V   K   Y   D   Q   A   A   L   K   G   I   A   V   K   S   N   K   S   I   V ggtgttggcgacaagggtgtcctcaagggcaagggcctcagcctgactggtggcgttgag
 G   V   G   D   K   G   V   L   K   G   K   G   L   S   L   T   G   G   V   E aacgttatcatccagaacatccacatcaccgacctgaaccccgagtacatctggggtggt
 N   V   I   I   Q   N   I   H   I   T   D   L   N   P   E   Y   I   W   G   G gatgccatcacgctcgctggttccgacaaggtctggatgcgtttcctgagagagcatccc
 D   A   I   T   L   A   G   S   D   K   V   W   M   R   F   L   R   E   H   P acatcatgctatatcctttactatgctttcaacagtaaaactaacgcccgaaacgtcgat
 T   S   C   Y   I   L   Y   Y   A   F   N   S   K   T   N   A   R   N   V   D catgtcaaaatttctctcgtcggtcgccagatgatcgttaccggctacgacaaggccggt
 H   V   K   I   S   L   V   G   R   Q   M   I   V   T   G   Y   D   K   A   G agggtcacgatctccaactccgagttcgacggccagaccgactggtccgcctcctgcaac
 R   V   T   I   S   N   S   E   F   D   G   Q   T   D   W   S   A   S   C   N ggcgaacactactggaccgtcctcgtgtacggtgccgacgaccagatcaccttcgcaaac
 G   E   H   Y   W   T   V   L   V   Y   G   A   D   D   Q   I   T   F   A   N
```

```
aactacatgcacgacacctcgggccgttcgcccaagatcggtggtgccgacggcgctggc
 N  Y  M  H  D  T  S  G  R  S  P  K  I  G  G  A  D  G  A  G atcaccttccacgcggtcaacaacgtcttccagaccaacaagggccataacttcgacatc
 I  T  F  H  A  V  N  N  V  F  Q  T  N  K  G  H  N  F  D  I ggctccggtgccgaggttttgctcgagggtaacaccttcaacgagtgcaaccagcccatc
 G  S  G  A  E  V  L  L  E  G  N  T  F  N  E  C  N  Q  P  I acctccaagtcggccaacgagggcggcgccatcttcaacacccctccggctccgagagc
 T  S  K  S  A  N  E  G  G  A  I  F  N  T  P  S  G  S  E  S tcctgctccagctacctcaagcgcgcctgccaggccaacactctcaccagctccggtgac
 S  C  S  S  Y  L  K  R  A  C  Q  A  N  T  L  T  S  S  G  D ttcggcacttacaaggacacctcggttctcgagggcttcaacggcgccacctccatctgg
 F  G  T  Y  K  D  T  S  V  L  E  G  F  N  G  A  T  S  I  W gaggccgtcagcgctgaggaggctgctgcgtccgtcatcgccaacgccggtattggcaag
 E  A  V  S  A  E  E  A  A  A  S  V  I  A  N  A  G  I  G  K ctccagggcggtgctagcaactccactgccaagttcaggcgcttccaatcctag
 L  Q  G  G  A  S  N  S  T  A  K  F  R  R  F  Q  S  -

SEQ ID NO:            30
LENGTH:               437
TYPE:                 PRT
ORGANISM:             M. phaseolina
MVNIAAVCRAAAFFLPVLAAAQSGVVGTPSGFAAGTTGGGDAAAAAPSDVAELISWLEDETPRVILIDKEFNF

LGTEGTKSDQGCRPDSNKCPGKGGQDAINQANWCDNGNAGEGVSAVTVKYDQAALKGIAVKSNKSIVGVGDKG

VLKGKGLSLTGGVENVIIQNIHITDLNPEYIWGGDAITLAGSDKVWMRFLREHPTSCYILYYAFNSKTNARNV

DHVKISLVGRQMIVTGYDKAGRVTISNSEFDGQTDWSASCNGEHYWTVLVYGADDQITFANNYMHDTSGRSPK

IGGADGAGITFHAVNNVFQTNKGHNFDIGSGAEVLLEGNTFNECNQPITSKSANEGGAIFNTPSGSESSCSSY

LKRACQANTLTSSGDFGTYKDTSVLEGFNGATSIWEAVSAEEAAASVIANAGIGKLQGGASNSTAKFRRFQS*

SEQ ID NO:            31
LENGTH:               1326 (including 150 bp 5' UTR and 150 bp 3' UTR)
TYPE:                 DNA
ORGANISM:             M. phaseolina
ACCAATCGTCACAGATCCGCTGGACACGATGCAGCGTGCACATATAGATCGGCTCCGCAGCGTTAATGCTGTC

CTCCAGCAGCAGCCTCAACTTTCTCTTCACCTTTCTCTTCACCTTTCTCTTCACCACCAGCCCAGCCCACCCT

CACCATGAAGTTTCTTTCCACTTTGGCCCTGGCGCCCTCGCGCACCTGGCGTGCGCCGTCCCCATGGCCGAG

AAGCGTGCCCCCGCGGCCACGCCCGTCGGCTACGCCTCGCAGAACGGCGGCGTGACCGGCGGTCAGGGCGGCA

CCACCACCACCGTCTCCTCGCTGCCCGAGATGACGGCTGCCCTTAAGAAGGGGGACACGGAGAAGAAGGTCGT

CTACGTCAAGGGCAAGATCTCCGGCAAGGCGAAGATCTACGTTGGCTCGAACAAGGTGCGGCCTCACCCCTTC

ACTCCATGACATCCGGGTAGCTAACGCAGCCTGCAGTCCATCCTCGGCGTTGACTCCAGCTCCGGCCTCGAGG

GCATCGGACTCCTCGTCCGTGACGCCAAGAACGTCATCATCCGCAACCTGGCCATCTCCAAGGTCGAGGCCGA

CACGGGCGGCGACGCCATCGCCATCGACGGCTCCACCAACGTCTGGGTCGACCACTGCGACCTGTCCAGCGAC

CTGGCCGCCGACAAGGACTTCTACGACGGCCTGCTCGACATCTCCCACGGCGCCGACTACGTCACCGTCTCGA

ACGTCTACTTCCACGACCACCACAAGAACTCGCTCGTCGGCCACTCCGACTCCAACGCCGGCGAGGACACGGG

CAAGCTGCACGTCACCTACGCCAACAACTACTGGAGCAACGTCGGCTCGCGCTGCCCGCTCGTGCGCTTCGGC

ACCGTCCACATCGTCAACAACTACTTCGAGGACGTCTCCGTCTCCGGCATCAACACCCGCATGGGCGCCCAGG

TCCTCGTCGAGAACAACGTCTTCAACAACGTCGTGCAGGCCCTCGTCTCGATCGACTCCAAGGAGCTCGGCTA

CGCCGTCGCGCGAGGCAACGACTGGGGCACCTCCAAGAACGAGGCCCCCGAGGGTACCCTTACCAAGGTGCCT

TACACCTACACCGCTGTTGAAGCGAGCGCGGTCAAGGCTGCTGTTGTTGGCAGCGCGGGCAACACCCTCTCTG

GCTTGTAAACATTTGACCTCGACGGGTTGCTCGAGAGAAGCCTATCTACATAGCCTGTGTTTACAAGCAATTC

TCTGTAGATATTTTTATACAATCTCTAATTGTAAATACGAAATCAAATCCGAATTAGTGGAATGCTTGCCTTA
```

AGCTCTTCGGAG

```
SEQ ID NO:              32
LENGTH:                 972
TYPE:                   DNA
ORGANISM:               M. phaseolina
FEATURE NAME/KEY:       CDS
LOCATION:               (1) ... (972)
``` atgaagtttctttccactttggccctggcggccctcgcgcacctggcgtgcgccgtcccc
 M  K  F  L  S  T  L  A  L  A  A  L  A  H  L  A  C  A  V  P atggccgagaagcgtgcccccgcggccacgcccgtcggctacgcctcgcagaacggcggc
 M  A  E  K  R  A  P  A  A  T  P  V  G  Y  A  S  Q  N  G  G gtgaccggcggtcagggcggcaccaccaccaccgtctcctcgctgcccgagatgacggct
 V  T  G  G  Q  G  G  T  T  T  T  V  S  S  L  P  E  M  T  A gcccttaagaaggggganacacggagaagaaggtcgtctacgtcaagggcaagatctccggc
 A  L  K  K  G  D  T  E  K  K  V  V  Y  V  K  G  K  I  S  G aaggcgaagatctacgttggctcgaacaagtccatcctcggcgttgactccagctccggc
 K  A  K  I  Y  V  G  S  N  K  S  I  L  G  V  D  S  S  S  G ctcgagggcatcggactcctcgtccgtgacgccaagaacgtcatcatccgcaacctggcc
 L  E  G  I  G  L  L  V  R  D  A  K  N  V  I  I  R  N  L  A atctccaaggtcgaggccgacacgggcggcgacgccatcgccatcgacggctccaccaac
 I  S  K  V  E  A  D  T  G  G  D  A  I  A  I  D  G  S  T  N gtctgggtcgaccactgcgacctgtccagcgacctggccgccgacaaggacttctacgac
 V  W  V  D  H  C  D  L  S  S  D  L  A  A  D  K  D  F  Y  D ggcctgctcgacatctcccacggcgccgactacgtcaccgtctcgaacgtctacttccac
 G  L  L  D  I  S  H  G  A  D  Y  V  T  V  S  N  V  Y  F  H gaccaccacaagaactcgctcgtcggccactccgactccaacgccggcgaggacacgggc
 D  H  H  K  N  S  L  V  G  H  S  D  S  N  A  G  E  D  T  G aagctgcacgtcacctacgccaacaactactggagcaacgtcggctcgcgctgcccgctc
 K  L  H  V  T  Y  A  N  N  Y  W  S  N  V  G  S  R  C  P  L gtgcgcttcggcaccgtccacatcgtcaacaactacttcgaggacgtctccgtctccggc
 V  R  F  G  T  V  H  I  V  N  N  Y  F  E  D  V  S  V  S  G atcaacacccgcatgggcgcccaggtcctcgtcgagaacaacgtcttcaacaacgtcgtg
 I  N  T  R  M  G  A  Q  V  L  V  E  N  N  V  F  N  N  V  V caggcccttgtctcgatcgactccaaggagctcggctacgccgtcgcgcgaggcaacgac
 Q  A  L  V  S  I  D  S  K  E  L  G  Y  A  V  A  R  G  N  D tggggcacctccaagaacgaggcccccgagggtacccttaccaaggtgccttacacctac
 W  G  T  S  K  N  E  A  P  E  G  T  L  T  K  V  P  Y  T  Y accgctgttgaagcgagcgcggtcaaggctgctgttgttggcagcgcgggcaacaccctc
 T  A  V  E  A  S  A  V  K  A  A  V  V  G  S  A  G  N  T  L tctggcttgtaa
 S  G  L  -

```
SEQ ID NO:              33
LENGTH:                 323
TYPE:                   PRT
ORGANISM:               M. phaseolina
```
MKFLSTLALAALAHLACAVPMAEKRAPAATPVGYASQNGGVTGGQGGTTTTVSSLPEMTAALKKGDTEKKVVY

VKGKISGKAKIYVGSNKSILGVDSSSGLEGIGLLVRDAKNVIIRNLAISKVEADTGGDAIAIDGSTNVWVDHC

DLSSDLAADKDFYDGLLDISHGADYVTVSNVYFHDHHKNSLVGHSDSNAGEDTGKLHVTYANNYWSNVGSRCP

LVRFGTVHIVNNYFEDVSVSGINTRMGAQVLVENNVFNNVVQALVSIDSKELGYAVARGNDWGTSKNEAPEGT

LTKVPYTYTAVEASAVKAAVVGSAGNTLSGL*

```
SEQ ID NO:              34
LENGTH:                 1320 (including 150 bp 5' UTR and 150 bp 3' UTR)
TYPE:                   DNA
ORGANISM:               M. phaseolina
```
TCTCCAAGTTCATCTTCATCTTCAGTCTTTCTCTATTAAACGCGTTGACTCGCGCCATTCTTTGACAGCCATC

AGCCTGCTGAGCACGCTTGACCACATATTCCTTCCCTTGAAAGTTCCCGTTTGCTCAACAACACTTCCACCGC

```
AACCATGAAGGCCACCACCCTCGCTACTTTTGCTCTTTCCGCCGTGAGCGCTCTGGCAGCGCCCACCAAGACC

TTCGCCAAGCGTGCCGCCATCACTGACGGCCCCGACGTCGGCTATGCCACCCTGAACGGTGGCACCACTGGCG

GTGCTGGCGGTTCCACCACCACCGTCTCCAGCCTGGCCCAGTTCACCGCTGCCGCCGAGGCTGATGGCGCCGC

CGTCATTGTCGTCTCCGGCAACATCTCTGGCGCCGCCAAGGTCCGCGTCGGCAGCGACAAGACCATCATCGGC

AAGGACTCCAGCGCCGTGCTCGAGGGCGTCGGTCTCTACATCAACAAGCAGAAGAACGTCATCGTCCGCAACC

TGTCCATCAAGAATGTGCTTGCGGAGAATGGTGACGCCATCGGCATCCAGGCTTCCCAGAACGTCTGGATCGA

CCACTGCGACCTGTCCTCGGACCGTGACCACGACAAGGACTACTACGACGGTCTCCTCGACGTGACCCACGCC

TCTGACTACATCACCCTGTCCAACAACTACCTCCATGACCACTGGAAGGCCTCGCTCGTCGGCCACTCCGACT

CCAACGGCTCTGAGGACAAGGGCCACTTGACCGTCACCTACTACCAGAACCACTTCGAGAACCTGAACTCGCG

TGGTCCTTCTTTCCGCTTCGGCACCGGTCACATTGTATGTTGCCCACCAACCTGACACCACAGTAATGATTCT

AACGGCAAATGCTAGGTCAACAACCTCTACACCAGCGTCAGCGACGGTATCAACGCTCGCCAGGGCGCCCAGC

TCCTTGTTGAGGGCAACGTCTTCACTGGCAGCAAGAAGCCGCTGTACAGCACCGATGCCGGCTACGCCGCCGT

CAACGACAACGACTTCGGCGGCGCTGAGAACACTGCTGAGGCTGGCACCCTCACTGCCTCTGACCTCGGCTAC

AAGTATACCGCTCTGAAGTCTTCCGAGGTCTCTGCCGCCGTCTCCAAGTCGGCTGGCGCCACGCTCACTTTCT

AAACGAAGTCGCGACGCTCTCTCGTTTTGGAACTCGCCGCAATGCCCGAGCCAGGGTTCGGATGCATGGAAGG

AATGCATTGTGATGGATGAAGAGCAACATACTTTTTTGGGGGGAAAAAGCACAGGGCGTGCTACTTTTTCAT

GTACAT
```

```
SEQ ID NO:         35
LENGTH:            966
TYPE:              DNA
ORGANISM:          M. phaseolina
FEATURE NAME/KEY:  CDS
LOCATION:          (1) ... (966)
atgaaggccaccaccctcgctacttttgctctttccgccgtgagcgctctggcagcgccc
 M   K   A   T   T   L   A   T   F   A   L   S   A   V   S   A   L   A   A   P accaagaccttcgccaagcgtgccgccatcactgacggccccgacgtcggctatgccacc
 T   K   T   F   A   K   R   A   A   I   T   D   G   P   D   V   G   Y   A   T ctgaacggtggcaccactggcggtgctggcggttccaccaccaccgtctccagcctggcc
 L   N   G   G   T   T   G   G   A   G   G   S   T   T   T   V   S   S   L   A cagttcaccgctgccgccgaggctgatggcgccgccgtcattgtcgtctccggcaacatc
 Q   F   T   A   A   A   E   A   D   G   A   A   V   I   V   V   S   G   N   I tctggcgccgccaaggtccgcgtcggcagcgacaagaccatcatcggcaaggactccagc
 S   G   A   A   K   V   R   V   G   S   D   K   T   I   I   G   K   D   S   S gccgtgctcgagggcgtcggtctctacatcaacaagcagaagaacgtcatcgtccgcaac
 A   V   L   E   G   V   G   L   Y   I   N   K   Q   K   N   V   I   V   R   N ctgtccatcaagaatgtgcttgcggagaatggtgacgccatcggcatccaggcttcccag
 L   S   I   K   N   V   L   A   E   N   G   D   A   I   G   I   Q   A   S   Q aacgtctggatcgaccactgcgacctgtcctcggaccgtgaccacgacaaggactactac
 N   V   W   I   D   H   C   D   L   S   S   D   R   D   H   D   K   D   Y   Y gacggtctcctcgacgtgacccacgcctctgactacatcaccctgtccaacaactacctc
 D   G   L   L   D   V   T   H   A   S   D   Y   I   T   L   S   N   N   Y   L catgaccactggaaggcctcgctcgtcggccactccgactccaacggctctgaggacaag
 H   D   H   W   K   A   S   L   V   G   H   S   D   S   N   G   S   E   D   K ggccacttgaccgtcacctactaccagaaccacttcgagaacctgaactcgcgtggtcct
 G   H   L   T   V   T   Y   Y   Q   N   H   F   E   N   L   N   S   R   G   P tctttccgcttcggcaccggtcacattgtcaacaacctctacaccagcgtcagcgacggt
 S   F   R   F   G   T   G   H   I   V   N   N   L   Y   T   S   V   S   D   G atcaacgctcgccagggcgcccagctccttgttgagggcaacgtcttcactggcagcaag
 I   N   A   R   Q   G   A   Q   L   L   V   E   G   N   V   F   T   G   S   K aagccgctgtacagcaccgatgccggctacgccgccgtcaacgacaacgacttcggcggc
 K   P   L   Y   S   T   D   A   G   Y   A   A   V   N   D   N   D   F   G   G
```

```
gctgagaacactgctgaggctggcaccctcactgcctctgacctcggctacaagtatacc
 A   E   N   T   A   E   A   G   T   L   T   A   S   D   L   G   Y   K   Y   T gctctgaagtcttccgaggtctctgccgccgtctccaagtcggctggcgccacgctcact
 A   L   K   S   S   E   V   S   A   A   V   S   K   S   A   G   A   T   L   T ttctaa
 F   -
```

```
SEQ ID NO:          36
LENGTH:             321
TYPE:               PRT
ORGANISM:           M. phaseolina
MKATTLATFALSAVSALAAPTKTFAKRAAITDGPDVGYATLNGGTTGGAGGSTTTVSSLAQFTAAAEADGAAV

IVVSGNISGAAKVRVGSDKTIIGKDSSAVLEGVGLYINKQKNVIVRNLSIKNVLAENGDAIGIQASQNVWIDH

CDLSSDRDHDKDYYDGLLDVTHASDYITLSNNYLHDHWKASLVGHSDSNGSEDKGHLTVTYYQNHFENLNSRG

PSFRFGTGHIVNNLYTSVSDGINARQGAQLLVEGNVFTGSKKPLYSTDAGYAAVNDNDFGGAENTAEAGTLTA

SDLGYKYTALKSSEVSAAVSKSAGATLTF*

SEQ ID NO:          37
LENGTH:             1896 (including 150 bp 5' UTR and 150 bp 3' UTR)
TYPE:               DNA
ORGANISM:           M. phaseolina
CAGCCAATACGGTGGCCTGAAACATACTCATATTCCTATATCCAATTCCACCCAGAAACATATTTACACGGCC

CGTCCCTTAGCCCAATTGACCCCGGAAGCGTCTCTCTTTTTCCCTTACGCTCGTTTCTTTTTCTCCCTGTCAT

GCTGATGGCGTCCTGTCTTCCCCTGGCCCTAGTGGCCTTTTCTTCACTTTCCTATGCTCTTCAGCCCTACAGT

GGCCCGGCGCCAGACCTTCCTGATCGTAAGCCATTCGGCTTCGGTGCCGCCGCCACAGGTGGCGGTACCCCCA

CGCCGAACAATACCTACCTGGTCGACAACATGCCTGATCTGCGGACCGTTCTAAAGATGGAGACTCCCCGCAC

AGTTTACGTGAAGGGCGAGATCAAAGGCAACGAAATCAACGAGACCACGACCGGCAATTGCCAATTCTACATT

GACAGCAGCAACAACTCCAAGTTCAACTTTACCCTCTACATCCAGAGCTACAACGAGACCTACATGGGCCAGG

TTAAGGCTGCCTCCGAAGCGGGCCAGCTATTCGACGGACAGAACGCCACCGAGCTCCTCAATCTACTCGGCCG

CCAGAACGTGAGCTTCCATGTGCCCGGAAAGGTTTCAAAATAACAGCAACGCTAACCCACCTCGCAGGGCTGG

CGCGGCCAAGTGCAAAACGTGCAAAAGTCCTACGAAGCCATTGACGTGGCCAGCAACCTTACGCTTATCGGCT

GGGACTCGTCCGCGTACCTGAATGGCGTCAATCTCGGGTTCAACTCGCGCTCCAACATCATCATGCGCAACCT

GCGCATTTCGTCGCCGCGTGACTGCTTCCCGTCGCCGGAAACCTACCCCAGCAGCTGGAACGCGCGTTACGAC

GCCGTGTCCATGGTGTCGACGACGACCGCGTGGCTCGACGGCAACATCTTCGAGGACGGCCCCGTCGCCGTCG

CGCCCGACGACTTCGCGGGCGGGTGGAAGGTCGACCGGTACGACGGCTTGTTTGACGCCGAGGACGGCAGCGA

CGACATCACCTTCTCGCACAACATCGTCACCAACCACCACAAGAGCCTGCTGTGGGCGGCGGCAACAAGGAG

GCGGACCGCGACATCGGCAAGATGAAGTTCACCGTCTTCGGCAACCGCTTCGTCGACAGCTTGTCGCGCAACC

CGCTGATGCGCTTCGGCACCTTCTACATCGTCGCCAACGTCTTCGAGAACTACGCCGAGCGCGCGCCGCTGTT

CGAGGACGACAGCGTCGCCGCGAGCGCGGCCGCCTCGCGGCTCGTTCGACGCGCGGACAATGCCACCACCTAC

AGGCCGGACTTCCAGTACAACATGGGCATCTACAACGCCAGCACCGTGTACGTCGCGGCGAATGCGTTTGTCC

AGACGGGCACCTATGCGGACGATTCGTCGCGCGTCTTCTCCTTCTCGGACCTTGCGACGCCGGGCCTGCCCGC

GACGCTGTGCTCGCCGGCTGATGGCGCGAACGGGACGGCGTCGGCGTCGTCCCTGCCGAAGAGCGTTTTCAAT

GGCAGGCCTATCGACCTTGCGAAGAATGCCAAGAACACGTGGGCGTATTTCCTGGAGAGCAAGAATGAGGACG

GCGAGTTCGCCGAGGGTGGGTTCGTGATTGGATGTGACGGGCTGGAGGAGCAGGAGACGCCGGTTGCGTTTAA

GGATGGTAACGAGGTCGATGCATATGTGCGGAAGAATGCAGGGCAGGTAGGGAGGGCGACGCCGTAGGGGTGC

AAGTGGATGCCAGGCTGATGGTTGGTGGTGGAATGTTTGTGGAACCGCGAGCGGATAGACTTGGCGGGAAGTG

CCTCCTCTTGGCGGAAGGTATGCATGTACAATGGGTCAACGGTAGAGATCTGCGGCTTTTCCGGCGGCGGG
```

```
SEQ ID NO:          38
LENGTH:             1536
TYPE:               DNA
ORGANISM:           M. phaseolina
FEATURE NAME/KEY:   CDS
LOCATION:           (1)...(1536)
atggcgtcctgtcttccctggccctagtggccttttcttcactttcctatgctcttcag
 M   A   S   C   L   P   L   A   L   V   A   F   S   S   L   S   Y   A   L   Q ccctacagtggcccggcgccagaccttcctgatcgtaagccattcggcttcggtgccgcc
 P   Y   S   G   P   A   P   D   L   P   D   R   K   P   F   G   F   G   A   A gccacaggtggcggtaccccacgccgaacaatacctacctggtcgacaacatgcctgat
 A   T   G   G   T   P   T   P   N   N   T   Y   L   V   D   N   M   P   D ctgcggaccgttctaaagatggagactccccgcacagtttacgtgaagggcgagatcaaa
 L   R   T   V   L   K   M   E   T   P   R   T   V   Y   V   K   G   E   I   K ggcaacgaaatcaacgagaccacgaccggcaattgccaattctacattgacagcagcaac
 G   N   E   I   N   E   T   T   T   G   N   C   Q   F   Y   I   D   S   S   N aactccaagttcaactttaccctctacatccagagctacaacgagacctacatgggccag
 N   S   K   F   N   F   T   L   Y   I   Q   S   Y   N   E   T   Y   M   G   Q gttaaggctgcctccgaagcgggccagctattcgacggacagaacgccaccgagctcctc
 V   K   A   A   S   E   A   G   Q   L   F   D   G   Q   N   A   T   E   L   L aatctactcggccgccagaacggctggcgcggccaagtgcaaaacgtgcaaaagtcctac
 N   L   L   G   R   Q   N   G   W   R   G   Q   V   Q   N   V   Q   K   S   Y gaagccattgacgtggccagcaaccttacgcttatcggctgggactcgtccgcgtacctg
 E   A   I   D   V   A   S   N   L   T   L   I   G   W   D   S   S   A   Y   L aatggcgtcaatctcgggttcaactcgcgctccaacatcatcatgcgcaacctgcgcatt
 N   G   V   N   L   G   F   N   S   R   S   N   I   I   M   R   N   L   R   I tcgtcgccgcgtgactgcttcccgtcgccggaaacctaccccagcagctggaacgcgcgt
 S   S   P   R   D   C   F   P   S   P   E   T   Y   P   S   S   W   N   A   R tacgacgccgtgtccatggtgtcgacgacgaccgcgtggctcgacggcaacatcttcgag
 Y   D   A   V   S   M   V   S   T   T   T   A   W   L   D   G   N   I   F   E gacggccccgtcgccgtcgcgcccgacgacttcgcgggcgggtggaaggtcgaccggtac
 D   G   P   V   A   V   A   P   D   D   F   A   G   G   W   K   V   D   R   Y gacggcttgtttgacgccgaggacggcagcgacgacatcaccttctcgcacaacatcgtc
 D   G   L   F   D   A   E   D   G   S   D   D   I   T   F   S   H   N   I   V accaaccaccacaagagcctgctgtggggcggcggcaacaaggaggcggaccgcgacatc
 T   N   H   H   K   S   L   L   W   G   G   G   N   K   E   A   D   R   D   I ggcaagatgaagttcaccgtcttcggcaaccgcttcgtcgacagcttgtcgcgcaacccg
 G   K   M   K   F   T   V   F   G   N   R   F   V   D   S   L   S   R   N   P ctgatgcgcttcggcaccttctacatcgtcgccaacgtcttcgagaactacgccgagcgc
 L   M   R   F   G   T   F   Y   I   V   A   N   V   F   E   N   Y   A   E   R gcgccgctgttcgaggacgacagcgtcgccgcgagcgcggccgcctcgcggctcgttcga
 A   P   L   F   E   D   D   S   V   A   A   S   A   A   A   S   R   L   V   R cgcgcggacaatgccaccacctacaggccggacttccagtacaacatgggcatctacaac
 R   A   D   N   A   T   T   Y   R   P   D   F   Q   Y   N   M   G   I   Y   N gccagcaccgtgtacgtcgcggcgaatgcgtttgtccagacgggcacctatgcggacgat
 A   S   T   V   Y   V   A   A   N   A   F   V   Q   T   G   T   Y   A   D   D tcgtcgcgcgtcttctccttctcggaccttgcgacgccgggcctgcccgcgacgctgtgc
 S   S   R   V   F   S   F   S   D   L   A   T   P   G   L   P   A   T   L   C tcgccggctgatggcgcgaacgggacggcgtcggcgtcgtccctgccgaagagcgttttc
 S   P   A   D   G   A   N   G   T   A   S   A   S   S   L   P   K   S   V   F aatggcaggcctatcgaccttgcgaagaatgccaagaacacgtgggcgtatttcctggag
 N   G   R   P   I   D   L   A   K   N   A   K   N   T   W   A   Y   F   L   E agcaagaatgaggacggcgagttcgccgagggtgggttcgtgattggatgtgacgggctg
 S   K   N   E   D   G   E   F   A   E   G   G   F   V   I   G   C   D   G   L gaggagcaggagacgccggttgcgtttaaggatggtaacgaggtcgatgcatatgtgcgg
 E   E   Q   E   T   P   V   A   F   K   D   G   N   E   V   D   A   Y   V   R
```

```
aagaatgcagggcaggtagggagggcgacgccgtag
  K  N  A  G  Q  V  G  R  A  T  P  -

SEQ ID NO:       39
LENGTH:          511
TYPE:            PRT
ORGANISM:        M. phaseolina
MASCLPLALVAFSSLSYALQPYSGPAPDLPDRKPFGFGAAATGGGTPTPNNTYLVDNMPDLRTVLKMETPRTV

YVKGEIKGNEINETTTGNCQFYIDSSNNSKFNFTLYIQSYNETYMGQVKAASEAGQLFDGQNATELLNLLGRQ

NGWRGQVQNVQKSYEAIDVASNLTLIGWDSSAYLNGVNLGFNSRSNIIMRNLRISSPRDCFPSPETYPSSWNA

RYDAVSMVSTTTAWLDGNIFEDGPVAVAPDDFAGGWKVDRYDGLFDAEDGSDDITFSHNIVTNHHKSLLWGGG

NKEADRDIGKMKFTVFGNRFVDSLSRNPLMRFGTFYIVANVFENYAERAPLFEDDSVAASAAASRLVRRADNA

TTYRPDFQYNMGIYNASTVYVAANAFVQTGTYADDSSRVFSFSDLATPGLPATLCSPADGANGTASASSLPKS

VFNGRPIDLAKNAKNTWAYFLESKNEDGEFAEGGFVIGCDGLEEQETPVAFKDGNEVDAYVRKNAGQVGRATP

*

SEQ ID NO:       40
LENGTH:          1798 (including 150 bp 5' UTR and 150 bp 3' UTR)
TYPE:            DNA
ORGANISM:        M. phaseolina
CGGGTTTTGGGAATATCTCCGGGCTTCGGTGGACCGTCCTATCCGTCTGAGCATGCCAATATGTTTTCTTGCC

TTTCTGTCCGTATATAAAATGCCAGTCAAGAAGAATTCTCGTGTTTCACACCTTTCTTCATCCGATCTCGCCT

CAGTATGCGTGCATCAGTCTCAATTACGGTCTCGCTACTGGCATTTGCCCTGAGGGCGTGCGCTGTTGGTGTG

GTTGGGAGTCCGGAGGGATTTGGCTCCGGGACAACAGGTGGAGGTAGTGCCACGCCGGTTTATCCTTCGACCA

CGAGCGAATTGCAGTCCTACTTGGAAGACGATGTTGCCCGAGTTATCGTCCTGAACAAGGAGTATGCAACCAA

ACAATTGTTTAATAAGCCTAAAACTGACCATGTCCAGGTTCAACTTCAAGGGCACCACCACCACTGCGACGGG

CTGCAGACCCACATCCAACACTTGCCCCGGTAATGGTGGCCAAGATGCAATTAATGCCAACGGTTGGTTAGTA

TCTGCTGGTTGCTCTCATCTGGTTCTTTGTGACTAATGTTCAACGCAGGTGCGGAAGTGCTCCGGCGGTCTCC

GTGAAGTACGACACGGCCGCTATTACGCCCATAAATCTCGGCTCTAACAAGTCTCTTATCGGCATTGGCACAT

CTGGTGTCATCCGCGGAAAGGGTCTCCGTATCGTCAGTAAAACTAATTCTTGCTATCAGTTGACGAAGAAACT

TACAGTTGATGAAATCTCTTCAGGCCAACGGAGCTAAAAATGTCATCATCCAAAATATTCATATTACCGATCT

CAACCCGCAGTACATCTGGGGTGGAGATGCCATTACCCTGGATGGTGCTGATCTGGTTTGGGTGGACCACGTT

AAGGGACGTATACTCCCGAACCCTCGCTCGAGCATTATTCTGACCTTGCCAACTACAGATCTCTCTCATCGGC

CGCCAGATGTTTGTCGCGGGCTACGGGGCATCTAACAGAGTAACTATCAGCAACACGGAGTTCGACGGCTCAA

CCTCCTGGAGCGCAACTTGCGACGGGCATGTACGTGCCGCCTCCCAGCCCACCACCACCTCCTTTCTTTCACT

GGAGTAGCTTAGATGCTAATATGCCTTATCTTTCCTTCTAGCACTACTGGACTATTTTGCTTTTGGGCTCAAA

CGACTTGATCACAATGAAAGGCAACTATATCCACCACACCAGCGGCCGTGGACCCAAGATCGGAGGCAACACC

CTGCTCCACGCCGTAAGTTCCGCCCCACAAACACCCTTGCCTCACCAATCGCCTGCTGAAACATGCTATTTCC

ACAGGTCAATAATGAGTGGTACGCCGTTTCGGGCCACGCCTTCGACCTGGGCGAGTCGGGCGCCATGGCCGTT

GCCGAGGGCAACGTTTTCCAGAACGTCGTCACGCCGCTGCTTTCGCCCGTCGAGGGCCGCATCTTCACGGCGC

CCAGCACTAGCGCCAACACCGCCTGCGCGACCTACCTTGGCCGCAACTGCGTCGTCAACGCCTTCGGCAGCAG

CGGCACCTTCTCCGGAACCGACACCAGCTTCTTCTCCAACTTCAACGGCAAGACGATCGCGAGTGCAGCCGCC

GCCGCATACAAGGATTCGACAGCGGGTGTGGGGAAGATTTAAGGGCGGAGCGGGTGGTTTTGCATTTAGGGGC

TGTGATATTGCGTTGGATGTTGGAATGAGGTCAGCAAAAGAAAATCTAAATCAACGATCATGAATGCTGGCT

GGAAGGAAATTGTTTGAGAACTACTTGTGCTTTTTTTTtATTACTG

SEQ ID NO:       41
LENGTH:          1137
TYPE:            DNA
```

ORGANISM: M. phaseolina
FEATURE NAME/KEY: CDS
LOCATION: (1) ... (1137)

```
atgcgtgcatcagtctcaattacggtctcgctactggcatttgccctgagggcgtgcgct
 M   R   A   S   V   S   I   T   V   S   L   L   A   F   A   L   R   A   C   A gttggtgtggttgggagtccggagggatttggctccgggacaacaggtggaggtagtgcc
 V   G   V   V   G   S   P   E   G   F   G   S   G   T   T   G   G   G   S   A acgccggtttatccttcgaccacgagcgaattgcagtcctacttggaagacgatgttgcc
 T   P   V   Y   P   S   T   T   S   E   L   Q   S   Y   L   E   D   D   V   A cgagttatcgtcctgaacaaggagttcaacttcaagggcaccaccaccactgcgacgggc
 R   V   I   V   L   N   K   E   F   N   F   K   G   T   T   T   T   A   T   G tgcagacccacatccaacacttgccccggtaatggtggccaagatgcaattaatgccaac
 C   R   P   T   S   N   T   C   P   G   N   G   G   Q   D   A   I   N   A   N ggttggtgcggaagtgctccggcggtctccgtgaagtacgacacggccgctattacgccc
 G   W   C   G   S   A   P   A   V   S   V   K   Y   D   T   A   A   I   T   P ataaatctcggctctaacaagtctcttatcggcattggcacatctggtgtcatccgcgga
 I   N   L   G   S   N   K   S   L   I   G   I   G   T   S   G   V   I   R   G aagggtctccgtatcttgatgaaatctcttcaggccaacggagctaaaaatgtcatcatc
 K   G   L   R   I   L   M   K   S   L   Q   A   N   G   A   K   N   V   I   I caaaatattcatattaccgatctcaacccgcagtacatctggggtggagatgccattacc
 Q   N   I   H   I   T   D   L   N   P   Q   Y   I   W   G   G   D   A   I   T ctggatggtgctgatctggtttggtggaccacatctctctcatcggccgccagatgttt
 L   D   G   A   D   L   V   W   V   D   H   I   S   L   I   G   R   Q   M   F gtcgcgggctacggggcatctaacagagtaactatcagcaacacggagttcgacggctca
 V   A   G   Y   G   A   S   N   R   V   T   I   S   N   T   E   F   D   G   S acctcctggagcgcaacttgcgacgggcatcactactggactattttgcttttgggctca
 T   S   W   S   A   T   C   D   G   H   H   Y   W   T   I   L   L   L   G   S aacgacttgatcacaatgaaaggcaactatatccaccacaccagcggccgtggacccaag
 N   D   L   I   T   M   K   G   N   Y   I   H   H   T   S   G   R   G   P   K atcggaggcaacacccctgctccacgccgtcaataatgagtggtacgccgtttcgggccac
 I   G   G   N   T   L   L   H   A   V   N   N   E   W   Y   A   V   S   G   H gccttcgacctgggcgagtcgggcgccatggccgttgccgagggcaacgttttccagaac
 A   F   D   L   G   E   S   G   A   M   A   V   A   E   G   N   V   F   Q   N gtcgtcacgccgctgctttcgcccgtcgagggccgcatcttcacggcgcccagcactagc
 V   V   T   P   L   L   S   P   V   E   G   R   I   F   T   A   P   S   T   S gccaacaccgcctgcgcgacctaccttggccgcaactgcgtcgtcaacgccttcggcagc
 A   N   T   A   C   A   T   Y   L   G   R   N   C   V   V   N   A   F   G   S agcggcaccttctccggaaccgacaccagcttcttctccaacttcaacggcaagacgatc
 S   G   T   F   S   G   T   D   T   S   F   F   S   N   F   N   G   K   T   I gcgagtgcagccgccgccgcatacaaggattcgacagcgggtgtggggaagatttaa
 A   S   A   A   A   A   A   Y   K   D   S   T   A   G   V   G   K   I   -
```

SEQ ID NO: 42
LENGTH: 378
TYPE: PRT
ORGANISM: M. phaseolina

MRASVSITVSLLAFALRACAVGVVGSPEGFGSGTTGGGSATPVYPSTTSELQSYLEDDVARVIVLNKEFNFKG

TTTTATGCRPTSNTCPGNGGQDAINANGWCGSAPAVSVKYDTAAITPINLGSNKSLIGIGTSGVIRGKGLRIL

MKSLQANGAKNVIIQNIHITDLNPQYIWGGDAITLDGADLVWVDHISLIGRQMFVAGYGASNRVTISNTEFDG

STSWSATCDGHHYWTILLLGSNDLITMKGNYIHHTSGRGPKIGGNTLLHAVNNEWYAVSGHAFDLGESGAMAV

AEGNVFQNVVTPLLSPVEGRIFTAPSTSANTACATYLGRNCVVNAFGSSGTFSGTDTSFFSNFNGKTIASAAA

AAYKDSTAGVGKI*

SEQ ID NO: 43
LENGTH: 1631 (including 150 bp 5' UTR and 150 bp 3' UTR)
TYPE: DNA
ORGANISM: M. phaseolina
GGTGGTGGTCTTGCACCTCTTCCGGTCCACTACTCACATTAACCCGTTCAATCGTTCCCACACATTCACTTAT -continued

```
ATTCCAACTCTCACACATTCGTTCTGTATCACGCAATCAATCTTTTTGTTTTTGTTTTTGATCTATTTTAGC

AAACATGAAGCTCACTCTCTTGTCTATTGTTCTCGCTCTTGCCCACCAGACTCGGGCCACCAGGGTTACGGGC

GCTGCCGAAGGCTTCGCCAAAGGCGTCACAGGGGGTGGCTCTGCTGCCCCTGTCACCCCCAAAAATATTGTTG

AGCTGACCAAATACCTTGCCGACGCTCAGCCCCGTGTCATCATCTTGGACAAGGAGTAAGTCCGCTATCACGG

GAGGGCTTCAACCGCTCTATCTGGGGGATTTTCTCCAGCCGAACGAACGCTGACATCTATCTTCCTCAGATTC

AACTTCAAGGGCTCAGAGGGAACCGTCAAGGAGATGGGCTGCCGTCCTCGTACCAAATGCTCCGAGACTGGCG

GTGGCCAAGATGCCATCAACCACGCTAGCTGGTGCACAAACGGCAACGCTGGTGCCGGCTCCAAAGCCGTTTC

TGTCACCTATGATAGAGCGGGAACCCTCGCCTTAAAGGTAAACTCCAACAAATCCATTGTCGGTGTCGGCAAC

AAGGGTGTCATCCGCGGCAAGGGTCTCCGTCTCGCCGGCGCTAAGAACGTCATCATCCAAAACATCCACATTA

CCGAGCTTAACCCTCAGTACATCTGGGGCGGTGACGGCATTCAGATCGACGGCGCCGACATGGTCTGGATCGA

CAGGTCCAAGATCTCTCTCGTGGGCCGGCAGATGCTTGTCCTTGGCAACGGCGCGTCCGGCAGGGTCTCGGTC

ACCAACAACGAATTCGACGGCTCTACTAGTATGCTGATCTCCATAGCCCCCTTGATCACCAAACGGCTAATCG

CTCTTTCCAGGCTGGTCGGCTACCTGTGACGGTCACCACTACTGGGCCCTCTACTTCACCGGTTCCAACGACA

TGGTCACGTTCAAGGGTAACTACATCCACCACACTTCTGGCCGGAGCCCAAGATCGGCGGTACCACGCTCCT

CCACGCTGTAAGATCCCCAATGATCCGTGTCTCGTGACTCGCGCTGATTCCACGCCCAGGTCAACAACGTCTG

GTATGCCAACTCCGGCCACGCTTTCGAGATCCTCGCGCCCAAGTCGAACGCCCTCATCGAGGGCAACATCTTC

CAGAACGTCGTCCGACCCATGAAGGCCAGCACGGGCAAGGTCTTTGCTCCCTCTTCGGTCCAGGCCGTCTGCA

ATCGCGCTCTTGGCCGCGCTTGCCAGGCCAACTCTTTCGGCTCCTCTGGCCCCTTGACCGGCACCGACAGCAG

CTTCCTCGGTCTGTTCAAGGGCAAGAACCCCGCTACTGCTTCCGCCGCCAGCCCCGCCATTTCTGGCCGCGCT

GGTGTCGGGAAGATTGCCTAAATGCTGGCTATGTTCTGGGTTGGACGCTTGCTGAGCAAGCTGTCTTGGCTGG

TTGGGTGCATGCACTCAGTTGATAGGCACAACCAACAATCTCTGGACGTGTTATCTCACTTGTCTGGCACTGA

GTGGGAATGATTTATGACAGTTTTT
```

```
SEQ ID NO:         44
LENGTH:            1137
TYPE:              DNA
ORGANISM:          M. phaseolina
FEATURE NAME/KEY:  CDS
LOCATION:          (1) ... (1137)
atgaagctcactctcttgtctattgttctcgctcttgcccaccagactcgggccaccagg
 M   K   L   T   L   L   S   I   V   L   A   L   A   H   Q   T   R   A   T   R gttacgggcgctgccgaaggcttcgccaaaggcgtcacaggggtggctctgctgcccct
 V   T   G   A   A   E   G   F   A   K   G   V   T   G   G   G   S   A   A   P gtcaccccaaaaatattgttgagctgaccaaataccttgccgacgctcagccccgtgtc
 V   T   P   K   N   I   V   E   L   T   K   Y   L   A   D   A   Q   P   R   V atcatcttggacaaggaattcaacttcaagggctcagagggaaccgtcaaggagatgggc
 I   I   L   D   K   E   F   N   F   K   G   S   E   G   T   V   K   E   M   G tgccgtcctcgtaccaaatgctccgagactggcggtggccaagatgccatcaaccacgct
 C   R   P   R   T   K   C   S   E   T   G   G   G   Q   D   A   I   N   H   A agctggtgcacaaacggcaacgctggtgccggctccaaagccgtttctgtcacctatgat
 S   W   C   T   N   G   N   A   G   A   G   S   K   A   V   S   V   T   Y   D agagcgggaaccctcgccttaaaggtaaactccaacaaatccattgtcggtgtcggcaac
 R   A   G   T   L   A   L   K   V   N   S   N   K   S   I   V   G   V   G   N aagggtgtcatccgcggcaagggtctccgtctcgccggcgctaagaacgtcatcatccaa
 K   G   V   I   R   G   K   G   L   R   L   A   G   A   K   N   V   I   I   Q aacatccacattaccgagcttaaccctcagtacatctggggcggtgacggcattcagatc
 N   I   H   I   T   E   L   N   P   Q   Y   I   W   G   G   D   G   I   Q   I gacggcgccgacatggtctggatcgacaggtccaagatctctctcgtgggccggcagatg
 D   G   A   D   M   V   W   I   D   R   S   K   I   S   L   V   G   R   Q   M
```

```
cttgtccttggcaacggcgcgtccggcagggtctcggtcaccaacaacgaattcgacggc
 L  V  L  G  N  G  A  S  G  R  V  S  V  T  N  N  E  F  D  G tctactagctggtcggctacctgtgacggtcaccactactgggccctctacttcaccggt
 S  T  S  W  S  A  T  C  D  G  H  H  Y  W  A  L  Y  F  T  G tccaacgacatggtcacgttcaagggtaactacatccaccacacttctggccggagcccc
 S  N  D  M  V  T  F  K  G  N  Y  I  H  H  T  S  G  R  S  P aagatcggcggtaccacgctcctccacgctgtcaacaacgtctggtatgccaactccggc
 K  I  G  G  T  T  L  L  H  A  V  N  N  V  W  Y  A  N  S  G cacgctttcgagatcctcgcgcccaagtcgaacgccctcatcgagggcaacatcttccag
 H  A  F  E  I  L  A  P  K  S  N  A  L  I  E  G  N  I  F  Q aacgtcgtccgacccatgaaggccagcacgggcaaggtctttgctccctcttcggtccag
 N  V  V  R  P  M  K  A  S  T  G  K  V  F  A  P  S  S  V  Q gccgtctgcaatcgcgctcttggccgcgcttgccaggccaactcttcggctcctctggc
 A  V  C  N  R  A  L  G  R  A  C  Q  A  N  S  F  G  S  S  G cccttgaccggcaccgacagcagcttcctcggtctgttcaagggcaagaaccccgctact
 P  L  T  G  T  D  S  S  F  L  G  L  F  K  G  K  N  P  A  T gcttccgccgccagccccgccatttctggccgcgctggtgtcgggaagattgcctaa
 A  S  A  A  S  P  A  I  S  G  R  A  G  V  G  K  I  A  -
```

SEQ ID NO:           45
LENGTH:              378
TYPE:                PRT
ORGANISM:            M. phaseolina

MKLTLLSIVLALAHQTRATRVTGAAEGFAKGVTGGGSAAPVTPKNIVELTKYLADAQPRVIILDKEFNFKGSE

GTVKEMGCRPRTKCSETGGGQDAINHASWCTNGNAGAGSKAVSVTYDRAGTLALKVNSNKSIVGVGNKGVIRG

KGLRLAGAKNVIIQNIHITELNPQYIWGGDGIQIDGADMVWIDRSKISLVGRQMLVLGNGASGRVSVTNNEFD

GSTSWSATCDGHHYWALYFTGSNDMVTFKGNYIHHTSGRSPKIGGTTLLHAVNNVWYANSGHAFEILAPKSNA

LIEGNIFQNVVRPMKASTGKVFAPSSVQAVCNRALGRACQANSFGSSGPLTGTDSSFLGLFKGKNPATASAAS

PAISGRAGVGKIA*

SEQ ID NO:           46
LENGTH:              1573 (including 150 bp 5' UTR and 150 bp 3' UTR)
TYPE:                DNA
ORGANISM:            M. phaseolina

CGGATGCCGTGCAGCTGTCAAAGTCATGATAAAAGTCCCCACTCCCAGGTACATAATGTGATCGGTAGTTCTG

CGCTCTCCTTTCCAACGGTTGTCCCTTGAGCTTCCCGTGCCATGGTAGCCTTTTCTTCCCTTACGTCTGGCAA

TGCCATGGCGTCCCTCCTGTCTCTATCCGTCCTTTCAGCTTTTCTTGCTTCACCGACACTTGCATACAGTCGT

GCTGAATGCCAGGCTCCATCTGCCGACCCCCTGGCGGGCTGCGTACCCGAACGCTGCTCGTCAGTCCAAACA

GCACCGTGACGGCTAACAACAGCACCTCCTTTACCTCTGTCCAATCAGCTATCCTTTCCCTCGGCAACACCAC

CACACCCGCCACCATCCTCATTCTTCCCGGCACCTATGTTGAGCAAGTCAATATCACCCGCCCGGGACCAGTG

ACGCTCCTCGGGCAGACTTCATCCCCGAACAATTCCTCCACCAACGGCGTTAAGATCCTCTGGCGTCAGGCCA

CTGGCAACTCGGTCAACACCTTCGACAACGCCTATACCTCTGTCCTCACTGTCGCGCCGACCCTCGAGAGCAG

CCTAACAGGCAGCGGGCCCACCGGATACGCCGTCCCCGCCGGCACGCCCTTCGGCAACGAGGACTTCCGCGCA

TACAACGTCGACTTCGTCAACGACTACGCGCCCTACTCGGCCGGCCCGGCACTCGCCATTAGCATCAGCTACG

CCAACGCGGGCTTCTACTTCTGCGGCTTCTACAGCTATCAGGACACCGTAAGTGTCATCTCCACTCGTCCACT

ACACGCAACAAACAAACATGCATCCGAGAATCCCTTTTCCCCACCAACTAACGCCAAACCGCAAGGTCTACAT

CGGCAAGCTCGGCAACGCCTACTTCTACGACTCCATCATCGCCGGCCAAACCGACTTCCTCTACGGCTTCGGC

ACCGCCTGGATCCAGTCATCGCAGCTCTCTCTCCGCTCCTGCGGCGGCGCATCACCGCCTGGAAGGGCACCA

ATACGTCCTTCCCCAACGCCTACGGCGTCTACATCCACGACAGCGTCGTCGAGAAGGCCAACGCCTCGCTCTC

CATCGCCGGGCTCTGCGCCCTCGGCAGGCCCTGGAATGCGCAGCATCGCTCCATCTTCGCGAACACGTGGCTC

GATGACAGCATCAAGCCGAGCGGGTACATCATCTGGGGGAGCACGGATCCGAGGACCAACAATTACACGTTTA

```
TGGCGGAGTATGAGGACTTTGGGCCGGGTTGGAATGAGACCGGGAGGAGGGCGGCGAATATTACGAAGGTGTT

GACGGAGGCCGAGTATGAGCCGTATGACAGTCTGGAGAAGGTGTTCCAGTATCCGTTCAGTGGCGAGTTCGGG

AACGTGGGGTGGATCGATGAGAGTCCGGAGGCTTGAGCCGGTGGGGATAGTGTGGATTGTGGTGGCCAGCGGC

GTAGACGAGGCGGATCTGGTAAGAACTGCGTAGCATGAATGAAATTCGTTTGTACATACGTCTTTATATCGAG

CAGCGCTTATGCAAGTTAAATGACGCCGTATTTGCATGCG
```

```
SEQ ID NO:        47
LENGTH:           1182
TYPE:             DNA
ORGANISM:         M. phaseolina
FEATURE NAME/KEY: CDS
LOCATION:         (1)...(1182)
atggcgtccctcctgtctctatccgtcctttcagcttttcttgcttcaccgacacttgca
 M   A   S   L   L   S   L   S   V   L   S   A   F   L   A   S   P   T   L   A tacagtcgtgctgaatgccaggctccatctgccgacccctggcgggctgcgtacccgga
 Y   S   R   A   E   C   Q   A   P   S   A   D   P   L   A   G   C   V   P   G acgctgctcgtcagtccaaacagcaccgtgacggctaacaacagcacctcctttacctct
 T   L   L   V   S   P   N   S   T   V   T   A   N   N   S   T   S   F   T   S gtccaatcagctatcctttccctcggcaacaccaccacacccgccaccatcctcattctt
 V   Q   S   A   I   L   S   L   G   N   T   T   T   P   A   T   I   L   I   L cccggcacctatgttgagcaagtcaatatcacccgcccgggaccagtgacgctcctcggg
 P   G   T   Y   V   E   Q   V   N   I   T   R   P   G   P   V   T   L   L   G cagacttcatccccgaacaattcctccaccaacggcgttaagatcctctggcgtcaggcc
 Q   T   S   S   P   N   N   S   S   T   N   G   V   K   I   L   W   R   Q   A actggcaactcggtcaacaccttcgacaacgcctatacctctgtcctcactgtcgcgccg
 T   G   N   S   V   N   T   F   D   N   A   Y   T   S   V   L   T   V   A   P accctcgagagcagcctaacaggcagcgggcccaccggatacgccgtccccgccggcacg
 T   L   E   S   S   L   T   G   S   G   P   T   G   Y   A   V   P   A   G   T cccttcggcaacgaggacttccgcgcatacaacgtcgacttcgtcaacgactacgcgccc
 P   F   G   N   E   D   F   R   A   Y   N   V   D   F   V   N   D   Y   A   P tactcggccggcccggcactcgccattagcatcagctacgccaacgcgggcttctacttc
 Y   S   A   G   P   A   L   A   I   S   I   S   Y   A   N   A   G   F   Y   F tgcggcttctacagctatcaggacaccgtctacatcggcaagctcggcaacgcctacttc
 C   G   F   Y   S   Y   Q   D   T   V   Y   I   G   K   L   G   N   A   Y   F tacgactccatcatcgccggccaaaccgacttcctctacggcttcggcaccgcctggatc
 Y   D   S   I   I   A   G   Q   T   D   F   L   Y   G   F   G   T   A   W   I cagtcatcgcagctctctctccgctcctgcggcggcggcatcaccgcctggaagggcacc
 Q   S   S   Q   L   S   L   R   S   C   G   G   G   I   T   A   W   K   G   T aatacgtccttccccaacgcctacggcgtctacatccacgacagcgtcgtcgagaaggcc
 N   T   S   F   P   N   A   Y   G   V   Y   I   H   D   S   V   V   E   K   A aacgcctcgctctccatcgccgggctctgcgccctcggcaggccctggaatgcgcagcat
 N   A   S   L   S   I   A   G   L   C   A   L   G   R   P   W   N   A   Q   H cgctccatcttcgcgaacacgtggctcgatgacagcatcaagccgagcgggtacatcatc
 R   S   I   F   A   N   T   W   L   D   D   S   I   K   P   S   G   Y   I   I tgggggagcacggatccgaggaccaacaattacacgtttatggcggagtatgaggacttt
 W   G   S   T   D   P   R   T   N   N   Y   T   F   M   A   E   Y   E   D   F gggccgggttggaatgagaccgggaggagggcggcgaatattacgaaggtgttgacggag
 G   P   G   W   N   E   T   G   R   R   A   A   N   I   T   K   V   L   T   E gccgagtatgagccgtatgacagtctggagaaggtgttccagtatccgttcagtggcgag
 A   E   Y   E   P   Y   D   S   L   E   K   V   F   Q   Y   P   F   S   G   E ttcgggaacgtggggtggatcgatgagagtccggaggcttga
 F   G   N   V   G   W   I   D   E   S   P   E   A   -
```

```
SEQ ID NO:  48
LENGTH:     393
TYPE:       PRT
ORGANISM:   M. phaseolina
MASLLSLSVLSAFLASPTLAYSRAECQAPSADPLAGCVPGTLLVSPNSTVTANNSTSFTSVQSAILSLGNTTT
```

PATILILPGTYVEQVNITRPGPVTLLGQTSSPNNSSTNGVKILWRQATGNSVNTFDNAYTSVLTVAPTLESSL

TGSGPTGYAVPAGTPFGNEDFRAYNVDFVNDYAPYSAGPALAISISYANAGFYFCGFYSYQDTVYIGKLGNAY

FYDSIIAGQTDFLYGFGTAWIQSSQLSLRSCGGGITAWKGTNTSFPNAYGVYIHDSVVEKANASLSIAGLCAL

GRPWNAQHRSIFANTWLDDSIKPSGYIIWGSTDPRTNNYTFMAEYEDFGPGWNETGRRAANITKVLTEAEYEP

YDSLEKVFQYPFSGEFGNVGWIDESPEA*

```
SEQ ID NO:        49
LENGTH:           1330 (including 150 bp 5' UTR and 150 bp 3' UTR)
TYPE:             DNA
ORGANISM:         M. phaseolina
```
TCAGGCTCGTATGCCTTGTCCTTCATTTGCTTGCACTCTAGGGCTGGCTAAGACCTCCTTACTTGAATAATGT

ATCTCTCTACGTCCGCCTTTATAGTCTGCCTGGCGGCTCCAAAACCCCTGAGCCTCACAACATTCATTCGCTT

AACC

ATGCATAGTTCTTCCATCCTTTTCAGCCTTTTCGGCTCCGCACTCGCTCTGACATCTCCACCGCCAGGAGCGC

TGACTGTTGGAGGCTCTGAGGGAAAATTCTCCACCGTTCAAGCTGCGGTTGACGCTCTCCAGAACACCACTGC

TCGGCAATCCATATTCATCTACTCCGGCACTTACGAGGAGCAGGTGTATATCGCCAAACACAATGGCCCCATT

TCCATTTATGGACAAGCCTCGGATGACAGCTCATACCACACCAATACTGTCACTCTCTCTTTCGGCCTCAGCC

AGGCCTTCAACCTTAGCAACGACCTCACGGCCACCCTCCGCGCTCACTCTCCCGATTTCAACTTGTACAACGT

GAATGTGGAGAACACCTACGGCAAAGGGAGCCAGGCCGTCGCTGTCTCGGCCTACGGTACCGAGCAGGCATAC

TACGGCTGCAAGCTCACGGGCTTCCAAGACACCCTCCTCACCCAGAGAGGCAGGCACTACTTCGTAAACACCT

ACATTGAAGGTAAGGAGGTCTTTCTCAAGCTGCGGAAAGCGCGGTCTCTGACGGACATGCACAGGCGCCACCG

ACTTCATTTTCGGCCAGTATTCCGCGGCCTGGTTTGAGAACTGCGACCTGCGCGTCCCCGCGGCCAAGCAGGG

ATGGGTCACCGCGAGCGGCCGCAACACGACCAACGACGGCTGGTATGTCATCAACGGAGGCAGCGTGCAAGCG

GCACCCGGCCAGAACGTAACTGCCGGCGCGTACTTCCTGGGCCGGCCGTGGCGCAGCTTCGCGCGCGCCGTCT

TCCAGAACGTCTACTTGAGCGAGGTCATCAACCCTGCGGGCTGGGCCATCTGGTCCACGAGCACGCCCAACAC

GGGCAACGTCACGTTCGCGGAGTACAACAACACCGGACCTGGTGCTTCCAACGGGACGCGGGCCAGCTTTTCG

CAGCAGCTGGCGGAGCCGGTGGACATCACGGAGGTGCTAGGATCGAACTACACACTCTGGATTGATCCCAAGT

TCTTGTGAATAGCAAGCGGGTAGAAAGCCGCGGTACGAACGCCTTTGCCGTAATTAGATAATCCCAGGAAGAC

GGAGAGAATGATTATCTTCTCCTCTAATGCGCCGTGGGACGACGGATCCGTGACTGAATAGTGAGAGCAAAAG

TGCGCCTGCATG

SEQ ID NO: 50
LENGTH: 975
TYPE: DNA
ORGANISM: *M. phaseolina*
FEATURE NAME/KEY: CDS
LOCATION: (1) ... (975)

```
atgcatagttcttccatccttttcagccttttcggctccgcactcgctctgacatctcca
 M  H  S  S  S  I  L  F  S  L  F  G  S  A  L  A  L  T  S  P ccgccaggagcgctgactgttggaggctctgagggaaaattctccaccgttcaagctgcg
 P  P  G  A  L  T  V  G  G  S  E  G  K  F  S  T  V  Q  A  A gttgacgctctccagaacaccactgctcggcaatccatattcatctactccggcacttac
 V  D  A  L  Q  N  T  T  A  R  Q  S  I  F  I  Y  S  G  T  Y gaggagcaggtgtatatcgccaaacacaatggccccatttccatttatggacaagcctcg
 E  E  Q  V  Y  I  A  K  H  N  G  P  I  S  I  Y  G  Q  A  S gatgacagctcataccacaccaatactgtcactctctctttcggcctcagccaggccttc
 D  D  S  S  Y  H  T  N  T  V  T  L  S  F  G  L  S  Q  A  F aaccttagcaacgacctcacggccaccctccgcgctcactctcccgatttcaacttgtac
 N  L  S  N  D  L  T  A  T  L  R  A  H  S  P  D  F  N  L  Y aacgtgaatgtggagaacacctacggcaaagggagccaggccgtcgctgtctcggcctac
 N  V  N  V  E  N  T  Y  G  K  G  S  Q  A  V  A  V  S  A  Y
```

```
ggtaccgagcaggcatactacggctgcaagctcacgggcttccaagacaccctcctcacc
 G  T  E  Q  A  Y  Y  G  C  K  L  T  G  F  Q  D  T  L  L  T cagagaggcaggcactacttcgtaaacacctacattgaaggcgccaccgacttcattttc
 Q  R  G  R  H  Y  F  V  N  T  Y  I  E  G  A  T  D  F  I  F ggccagtattccgcggcctggtttgagaactgcgacctgcgcgtccccgcggccaagcag
 G  Q  Y  S  A  A  W  F  E  N  C  D  L  R  V  P  A  A  K  Q ggatgggtcaccgcgagcggccgcaacacgaccaacgacggctggtatgtcatcaacgga
 G  W  V  T  A  S  G  R  N  T  T  N  D  G  W  Y  V  I  N  G ggcagcgtgcaagcggcacccggccagaacgtaactgccggcgcgtacttcctgggccgg
 G  S  V  Q  A  A  P  G  Q  N  V  T  A  G  A  Y  F  L  G  R ccgtggcgcagcttcgcgcgcgccgtcttccagaacgtctacttgagcgaggtcatcaac
 P  W  R  S  F  A  R  A  V  F  Q  N  V  Y  L  S  E  V  I  N cctgcgggctgggccatctggtccacgagcacgcccaacacgggcaacgtcacgttcgcg
 P  A  G  W  A  I  W  S  T  S  T  P  N  T  G  N  V  T  F  A gagtacaacaacaccggacctggtgcttccaacgggacgcgggccagcttttcgcagcag
 E  Y  N  N  T  G  P  G  A  S  N  G  T  R  A  S  F  S  Q  Q ctggcggagccggtggacatcacggaggtgctaggatcgaactacacactctggattgat
 L  A  E  P  V  D  I  T  E  V  L  G  S  N  Y  T  L  W  I  D cccaagttcttgtga
 P  K  F  L  -

SEQ ID NO:      51
LENGTH:         324
TYPE:           PRT
ORGANISM:       M. phaseolina
MHSSSILFSLFGSALALTSPPPGALTVGGSEGKFSTVQAAVDALQNTTARQSIFIYSGTYEEQVYIAKHNGPI

SIYGQASDDSSYHTNTVTLSFGLSQAFNLSNDLTATLRAHSPDFNLYNVNVENTYGKGSQAVAVSAYGTEQAY

YGCKLTGFQDTLLTQRGRHYFVNTYIEGATDFIFGQYSAAWFENCDLRVPAAKQGWVTASGRNTTNDGWYVIN

GGSVQAAPGQNVTAGAYFLGRPWRSFARAVFQNVYLSEVINPAGWAIWSTSTPNTGNVTFAEYNNTGPGASNG

TRASFSQQLAEPVDITEVLGSNYTLWIDPKFL*

SEQ ID NO:      52
LENGTH:         7706 (including 150 bp 5' UTR and 150 bp 3' UTR)
TYPE:           DNA
ORGANISM:       M. phaseolina
GCTGCTTCTCTGAGCGGCTCCAAGAACGCCTTTTACAACTGCCAATTCATCTCCGCCGGCGATTTAGGAATAT

CCTCGTCCACCGGTACCACGTTCGTCTACAATTCGTACATCGAAGCGCGTTCTAAGCTCATCTACAATACGCC

TAACATGTACATTTACGGCTCAACTCTCACGCCTACGGCGAGCAACGCACTCTTGGTTTATAACAAGGGCGTG

TCTTCTGGCACGGTGGTGACCACCAACTCCACCGTTGTCTTCGACTCCTGCACCGTCACTCCGAAGCCGGGCA

CCACTGTGACCGGTATTTCCCTTGCCGCAGCGAACGGTGTTGGGTCAATTGTGGTCTATAGAAACTCCGTCCT

GCCAGGCTTCATTCTCAGCACCGGTATTCACGTTGACGCCAAGACCCAGGCAGCACAGAACTTCTACGGCGAG

TTCGGTAACACAGGTGCCGGATCCTACTCTTCCAACTCCGCCGCGAGGGCCTCCTACGTGAAGAGCCTGAGCG

TCGATCAGCTTTCTCAATTCTCCGTTGATCAAGTGTTCGGCACCGCAAACACTAACTGGATCGACTCTTCAGT

CATCTCCCTCGTCCAGGATTCGGATGCATCTCAAGCGGCAAAGGCGACCACGGCAGGTGTGGTGTCATACACT

ACTACGTCTTCCTCTTCAAGTACTACAAGCTCTGTACTGTCGAGCAGCTTGGTCACCGCATCGGGCAGCTCCG

TGTCCACATCATCAAGCTCGGTGTCGTCTACGTCTTCAACCTCCGCCTCTGCCAGTGACGCGCCTTCGCTTTC

CAGCAGTGCTGCTCTCGCTTCATCAGTACCTGGATCTTCCTCCAACACTACAGTGACCACCAGCGGCACAGCA

AGCTCAAGCTCTGTCACTGGTTCCTCGTTCGCACTGTCCACTAGCTCGATCTCCTCCAGCGTGAGCACTCCGG

GGGACACAGCGAGCTCCACCGCCGCTGCGTCTAATTCGACTTCGAGTTGCGCTCTTCCTTCCTCAGTGCCCAC

CACTGCTCGCGTCGTGGGTCCGGCTGGGTCCTGCGCCAACTACACCAGCATCGCCGATGCCGTCAAAGACCTT

TCTACGGATCAATCTAAGACGGAATATGTGTACATTCTCGCTGGCACCTATACCGAGCAGATCATTTTCAGCC
```

-continued

```
GTGTAGGTCCCACCGTCTTCCGCGGCGAGACATCAAGCGAGCTCGATCAGTCCAGCAACAAAGTGACTATCAA
GTCTTCTACTGGTGTGCCCTCCAGTAGCGGGGGATCTTCCAGTACCGCCCCGTTCCAGGCGACTCAGTACTAC
AGCAAGAGTATCAGTTTCTATAACATCAATTTCGAGAACACCTACGCTGCAGCTACGGGTTACAATGCGGTTG
CATTGTCCAGCAAAGCTTTGAAGGCCTATTATTACAACTGCGGGATCACTTCCTCTCAAGGAGCTCTGCTGCT
CAACTTCGGCGCCCACTTCTTCTCGGGCTGCAAGATTACCGGTACCACCGACATCGTCTGGGGCCAAGGTGGC
GCTTACATCTACAATTCGAAGATCGTTAGCACCGGAACCACGACTGGTCAGTCTCTCTCCGCACAGTCGTACC
AGTCACAATACAATCCTTCGCAGTTTGTCTTCGACACTTGCGCTTTCGTGCCGAACGACAGCACCGTGCCGAA
GGCGAGCACGTACTTGGGCCGCGACTATACAGCTTCGGCACGTGTTGCGGTGATCAACTCTTACCTGGACGCT
CATATTACTCCTGTTGGATGGTTGATTGCGTCCAAGACTACGAACGTGACGTTTGTTGAGGCCAGCAACTCCG
GGCCTGGAGCGTCGACCGCATCTAGAGTTTCCCAGATTGTGACCGATACGTCTGCCTACGCCGCCAACAACGT
GCTCGGTTCTCTTTCGATCGACACCGCCGCTGTTGCTCCTGTTGCTGCCTTCCCCGACAGCGTCTACGGTAGT
CCTCTTTCCCCCAGCTCTTCTACTGTCTTGGCCAACTCAACGACAGCGACTTCCGTGTCTGCTTCGACATCCA
GCACTTCTGCTGCTGCAACTGCGGCCAACACCCTCATTGTCTCAACCACGCCTGCCTCTGGCGAATACGGCAA
CGTCACAGCAGCCATCGCCGCCCTTCCCAACGATAGCAAGGAGTACACCATCTACATCCGCGCCGGCACCTAC
CAGGAGCAGTTCACCATTGTGCGGAATGGCAAGGTCACACTGCGTGGCGAGACGGCGTTCCCCAACGACTTCT
CGCAGAACCAGGTCACCATCCAGTTCTCCTATGGTGTTCTCACCAGCGCTGGCCAGAACGAGTTGACGCCCGT
TATCAACGCCAAGAAGAACGATGGCTCCGGCCTCGCGTTGTACAACATCAACTTCATCAACACGTACCCGCAG
ACGAAGAACACGGCTGCGCTTGCGGCTGACTTCTACGGTACCAATATGGCTGCCTATGGCTGCAAGTTCGTCG
GCTACCAGGACACCCTCCTCGCCAACAAGGGCACCCAAGTCTTTTCCAACAGCTACATTGAAGGCTCTATTGA
CTATATCTGGGGTTTCTCGACGGCCTACTTCCACCAGTGCTACATCGCATCCAACACAGCTGGTGGCTACATT
TCTGCCATGAGCCGCGCTTCGGCTTCGGCTACTGGAGGTTATGTCTTTGACAGCTGCTATGTCACCTACACGA
GCACCTACGGATCGACCTTTGGCACCAGCTACCTCGGTCGCCCGTACTCGAGCTACAGCATCGCCGTCTACAT
GAACTCGTTCATTGACAAGCACATTAGCCCCGCCGGTTGGGCTGTGTGGCAAACGAGTAACCCGCAGACGGAC
AACGTCCTGTTTGGAGAGTTCAACAACACCGGCCCCGGAAGCTGGTCCAGCTCTCGCGCGTCTTTCGCGACGA
ACTTGACCGAGTCCCAGGCGGATGCTTACAAGCTGTCTACTTGGATCGGCAGCACGTCGTGGCTTGACATGGA
TGCTTACAACTACGTGCCTTCGTACGATATTTCCGGCGCAGCTGGTGCATCAACCACGACCCCCTCGGCGTCA
GCTTCCTCTACCACTGCCACAGCCACTGCCACCTGGGCGCATCCCTCGAGTGGTGCTACCCCACCTATCGGTG
CCGTCCTGGTGTCCGTTGGAGGCTCCGTCAACGGGTCATACAGCAATCTTACCGCCGCCCTCGCGTCTCTGCC
ATCGGATAGCTCGACACAGGTCATCTTCATGTACCCCGGAACCTACAACGAGCAGCCCCCGGCCGTAAACAGG
CCCGGCCCCATCCAGATCATCGGTGCTCAAGATGGCAATCCAGGCCAGAGCTACAAGACCAATAAAGTCATTC
TGACCCAGTCTCGCGGCTTGTCGGTCTCTCCGTTGCCGACCGGACACTCTGACGCTGAAACCGCAACATTCTC
CACTACCAGCAACAAAATTGCCATGTACAACATCGACATCATCAACTCCGATAATCTTGACGGTTCGCTTTCC
TCTTACGTGACGCTGGCCGGCTCAATTTATGGCTCGCGCATTGCGTTCTATGGGTGCAGCTTCATTGGCTGGC
AGGATACGCTGTTGACTGGAAGCACCAGTGGCTACCAGTACTACGAATCCTGCTACATTGATGGCGCCATCGA
TTTCATCTGGGGCTACTCTAAGGCTTACTTCAAAGGCTGCACCATCGGCGCCAAAAGGCAAAAGTCGGCCATC
ACGGCTCACAGCCGTGCTTCCTCCAGCGCAGTCGGAGGCTACATCTTCGACCAGTGCCTGTTCACTGCTGCCT
CGTCTGCGACGGTTGACCTTACGCAGTCTGTTTACCTCGGCCGCCCTTACAGCAAGTACGCCCTCGTGGTTGT
CAAGAACTCGTACCTGGACAAGACGATCCAGCCTGCTGGTTGGAAGATCTGGTCTGCCACCGACCCGCGTACC
GACTACGTTACCTTCGCCGAGTTCAACAACTCCGGACCTGGTAACTGGGAGAACAACGCCGCGGCGCGTACCG
CTTTCGGCTACTGCACCCTGTTGACGTCGGACACGTACTCCCTATCTGCCGTCATGGACTCACCCTCTGACTG
GATTGACATGACGTACTGGGACTCGATCACCACACCGACAGTGGCCGCTGTTGCTACGGGAAACACCACTACG
```

-continued

```
GCGGTCAACGGTACTTCGGTCTATGATGGCACCACCCCACCTGCCGGCGCATTGATTGTCTCCAAGACGGCCA

TTGAGGGCGTGACGACGTACGATACCATCCAGAGCGCTCTGAATGCGCTGCCTACTTCGAGCAGCAAGACCGG

CACCATCTTCATCTACCCCGGTGTGTACTCGGAGCAGCTTGTGCTGAGCAAGTCTGGTACCACCGTGTTCATC

GGCTACTCAAACTCCACCGACGATTACCTGCAGAACCAGGTGACGATCGACTTCAACAAGGGAATCGATACGC

AAGCAGATGCTTCCAACTCTGACAGCGCTACTGTGTATGCCACAGGCAACTACTTCCAGGCATACAACATCAA

CTTCAAGAACTCTTTCGGCACAACCGAGGACTACGCCTCGCTCGGCTTCGGTGTCAAGTCCAGCAAGTACGCA

TCGCTGTATGGCTGCCAGGTCTGGGGCAATCAGGACTCGCTACTCATCAACGGCTACTTCTTCGCCTTCAACT

CGCTGATTGTCGGTAACATCGACATGATCTGGGGCTCCGGCGCGGGCTATTTCCTCAGCTCAACCATCTCACC

CAACACCGACGACGTCAGCCTGACCGCCAGCAAGCGCGCGACCAACACTACAGCTGCCGGTTTTGTCTTCGAC

CAGTGCACCGTTAAGCCCGCCCCCGGTACCGGCCCCTTCACCGAGATCAGCCTCGGACGTCCGTGGAACAACC

TTGCCCGTGTCGCGTATATCGAGACGTATCTCGATTCCAGCGTTGAGGCTGCAGGCTGGAGCCAGTGGTCCAA

GTCCAATCCACAGACCGAAGGAGTGACTTTTGCCGAGTACGGGAACTATGGACCGGGTGCAAGCACTTCGGGC

CGTGCGAAATTTTCCACGCAGCTCTCGGCTGCCGATGCCGCCCAGTTTCAGCTCGCCAACTTCTTCGCCGTCA

CCTCCTGGATCAACTTCACGCGGATCGATGTCCAACCCTTCGTGGCCAGCGAGGTTGTTGTTCCAACCTCGGC

GGTCACTTCGTCTGTCCTTCTCTCTTCCACCCTTAGCACTCCGATCTCGTCTTCAACGCTTATACTGAGCACC

CTCTTCCTCACTAAAGTCACTACCGACAAGGAGACTCTCTTCACAACCGTCACTGGCGCTGTTCCGACCCTCA

CTTCAACGCAGACTATCACGCTGGACATGGGTGCCACCGTTACCCCCGACCCAGTGTACAAGACCAGCACCGT

GAAGAGTACGACAACGATCATTGAGACCGTATCGCAGCCCGATGTTACGCAGACGTCTACTGTGGTCGTCACC

AGCGATATCGGAACCACAATCACACCGGAGCCGAGCACGATCACCACTGTGCTCAAGCAGACGACTACTGTTT

TCGCCACCTCGACCAAGGCGCCCCAGACGATTACTGAGAAGAGTACCATTACTTCGACGAGTTTGGCTACCCG

GACGCTCGATCCCATTACGTCAACACTCAGCCTCGGATCTACCGTTTATGTGACCAGCGTTTTCACCCCGAAG

GCCGCGCGGGTCACCTCTAGTCTAACCATCACTACGGGCACTGGCGGCACGTCAACTAAGACGACCAAAGCAA

CCACGACTTACGTCACTGTCACTTCTGTGAAAATGACAACGAAGAAATCCACAACAACCCTCTCCTGTGTGCC

CACCGACAGTCTCCAAAGGCGCTCGTACCCCTTAGGTCCCCGCCGCCGGTGACAGCGTCACCACATCCACC

ATTTTCTCCACCCTCCTCACCTACGTCAAGACCTCTACAGCAACCTTAGCCCCGGCTCGACCGCCACGACCC

TTGTGTCGATCACCAAGACCGTCGGCTCCACCACCACCCTCAAGCCCACCACCATCACGGTCTCCACTGTCTC

CATCGCCACCAAGTCCTCCACCCTCACCCACCCGGCATCCACCTTCTTCACAACCGTAACCTCGACCAAACTC

ACCGGCAAAACCACCTCGCTGAAAGCCTCAACACTGACGGTGACATCCACCTCCCTTGCAGCCACCCGCACCT

CCGTCACCACCCTCTCCGCTGCGGGCGCCGCTACAACGACTTCTCTCGCCACCGTGACGCGGAAATCGACGAT

AACGCTCCCCGCGAGCACCGTCGTCAAAACATCTTCGCGGGACGCCACGAGCAGTGTAGTCATCACGGCGGCG

GCGAGCACGAGTACGGTGTGGAAGACGGCCACGATCACGCTGGCACCGAGCCAGACAGTGGTGTTGCAGAGCA

CAGTCGTCAAAGAAACGACGGCAAAGGTAACAAGCACGGTTCTTAGTACGATAACAAAGACGGCGAAAGGGGC

GGCGGCGTGTACAGAGGTATAAGTAAAGATTGGAAGAGAAGAAGGAGGGGAATAGAGTTGAAAATAAATAAAG

AGAATAAATAGTAGCGGGGGTTTTATATATTTATAATATTTTAAGTAACTAGTTACTTAATTATTAAATTTCC

TAAAGGCCGAATTCTACACCTGCTCACTGCTGATGGACGATACGGGCTGTGTTCCACGATCTATAGTCACATG

GAAAAGCAGAAGTTGCAAAATTATATTATACTTACACGAAATATTTCCCGGAAAATCAGACACCTTAGTGTAT

TACAGTTGTGCCAAGGTTCTATCTAAGTTGAAACTCCTTTATCTACTGTGAGAAAGAGACTTGCATAGACTTA

GGTATATTTCACGAGAATAACAGCAATCAACATATTTGTAGCAGTAGAGCATTGCTTGCACAGGATAGGTTCA

ATTGCCTTTGAAGTTTCTAAGTCACTAGAGCTGCCTCGTTCAGTCAGAGTCGTTCTTTCTGGCGTTCAGCGAA

TGACTGCTGGCATCCAAAATCGAGAATGAAGTGATTCCATATGTGAGGATGCAATGCGACCATTCAATCGAAC
```

-continued

```
AGCGCCTCCGCACTCGCAGCCTGAGCGAGTTCCCCTCTCAATCGTGTGGATATAATCCCTTGTCGACTGAATC

AAGTAAGGGGCATAAGCCTGAGTAGCTCTCTTGTGTCCAGCCACAACAATGTGCGGGTTCAAAGCCTCGATGC

GATCAATAGCATCAAGCCGCTCCCTGCGTTTGGCCGGGGCGTTTGCCTCCCCGAAATGTGGATGACAATCGCC

GTAGATGATATCGCCAGAGACAACGAGACGGACGGAAGGGACGTGGGGGAAGCTGGAAAACTCGTTGTCGGTG

TGCCCAACTTCAATTCCGTGCCATTTATGGCCGTTCGACGGAGAACTCCCCCGACGCTGGAAGCGCCTTGGGC

ACTGGCTTGGCAGTATCGAGCTGGCCGGGGAACATGCCAGGCCAGATGTGCTCGCAACTCGTATTGCATACGG

GATAATACAACGTGCACACTCTTGGCGTGCAATATAACACTTTGCACACTTGCGTAGCAAAATACACACCTGT

TTTACTAAGAAATACGATCTTTTCTTAAATATCTCTACTACAACGCAGTAATATATAAATAGCTAACTTAAAT

ATAGAAATTTAGGGTCTTCTTTAGGATTAGGAGGGTTAGGG
```

```
SEQ ID NO:         53
LENGTH:            5895
TYPE:              DNA
ORGANISM:          M. phaseolina
FEATURE NAME/KEY:  CDS
LOCATION:          (1) ... (5895)
```

```
atgtacatttacggctcaactctcacgcctacggcgagcaacgcactcttggtttataac
 M   Y   I   Y   G   S   T   L   T   P   T   A   S   N   A   L   L   V   Y   N aagggcgtgtcttctggcacggtggtgaccaccaactccaccgttgtcttcgactcctgc
 K   G   V   S   S   G   T   V   V   T   T   N   S   T   V   V   F   D   S   C accgtcactccgaagccgggcaccactgtgaccggtatttcccttgccgcagcgaacggt
 T   V   T   P   K   P   G   T   T   V   T   G   I   S   L   A   A   A   N   G gttgggtcaattgtggtctatagaaactccgtcctgccaggcttcattctcagcaccggt
 V   G   S   I   V   V   Y   R   N   S   V   L   P   G   F   I   L   S   T   G attcacgttgacgccaagacccaggcagcacagaacttctacggcgagttcggtaacaca
 I   H   V   D   A   K   T   Q   A   A   Q   N   F   Y   G   E   F   G   N   T ggtgccggatcctactcttccaactccgccgcgagggcctcctacgtgaagagcctgagc
 G   A   G   S   Y   S   S   N   S   A   A   R   A   S   Y   V   K   S   L   S gtcgatcagctttctcaattctccgttgatcaagtgttcggcaccgcaaacactaactgg
 V   D   Q   L   S   Q   F   S   V   D   Q   V   F   G   T   A   N   T   N   W atcgactcttcagtcatctccctcgtccaggattcggatgcatctcaagcggcaaaggcg
 I   D   S   S   V   I   S   L   V   Q   D   S   D   A   S   Q   A   A   K   A accacggcaggtgtggtgtcatacactactacgtcttcctcttcaagtactacaagctct
 T   T   A   G   V   V   S   Y   T   T   T   S   S   S   S   T   T   S   S gtactgtcgagcagcttggtcaccgcatcgggcagctccgtgtccacatcatcaagctcg
 V   L   S   S   S   L   V   T   A   S   G   S   S   V   S   T   S   S   S   S gtgtcgtctacgtcttcaacctccgcctctgccagtgacgcgccttcgctttccagcagt
 V   S   S   T   S   S   T   S   A   S   A   S   D   A   P   S   L   S   S   S gctgctctcgcttcatcagtacctggatcttcctccaacactacagtgaccaccagcggc
 A   A   L   A   S   S   V   P   G   S   S   S   N   T   T   V   T   T   S   G acagcaagctcaagctctgtcactggttcctcgttcgcactgtccactagctcgatctcc
 T   A   S   S   S   V   T   G   S   S   F   A   L   S   T   S   S   I   S tccagcgtgagcactccggggacacagcgagctccaccgccgctgcgtctaattcgact
 S   S   V   S   T   P   G   D   T   A   S   S   T   A   A   A   S   N   S   T tcgagttgcgctcttccttcctcagtgcccaccactgctcgcgtcgtgggtccggctggg
 S   S   C   A   L   P   S   S   V   P   T   T   A   R   V   V   G   P   A   G tcctgcgccaactacaccagcatcgccgatgccgtcaaagacctttctacggatcaatct
 S   C   A   N   Y   T   S   I   A   D   A   V   K   D   L   S   T   D   Q   S aagacggaatatgtgtacattctcgctggcacctataccgagcagatcattttcagccgt
 K   T   E   Y   V   Y   I   L   A   G   T   Y   T   E   Q   I   I   F   S   R gtaggtcccaccgtcttccgcggcgagacatcaagcgagctcgatcagtccagcaacaaa
 V   G   P   T   V   F   R   G   E   T   S   S   E   L   D   Q   S   S   N   K gtgactatcaagtcttctactggtgtgccctccagtagcgggggatcttccagtaccgcc
 V   T   I   K   S   S   T   G   V   P   S   S   S   G   G   S   S   T   A
```

```
ccgttccaggcgactcagtactacagcaagagtatcagtttctataacatcaatttcgag
 P  F  Q  A  T  Q  Y  Y  S  K  S  I  S  F  Y  N  I  N  F  E aacacctacgctgcagctacgggttacaatgcggttgcattgtccagcaaagctttgaag
 N  T  Y  A  A  A  T  G  Y  N  A  V  A  L  S  S  K  A  L  K gcctattattacaactgcgggatcacttcctctcaaggagctctgctgctcaacttcggc
 A  Y  Y  Y  N  C  G  I  T  S  S  Q  G  A  L  L  L  N  F  G gcccacttcttctcgggctgcaagattaccggtaccaccgacatcgtctggggccaaggt
 A  H  F  F  G  C  I  T  S  T  G  T  T  D  I  V  W  G  Q  G ggcgcttacatctacaattcgaagatcgttagcaccggaaccacgactggtcagtctctc
 G  A  Y  I  Y  N  S  K  I  V  S  T  G  T  T  T  G  Q  S  L tccgcacagtcgtaccagtcacaatacaatccttcgcagtttgtcttcgacacttgcgct
 S  A  Q  S  Y  Q  S  Q  Y  N  P  S  Q  F  V  F  D  T  C  A ttcgtgccgaacgacagcaccgtgccgaaggcgagcacgtacttgggccgcgactataca
 F  V  P  N  D  S  T  V  P  K  A  S  T  Y  L  G  R  D  Y  T gcttcggcacgtgttgcggtgatcaactcttacctggacgctcatattactcctgttgga
 A  S  A  R  V  A  V  I  N  S  Y  L  D  A  H  I  T  P  V  G tggttgattgcgtccaagactacgaacgtgacgtttgttgaggccagcaactccgggcct
 W  L  I  A  S  K  T  T  N  V  T  F  V  E  A  S  N  S  G  P ggagcgtcgaccgcatctagagtttcccagattgtgaccgatacgtctgcctacgccgcc
 G  A  S  T  A  S  R  V  S  Q  I  V  T  D  T  S  A  Y  A  A aacaacgtgctcggttctctttcgatcgacaccgccgctgttgctcctgttgctgccttc
 N  N  V  L  G  S  L  S  I  N  T  A  A  V  A  P  V  A  A  F cccgacagcgtctacggtagtcctcttccccagctcttctactgtcttggccaactca
 P  D  S  V  Y  G  S  P  L  S  P  S  S  S  T  V  L  A  N  S acgacagcgacttccgtgtctgcttcgacatccagcacttctgctgctgcaactgcggcc
 T  T  A  T  S  V  S  A  S  T  S  S  T  S  A  A  A  T  A  A aacaccctcattgtctcaaccacgcctgcctctggcgaatacggcaacgtcacagcagcc
 N  T  L  I  V  S  T  T  P  A  S  G  E  Y  G  N  V  T  A  A atcgccgcccttcccaacgatagcaaggagtacaccatctacatccgcgccggcacctac
 I  A  A  L  P  N  D  S  K  E  Y  T  I  Y  I  R  A  G  T  Y caggagcagttcaccattgtgcggaatggcaaggtcacactgcgtggcgagacggcgttc
 Q  E  Q  F  T  I  V  R  N  G  K  V  T  L  R  G  E  T  A  F cccaacgacttctcgcagaaccaggtcaccatccagttctcctatggtgttctcaccagc
 P  N  D  F  S  Q  N  Q  V  T  I  Q  F  S  Y  G  V  L  T  S gctggccagaacgagttgacgcccgttatcaacgccaagaagaacgatggctccggcctc
 A  G  Q  N  E  L  T  P  V  I  N  A  K  K  N  D  G  S  G  L gcgttgtacaacatcaacttcatcaacacgtacccgcagacgaagaacacggctgcgctt
 A  L  Y  N  I  N  F  I  N  T  Y  P  Q  T  K  N  T  A  A  L gcggctgacttctacggtaccaatatggctgcctatggctgcaagttcgtcggctaccag
 A  A  D  F  Y  G  T  N  M  A  A  Y  G  C  K  F  V  G  Y  Q gacacccttctcgccaacaagggcacccaagtcttttccaacagctacattgaaggctct
 D  T  L  L  A  N  K  G  T  Q  V  F  S  N  S  Y  I  E  G  S attgactatatctggggtttctcgacggcctacttccaccagtgctacatcgcatccaac
 I  D  Y  I  W  G  F  S  T  A  Y  F  H  Q  C  Y  I  A  S  N acagctggtggctacatttctgccatgagccgcgcttcggcttcggctactggaggttat
 T  A  G  G  Y  I  S  A  M  S  R  A  S  A  S  A  T  G  G  Y gtctttgacagctgctatgtcacctacacgagcacctacggatcgacctttggcaccagc
 V  F  D  S  C  Y  V  T  Y  T  S  T  Y  G  S  T  F  G  T  S tacctcggtcgcccgtactcgagctacagcatcgccgtctacatgaactcgttcattgac
 Y  L  G  R  P  Y  S  S  Y  S  I  A  V  Y  M  N  S  F  I  D aagcacattagccccgccggttgggctgtgtggcaaacgagtaacccgcagacggacaac
 K  H  I  S  P  A  G  W  A  V  W  Q  T  S  N  P  Q  T  D  N gtcctgtttggagagttcaacaacaccggccccggaagctggtccagctctcgcgcgtct
 V  L  F  G  E  F  N  N  T  G  P  G  S  W  S  S  S  R  A  S
```

```
ttcgcgacgaacttgaccgagtcccaggcggatgcttacaagctgtctacttggatcggc
 F   A   T   N   L   T   E   S   Q   A   D   A   Y   K   L   S   T   W   I   G agcacgtcgtggcttgacatggatgcttacaactacgtgccttcgtacgatatttccggc
 S   T   S   W   L   D   M   D   A   Y   N   Y   V   P   S   Y   D   I   S   G gcagctggtgcatcaaccacgaccccctcggcgtcagcttcctctaccactgccacagcc
 A   A   G   A   S   T   T   T   P   S   A   S   A   S   S   T   T   A   T   A actgccacctgggcgcatccctcgagtggtgctaccccacctatcggtgccgtcctggtg
 T   A   T   W   A   H   P   S   S   G   A   T   P   P   I   G   A   V   L   V tccgttggaggctccgtcaacgggtcatacagcaatcttaccgccgccctcgcgtctctg
 S   V   G   G   S   V   N   G   S   Y   S   N   L   T   A   A   L   A   S   L ccatcggatagctcgacacaggtcatcttcatgtaccccggaacctacaacgagcagccc
 P   S   D   S   S   T   Q   V   I   F   M   Y   P   G   T   Y   N   E   Q   P ccggccgtaaacaggcccggccccatccagatcatcggtgctcaagatggcaatccaggc
 P   A   V   N   R   P   G   P   I   Q   I   I   G   A   Q   D   G   N   P   G cagagctacaagaccaataaagtcattctgacccagtctcgcggcttgtcggtctctccg
 Q   S   Y   K   T   N   K   V   I   L   T   Q   S   R   G   L   S   V   S   P ttgccgaccggacactctgacgctgaaaccgcaacattctccactaccagcaacaaaatt
 L   P   T   G   H   S   D   A   E   T   A   T   F   S   T   T   S   N   K   I gccatgtacaacatcgacatcatcaactccgataatcttgacggttcgctttcctcttac
 A   M   Y   N   I   D   I   I   N   S   D   N   L   D   G   S   L   S   S   Y gtgacgctggccggctcaatttatggctcgcgcattgcgttctatgggtgcagcttcatt
 V   T   L   A   G   S   I   Y   G   S   R   I   A   F   Y   G   C   S   F   I ggctggcaggatacgctgttgactggaagcaccagtggctaccagtactacgaatcctgc
 G   W   Q   D   T   L   L   T   G   S   T   S   G   Y   Q   Y   Y   E   S   C tacattgatggcgccatcgatttcatctggggctactctaaggcttacttcaaaggctgc
 Y   I   D   G   A   I   D   F   I   W   G   Y   S   K   A   Y   F   K   G   C accatcggcgccaaaaggcaaaagtcggccatcacggctcacagccgtgcttcctccagc
 T   I   G   A   K   R   Q   K   S   A   I   T   A   H   S   R   A   S   S   S gcagtcggaggctacatcttcgaccagtgcctgttcactgctgcctcgtctgcgacggtt
 A   V   G   G   Y   I   F   D   Q   C   L   F   T   A   A   S   S   A   T   V gaccttacgcagtctgtttacctcggccgcccttacagcaagtacgccctcgtggttgtc
 D   L   T   Q   S   V   Y   L   G   R   P   Y   S   K   Y   A   L   V   V   V aagaactcgtacctggacaagacgatccagcctgctggttggaagatctggtctgccacc
 K   N   S   Y   L   D   K   T   I   Q   P   A   G   W   K   I   W   S   A   T gacccgcgtaccgactacgttaccttcgccgagttcaacaactccggacctggtaactgg
 D   P   R   T   D   Y   V   T   F   A   E   F   N   N   S   G   P   G   N   W gagaacaacgccgcggcgcgtaccgctttcggctactgcaccctgttgacgtcggacacg
 E   N   N   A   A   A   R   T   A   F   G   Y   C   T   L   L   T   S   D   T tactccctatctgccgtcatggactcacccctctgactggattgacatgacgtactgggac
 Y   S   L   S   A   V   M   D   S   P   S   D   W   I   D   M   T   Y   W   D tcgatcaccacaccgacagtggccgctgttgctacgggaaacaccactacggcggtcaac
 S   I   T   T   P   T   V   A   A   V   A   T   G   N   T   T   A   V   N ggtacttcggtctatgatggcaccacccacctgccggcgcattgattgtctccaagacg
 G   T   S   V   Y   D   G   T   T   P   P   A   G   A   L   I   V   S   K   T gccattgagggcgtgacgacgtacgataccatccagagcgctctgaatgcgctgcctact
 A   I   E   G   V   T   T   Y   D   T   I   Q   S   A   L   N   A   L   P   T tcgagcagcaagaccggcaccatcttcatctacccggtgtgtactcggagcagcttgtg
 S   S   S   K   T   G   T   I   F   I   Y   P   G   V   Y   S   E   Q   L   V ctgagcaagtctggtaccaccgtgttcatcggctactcaaactccaccgacgattacctg
 L   S   K   S   G   T   T   V   F   I   G   Y   S   N   S   T   D   D   Y   L cagaaccaggtgacgatcgacttcaacaagggaatcgatacgcaagcagatgcttccaac
 Q   N   Q   V   T   I   D   F   N   K   G   I   D   T   Q   A   D   A   S   N tctgacagcgctactgtgtatgccacaggcaactacttccaggcatacaacatcaacttc
 S   D   S   A   T   V   Y   A   T   G   N   Y   F   Q   A   Y   N   I   N   F
```

-continued

```
aagaactctttcggcacaaccgaggactacgcctcgctcggcttcggtgtcaagtccagc
 K  N  S  F  G  T  T  E  D  Y  A  S  L  G  F  G  V  K  S  S aagtacgcatcgctgtatggctgccaggtctggggcaatcaggactcgctactcatcaac
 K  Y  A  S  L  Y  G  C  Q  V  W  G  N  Q  D  S  L  L  I  Y ggctacttcttcgccttcaactcgctgattgtcggtaacatcgacatgatctggggctcc
 G  Y  F  F  A  F  N  S  L  I  V  G  N  I  D  M  I  W  G  S ggcgcgggctatttcctcagctcaaccatctcacccaacaccgacgacgtcagcctgacc
 G  A  G  Y  F  L  S  S  T  I  S  P  N  T  D  D  V  S  L  T gccagcaagcgcgcgaccaacactacagctgccggttttgtcttcgaccagtgcaccgtt
 A  S  K  R  A  T  N  T  T  A  A  G  F  V  F  D  Q  C  T  V aagcccgccccggtaccggcccttcaccgagatcagcctcggacgtccgtggaacaac
 K  P  A  P  G  T  G  P  F  T  E  I  S  L  G  R  P  W  N  N cttgcccgtgtcgcgtatatcgagacgtatctcgattccagcgttgaggctgcaggctgg
 L  A  R  V  A  Y  I  E  T  Y  L  D  S  S  V  E  A  A  G  W agccagtggtccaagtccaatccacagaccgaaggagtgacttttgccgagtacgggaac
 S  Q  W  S  K  S  N  P  Q  T  E  G  V  T  F  A  E  Y  G  N tatggacccgggtgcaagcacttcgggccgtgcgaaattttccacgcagctctcggctgcc
 Y  G  P  G  A  S  T  S  G  R  A  K  F  S  T  Q  L  S  A  A gatgccgcccagtttcagctcgccaacttcttcgccgtcacctcctggatcaacttcacg
 D  A  A  Q  F  Q  L  A  N  D  F  A  V  T  S  W  I  N  F  T cggatcgatgtccaacccttcgtggccagcgaggttgttgttccaacctcggcggtcact
 R  I  D  V  Q  P  F  V  A  S  E  V  V  V  P  T  S  A  V  T tcgtctgtccttctctcttccacccttagcactccgatctcgtcttcaacgcttatactg
 S  S  V  L  L  S  S  T  L  S  T  P  I  S  S  S  T  L  I  L agcaccctcttcctcactaaagtcactaccgacaaggagactctcttcacaaccgtcact
 S  T  L  F  L  T  K  V  T  T  D  K  E  T  L  F  T  T  V  T ggcgctgttccgaccctcacttcaacgcagactatcacgctggacatgggtgccaccgtt
 G  A  V  P  T  L  T  S  T  Q  T  I  T  L  D  M  G  A  T  V acccccgacccagtgtacaagaccagcaccgtgaagagtacgacaacgatcattgagacc
 T  P  D  P  V  Y  K  T  S  T  V  K  S  T  T  T  I  I  E  T gtatcgcagcccgatgttacgcagacgtctactgtggtcgtcaccagcgatatcggaacc
 V  S  Q  P  D  V  T  Q  T  S  T  V  V  V  T  S  D  I  G  T acaatcacaccggagccgagcacgatcaccactgtgctcaagcagacgactactgttttc
 T  I  T  P  E  P  S  T  I  T  T  V  L  K  Q  T  T  T  V  F gccacctcgaccaaggcgccccagacgattactgagaagagtaccattacttcgacgagt
 A  T  S  T  K  A  P  Q  T  I  T  E  K  S  T  I  T  S  T  S ttggctacccggacgctcgatcccattacgtcaacactcagcctcggatctaccgtttat
 L  A  T  R  T  L  D  P  I  T  S  T  L  S  L  G  S  T  V  Y gtgaccagcgttttcaccccgaaggccgcgcgggtcacctctagtctaaccatcactacg
 V  T  S  V  F  T  P  K  A  A  R  V  T  S  S  L  T  I  T  T ggcactggcggcacgtcaactaagacgaccaaagcaaccacgacttacgtcactgtcact
 G  T  G  G  T  S  T  G  T  T  K  A  T  T  T  Y  V  T  V  T tctatgatatcgccagagacaacgagacggacggaagggacgtgggggaagctggaaaac
 S  M  I  S  P  E  T  T  R  R  T  E  G  T  W  G  K  L  E  N tcgttgtcggtgtgcccaacttcaattccgtgccatttatggccgttcgacggagaactc
 S  L  S  V  C  P  T  S  I  P  C  H  L  W  P  F  D  G  E  L ccccgacgctggaagcgccttgggcactggcttggcagtatcgagctggccggggaacat
 P  R  R  W  K  R  L  G  H  W  L  G  S  I  E  L  A  G  E  H gccaggccagatgtgctcgcaactcgtattgcatacgggataatacaacgtgcacactct
 A  R  P  D  V  L  A  T  R  I  A  Y  G  I  I  Q  R  A  H  S tggcgtgcaatataa
 W  R  A  I  -
```

```
SEQ ID NO:      54
LENGTH:         1964
TYPE:           PRT
ORGANISM:       M. phaseolina
MYIYGSTLTPTASNALLVYNKGVSSGTVVTTNSTVVFDSCTVTPKPGTTVTGISLAAANGVGSIVVYRNSVLP
GFILSTGIHVDAKTQAAQNFYGEFGNTGAGSYSSNSAARASYVKSLSVDQLSQFSVDQVFGTANTNWIDSSVI
SLVQDSDASQAAKATTAGVVSYTTTSSSSSTTSSVLSSSLVTASGSSVSTSSSSVSSTSSTSASASDAPSLSS
SAALASSVPGSSSNTTVTTSGTASSSSVTGSSFALSTSSISSSVSTPGDTASSTAAASNSTSSCALPSSVPTT
ARVVGPAGSCANYTSIADAVKDLSTDQSKTEYVYILAGTYTEQIIFSRVGPTVFRGETSSELDQSSNKVTIKS
STGVPSSSGGSSSTAPFQATQYYSKSISFYNINFENTYAAATGYNAVALSSKALKAYYYNCGITSSQGALLLN
FGAHFFSGCKITGTTDIVWGQGGAYIYNSKIVSTGTTTGQSLSAQSYQSQYNPSQFVFDTCAFVPNDSTVPKA
STYLGRDYTASARVAVINSYLDAHITPVGWLIASKTTNVTFVEASNSGPGASTASRVSQIVTDTSAYAANNVL
GSLSIDTAAVAPVAAFPDSVYGSPLSPSSSTVLANSTTATSVSASTSSTSAAATAANTLIVSTTPASGEYGNV
TAAIAALPNDSKEYTIYIRAGTYQEQFTIVRNGKVTLRGETAFPNDFSQNQVTIQFSYGVLTSAGQNELTPVI
NAKKNDGSGLALYNINFINTYPQTKNTAALAADFYGTNMAAYGCKFVGYQDTLLANKGTQVFSNSYIEGSIDY
IWGFSTAYFHQCYIASNTAGGYISAMSRASASATGGYVFDSCYVTYTSTYGSTFGTSYLGRPYSSYSIAVYMN
SFIDKHISPAGWAVWQTSNPQTDNVLFGEFNNTGPGSWSSSRASFATNLTESQADAYKLSTWIGSTSWLDMDA
YNYVPSYDISGAAGASTTTPSASASSTTATATATWAHPSSGATPPIGAVLVSVGGSVNGSYSNLTAALASLPS
DSSTQVIFMYPGTYNEQPPAVNRPGPIQIIGAQDGNPGQSYKTNKVILTQSRGLSVSPLPTGHSDAETATFST
TSNKIAMYNIDIINSDNLDGSLSSYVTLAGSIYGSRIAFYGCSFIGWQDTLLTGSTSGYQYYESCYIDGAIDF
IWGYSKAYFKGCTIGAKRQKSAITAHSRASSSAVGGYIFDQCLFTAASSATVDLTQSVYLGRPYSKYALVVVK
NSYLDKTIQPAGWKIWSATDPRTDYVTFAEFNNSGPGNWENNAAARTAFGYCTLLTSDTYSLSAVMDSPSDWI
DMTYWDSITTPTVAAVATGNTTTAVNGTSVYDGTTPPAGALIVSKTAIEGVTTYDTIQSALNALPTSSSKTGT
IFIYPGVYSEQLVLSKSGTTVFIGYSNSTDDYLQNQVTIDFNKGIDTQADASNSDSATVYATGNYFQAYNINF
KNSFGTTEDYASLGFGVKSSKYASLYGCQVWGNQDSLLINGYFFAFNSLIVGNIDMIWGSGAGYFLSSTISPN
TDDVSLTASKRATNTTAAGFVFDQCTVKPAPGTGPFTEISLGRPWNNLARVAYIETYLDSSVEAAGWSQWSKS
NPQTEGVTFAEYGNYGPGASTSGRAKFSTQLSAADAAQFQLANFFAVTSWINFTRIDVQPFVASEVVVPTSAV
TSSVLLSSTLSTPISSSTLILSTLFLTKVTTDKETLFTTVTGAVPTLTSTQTITLDMGATVTPDPVYKTSTVK
STTTIIETVSQPDVTQTSTVVVTSDIGTTITPEPSTITTVLKQTTTVFATSTKAPQTITEKSTITSTSLATRT
LDPITSTLSLGSTVYVTSVFTPKAARVTSSLTITTGTGGTSTKTTKATTTYVTVTSMISPETTRRTEGTWGKL
ENSLSVCPTSIPCHLWPFDGELPRRWKRLGHWLGSIELAGEHARPDVLATRIAYGIIQRAHSWRAI*
SEQ ID NO:      55
LENGTH:         1281 (including 150 bp 5' UTR and 150 bp 3' UTR)
TYPE:           DNA
ORGANISM:       M. phaseolina
CACCGGTTGTTGATCATTTACACCCTCAGCGAGCATTCCCGGCCAGGCGCCTCTTGTTGAACACTGTCCAGTC
CTTCACTCCTCTCCTTCCACCCGCTACCCGGTCTTTTTCCTTTTGCCATTCCAATTGCGTGAACCGTCCATCA
CAGCATGCCTCGCCTCGCCAGCCTCCTCGCCCTTGCAAGCCCAGTGCTTGCCCTGACCTCCCCTCCGTCAGGC
GCCCTCACCGTCGGCTCCAGCGGCAAGTACTCGACCATCCAGGACGCCGTCGACGCGCTCAGCACCAGCTCCT
CGTCGGCCCAGACCATCTTCATCTACCAGGGCACCTACAAGGAACAAGTCGTGATCCCGAAGCTATCGGCGC
CCTCACCATCTACGGCTACTCGAAGGATGGATCATCGTACAGCGGCAACACCGTGACCATCAGCGCGGGCAAG
TCGCAGGCCGACGGCCTCTCCAACGACGGCACCGCCACCCTCGCCGTCCACACGGGCAACATCAAGGTCTACA
ACATCAACGTCGCCAACACGTACGGCTCCGGCTCGCAGGCCGTCGCGCTGTCGGCCTACGCCAGCGGCAACCA
CGGCTACTACGGCGTCAAGCTCACGGGCTTCCAAGACACGCTCCTGGCGCAGGAGGGCAAACAAGTCTACGCC
```

```
AACTCGTACATCGAGGGCGCGACCGATTTCATTTTCGGCCAGAAGGCCGTCGCGTGGTTTGAGAACTGCGACC

TGCGCATCGCCTCGGCCTCGCTCGGCTACGTGACGGCCAACGGCCGCGACAGCAGCTCCAACCCATCCTACTA

CGTCATCAACAACTCGACCGTCGCCGCCGCCGACGGCGCCACCGTCAAGAGCGGCGGCATCTACCTCGGCCGC

CCCTGGCGCAACTACGCCCGCGTCGTCTTCCAGGAGACCAGCCTGTCCAACATCATCAACAGCGCCGGCTGGG

TCCAATGGGGCAGCAGCGACCCACGCACCGACAATGTCAACTTCGCCGAGTACAAAAACTCGGGCGCCGGCGC

CTCTACCAGCGGCCGTGCTAGCTTTTCCAAGCAGTTGAGCAGCCCCGTCAGCATCTCGGAAGTCTTGGGCAGC

AACTACGCCGACTGGATCGACACCAGCTACTTCTAAACGCGTGAGGCTTCGCTAATGTCGGTTGGATCGGATG

GAGGCGGGATGTAGCATGCAAGGAACCGGCAGGACTGTTTTAACTTTCTAATGTGGATATTtttGTCTCTCGG

ACAAATATAAAAATAAGCTTTCTGGAGTGACTTTTGATGA
```

```
SEQ ID NO:         56
LENGTH:            981
TYPE:              DNA
ORGANISM:          M. phaseolina
FEATURE NAME/KEY:  CDS
LOCATION:          (1) ... (981)
```

```
atgcctcgcctcgccagcctcctcgcccttgcaagcccagtgcttgccctgacctcccct
 M   P   R   L   A   S   L   L   A   L   A   S   P   V   L   A   L   T   S   P ccgtcaggcgccctcaccgtcggctccagcggcaagtactcgaccatccaggacgccgtc
 P   S   G   A   L   T   V   G   S   S   G   K   Y   S   T   I   Q   D   A   V gacgcgctcagcaccagctcctcgtcggcccagaccatcttcatctaccagggcacctac
 D   A   L   S   T   S   S   S   S   A   Q   T   I   F   I   Y   Q   G   T   Y aaggaacaagtcgtgatcccgaagctatcgggcgccctcaccatctacggctactcgaag
 K   E   Q   V   V   I   P   K   L   S   G   A   L   T   I   Y   G   Y   S   K gatggatcatcgtacagcggcaacaccgtgaccatcagcgcgggcaagtcgcaggccgac
 D   G   S   S   Y   S   G   N   T   V   T   I   S   A   G   K   S   Q   A   D ggcctctccaacgacggcaccgccacccctcgccgtccacacgggcaacatcaaggtctac
 G   L   S   N   D   G   T   A   T   L   A   V   H   T   G   N   I   K   V   Y aacatcaacgtcgccaacacgtacggctccggctcgcaggccgtcgcgctgtcggcctac
 N   I   N   V   A   N   T   Y   G   S   G   S   Q   A   V   A   L   S   A   Y gccagcggcaaccacggctactacggcgtcaagctcacgggcttccaagacacgctcctg
 A   S   G   N   H   G   Y   Y   G   V   K   L   T   G   F   Q   D   T   L   L gcgcaggagggcaaacaagtctacgccaactcgtacatcgagggcgcgaccgatttcatt
 A   Q   E   G   K   Q   V   Y   A   N   S   Y   I   E   G   A   T   D   F   I ttcggccagaaggccgtcgcgtggtttgagaactgcgacctgcgcatcgcctcggcctcg
 F   G   Q   K   A   V   A   W   F   E   N   C   D   L   R   I   A   S   A   S ctcggctacgtgacggccaacggccgcgacagcagctccaacccatcctactacgtcatc
 L   G   Y   V   T   A   N   G   R   D   S   S   S   N   P   S   Y   Y   V   I aacaactcgaccgtcgccgccgccgacggcgccaccgtcaagagcggcggcatctacctc
 N   N   S   T   V   A   A   A   D   G   A   T   V   K   S   G   G   I   Y   L ggccgcccctggcgcaactacgcccgcgtcgtcttccaggagaccagcctgtccaacatc
 G   R   P   W   R   N   Y   A   R   V   V   F   Q   E   T   S   L   S   N   I atcaacagcgccggctgggtccaatggggcagcagcgacccacgcaccgacaatgtcaac
 I   N   S   A   G   W   V   Q   W   G   S   S   D   P   R   T   D   N   V   N ttcgccgagtacaaaaactcgggcgccggcgcctctaccagcggccgtgctagcttttcc
 F   A   E   Y   K   N   S   G   A   G   A   S   T   S   G   R   A   S   F   S aagcagttgagcagccccgtcagcatctcggaagtcttgggcagcaactacgccgactgg
 K   Q   L   S   S   P   V   S   I   S   E   V   L   G   S   N   Y   A   D   W atcgacaccagctacttctaa
 I   D   T   S   Y   F   -
```

```
SEQ ID NO:    57
LENGTH:       326
TYPE:         PRT
ORGANISM:     M. phaseolina
```

MPRLASLLALASPVLALTSPPSGALTVGSSGKYSTIQDAVDALSTSSSSAQTIFIYQGTYKEQVVIPKLSGAL

-continued

TIYGYSKDGSSYSGNTVTISAGKSQADGLSNDGTATLAVHTGNIKVYNINVANTYGSGSQAVALSAYASGNHG

YYGVKLTGFQDTLLAQEGKQVYANSYIEGATDFIFGQKAVAWFENCDLRIASASLGYVTANGRDSSSNPSYYV

INNSTVAAADGATVKSGGIYLGRPWRNYARVVFQETSLSNIINSAGWVQWGSSDPRTDNVNFAEYKNSGAGAS

TSGRASFSKQLSSPVSISEVLGSNYADWIDTSYF*

```
SEQ ID NO:          58
LENGTH:             1943 (including 150 bp 5' UTR and 150 bp 3' UTR)
TYPE:               DNA
ORGANISM:           M. phaseolina
```
CTATATTTCCATTTTTGGGAACGTACGCGTACGCCTTCTGTGGGGCCCCTTACTCCCGGAGGATTGCTGCGGG

ACTTGGAGAATGTATAAAGTACAGCAATCGAGTTGTCTGCGAGCTAGAGCGTTCTCCAGGCAGTGTCTAAACG

TTTCATGATGTTGTCTAACGTCATCGTCGGCCTTCTAGCTGCCGCCTATGGAAAGCCTGTGCTGGCAGCGTTT

GGGCTCACAGACAATGGCGACAGTTACACCATTGATGCTGGCTCCACCAATCCCCTGGTAATCACTGTCGACA

GTTCCAACTGCGACATCACCTCTTTCGTCTACCGGAGCCAGAAATACCAGTATGCCTCGAAAGGATCCCACAT

TAGCTCAGGCCTTGGCTCGGCTGATGTGACGGCAGAGACTATTGATGGTAAAGCCTGAAGACTGTGATGCAAC

TTCCCATCCGCTGACCACCCGCAGATGTAATCAAGGTCACTTGCACAACCGACACACTGATCCACTACTATGT

CGTCAAATCCGGAGAGAGCAACGTCTACATGGCTACGTACACTTCAGCTGAGCCTTCAGTGGGAGAGCTGCGC

TACATCGCACGACTTGATCCTTCGCTGCTTCCATATGAGTACCCCTTCGGCGACGTCTCCACCACCGCCGACA

GCACTTCGACAGTGGAAGGTTCTGACGTCTTCATCGTCGACGGAGAGACTCGCAGCAAATTCTACTCCAGCCA

GCGCTTCATCGACGACGACGTCCACTGCGTCTACAGCGACGACGTCCACGCGTGCATGCTGATGCCCCAGTAC

GAGACCTCGTCCGGCGGGCCGTTCCACCGAGACATCAACACCAACAACGCCGGCGACTCGACCAACCTGTACT

GGTACATGAACAGCGGACACGTGCAGACCGAGGCCTTCCGGATGGGCCTCCACGGGCCCTACGCCCTCACGTG

GTCGCGCTCTGGCGTGCCCAGTCTCAGCGGCCTCGACTTCTCCTTCATGGCGGACCTCGACCTGGAAGGCTAC

GTCGCCGACAGCGGGCGCGGCACCGTCTCGGGCACAGCATCCGGCGTCTCCAGCGACTATGAGGTCGTGGTGC

ACTGGTACAACGACGACGCGCAGTACTGGACGTACGCCTCTTCGTCCGGCGCCTTCACGTCGCCCGCCATGAA

GCCGGGGACCTACACCATGGCCCTGTACCAGACCGAACTCAAAGTGGCCACGTCCTCGGTGACGGTCAAGGCC

GGATCGGCCACCAGCGCCAACATCGCCAGCACCTGGAGCTCCAATACCACGCTCTTCCAGATCGGCGACTGGG

ACGGGCAGCCGACCGGCTTCCTCAACGCGGCCAGCCAGCTGCGCATGCACCCGTCCGACTCGCGCATGGCCGA

CTGGGGCCCCGTCACCTACACCGTCGGCTCGTCCTCCGACAGCTCCGTCCCGATGGCGCTGTTCAAGGACGTC

AACGACCCGCTGACCATCAGCTTCACGCTGGCGTCTTCGCAGGCCAGCGGCGCGGCGACGCTGCGCGTCGGCA

CCACGCTGTCGTTCGCGGGCGGGCGGCCGAGCGTCACCGTCAACGACTACAGCGACTCCGCCGCCGCGCCGAC

CAAGATCGACTCCCGGGGCGTGACGCGCGGCGCGTATCGCGGGTACGGCGAGATCTACGACTTCGAGCTGCCG

GACGGGACGCTGTCGACGAGCAATACGATCACCATTTCGGTGATTTCGGGGAGCAGTGGGGCGGATTTCCTGG

AGCCGAATTTTGTGAGTTCTCGCATTCCTCTTGGCCACTAGCATGTTTGAGAGGAATGTGACGCTGACGGTGT

GACAGATCCTTGATGCTATTGAGCTGTGGAGATAGGGTTGATAGGTCTGCGGACGTGTTGTGGATGGTTTCGC

GGGTCTGGGATCTTGATTGGTTGTTGGGATGGTATGCAGCAAAGA

```
SEQ ID NO:          59
LENGTH:             1593
TYPE:               DNA
ORGANISM:           M. phaseolina
FEATURE NAME/KEY:   CDS
LOCATION:           (1) ... (1593)
```
atgatgttgtctaacgtcatcgtcggccttctagctgccgcctatggaaagcctgtgctg
 M  M  L  S  N  V  I  V  G  L  L  A  A  A  Y  G  K  P  V  L gcagcgtttgggctcacagacaatggcgacagttacaccattgatgctggctccaccaat
 A  A  F  G  L  T  D  N  G  D  S  Y  T  I  D  A  G  S  T  N cccctggtaatcactgtcgacagttccaactgcgacatcacctctttcgtctaccggagc
 P  L  V  I  T  V  D  S  S  N  C  D  I  T  S  F  V  Y  R  S

```
                                         -continued
cagaaataccagtatgcctcgaaaggatcccacattagctcaggccttggctcggctgat
 Q  K  Y  Q  Y  A  S  K  G  S  H  I  S  S  G  L  G  S  A  D gtgacggcagagactattgatgatgtaatcaaggtcacttgcacaaccgacacactgatc
 V  T  A  E  T  I  D  D  V  I  K  V  T  C  T  T  D  T  L  I cactactatgtcgtcaaatccggagagagcaacgtctacatggctacgtacacttcagct
 H  Y  Y  V  V  K  S  G  E  S  N  V  Y  M  A  T  Y  T  S  A gagccttcagtgggagagctgcgctacatcgcacgacttgatccttcgctgcttccatat
 E  P  S  V  G  E  L  R  Y  I  A  R  L  D  P  S  L  L  P  Y gagtaccccttcggcgacgtctccaccaccgccgacagcacttcgacagtggaaggttct
 E  Y  P  F  G  D  V  S  T  T  A  D  S  T  S  T  V  E  G  S gacgtcttcatcgtcgacggagagactcgcagcaaattctactccagccagcgcttcatc
 D  V  F  I  V  D  G  E  T  R  S  K  F  Y  S  S  Q  R  F  I gacgacgacgtccactgcgtctacagcgacgacgtccacgcgtgcatgctgatgccccag
 D  D  D  V  H  C  V  Y  S  D  D  V  H  A  C  M  L  M  P  Q tacgagacctcgtccggcgggccgttccaccgagacatcaacaccaacaacgccggcgac
 Y  E  T  S  S  G  G  P  F  H  R  D  I  N  T  N  N  A  G  D tcgaccaacctgtactggtacatgaacagcggacacgtgcagaccgaggccttccggatg
 S  T  N  L  Y  W  Y  M  N  S  G  H  V  Q  T  E  A  F  R  M ggcctccacgggccctacgcctcacgtggtcgcgctctggcgtgcccagtctcagcggc
 G  L  H  G  P  Y  A  L  T  W  S  R  S  G  V  P  S  L  S  G ctcgacttctccttcatggcggacctcgacctggaaggctacgtcgccgacagcgggcgc
 L  D  F  S  F  M  A  D  L  D  L  E  G  Y  V  A  D  S  G  R ggcaccgtctcgggcacagcatccggcgtctccagcgactatgaggtcgtggtgcactgg
 G  T  V  S  G  T  A  S  G  V  S  S  D  Y  E  V  V  V  H  W tacaacgacgacgcgcagtactggacgtacgcctcttcgtccggcgccttcacgtcgccc
 Y  N  D  D  A  Q  Y  W  T  Y  A  S  S  S  G  A  F  T  S  P gccatgaagccggggacctacaccatggccctgtaccagaccgaactcaaagtggccacg
 A  M  K  P  G  T  Y  T  M  A  L  Y  Q  T  E  L  K  V  A  T tcctcggtgacggtcaaggccggatcggccaccagcgccaacatcgccagcacctggagc
 S  S  V  T  V  K  A  G  S  A  T  S  A  N  I  A  S  T  W  S tccaataccacgctcttccagatcggcgactgggacgggcagccgaccggcttcctcaac
 S  N  T  T  L  F  Q  I  G  D  W  D  G  Q  P  T  G  F  L  N gcggccagccagctgcgcatgcacccgtccgactcgcgcatggccgactggggcccggtc
 A  A  S  Q  L  R  M  H  P  S  D  S  R  M  A  D  W  G  P  V acctacaccgtcggctcgtcctccgacagctccgtcccgatggcgctgttcaaggacgtc
 T  Y  T  V  G  S  S  S  D  S  S  V  P  M  A  L  F  K  D  V aacgacccgctgaccatcagcttcacgctggcgtcttcgcaggccagcggcgcggcgacg
 N  D  P  L  T  I  S  F  T  L  A  S  S  Q  A  S  G  A  A  T ctgcgcgtcggcaccacgctgtcgttcgcgggcgggcggccgagcgtcaccgtcaacgac
 L  R  V  G  T  T  L  S  F  A  G  G  R  P  S  V  T  V  N  D tacagcgactccgccgccgcgccgaccaagatcgactcccggggcgtgacgcgcggcgcg
 Y  S  D  S  A  A  A  P  T  K  I  D  S  R  G  V  T  R  G  A tatcgcgggtacggcgagatctacgacttcgagctgccggacgggacgctgtcgacgagc
 Y  R  G  Y  G  E  I  Y  D  F  E  L  P  D  G  T  L  S  T  S aatacgatcaccatttcggtgatttcggggagcagtggggcggatttcctggagccgaat
 N  T  I  T  I  S  V  I  S  G  S  S  G  A  D  F  L  E  P  N tttgtgagttctcgcattcctcttggccactag
 F  V  S  S  R  I  P  L  G  H  -

SEQ ID NO:       60
LENGTH:          530
TYPE:            PRT
ORGANISM:        M. phaseolina
MMLSNVIVGLLAAAYGKPVLAAFGLTDNGDSYTIDAGSTNPLVITVDSSNCDITSFVYRSQKYQYASKGSHIS

SGLGSADVTAETIDDVIKVTCTTDTLIHYYVVKSGESNVYMATYTSAEPSVGELRYIARLDPSLLPYEYPFGD

VSTTADSTSTVEGSDVFIVDGETRSKFYSSQRFIDDDVHCVYSDDVHACMLMPQYETSSGGPFHRDINTNNAG
```

DSTNLYWYMNSGHVQTEAFRMGLHGPYALTWSRSGVPSLSGLDFSFMADLDLEGYVADSGRGTVSGTASGVSS
DYEVVVHWYNDDAQYWTYASSSGAFTSPAMKPGTYTMALYQTELKVATSSVTVKAGSATSANIASTWSSNTTL
FQIGDWDGQPTGFLNAASQLRMHPSDSRMADWGPVTYTVGSSSDSSVPMALFKDVNDPLTISFTLASSQASGA
ATLRVGTTLSFAGGRPSVTVNDYSDSAAAPTKIDSRGVTRGAYRGYGEIYDFELPDGTLSTSNTITISVISGS
SGADFLEPNFVSSRIPLGH*

```
SEQ ID NO:          61
LENGTH:             2009 (including 150 bp 5' UTR and 150 bp 3' UTR)
TYPE:               DNA
ORGANISM:           M. phaseolina
```
TCGCTGATCGTCTTGGATATGCGCCTGGCAGTGCATTCGCGCCGGGGACTACAAAAGCAGGGGACGCATGCCA

CAACAGAATTGGCTTTTCTTGTCACTGCACTTCCTGCCGCTCCAAGTCCCCCCCTCGCGTTTGAGGGAACCGC

CACAATGGCTCTCTTTGCTCTGTTTCTGACCTTTATCTCTCTTTTCGCACCGTCGGTGCTGGCCGCCTTTGGA

GTGACTACATCCTCTTCCAGCTATGTTGTCGATGCCGGCTCATCCAACCCCTTCGTTGTTACCATTTCGCGCA

GCAGTTGCGACATTACCTCGATCAAGTACCGTGGAGAGGAATTCCAGTACTCCGGCAAGGGTTCGCACATCTC

GTCCGGCCTTGGATCTGCGACCGTAACGTCAGAGATCGTCAGCAGTGAGCGTCTCTTGCAACCCGTCATACGC

CCCTCAGGCTAACAATCGACAGGCACTTATGCCAAGATCACCTGCACGGCTGGCAGCTTGACCCATTACATTA

TTGTCAAGTCCGGAGAGAGCTCTTTGTACATGGGCACTTACTTCACTGAGGAGCCCTCGATTGGTGAAGCCCG

TTTCATCGCTCGCTTGGACCCGGCCAAGCTCCCTCTCGAATACCCCTACGGCACTGCCTCCACTACTGCTGGG

AGCAGCAGCACCGTCGAGGGATCCGACGTCTTTGTTGTGAATGGCCAGACCCGCAGCAAGTTCTACTCTAGCC

AACGTTTCATCGACGACAAGGTGCAGTGCGTGTACCGCGATGATGATGCTGTCCACGCTTGCATGATCTTGCA

GCCTCTCTCCTACGAGGGATCCAGCGGCGGTCCCTTCTTCAGGGACATCAACACCAACAACGCCGGTGACTCG

ACCAACCTGTACTTCTACATGAACTCCAACCATGCTCAGACTGAGAGTTACCGTATGGGCTTCCACGGCCCGT

ACCAGTTGCAGTTCAGCCGCTCTGGTATTCCCAACAGCTTTGACGCTTCGTTCTTCGCCGACCTCAAGCTCTC

CGGCTACGTTGCTGAGTCTGCTCGTGGCTACGTCAAGGGTACTGCTTCTGGAGTTGGTAGCTCTTACCAGAAA

GTCCTTCATTGGTACAACAGCAACGCGCAGTACTGGGTCTATGCCTCGTCTAACGGTGCCTTTACTTCTCCTG

CCATGAAGCCTGGCACCTACACCCAGGTCCTCTACCAGGACGAACTCAAGGTTGCCACCGACTCGGTCACTGT

CTCTGCTGGATCGACGGTCACCAAGAACATTGCATCTACCTTCTCTTTCCCTTCGACCATCTGGACAATTGGC

GACTGGGACGGCCAGCCATTCGGCTTCCGCAACGCCGACAAGATCGAGCGCATGCACCCGTCCGACAGCCGCA

TGAGCAGCTGGGGGCCGTTGACCTACACGGTCGGCTCCAGCGCACTGACTGACGTTCCCATGGCGCTCTTCAA

GGGCGTCAACACGCCTTTCACCATCAAGTTCACGCTCTCCTCGTCGCAGACAGGTGCGGCGGTCCTCCGGATC

GGCACGACTCTGGCCTTCGCCAGCGGCAGGCCGCAGCCCAAGATCAACAGCTACAGCCCTTCGGCGCCGGCGG

CACCGACGAAGATCGATTCGCGCGGCGTCACACGTGGCACTTACCGCGGTTTGGGTGAGATCTACACCTTCGA

CATTCCCGCGGGCACTCTCGTGAGTGGCTCGAACACGATCACCATCGACTGCATCTCGGGAAGCTCGGGCGAC

ACCTACCTGTCTCCCAACTTTGTAAGTTTCGCTCTGCATACCTCCGCCATGCGCCGTGCTAACGCAAGAAACA

GATCCTTGACGCCATTGACCTGTACCTCAAGTGAGCGAGGGTCAGGAGAAGGGTGCTAGCTGAGGTTCGCTTC

TGTAAATAAGTTTACGTCCTACATTGAACATACATTTTGGCTTTGATTGCCGGTCTGCATTACTCGTCAATAC

GAAGCTTCGCGAGCGCGCAGCTCCACCGAATGCGTGGC

SEQ ID NO: 62
LENGTH: 1605
TYPE: DNA
ORGANISM: *M. phaseolina*
FEATURE NAME/KEY: CDS
LOCATION: (1) ... (1605)

atggctctctttgctctgtttctgacctttatctctcttttcgcaccgtcggtgctggcc
 M  A  L  F  A  L  F  L  T  F  I  S  L  F  A  P  S  V  L  A -continued

```
gcctttggagtgactacatcctcttccagctatgttgtcgatgccggctcatccaacccc
 A  F  G  V  T  T  S  S  S  S  Y  V  V  D  A  G  S  S  N  P ttcgttgttaccatttcgcgcagcagttgcgacattacctcgatcaagtaccgtggagag
 F  V  V  T  I  S  R  S  S  C  D  I  T  S  I  K  Y  R  G  E gaattccagtactccggcaagggttcgcacatctcgtccggccttggatctgcgaccgta
 E  F  Q  Y  S  G  K  G  S  H  I  S  S  G  L  G  S  A  T  V acgtcagagatcgtcagcagcacttatgccaagatcacctgcacggctggcagcttgacc
 T  S  E  I  V  S  S  T  Y  A  K  I  T  C  T  A  G  S  L  T cattacattattgtcaagtccggagagagctctttgtacatgggcacttacttcactgag
 H  Y  I  I  V  K  S  G  E  S  S  L  Y  M  G  T  Y  F  T  E gagccctcgattggtgaagcccgtttcatcgctcgcttggacccggccaagctccctctc
 E  P  S  I  G  E  A  R  F  I  A  R  L  D  P  A  K  L  P  L gaataccccctacggcactgcctccactactgctgggagcagcagcaccgtcgagggatcc
 E  Y  P  Y  G  T  A  S  T  T  A  G  S  S  S  T  V  E  G  S gacgtctttgttgtgaatggccagacccgcagcaagttctactctagccaacgtttcatc
 D  V  F  V  V  N  G  Q  T  R  S  K  F  Y  S  S  Q  R  F  I gacgacaaggtgcagtgcgtgtaccgcgatgatgatgctgtccacgcttgcatgatcttg
 D  D  K  V  Q  C  V  Y  R  D  D  D  A  V  H  A  C  M  I  L cagcctctctcctacgagggatccagcggcggtcccttcttcagggacatcaacaccaac
 Q  P  L  S  Y  E  G  S  S  G  G  P  F  F  R  D  I  N  T  N aacgccggtgactcgaccaacctgtacttctacatgaactccaaccatgctcagactgag
 N  A  G  D  S  T  N  L  Y  F  Y  M  N  S  N  H  A  Q  T  E agttaccgtatgggcttccacggcccgtaccagttgcagttcagccgctctggtattccc
 S  Y  R  M  G  F  H  G  P  Y  Q  L  Q  F  S  R  S  G  I  P aacagctttgacgcttcgttcttcgccgacctcaagctctccggctacgttgctgagtct
 N  S  F  D  A  S  F  F  A  D  L  K  L  S  G  Y  V  A  E  S gctcgtggctacgtcaagggtactgcttctggagttggtagctcttaccagaaagtcctt
 A  R  G  Y  V  K  G  T  A  S  G  V  G  S  S  Y  Q  K  V  L cattggtacaacagcaacgcgcagtactgggtctatgcctcgtctaacggtgcctttact
 H  W  Y  N  S  N  A  Q  Y  W  V  Y  A  S  S  N  G  A  F  T tctcctgccatgaagcctggcacctacacccaggtcctctaccaggacgaactcaaggtt
 S  P  A  M  K  P  G  T  Y  T  Q  V  L  Y  Q  D  E  L  K  V gccaccgactcggtcactgtctctgctggatcgacggtcaccaagaacattgcatctacc
 A  T  D  S  V  T  V  S  A  G  S  T  V  T  K  N  I  A  S  T ttctctttccccttcgaccatctggacaattggcgactgggacggccagccattcggcttc
 F  S  F  P  S  T  I  W  T  I  G  D  W  D  G  Q  P  F  G  F cgcaacgccgacaagatcgagcgcatgcacccgtccgacagccgcatgagcagctggggg
 R  N  A  D  K  I  E  R  M  H  P  S  D  S  R  M  S  S  W  G ccgttgacctacacggtcggctccagcgcactgactgacgttcccatggcgctcttcaag
 P  L  T  Y  T  V  G  S  S  A  L  T  D  V  P  M  A  L  F  K ggcgtcaacacgccttttcaccatcaagttcacgctctcctcgtcgcagacaggtgcggcg
 G  V  N  T  P  F  T  I  K  F  T  L  S  S  S  Q  T  G  A  A gtcctccggatcggcacgactctggccttcgccagcggcaggccgcagcccaagatcaac
 V  L  R  I  G  T  T  L  A  F  A  S  G  R  P  Q  P  K  I  N agctacagcccttcggcgccggcggcaccgacgaagatcgattcgcgcggcgtcacacgt
 S  Y  S  P  S  A  P  A  A  P  T  K  I  D  S  R  G  V  T  R ggcacttaccgcggtttgggtgagatctacaccttcgacattcccgcgggcactctcgtg
 G  T  Y  R  G  L  G  E  I  Y  T  F  D  I  P  A  G  T  L  V agtggctcgaacacgatcaccatcgactgcatctcgggaagctcgggcgacacctacctg
 S  G  S  N  T  I  T  I  D  C  I  S  G  S  S  G  D  T  Y  L tctcccaactttatccttgacgccattgacctgtacctcaagtga
 S  P  N  F  I  L  D  A  I  D  L  Y  L  K  -
```

SEQ ID NO: 63
LENGTH: 534
TYPE: PRT
ORGANISM: M. phaseolina

MALFALFLTFISLFAPSVLAAFGVTTSSSSYVVDAGSSNPFVVTISRSSCDITSIKYRGEEFQYSGKGSHISS

GLGSATVTSEIVSSTYAKITCTAGSLTHYIIVKSGESSLYMGTYFTEEPSIGEARFIARLDPAKLPLEYPYGT

ASTTAGSSSTVEGSDVFVVNGQTRSKFYSSQRFIDDKVQCVYRDDDAVHACMILQPLSYEGSSGGPFFRDINT

NNAGDSTNLYFYMNSNHAQTESYRMGFHGPYQLQFSRSGIPNSFDASFFADLKLSGYVAESARGYVKGTASGV

GSSYQKVLHWYNSNAQYWVYASSNGAFTSPAMKPGTYTQVLYQDELKVATDSVTVSAGSTVTKNIASTFSFPS

TIWTIGDWDGQPFGFRNADKIERMHPSDSRMSSWGPLTYTVGSSALTDVPMALFKGVNTPFTIKFTLSSSQTG

AAVLRIGTTLAFASGRPQPKINSYSPSAPAAPTKIDSRGVTRGTYRGLGEIYTFDIPAGTLVSGSNTITIDCI

SGSSGDTYLSPNFILDAIDLYLK*

INCORPORATION BY REFERENCE

All of the U.S. patents, U.S. published patent applications, and published PCT applications that cited herein are hereby incorporated by reference.

EQUIVALENTS

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed.

What is claimed is:

1. An expression construct comprising a polynucleotide sequence having at least 90% identity to a nucleotide sequence set forth in SEQ ID NO. 2, wherein the polynucleotide sequence encodes a pectate lyase having pectate lyase activity and is operatively associated with a heterologous regulatory nucleotide sequence containing transcriptional or translational regulatory signals, or both, that controls expression of the polynucleotide sequence in a host cell.

2. A genetically engineered host cell comprising the expression construct of claim 1.

3. A method of making a polypeptide comprising the steps of:

i. culturing a cell transformed with an expression construct of claim 1 under effective conditions to produce the polypeptide; and ii. isolating the polypeptide.

4. A transformant comprising the expression construct of claim 1.

5. A transgenic fungi of *M. phaseolina*, comprising the expression construct of claim 1.

6. The expression construct of claim 1, wherein the polynucleotides sequence has at least 95% identity to the nucleotide sequence set forth in SEQ ID No. 2.

7. The expression construct of claim 1, wherein the polynucleotides sequence has 100% identity to the nucleotide sequence set forth in SEQ ID No. 2.

* * * * *

SEQUENCE LISTING

```
<160> NUMBER OF SEQ ID NOS: 105

<210> SEQ ID NO 1
<211> LENGTH: 1047
<212> TYPE: DNA
<213> ORGANISM: M. phaseolina

<400> SEQUENCE: 1
gaagagtata tagaggtggc cacgactgca ctgttgaact catcaccgac ccacaatcgc    60
tttctttctg cccactctcg ttcacaacac agatctctga tctaccacat tcgttcttac   120
cgaggatcaa aaattcctcc catctccaca atgcagtaca agtacaccgt ccttgccgcc   180
actatggccg ccgttgcctt cgcccagcag aacttgattg gcattcctac cggtactaaa   240
gctaagcctt tcacccagcc cgagaccatt accttcttcg acggtaaaat gatggaatac   300
ggccgcggca agccctgtgg caccgacgat gacaagggtg accttgaggc cgtcttcatc   360
atcaagcccg gcggcacgct gcagaacgcc atcatcggcg ccgactccct tgagggcgtg   420
cactgcgagg gcgcctgcac catcaagaac gtctggttca aggacgtgtg cgaagacgcc   480
atcaccctca agggcaacgg cccgtacctg atcaccggtg gcggtgcgca gcacgccaag   540
gacaaggtcg tccagcacaa cggcaagggc accgtgacca tctccgatta caagatcggc   600
gccgtcggta agctgtaccg cagctgtggc aactgcagca caacggcgg ccccgcaac    660 gtcgtcctcg accgcatctc ttccttcggc cccggcacca cgtccgacct tgtcggcatc   720
aactccaact acaacgacgt cgccaccatc agtggcgtct gcggccctgt caagaacatg   780
tgtcaggagt tcaccggcat cgagaaggac ggcaacaagg agagccccca cagggagccc   840
ccgattggtg cttgcaaggg cccccagggc cagctcaaga cggctcccgc ttgctaagcg   900
```

-continued

```
cctcacggaa ttatcatggg tgtgcagtta cgggaaagga aatcgatatc gacctcccta    960
ttggtaacat caatctggct ccaaattgca tcatccgcca ctggtcggcc atgacaggac   1020
agagcgaagt caaaagtttc ggtgtac                                       1047
```

<210> SEQ ID NO 2
<211> LENGTH: 747
<212> TYPE: DNA
<213> ORGANISM: M. phaseolina

<400> SEQUENCE: 2

```
atgcagtaca agtacaccgt ccttgccgcc actatggccg ccgttgcctt cgcccagcag     60
aacttgattg gcattcctac cggtactaaa gctaagcctt tcacccagcc cgagaccatt    120
accttcttcg acggtaaaat gatggaatac ggccgcggca agccctgtgg caccgacgat    180
gacaagggtg accttgaggc cgtcttcatc atcaagcccg gcggcacgct gcagaacgcc    240
atcatcggcg ccgactccct tgagggcgtg cactgcgagg gcgcctgcac catcaagaac    300
gtctggttca aggacgtgtg cgaagacgcc atcaccctca agggcaacgg cccgtacctg    360
atcaccggtg gcggtgcgca gcacgccaag gacaaggtcg tccagcacaa cggcaagggc    420
accgtgacca tctccgatta caagatcggc gccgtcggta agctgtaccg cagctgtggc    480
aactgcagca caacggcggc ccccgcaac gtcgtcctcg accgcatctc ttccttcggc    540
cccggcacca cgtccgacct tgtcggcatc aactccaact acaacgacgt cgccaccatc    600
agtggcgtct gcggccctgt caagaacatg tgtcaggagt tcaccggcat cgagaaggac    660
ggcaacaagg agagccccca cagggagccc ccgattggtg cttgcaaggg cccccagggc    720
cagctcaaga cggctcccgc ttgctaa                                        747
```

<210> SEQ ID NO 3
<211> LENGTH: 248
<212> TYPE: PRT
<213> ORGANISM: M. phaseolina

<400> SEQUENCE: 3

```
Met Gln Tyr Lys Tyr Thr Val Leu Ala Ala Thr Met Ala Ala Val Ala
1               5                   10                  15

Phe Ala Gln Gln Asn Leu Ile Gly Ile Pro Thr Gly Thr Lys Ala Lys
            20                  25                  30

Pro Phe Thr Gln Pro Glu Thr Ile Thr Phe Phe Asp Gly Lys Met Met
        35                  40                  45

Glu Tyr Gly Arg Gly Lys Pro Cys Gly Thr Asp Asp Lys Gly Asp
    50                  55                  60

Leu Glu Ala Val Phe Ile Ile Lys Pro Gly Gly Thr Leu Gln Asn Ala
65                  70                  75                  80

Ile Ile Gly Ala Asp Ser Leu Glu Gly Val His Cys Glu Gly Ala Cys
                85                  90                  95

Thr Ile Lys Asn Val Trp Phe Lys Asp Val Cys Glu Asp Ala Ile Thr
            100                 105                 110

Leu Lys Gly Asn Gly Pro Tyr Leu Ile Thr Gly Gly Ala Gln His
        115                 120                 125

Ala Lys Asp Lys Val Val Gln His Asn Gly Lys Gly Thr Val Thr Ile
    130                 135                 140

Ser Asp Tyr Lys Ile Gly Ala Val Gly Lys Leu Tyr Arg Ser Cys Gly
145                 150                 155                 160

Asn Cys Ser Asn Asn Gly Gly Pro Arg Asn Val Val Leu Asp Arg Ile
```

|   |   |   | 165 |   |   |   | 170 |   |   |   | 175 |   |
|---|---|---|---|---|---|---|---|---|---|---|---|---|
| Ser | Ser | Phe | Gly | Pro | Gly | Thr | Thr | Ser | Asp | Leu | Val | Gly | Ile | Asn | Ser |
|   |   |   | 180 |   |   |   | 185 |   |   |   | 190 |   |

Ser Ser Phe Gly Pro Gly Thr Thr Ser Asp Leu Val Gly Ile Asn Ser
            180                 185                 190

Asn Tyr Asn Asp Val Ala Thr Ile Ser Gly Val Cys Gly Pro Val Lys
        195                 200                 205

Asn Met Cys Gln Glu Phe Thr Gly Ile Glu Lys Asp Gly Asn Lys Glu
    210                 215                 220

Ser Pro His Arg Glu Pro Pro Ile Gly Ala Cys Lys Gly Pro Gln Gly
225                 230                 235                 240

Gln Leu Lys Thr Ala Pro Ala Cys
            245

<210> SEQ ID NO 4
<211> LENGTH: 1167
<212> TYPE: DNA
<213> ORGANISM: M. phaseolina

<400> SEQUENCE: 4

```
ctaccacgaa tcggaattaa acgacgaatc tcctggtgaa gactataaaa ggcagacaac     60
ggcgtcgaca gtaaagacca tcgcaatcca acagtccagt tcctcctcaa gtctctcact    120
cccatcctcc actttccaat cacttccaac atgaagttca tctacgccgc tatcaccgcc    180
accgtggctg gccttgcctc tgcgcagtcc ctgaccatcc ccaccgctc cggcagcaag     240
gtcgtcctct ccgcgcccag taccatctcc ggctcgcaag actttggtaa caaggagttc    300
gaccgcggaa tccctgcga ctcggacgat gacactggca gctccagcgc cgtcttcatc     360
ctcaagaacg gcgccagcat ctccaacgtc atcattggta ccgacgcgct cgagggcgtc    420
cactgcgagg gtgcctgcac cctgaccaac gtctggttcc gtgacgtctg cgagggtgag    480
ctaaatccac aacataccat caaacactca gtagtgcac acgaatgcta atgggaaaat     540
ccagacgcca tctccgcgct cggcaccggc aatgtcctca tccagggcgg cggtgcgcag    600
aacgccaagg acaaggtcgt ccagcacaac ggccgcggca ccgtcaccat caagaactac    660
accgtcgtca acgccggcaa gctgtaccgc agctgcggcg actgcaccaa caacggcggc    720
ccccgcaacg tcgtcgtgga acgtccgc gtcaacggca tgacctctga cctcgtcggc      780
atcaactcca actacggtga cagtaagtcg gcaaaagata cttcaaatcg ttggaggaac    840
actcaatact gactgtcgat tccagctgct accatcagca actcttgcgg cgtctccaag    900
aaggtctgcc aggagtacaa gggcgtcacc aagggcaacg cgacagcga aaggtctcc      960
accactgcca actgcaaggg tgctcagggt actctgtcta agcttccac ttgctagaca     1020
acctaaaagc aaaaccaaac tagagcttgg gcacggatca ctcgcgttgg atgtggtccg    1080
tggaatcctt ggtcagtgct caatcgcctg cttcgagtgg aaacggccg tctcaattga     1140
taccgggcga gtgtctgcgc atggatg                                      1167
```

<210> SEQ ID NO 5
<211> LENGTH: 735
<212> TYPE: DNA
<213> ORGANISM: M. phaseolina

<400> SEQUENCE: 5

```
atgaagttca tctacgccgc tatcaccgcc accgtggctg gccttgcctc tgcgcagtcc     60
ctgaccatcc ccaccgctc cggcagcaag gtcgtcctct ccgcgcccag taccatctcc    120
ggctcgcaag actttggtaa caaggagttc gaccgcggaa tccctgcga ctcggacgat    180
```

```
gacactggca gctccagcgc cgtcttcatc ctcaagaacg gcgccagcat ctccaacgtc    240
atcattggta ccgacgcgct cgagggcgtc cactgcgagg gtgcctgcac cctgaccaac    300
gtctggttcc gtgacgtctg cgaggacgcc atctccgcgc tcggcaccgg caatgtcctc    360
atccagggcg gcggtgcgca gaacgccaag gacaaggtcg tccagcacaa cggccgcggc    420
accgtcacca tcaagaacta caccgtcgtc aacgccggca agctgtaccg cagctgcggc    480
gactgcacca caacggcggc ccccgcaac gtcgtcgtgg acaacgtccg cgtcaacggc    540
atgacctctg acctcgtcgg catcaactcc aactacggtg acactgctac catcagcaac    600
tcttgcggcg tctccaagaa ggtctgccag gagtacaagg gcgtcaccaa gggcaacggc    660
gacagcgaga aggtctccac cactgccaac tgcaagggtg ctcagggtac tctgtctaag    720
cttcccactt gctag                                                    735
```

```
<210> SEQ ID NO 6
<211> LENGTH: 244
<212> TYPE: PRT
<213> ORGANISM: M. phaseolina

<400> SEQUENCE: 6

Met Lys Phe Ile Tyr Ala Ala Ile Thr Ala Thr Val Ala Gly Leu Ala
1               5                   10                  15

Ser Ala Gln Ser Leu Thr Ile Pro Thr Arg Ser Gly Ser Lys Val Val
            20                  25                  30

Leu Ser Ala Pro Ser Thr Ile Ser Gly Ser Gln Asp Phe Gly Asn Lys
        35                  40                  45

Glu Phe Asp Arg Gly Ile Pro Cys Asp Ser Asp Asp Thr Gly Ser
    50                  55                  60

Ser Ser Ala Val Phe Ile Leu Lys Asn Gly Ala Ser Ile Ser Asn Val
65                  70                  75                  80

Ile Ile Gly Thr Asp Ala Leu Glu Gly Val His Cys Glu Gly Ala Cys
                85                  90                  95

Thr Leu Thr Asn Val Trp Phe Arg Asp Val Cys Glu Asp Ala Ile Ser
            100                 105                 110

Ala Leu Gly Thr Gly Asn Val Leu Ile Gln Gly Gly Gly Ala Gln Asn
        115                 120                 125

Ala Lys Asp Lys Val Val Gln His Asn Gly Arg Gly Thr Val Thr Ile
    130                 135                 140

Lys Asn Tyr Thr Val Val Asn Ala Gly Lys Leu Tyr Arg Ser Cys Gly
145                 150                 155                 160

Asp Cys Thr Asn Asn Gly Gly Pro Arg Asn Val Val Asp Asn Val
                165                 170                 175

Arg Val Asn Gly Met Thr Ser Asp Leu Val Gly Ile Asn Ser Asn Tyr
            180                 185                 190

Gly Asp Thr Ala Thr Ile Ser Asn Ser Cys Gly Val Ser Lys Lys Val
        195                 200                 205

Cys Gln Glu Tyr Lys Gly Val Thr Lys Gly Asn Gly Asp Ser Glu Lys
    210                 215                 220

Val Ser Thr Thr Ala Asn Cys Lys Gly Ala Gln Gly Thr Leu Ser Lys
225                 230                 235                 240

Leu Pro Thr Cys

<210> SEQ ID NO 7
<211> LENGTH: 1110
<212> TYPE: DNA
```

<213> ORGANISM: M. phaseolina

<400> SEQUENCE: 7

```
cagcggtata taaatgccct ggtaccctgc cccaaaatgc cttcttcacc accacagtcc      60
ttcgtttcaa tcgttcagca cattcactct ttcattcaca ctcactaacc gatctgcgat     120
cgtgttcttt gccttccact accagacaca atgttctcca agcttttcct gcttcccctc     180
ctggcggctt ccgccctggc tgctcctgcc gacgacactt tcggctacga gctcgttcgc     240
cgcgcgaact tccccattcc tgcctccaag ggcaacgtca agctcagcgc tgccaagtcc     300
gtgtccggca ccttcgatgg tggcatgaag acctacggcc gtggtgtcaa gtgcaccggt     360
caggccgagg gtggtgacaa ggacgccgtc ttcatcctcg agaacggtgc taccctcaag     420
aacgccatca ttggtaccga ccagatcgag ggcgtccact gcaagggctc ctgcaccatc     480
gaaaacgtct ggtgggccgg tgtctgcgag gacgcgctct ccctgaaggg tgacggttcc     540
gccaaggtca tcggcggcgg cgctactggc gctgaagaca aggtacgtac gcctctgata     600
cgccttcgct cagattgctg accagatctg gtacaggtca tccagcacaa cggcgttggc     660
tccgtctcga ttgatggctt cactgttgcc gacttcggca agctctaccg ctcgtgcgga     720
aactgcaaga agatgggcaa gagaaccgtc accatcaaga acgtgaaggc tagcaacgga     780
aagcttttgg ctggcatcaa ctccaactac ggcgacactg ctaccatcac cggcacctgc     840
gctacctccg tcaagaaggt ctgcaccgag ttcaagggca caacagcgg caaggagccc     900
accgagatca gctccggccc cagcaacgcc tgcaagtact cctccctcaa ggcctgctag     960
ggcctgctag acggttgctc aacaaacaaa catggcattt gccgcgtgag cccgggacct    1020
ttccgggctc gggagaagaa agtggatggc attctattct tgtatcgact tctagtacta    1080
gagcatcttc tatacctcta atttactgtg                                     1110
```

<210> SEQ ID NO 8
<211> LENGTH: 756
<212> TYPE: DNA
<213> ORGANISM: M. phaseolina

<400> SEQUENCE: 8

```
atgttctcca agcttttcct gcttcccctc ctggcggctt ccgccctggc tgctcctgcc      60
gacgacactt tcggctacga gctcgttcgc cgcgcgaact tccccattcc tgcctccaag     120
ggcaacgtca agctcagcgc tgccaagtcc gtgtccggca ccttcgatgg tggcatgaag     180
acctacggcc gtggtgtcaa gtgcaccggt caggccgagg gtggtgacaa ggacgccgtc     240
ttcatcctcg agaacggtgc taccctcaag aacgccatca ttggtaccga ccagatcgag     300
ggcgtccact gcaagggctc ctgcaccatc gaaaacgtct ggtgggccgg tgtctgcgag     360
gacgcgctct ccctgaaggg tgacggttcc gccaaggtca tcggcggcgg cgctactggc     420
gctgaagaca aggtcatcca gcacaacggc gttggctccg tctcgattga tggcttcact     480
gttgccgact tcggcaagct ctaccgctcg tgcgaaaact gcaagaagat gggcaagaga     540
accgtcacca tcaagaacgt gaaggctagc aacggaaagc ttttggctgg catcaactcc     600
aactacggcg acactgctac catcaccggc acctgcgcta cctccgtcaa gaaggtctgc     660
accgagttca agggcaacaa cagcggcaag agcccaccg atcagctc cggccccagc     720
aacgcctgca agtactcctc cctcaaggcc tgctag                               756
```

<210> SEQ ID NO 9
<211> LENGTH: 251

```
<212> TYPE: PRT
<213> ORGANISM: M. phaseolina

<400> SEQUENCE: 9

Met Phe Ser Lys Leu Phe Leu Pro Leu Leu Ala Ala Ser Ala Leu
1               5                   10                  15

Ala Ala Pro Ala Asp Asp Thr Phe Gly Tyr Glu Leu Val Arg Arg Ala
            20                  25                  30

Asn Phe Pro Ile Pro Ala Ser Lys Gly Asn Val Lys Leu Ser Ala Ala
            35                  40                  45

Lys Ser Val Ser Gly Thr Phe Asp Gly Met Lys Thr Tyr Gly Arg
    50                  55                  60

Gly Val Lys Cys Thr Gly Gln Ala Glu Gly Asp Lys Asp Ala Val
65              70                  75                  80

Phe Ile Leu Glu Asn Gly Ala Thr Leu Lys Asn Ala Ile Ile Gly Thr
                85                  90                  95

Asp Gln Ile Glu Gly Val His Cys Lys Gly Ser Cys Thr Ile Glu Asn
            100                 105                 110

Val Trp Trp Ala Gly Val Cys Glu Asp Ala Leu Ser Leu Lys Gly Asp
        115                 120                 125

Gly Ser Ala Lys Val Ile Gly Gly Ala Thr Gly Ala Glu Asp Lys
    130                 135                 140

Val Ile Gln His Asn Gly Val Gly Ser Val Ser Ile Asp Gly Phe Thr
145             150                 155                 160

Val Ala Asp Phe Gly Lys Leu Tyr Arg Ser Cys Gly Asn Cys Lys Lys
                165                 170                 175

Met Gly Lys Arg Thr Val Thr Ile Lys Asn Val Lys Ala Ser Asn Gly
            180                 185                 190

Lys Leu Leu Ala Gly Ile Asn Ser Asn Tyr Gly Asp Thr Ala Thr Ile
        195                 200                 205

Thr Gly Thr Cys Ala Thr Ser Val Lys Val Cys Thr Glu Phe Lys
    210                 215                 220

Gly Asn Asn Ser Gly Lys Glu Pro Thr Glu Ile Ser Ser Gly Pro Ser
225             230                 235                 240

Asn Ala Cys Lys Tyr Ser Ser Leu Lys Ala Cys
                245                 250

<210> SEQ ID NO 10
<211> LENGTH: 1127
<212> TYPE: DNA
<213> ORGANISM: M. phaseolina

<400> SEQUENCE: 10
ccgctcctct gtgcgttgtt gaaccttgct gtttgtaggt ataaagcccc cccgtcattg      60
ctgaggacgt gtatggacag gatccctcaa acagattgtc ttctacatct cagcgcatta    120
agaaccccat aaataccaag agttacaaac atgcgttcta caaatctgct cgtcctcctc    180
gcaacctccc tcagcctggt cgcagcgagc ccgttggatg cgccgaccaa agtgatgggc    240
aagcggttcg ccaccaatgt tctacccgca tcatctggac atgttgtcct ccctcagca    300 accactgtga gcactttga cggcggaatg aagaagtacg accgtggtac ctcttgcact    360
ggtcagtccg aagggggga tgcggacgct gtcttcctcg ttcagtccgg aggcacctc     420 aagaatgtca tcattggtgc ggaccaatct gaaggtgtcc actgtctcgg cccgtgcacg    480
atccagaacg tgtggtggga ggccgtctgc gagggtgaga gccagacgct tcgcgttgta    540
```

```
aagggggcgaa atgctgacct caagacccag acgccttgac catcaaacaa acttctggga    600
cctcctacgt cgttggcggc ggtgcttttg gcgcgtcaga caaaattatc cagcacaacg    660
gaggcggtac cgtctcgatc aaggacttct acgcccaaga tttcggcaaa gtttaccgca    720
gctgcggcaa ttgcggcact cagtacaaac gcaccgtcac catgtctggg atttgggccg    780
ttaatggtga tctccttgcc ggcgttaact ccaattacgg tgataccgcg accatttccg    840
gcacttgtgc agacaacgtg gacaacatct gcgcctggta cgaaggaaac gatgatggcg    900
atgagcccac caagttgggc actggcatca gctcttactg tgtctatacc gccaatggtg    960
tcgatgactg cccttgagtt gaacattggc ttctatttgc cacgacacta tgatcgtgtt   1020
gcggctctat cgctgttgtg tccggttggt gagggcaccc gtacatatgt ggaatggagg   1080
tcacgtggtg gatagcatgt acatattctt gcctgttatg cctacac                 1127
```

```
<210> SEQ ID NO 11
<211> LENGTH: 771
<212> TYPE: DNA
<213> ORGANISM: M. phaseolina

<400> SEQUENCE: 11
atgcgttcta caaatctgct cgtcctcctc gcaacctccc tcagcctggt cgcagcgagc      60
ccgttggatg cgccgaccaa agtgatgggc aagcggttcg ccaccaatgt tctacccgca    120
tcatctggac atgttgtcct ccctcagca accactgtga gcactttga cggcggaatg      180 aagaagtacg accgtggtac ctcttgcact ggtcagtccg aaggggggga tgcggacgct    240
gtcttcctcg ttcagtccgg aggcaccctc aagaatgtca tcattggtgc ggaccaatct    300
gaaggtgtcc actgtctcgg cccgtgcacg atccagaacg tgtggtggga ggccgtctgc    360
gaggacgcct tgaccatcaa acaaacttct gggacctcct acgtcgttgg cggcggtgct    420
tttggcgcgt cagacaaaat tatccagcac aacggaggcg gtaccgtctc gatcaaggac    480
ttctacgccc aagatttcgg caaagtttac cgcagctgcg gcaattgcgg cactcagtac    540
aaacgcaccg tcaccatgtc tgggatttgg gccgttaatg gtgatctcct tgccggcgtt    600
aactccaatt acggtgatac cgcgaccatt tccggcactt gtgcagacaa cgtggacaac    660
atctgcgcct ggtacgaagg aaacgatgat ggcgatgagc ccaccaagtt gggcactggc    720
atcagctctt actgtgtcta taccgccaat ggtgtcgatg actgcccttg a             771
```

```
<210> SEQ ID NO 12
<211> LENGTH: 256
<212> TYPE: PRT
<213> ORGANISM: M. phaseolina

<400> SEQUENCE: 12

Met Arg Ser Thr Asn Leu Leu Val Leu Leu Ala Thr Ser Leu Ser Leu
1               5                   10                  15

Val Ala Ala Ser Pro Leu Asp Ala Pro Thr Lys Val Met Gly Lys Arg
            20                  25                  30

Phe Ala Thr Asn Val Leu Pro Ala Ser Ser Gly His Val Val Leu Pro
        35                  40                  45

Ser Ala Thr Thr Val Ser Thr Phe Asp Gly Gly Met Lys Lys Tyr Asp
    50                  55                  60

Arg Gly Thr Ser Cys Thr Gly Gln Ser Glu Gly Gly Asp Ala Asp Ala
65                  70                  75                  80

Val Phe Leu Val Gln Ser Gly Gly Thr Leu Lys Asn Val Ile Ile Gly
                85                  90                  95
```

Ala Asp Gln Ser Glu Gly Val His Cys Leu Gly Pro Cys Thr Ile Gln
            100                 105                 110

Asn Val Trp Trp Glu Ala Val Cys Glu Asp Ala Leu Thr Ile Lys Gln
            115                 120                 125

Thr Ser Gly Thr Ser Tyr Val Gly Gly Ala Phe Gly Ala Ser
            130                 135                 140

Asp Lys Ile Ile Gln His Asn Gly Gly Thr Val Ser Ile Lys Asp
145                 150                 155                 160

Phe Tyr Ala Gln Asp Phe Gly Lys Val Tyr Arg Ser Cys Gly Asn Cys
                165                 170                 175

Gly Thr Gln Tyr Lys Arg Thr Val Thr Met Ser Gly Ile Trp Ala Val
            180                 185                 190

Asn Gly Asp Leu Leu Ala Gly Val Asn Ser Asn Tyr Gly Asp Thr Ala
            195                 200                 205

Thr Ile Ser Gly Thr Cys Ala Asp Asn Val Asp Asn Ile Cys Ala Trp
            210                 215                 220

Tyr Glu Gly Asn Asp Asp Gly Asp Glu Pro Thr Lys Leu Gly Thr Gly
225                 230                 235                 240

Ile Ser Ser Tyr Cys Val Tyr Thr Ala Asn Gly Val Asp Asp Cys Pro
                245                 250                 255

<210> SEQ ID NO 13
<211> LENGTH: 1164
<212> TYPE: DNA
<213> ORGANISM: M. phaseolina

<400> SEQUENCE: 13

```
agtgacatat aagtcctctg ttctgccatc ggaaaatgct tctcatcacc aacattctct      60
tccttctttc ctcaccacca cttcccctct ttcaaacaat taccggatag atctgtgatc     120
atcccctact ttcgtttaac aacatacaaa atgcagtcca agatcgttct cggcctttct     180
ctcctcgccg ccaccggcat ggcggctccc tccgagcccc tccgcgtccg cgccacccte     240
cccatcccct cctccaaggg ctctgtcacc tacgatgagg tcaagtccat caccggcact     300
ttcgacggtg gcatgaagac ctacggccgt ggtgtttcct gcactggcca agaggagggt     360
ggcaacaagg acgccgtctt ccagcttgag gacggtgcta ccctcaagaa cgtcatcatt     420
ggcgaggacc agatcgaggg tatccactgc atgggcagct gcaccctgga aacgtctgg      480
tggagcgccg tctgcgaggg tttgtcttct tccatccact gaagcacttc acagctaacg     540
tcatctcaga cgctcttacc ttcaagggt acggtgacgc caaggtcatc ggcggcggtg      600
cccagggcgc cgacgacaag gtcctccagc acaacggtgt cggcgatgtg accatcgacg    660
gcttcaccgt tgtcgatttc ggcaagctgt atcgctcttg cggcagtaag ttccccccgg     720
cttctgccca cctccatccc tcattcacct gctcacacac gtgttccaga ctgcaagcag     780
aacggcggca cccgcaacgt caacatctcc aacgtcaagg cctacaacgg caaggtcctc     840
accggcatca actccaacta cggcgacgtc gccaccttca aggacacctg cgcctcttcc     900
gtcaaggaca tctgcgtcga gtacaagggt accaacaaca acgacgagga gccctccaag     960
atcggctccg gtccttccga caactgcgtc tactccgaca tcccctcttg ctagacggct    1020
cgccaacggt cgcttgggct ggctttcgcg gatgcccatt gtgaataatc cgcttgtttc    1080
ttgtatgtaa ttatttttaaa ggcaagaaga ccatttaaat caataaatag agacggggct    1140
agacctcgct tgtactacgc acac                                            1164
```

<210> SEQ ID NO 14
<211> LENGTH: 750
<212> TYPE: DNA
<213> ORGANISM: M. phaseolina

<400> SEQUENCE: 14

```
atgcagtcca agatcgttct cggcctttct ctcctcgccg ccaccggcat ggcggctccc      60
tccgagcccc tccgcgtccg cgccaccctc cccatcccct cctccaaggg ctctgtcacc     120
tacgatgagg tcaagtccat caccggcact ttcgacggtg gcatgaagac ctacggccgt     180
ggtgttttcct gcactggcca gaaggagggt ggcaacaagg acgccgtctt ccagcttgag     240
gacggtgcta ccctcaagaa cgtcatcatt ggcgaggacc agatcgaggg tatccactgc     300
atgggcagct gcaccctgga gaacgtctgg tggagcgccg tctgcgagga cgctcttacc     360
ttcaagggtg acggtgacgc caaggtcatc ggcggcggtg cccagggcgc cgacgacaag     420
gtcctccagc acaacggtgt cggcgatgtg accatcgacg gcttcaccgt tgtcgatttc     480
ggcaagctgt atcgctcttg cggcaactgc aagcagaacg gcggcacccg caacgtcaac     540
atctccaacg tcaaggccta caacggcaag gtcctcaccg gcatcaactc caactacggc     600
gacgtcgcca ccttcaagga cacctgcgcc tcttccgtca aggacatctg cgtcgagtac     660
aagggtacca caacaacga cgaggagccc tccaagatcg gctccggtcc ttccgacaac     720
tgcgtctact ccgacatccc ctcttgctag                                     750
```

<210> SEQ ID NO 15
<211> LENGTH: 249
<212> TYPE: PRT
<213> ORGANISM: M. phaseolina

<400> SEQUENCE: 15

Met Gln Ser Lys Ile Val Leu Gly Leu Ser Leu Leu Ala Ala Thr Gly
1               5                   10                  15

Met Ala Ala Pro Ser Glu Pro Leu Arg Val Arg Ala Thr Leu Pro Ile
                20                  25                  30

Pro Ser Ser Lys Gly Ser Val Thr Tyr Asp Glu Val Lys Ser Ile Thr
            35                  40                  45

Gly Thr Phe Asp Gly Gly Met Lys Thr Tyr Gly Arg Gly Val Ser Cys
        50                  55                  60

Thr Gly Gln Lys Glu Gly Gly Asn Lys Asp Ala Val Phe Gln Leu Glu
65                  70                  75                  80

Asp Gly Ala Thr Leu Lys Asn Val Ile Ile Gly Glu Asp Gln Ile Glu
                85                  90                  95

Gly Ile His Cys Met Gly Ser Cys Thr Leu Glu Asn Val Trp Trp Ser
            100                 105                 110

Ala Val Cys Glu Asp Ala Leu Thr Phe Lys Gly Asp Gly Asp Ala Lys
        115                 120                 125

Val Ile Gly Gly Ala Gln Gly Ala Asp Asp Lys Val Leu Gln His
    130                 135                 140

Asn Gly Val Gly Asp Val Thr Ile Asp Gly Phe Thr Val Val Asp Phe
145                 150                 155                 160

Gly Lys Leu Tyr Arg Ser Cys Gly Asn Cys Lys Gln Asn Gly Gly Thr
                165                 170                 175

Arg Asn Val Asn Ile Ser Asn Val Lys Ala Tyr Asn Gly Lys Val Leu
            180                 185                 190

Thr Gly Ile Asn Ser Asn Tyr Gly Asp Val Ala Thr Phe Lys Asp Thr 195                 200                 205
Cys Ala Ser Ser Val Lys Asp Ile Cys Val Glu Tyr Lys Gly Thr Asn
            210                 215                 220

Asn Asn Asp Glu Glu Pro Ser Lys Ile Gly Ser Gly Pro Ser Asp Asn
225                 230                 235                 240

Cys Val Tyr Ser Asp Ile Pro Ser Cys
                245

<210> SEQ ID NO 16
<211> LENGTH: 1238
<212> TYPE: DNA
<213> ORGANISM: M. phaseolina

<400> SEQUENCE: 16

| | | | | | |
|---|---|---|---|---|---|
| ctataaagat | ggagaccagc | cagcttctag | aggcttttcc | ctccaggcaa | gcatcctctc | 60 |
| tccggccatc | actttcattc | tttcgcattc | ttccactctt | ttgtccaact | ccgacccgaa | 120 |
| cagatctgtg | atcgttcact | acactacaca | atgttgacca | agactcttct | tcccctcctc | 180 |
| gccatctctg | gcgccgtctc | tgccgtcaag | accaagacct | tcggcaagaa | cctcgtccgc | 240 |
| cgtgcggact | ccctatccc | tgaatcccag | ggttccgtca | cctttgacgc | cgccgaggag | 300 |
| gtcgatggcg | agtacgacgg | tggctacaag | acgtacggcc | gtggtgtttc | ttgcactggc | 360 |
| caggaggagg | gtggcgactc | tgacgccgtc | ttcatcctga | aggacggtgc | ttccctcaag | 420 |
| aacgccatca | tcggctctga | ccagattgag | ggtgtccact | gcgagggctc | ctgcactctt | 480 |
| gagaacgttt | ggtgggaggc | cgtctgcgag | gacgctctgt | ccttcaaggg | tgacggtgat | 540 |
| gccaccgtca | ctggcggtgg | tgcaactggt | gctgaggaca | aagtcctcca | gcaaaacggt | 600 |
| attggctcca | tcaccgtcga | tggcttcacc | gttgtggact | cggcaagct | gtaccgctct | 660 |
| tgcggtaact | gcgacgagat | gggccagcgc | actgtacgtc | aatgctatcg | ctcattctgt | 720 |
| agggcagaga | gtgctgacat | ggctgtgcga | cttagatcac | cctcaagaac | gtcaaggcct | 780 |
| actccggcaa | gaagcttgtc | ggcatcaact | ccaactacgg | tgacagtgcg | tcatgttcct | 840 |
| ttaggctttc | aacccttgag | ccatgtgcta | atagcatcct | cagctgccac | catcaccgac | 900 |
| acttgcgcga | ccgacgtctc | tgacatttgc | acggagtacg | tagtcactcg | gacgatgggc | 960 |
| ctcaggaacg | aagacactaa | cataattatc | tttacaggta | cgaaggaaac | gataccggag | 1020 |
| acgaacctga | agagatcagc | tccggcccct | ctgatgcctg | catttacagc | gacgttccgg | 1080 |
| agtgctagac | gcacagctcg | aacatgccgc | ctcaaagcaa | gcattctgat | ggagggccag | 1140 |
| ggggtgggaa | gggatttaga | gcctccgaaa | aggtggaagt | gggtttagga | cttcgttgta | 1200 |
| taatataaac | ttgtttccga | aaataagaac | catcctgc | | | 1238 |

<210> SEQ ID NO 17
<211> LENGTH: 756
<212> TYPE: DNA
<213> ORGANISM: M. phaseolina

<400> SEQUENCE: 17

| | | | | | |
|---|---|---|---|---|---|
| atgttgacca | agactcttct | tcccctcctc | gccatctctg | gcgccgtctc | tgccgtcaag | 60 |
| accaagacct | tcggcaagaa | cctcgtccgc | cgtgcggact | ccctatccc | tgaatcccag | 120 |
| ggttccgtca | cctttgacgc | cgccgaggag | gtcgatggcg | agtacgacgg | tggctacaag | 180 |
| acgtacggcc | gtggtgtttc | ttgcactggc | caggaggagg | gtggcgactc | tgacgccgtc | 240 |
| ttcatcctga | aggacggtgc | ttccctcaag | aacgccatca | tcggctctga | ccagattgag | 300 |

```
ggtgtccact gcgagggctc ctgcactctt gagaacgttt ggtgggaggc cgtctgcgag     360
gacgctctgt ccttcaaggg tgacggtgat gccaccgtca ctggcggtgg tgcaactggt     420
gctgaggaca aagtcctcca gcaaaacggt attggctcca tcaccgtcga tggcttcacc     480
gttgtggact tcggcaagct gtaccgctct gcggtaact gcgacgagat gggccagcgc      540
actatcaccc tcaagaacgt caaggcctac tccggcaaga agcttgtcgg catcaactcc     600
aactacggtg acactgccac catcaccgac acttgcgcga ccgacgtctc tgacatttgc     660
acggagtacg aaggaaacga taccggagac gaacctgaag agatcagctc cggcccctct     720
gatgcctgca tttacagcga cgttccggag tgctag                              756
```

<210> SEQ ID NO 18
<211> LENGTH: 251
<212> TYPE: PRT
<213> ORGANISM: M. phaseolina

<400> SEQUENCE: 18

```
Met Leu Thr Lys Thr Leu Leu Pro Leu Leu Ala Ile Ser Gly Ala Val
1               5                   10                  15
Ser Ala Val Lys Thr Lys Thr Phe Gly Lys Asn Leu Val Arg Arg Ala
            20                  25                  30
Asp Phe Pro Ile Pro Glu Ser Gln Gly Ser Val Thr Phe Asp Ala Ala
        35                  40                  45
Glu Val Asp Gly Glu Tyr Asp Gly Gly Tyr Lys Thr Tyr Gly Arg
    50                  55                  60
Gly Val Ser Cys Thr Gly Gln Glu Glu Gly Asp Ser Asp Ala Val
65                  70                  75                  80
Phe Ile Leu Lys Asp Gly Ala Ser Leu Lys Asn Ala Ile Ile Gly Ser
                85                  90                  95
Asp Gln Ile Glu Gly Val His Cys Glu Gly Ser Cys Thr Leu Glu Asn
            100                 105                 110
Val Trp Trp Glu Ala Val Cys Glu Asp Ala Leu Ser Phe Lys Gly Asp
        115                 120                 125
Gly Asp Ala Thr Val Thr Gly Gly Ala Thr Gly Ala Glu Asp Lys
    130                 135                 140
Val Leu Gln Gln Asn Gly Ile Gly Ser Ile Thr Val Asp Gly Phe Thr
145                 150                 155                 160
Val Val Asp Phe Gly Lys Leu Tyr Arg Ser Cys Gly Asn Cys Asp Glu
                165                 170                 175
Met Gly Gln Arg Thr Ile Thr Leu Lys Asn Val Lys Ala Tyr Ser Gly
            180                 185                 190
Lys Lys Leu Val Gly Ile Asn Ser Asn Tyr Gly Asp Thr Ala Thr Ile
        195                 200                 205
Thr Asp Thr Cys Ala Thr Asp Val Ser Asp Ile Cys Thr Glu Tyr Glu
    210                 215                 220
Gly Asn Asp Thr Gly Asp Glu Pro Glu Glu Ile Ser Ser Gly Pro Ser
225                 230                 235                 240
Asp Ala Cys Ile Tyr Ser Asp Val Pro Glu Cys
                245                 250
```

<210> SEQ ID NO 19
<211> LENGTH: 1245
<212> TYPE: DNA
<213> ORGANISM: M. phaseolina

<400> SEQUENCE: 19

```
ggttcacctc atcaactcgc ttcttcattc gttccttgct gtgcaagaca ccatccagac    60
ggacattcca ttacaacggt ctttgatagc caatccaact ttgtctactc cctgcctctc   120
catcctaccc taccaataag cccatccaaa atgcagtaca gcatccgctc gctcgccttc   180
ggcctcgccg ccctggccgt ctccaccgac gctttcatgg ttccccgtga ccctagcaag   240
ggctggggct tccccaacgc caacaacgct cgcgttgctg ctgccgccgc ctccactcct   300
gtccagaccc ccggcaacac ccctaccact cccgtggcca cccctggtgt cactggcggc   360
gccactgccg ccgctggctt ccccgcctcg tccggcacca gccagctcag cgcccccatg   420
accgtcaccg gcagcttcga cggtggcatg aaggccttcg gcgcggtgt ctcctgcact    480 ggccaggctg agggtggcga cagcgacgct gtcttcatga tcgaggaggg cggtactctc   540
tccaacgtca tcatcgccgc cgatcagatc gagggtgtcc actgcttcgg ttcctgcact   600
ctcaagaacg tctggtgggt cgccgtctgc gaggacgctt tcaccatcaa ggagcagggc   660
gcctctggca ctacccacat catcggcggt ggtgctcagg gcgccgaaga caaggttctc   720
cagcacaacg gcggcggcac tctcgctgtc tctggcttcc tcgccaagga cttcggtaag   780
ctctaccgca gctgcggcaa ctgcgacgag atgcccgagc gccacgttac catcgacggc   840
gttaccgctg agtctggtga catcctggtc ggcatcaact ccaacatggg cgacagtaag   900
taactcctga ttttgcaagc gatgaggcaa tgctaacaat gcgcagctgc taccatcacc   960
aacacctgcg ccaccggcgt cgagaccatc tgccaggagt tcaacggtgt cacggacggc  1020
agcgagcccg aggctgccgg cagcggccct agcactgctt gcaagtacac tgccgctgac  1080
gcccaggcct gctaagcaca tccctttctt gattgaccag taaaagttcg acggccacac  1140
ggttgggtaa tgcagggatt ggcaaaatgt ccgtccggca taattagcac ttctttgatg  1200
tagatattgg gccgggtgtc cacaatgtat aactctgaca tgtca                  1245
```

<210> SEQ ID NO 20
<211> LENGTH: 894
<212> TYPE: DNA
<213> ORGANISM: M. phaseolina

<400> SEQUENCE: 20

```
atgcagtaca gcatccgctc gctcgccttc ggcctcgccg ccctggccgt ctccaccgac    60
gctttcatgg ttccccgtga ccctagcaag ggctggggct tccccaacgc caacaacgct   120
cgcgttgctg ctgccgccgc ctccactcct gtccagaccc ccggcaacac ccctaccact   180
cccgtggcca cccctggtgt cactggcggc gccactgccg ccgctggctt ccccgcctcg   240
tccggcacca gccagctcag cgcccccatg accgtcaccg gcagcttcga cggtggcatg   300
aaggccttcg gcgcggtgt ctcctgcact ggccaggctg agggtggcga cagcgacgct    360
gtcttcatga tcgaggaggg cggtactctc tccaacgtca tcatcgccgc cgatcagatc   420
gagggtgtcc actgcttcgg ttcctgcact ctcaagaacg tctggtgggt cgccgtctgc   480
gaggacgctt tcaccatcaa ggagcagggc gcctctggca ctacccacat catcggcggt   540
ggtgctcagg gcgccgaaga caaggttctc cagcacaacg gcggcggcac tctcgctgtc   600
tctggcttcc tcgccaagga cttcggtaag ctctaccgca gctgcggcaa ctgcgacgag   660
atgcccgagc gccacgttac catcgacggc gttaccgctg agtctggtga catcctggtc   720
ggcatcaact ccaacatggg cgacactgct accatcacca acacctgcgc caccggcgtc   780
gagaccatct gccaggagtt caacggtgtc acggacggca gcgagcccga ggctgccggc   840
```
agcggcccta gcactgcttg caagtacact gccgctgacg cccaggcctg ctaa 894

<210> SEQ ID NO 21
<211> LENGTH: 297
<212> TYPE: PRT
<213> ORGANISM: M. phaseolina

<400> SEQUENCE: 21

```
Met Gln Tyr Ser Ile Arg Ser Leu Ala Phe Gly Leu Ala Ala Leu Ala
1               5                   10                  15

Val Ser Thr Asp Ala Phe Met Val Pro Arg Asp Pro Ser Lys Gly Trp
            20                  25                  30

Gly Phe Pro Asn Ala Asn Asn Ala Arg Val Ala Ala Ala Ala Ala Ser
        35                  40                  45

Thr Pro Val Gln Thr Pro Gly Asn Thr Pro Thr Pro Val Ala Thr
    50                  55                  60

Pro Gly Val Thr Gly Gly Ala Thr Ala Ala Gly Phe Pro Ala Ser
65              70                  75                  80

Ser Gly Thr Ser Gln Leu Ser Ala Pro Met Thr Val Thr Gly Ser Phe
                85                  90                  95

Asp Gly Gly Met Lys Ala Phe Gly Arg Gly Val Ser Cys Thr Gly Gln
            100                 105                 110

Ala Glu Gly Gly Asp Ser Asp Ala Val Phe Met Ile Glu Glu Gly Gly
        115                 120                 125

Thr Leu Ser Asn Val Ile Ile Ala Ala Asp Gln Ile Glu Gly Val His
    130                 135                 140

Cys Phe Gly Ser Cys Thr Leu Lys Asn Val Trp Trp Val Ala Val Cys
145                 150                 155                 160

Glu Asp Ala Phe Thr Ile Lys Glu Gln Gly Ala Ser Gly Thr Thr His
                165                 170                 175

Ile Ile Gly Gly Gly Ala Gln Gly Ala Glu Asp Lys Val Leu Gln His
            180                 185                 190

Asn Gly Gly Gly Thr Leu Ala Val Ser Gly Phe Leu Ala Lys Asp Phe
        195                 200                 205

Gly Lys Leu Tyr Arg Ser Cys Gly Asn Cys Asp Glu Met Pro Glu Arg
    210                 215                 220

His Val Thr Ile Asp Gly Val Thr Ala Glu Ser Gly Asp Ile Leu Val
225                 230                 235                 240

Gly Ile Asn Ser Asn Met Gly Asp Thr Ala Thr Ile Thr Asn Thr Cys
                245                 250                 255

Ala Thr Gly Val Glu Thr Ile Cys Gln Glu Phe Asn Gly Val Thr Asp
            260                 265                 270

Gly Ser Glu Pro Glu Ala Ala Gly Ser Gly Pro Ser Thr Ala Cys Lys
        275                 280                 285

Tyr Thr Ala Ala Asp Ala Gln Ala Cys
    290                 295
```

<210> SEQ ID NO 22
<211> LENGTH: 1047
<212> TYPE: DNA
<213> ORGANISM: M. phaseolina

<400> SEQUENCE: 22
gaatggtata aagagcggtg ggatatccat cattgagctc atcaccaacc cacaattact 60
ttcgttctac actcctctcg tttacacaac ggatcactga tctaccacat tcgctcttac 120

```
caaagatcct gtctaccaac catctacaac atgcagttca agtacgccgc tctcgctgcc      180
gccctggccg ccgtcggctc cacgcagagc ctccccatcc ccgcctcccg cggagttgat      240
cccaacaagg gccaaaggat cgtcaagccc ggcaatcctt tcgacggcgg gatgaaggag      300
tttggccgtg gtgtcgtctg caacgacaag gccgacactg gcgtcaggaa cgccgtcttc      360
gtcatcgagg acggcggtgt tctgcgcaac gccatcatcg gcgccgacgc cgtcgagggc      420
atccactgcg agggcaagtg caccatcgag aacgtctggt tccgcgacgt gtgcgaggac      480
gccatcacgc tgaagggcaa cggcccttac accatcactg gcggcggcgc ccagaacgcc      540
ggcgacaagg tcatccagca caacggcaag ggcgagctgc gcatctcaaa ctaccaggtc      600
aacaacgtcg gcaagctgtt ccgcacctgc ggcaactgca gcaacaacgg cggcccgcgc      660
agcatcgtcg ccaccggcat cagggccttc ggcgtcacca gcgacctcat cggcatcaac      720
tccaactacg gcgacaaggc ctccatcacc ggctcctgcg gcaacaccaa gacggtctgc      780
caggaatatg tcggcatcga agggcgcc aacggcggga aggacagcga agagggtc       840 ccgccggtcg gcgcttgcac cggccagggc ggtctcgcca ggctcccttc ctgctagacg      900
cctcgcggaa tcttgcgctg agtatgggat gggaggaatg gattgaccgc tcagttttgg      960
gatccgtgcg aacagtcggg aacttcgcaa ctgcctcatc cgtcaagagg tgtgggcccc     1020
tgccggacag gatgaaacgc gtttatg                                          1047

<210> SEQ ID NO 23
<211> LENGTH: 747
<212> TYPE: DNA
<213> ORGANISM: M. phaseolina

<400> SEQUENCE: 23
atgcagttca agtacgccgc tctcgctgcc gccctggccg ccgtcggctc cacgcagagc       60
ctccccatcc ccgcctcccg cggagttgat cccaacaagg gccaaaggat cgtcaagccc      120
ggcaatcctt tcgacggcgg gatgaaggag tttggccgtg gtgtcgtctg caacgacaag      180
gccgacactg gcgtcaggaa cgccgtcttc gtcatcgagg acggcggtgt tctgcgcaac      240
gccatcatcg gcgccgacgc cgtcgagggc atccactgcg agggcaagtg caccatcgag      300
aacgtctggt tccgcgacgt gtgcgaggac gccatcacgc tgaagggcaa cggcccttac      360
accatcactg gcggcggcgc ccagaacgcc ggcgacaagg tcatccagca caacggcaag      420
ggcgagctgc gcatctcaaa ctaccaggtc aacaacgtcg gcaagctgtt ccgcacctgc      480
ggcaactgca gcaacaacgg cggcccgcgc agcatcgtcg ccaccggcat cagggccttc      540
ggcgtcacca gcgacctcat cggcatcaac tccaactacg gcgacaaggc ctccatcacc      600
ggctcctgcg gcaacaccaa gacggtctgc caggaatatg tcggcatcga agggcgcc       660 aacggcggga aggacagcga agagggtc ccgccggtcg gcgcttgcac cggccagggc       720
ggtctcgcca ggctcccttc ctgctag                                          747

<210> SEQ ID NO 24
<211> LENGTH: 248
<212> TYPE: PRT
<213> ORGANISM: M. phaseolina

<400> SEQUENCE: 24

Met Gln Phe Lys Tyr Ala Ala Leu Ala Ala Ala Leu Ala Ala Val Gly
1               5                   10                  15

Ser Thr Gln Ser Leu Pro Ile Pro Ala Ser Arg Gly Val Asp Pro Asn
            20                  25                  30
```

```
Lys Gly Gln Arg Ile Val Lys Pro Gly Asn Pro Phe Asp Gly Gly Met
         35                  40                  45

Lys Glu Phe Gly Arg Gly Val Val Cys Asn Asp Lys Ala Asp Thr Gly
 50                  55                  60

Val Arg Asn Ala Val Phe Val Ile Glu Asp Gly Val Leu Arg Asn
 65                  70                  75                  80

Ala Ile Ile Gly Ala Asp Ala Val Glu Gly Ile His Cys Glu Gly Lys
                 85                  90                  95

Cys Thr Ile Glu Asn Val Trp Phe Arg Asp Val Cys Glu Asp Ala Ile
            100                 105                 110

Thr Leu Lys Gly Asn Gly Pro Tyr Thr Ile Thr Gly Gly Ala Gln
        115                 120                 125

Asn Ala Gly Asp Lys Val Ile Gln His Asn Gly Lys Gly Glu Leu Arg
    130                 135                 140

Ile Ser Asn Tyr Gln Val Asn Asn Val Gly Lys Leu Phe Arg Thr Cys
145                 150                 155                 160

Gly Asn Cys Ser Asn Asn Gly Gly Pro Arg Ser Ile Val Ala Thr Gly
                165                 170                 175

Ile Arg Ala Phe Gly Val Thr Ser Asp Leu Ile Gly Ile Asn Ser Asn
            180                 185                 190

Tyr Gly Asp Lys Ala Ser Ile Thr Gly Ser Cys Gly Asn Thr Lys Thr
        195                 200                 205

Val Cys Gln Glu Tyr Val Gly Ile Glu Lys Gly Ala Asn Gly Gly Lys
    210                 215                 220

Asp Ser Glu Lys Arg Val Pro Pro Val Gly Ala Cys Thr Gly Gln Gly
225                 230                 235                 240

Gly Leu Ala Arg Leu Pro Ser Cys
                245

<210> SEQ ID NO 25
<211> LENGTH: 2495
<212> TYPE: DNA
<213> ORGANISM: M. phaseolina

<400> SEQUENCE: 25
gtttggtgcg tgggaacgca tttaacggtg gatgaatcga tccaaggctt ccaaggcaga      60
gcctccgaaa cagtcaatat tccatccaaa ccaacgccta ttggattcaa gatttgggca    120
ctttgtaacg aggcttttt ggttgattgg atgttccatt caaatggcga aggaccgtgg    180
gatcttgaca gtattacac cgacgaacag tacgaaatta acctcacaca gacggctgca    240
gtggtgcccg atttggtggc tcagttatgc ccacatgagc tgccatttga cagcccaaaa    300
tacatcgttt ggatagacaa tctgcttact tctgcgcggc ttatgacaac gctccggaac    360
gagaatattg gcgctgcagg gactgttcga atgggcaaga cacagcgtga agaatgaa      420
gagaaggcag ctagcaaaaa gaagcaagcc accaagaag ataaccgtgg tttacaccaa    480
aggcttcgag atttgaggtc aaaaaatgaa ggacagatcg aatggggcac gcagtattgc    540
tgtctatcac aggacgagca gtcaatgcaa tttggctggc aggatgcaag aattgtgcta    600
ttcatgagca ctgttcatga cggtaaacaa tgggtgattc gacgacgacg gcggcccaca    660
aagacctcca ccaattcgaa gatcactcag aagccatttg gtgataacgt ggaacaagat    720
atggagattc cgaggtgggc agacgagtac aatcacaaca gaatgcggt tgaccgtttt    780
gaccaattca aagccgaacg ccaaatcaat cgactttgtt atcgaacatg gaagcctctt    840
```

| | |
|---|---|
| tggaacttcc tcttccaatc atcgatcatc agtgcatatc tgctcacttg tagaggcttg | 900 |
| gatgacgatg agaaacctcc attcgcgtcc ctgaacgcat tccgccagag gctttgggag | 960 |
| cagctctttg aacgctcaga acgcgttgac ggacgccgtg gacgagcaga gcctcgttat | 1020 |
| cgtgagattc cacgcgaaga acatcaatat gagaggctta aggtccaagg gaactgcagt | 1080 |
| gaatgtatgg ctaacatgcg caaatcaacg cgtattcgaa ggccacttgc agagcgttcc | 1140 |
| accaacattc ggccaccaag gccaaggtgg ggctgtgggc tatgtaatct gaatctttgt | 1200 |
| gaaggcattt gcttcaaaaa tcacttgaat cgggtgatag gaagcagttg aatttgatgt | 1260 |
| ggaagttggg ctcgatttgg tcgcgaattc gtcgcgattt agatctaaaa caccaagatt | 1320 |
| tgggccgtaa atcgaatata tataaatgca aatagactca tttgaatttg acagcttatg | 1380 |
| cgacctcaaa acactacgtt ttagttgaat tattgcgatt attgggctgc gaaaagcccc | 1440 |
| tgatgacttt ggtgttctga cccctgtcac caccctgtc gctctcaagc tctccataga | 1500 |
| ttgagagcat atccagccta cgaagggata ccactgcccc ctcctggcgg cttccgccct | 1560 |
| ggctgctcct gccgacgaca ctttcggcta cgagctcgtt cgccgtgcga acttccctat | 1620 |
| tcctgcctcc aagggcaccg tcaagtacag cgctgccaag tccatctccg gcactttcga | 1680 |
| tggtggcctg aagaccctac agccgtggtg tcaagtgcat cggtcaggct gagggcggtg | 1740 |
| acaaaaaagc cgtcttcatc cctgaggacg gtgctagcct caagagcgcc atcactggca | 1800 |
| ccgagcagat cgagggcgtc cactgcaagg ggctcctgca ctatcgagaa cgtctggtgg | 1860 |
| gctggtgtct gcgaggatgc tctctccctc aagggcaacg gcaacgccaa gatcattggt | 1920 |
| ggcggtgcca ctggtgccga agacaagggt aagctctctt ctgcaagagc gttgcgatcg | 1980 |
| gatttctaac actctctggt gcaggtcatc cagcaccggt tttggatccg tctctattga | 2040 |
| cggcttcact gttgccgatt tcggcaagct ctaccgctct tgcggaaact gcaagaagca | 2100 |
| gggcaagaga actgtcacca tcaagaatgt caaggcatca tccggcaagc tgctcgctgg | 2160 |
| tatcaactcc aactacggcg acactgctac catcaccggc acctgcgctg cctccgtcaa | 2220 |
| gaagatctgc accgagttca tgggcaacaa cagcggcaag gagcccagtg tggttttcaa | 2280 |
| tctcgatctt atcaatctta tcaatcgatc cctatcaatc gatatcaagt ccatcatgga | 2340 |
| attgaattga cgattgataa ggatcgacag cctcctggtt gccctgccaa acgccaccaa | 2400 |
| acaaacgcca taaacacgc ccgcaggag ccgcaggacc cgaaatgcat caaacagtcc | 2460 |
| tcttctattg cattatcaat tatcgggcat ggatg | 2495 |

<210> SEQ ID NO 26
<211> LENGTH: 1707
<212> TYPE: DNA
<213> ORGANISM: M. phaseolina

<400> SEQUENCE: 26

| | |
|---|---|
| atgttccatt caaatggcga aggaccgtgg gatcttgacg agtattacac cgacgaacag | 60 |
| tacgaaatta acctcacaca gacggctgca gtggtgcccg atttggtggc tcagttatgc | 120 |
| ccacatgagc tgccatttga cagcccaaaa tacatcgttt ggatagacaa tctgcttact | 180 |
| tctgcgcggc ttatgacaac gctccggaac gagaatattg gcgctgcagg gactgttcga | 240 |
| atgggcaaga cacagcgtga agaatgaa gagaaggcag ctagcaaaaa gaagcaagcc | 300 |
| accaaagaag ataaccgtgg tttacaccaa aggcttcgag atttgaggtc aaaaaatgaa | 360 |
| ggacagatcg aatggggcac gcagtattgc tgtctatcac aggacgagca gtcaatgcaa | 420 |
| tttggctggc aggatgcaag aattgtgcta ttcatgagca ctgttcatga cggtaaacaa | 480 |

```
tgggtgattc gacgacgacg gcggcccaca aagacctcca ccaattcgaa gatcactcag    540
aagccatttg gtgataacgt ggaacaagat atggagattc gaggtgggc agacgagtac     600 aatcacaaca agaatgcggt tgaccgtttt gaccaattca agccgaacg ccaaatcaat     660 cgactttgtt atcgaacatg gaagcctctt tggaacttcc tcttccaatc atcgatcatc    720
agtgcatatc tgctcacttg tagaggcttg gatgacgatg agaaacctcc attcgcgtcc    780
ctgaacgcat tccgccagag gctttgggag cagctctttg aacgctcaga acgcgttgac    840
ggacgccgtg gacgagcaga gcctcgttat cgtgagattc cacgcgaaga acatcaatat    900
gagaggctta aggtccaagg gaactgcagt gaatcctacg aagggatacc actgcccct    960 cctggcggct tccgccctgg ctgctcctgc cgacgacact ttcggctacg agctcgttcg    1020
ccgtgcgaac ttccctattc ctgcctccaa gggcaccgtc aagtacagcg ctgccaagtc    1080
catctccggc actttcgatg gtggcctgaa gaccctacag ccgtggtgtc aagtgcatcg    1140
gtcaggctga gggcggtgac aaaaaagccg tcttcatccc tgaggacggt gctagcctca    1200
agagcgccat cactggcacc gagcagatcg agggcgtcca ctgcaagggg ctcctgcact    1260
atcgagaacg tctggtgggc tggtgtctgc gaggatgctc tctccctcaa gggcaacggc    1320
aacgccaaga tcattggtgg cggtgccact ggtgccgaag acaagggtca tccagcaccg    1380
gttttggatc cgtctctatt gacggcttca ctgttgccga tttcggcaag ctctaccgct    1440
cttgcggaaa ctgcaagaag cagggcaaga gaactgtcac catcaagaat gtcaaggcat    1500
catccggcaa gctgctcgct ggtatcaact ccaactacgg cgacactgct accatcaccg    1560
gcacctgcgc tgcctccgtc aagaagatct gcaccgagtt catgggcaac aacagcggca    1620
aggagcccag tgtggttttc aatctcgatc ttatcaatct tatcaatcga tccctatcaa    1680
tcgatatcaa gtccatcatg gaattga                                        1707
```

<210> SEQ ID NO 27
<211> LENGTH: 568
<212> TYPE: PRT
<213> ORGANISM: M. phaseolina

<400> SEQUENCE: 27

```
Met Phe His Ser Asn Gly Glu Gly Pro Trp Asp Leu Asp Glu Tyr Tyr
1               5                   10                  15

Thr Asp Glu Gln Tyr Glu Ile Asn Leu Thr Gln Thr Ala Ala Val Val
                20                  25                  30

Pro Asp Leu Val Ala Gln Leu Cys Pro His Glu Leu Pro Phe Asp Ser
            35                  40                  45

Pro Lys Tyr Ile Val Trp Ile Asp Asn Leu Leu Thr Ser Ala Arg Leu
        50                  55                  60

Met Thr Thr Leu Arg Asn Glu Asn Ile Gly Ala Ala Gly Thr Val Arg
65                  70                  75                  80

Met Gly Lys Thr Gln Arg Glu Lys Asn Glu Lys Ala Ala Ser Lys
                85                  90                  95

Lys Lys Gln Ala Thr Lys Glu Asp Asn Arg Gly Leu His Gln Arg Leu
            100                 105                 110

Arg Asp Leu Arg Ser Lys Asn Glu Gly Gln Ile Glu Trp Gly Thr Gln
        115                 120                 125

Tyr Cys Cys Leu Ser Gln Asp Glu Gln Ser Met Gln Phe Gly Trp Gln
    130                 135                 140

Asp Ala Arg Ile Val Leu Phe Met Ser Thr Val His Asp Gly Lys Gln
```

-continued

```
            145                 150                 155                 160
        Trp Val Ile Arg Arg Arg Arg Pro Thr Lys Thr Ser Thr Asn Ser
                        165                 170                 175
        Lys Ile Thr Gln Lys Pro Phe Gly Asp Asn Val Glu Gln Asp Met Glu
                        180                 185                 190
        Ile Pro Arg Trp Ala Asp Glu Tyr Asn His Asn Lys Asn Ala Val Asp
                        195                 200                 205
        Arg Phe Asp Gln Phe Lys Ala Glu Arg Gln Ile Asn Arg Leu Cys Tyr
                        210                 215                 220
        Arg Thr Trp Lys Pro Leu Trp Asn Phe Leu Phe Gln Ser Ser Ile Ile
        225                 230                 235                 240
        Ser Ala Tyr Leu Leu Thr Cys Arg Gly Leu Asp Asp Glu Lys Pro
                        245                 250                 255
        Pro Phe Ala Ser Leu Asn Ala Phe Arg Gln Arg Leu Trp Glu Gln Leu
                        260                 265                 270
        Phe Glu Arg Ser Glu Arg Val Asp Gly Arg Arg Gly Arg Ala Glu Pro
                        275                 280                 285
        Arg Tyr Arg Glu Ile Pro Arg Glu His Gln Tyr Glu Arg Leu Lys
        290                 295                 300
        Val Gln Gly Asn Cys Ser Glu Ser Tyr Glu Gly Ile Pro Leu Pro Pro
        305                 310                 315                 320
        Pro Gly Gly Phe Arg Pro Gly Cys Ser Cys Arg Arg His Phe Arg Leu
                        325                 330                 335
        Arg Ala Arg Ser Pro Cys Glu Leu Pro Tyr Ser Cys Leu Gln Gly His
                        340                 345                 350
        Arg Gln Val Gln Arg Cys Gln Val His Leu Arg His Phe Arg Trp Trp
                        355                 360                 365
        Pro Glu Asp Pro Thr Ala Val Val Ser Ser Ala Ser Val Arg Leu Arg
                        370                 375                 380
        Ala Val Thr Lys Lys Pro Ser Ser Ser Leu Arg Thr Val Leu Ala Ser
        385                 390                 395                 400
        Arg Ala Pro Ser Leu Ala Pro Ser Arg Ser Arg Ala Ser Thr Ala Arg
                        405                 410                 415
        Gly Ser Cys Thr Ile Glu Asn Val Trp Trp Ala Gly Val Cys Glu Asp
                        420                 425                 430
        Ala Leu Ser Leu Lys Gly Asn Gly Asn Ala Lys Ile Ile Gly Gly Gly
                        435                 440                 445
        Ala Thr Gly Ala Glu Asp Lys Gly His Pro Ala Pro Val Leu Asp Pro
                        450                 455                 460
        Ser Leu Leu Thr Ala Ser Leu Leu Pro Ile Ser Ala Ser Ser Thr Ala
        465                 470                 475                 480
        Leu Ala Glu Thr Ala Arg Ser Arg Ala Arg Glu Leu Ser Pro Ser Arg
                        485                 490                 495
        Met Ser Arg His His Pro Ala Ser Cys Ser Leu Val Ser Thr Pro Thr
                        500                 505                 510
        Thr Ala Thr Leu Leu Pro Ser Pro Ala Pro Ala Leu Pro Pro Ser Arg
                        515                 520                 525
        Arg Ser Ala Pro Ser Ser Trp Ala Thr Thr Ala Ala Arg Ser Pro Val
                        530                 535                 540
        Trp Phe Ser Ile Ser Ile Leu Ser Ile Leu Ser Ile Asp Pro Tyr Gln
        545                 550                 555                 560
        Ser Ile Ser Ser Pro Ser Trp Asn
                        565
```

<210> SEQ ID NO 28
<211> LENGTH: 1922
<212> TYPE: DNA
<213> ORGANISM: M. phaseolina

<400> SEQUENCE: 28

```
caagatgtgc ttttgctctc caggacattc ctctccatcc ctcgtttcca atcactttca      60
gtctttgcca ctccttcgct gtccactgta gtccggaact acatcagtaa accaccttct     120
tttccaacag accccatcac atccgccaaa atggtcaaca ttgctgccgt ctgccgcgct     180
gcggctttct ttcttcctgt cctcgccgcc gcccagagcg gtgtcgttgg tacccctccc     240
ggtttcgccg ccggcaccac tggtggtggt gacgctgccg ccgccgctcc ctccgacgtt     300
gctgagctca tctcttggct tgaggatgag actccccgtg tcatcctcat cgacaaggag     360
ttcaacttcc tcggcacgga gggcaccaag agcgatcagg gctgccgtcc cgacagcaac     420
aagtgccctg gcaagggtgg ccaggatgcc atcaaccagg ccaactggtg cgacaacggc     480
aacgctggcg agggtgtctc ggccgtcacc gtcaagtacg accaggctgc gctcaagggc     540
atcgctgtca agagcaacaa gtccatcgtc ggtgttggcg acaagggtgt cctcaagggc     600
aagggcctca gcctgactgg tggcgttgag aacgttatca tccagaacat ccacatcacc     660
gacctgaacc ccgagtacat ctggggtggt gatgccatca cgctcgctgg ttccgacaag     720
gtctggagta agtacttccg aactgtttcg atcccatacg gttggccttg aaacccaaat     780
cgggaaacgc actataccca atatggcaat tttctacgaa catcgagaca ccgcagcaga     840
acacgagttt cacgccattg cttgtttctg tggctgtcaa tgctgtctcg aagtccctgt     900
atgctgtttg gcttgatgcg ctagtgcgtt tcctgagaga ggtgcccacc acaccatcat     960
gccccaagct cccttacccc tttcccagca tcccacatca tgctatatcc tttactatgc    1020
tttcaacagt aaaactaacg cccgaaacgt cgatcatgtc aaaatttctc tcgtcggtcg    1080
ccagatgatc gttaccggct acgacaaggc cggtagggtc acgatctcca actccgagtt    1140
cgacggccag accgactggt ccgcctcctg caacggcgaa cactactgga ccgtcctcgt    1200
gtacggtgcc gacgaccaga tcaccttcgc aaacaactac atgcacgaca cctcgggccg    1260
ttcgcccaag atcggtggtg ccgacggcgc tggcatcacc ttccacgcgg tcaacaacgt    1320
cttccagacc aacaagggcc ataacttcga catcggctcc ggtgccgagg ttttgctcga    1380
gggtaacacc ttcaacgagt gcaaccagcc catcacctcc aagtcggcca acgagggcgg    1440
cgccatcttc aacacccct ccggctccga gagctcctgc tccagctacc tcaagcgcgc    1500
ctgccaggcc aacactctca ccagctccgg tgacttcggc acttacaagg acacctcggt    1560
tctcgagggc ttcaacggcg ccacctccat ctgggaggcc gtcagcgctg aggaggctgc    1620
tgcgtccgtc atcgccaacg ccggtattgg caagctccag ggcggtgcta gcaactccac    1680
tgccaagttc agtatgtctt ctcccttcaa ccctgtatca caggagacat gtactaataa    1740
ttctctcctc tgcagggcgc ttccaatcct agattaataa gcacgatcga ccgaatacta    1800
gcatcagtac ggttttaga taaaaaggga tctgtctggt ttactgtaga tatttagcct    1860
tccttctttt ggcttcacat attttaact ttacagccca agaggctca atgcaaatac    1920
tt                                                                   1922
```

<210> SEQ ID NO 29
<211> LENGTH: 1314
<212> TYPE: DNA

<213> ORGANISM: M. phaseolina

<400> SEQUENCE: 29

```
atggtcaaca ttgctgccgt ctgccgcgct gcggctttct ttcttcctgt cctcgccgcc      60
gcccagagcg gtgtcgttgg taccccttcc ggtttcgccg ccggcaccac tggtggtggt     120
gacgctgccg ccgccgctcc ctccgacgtt gctgagctca tctcttggct tgaggatgag     180
actccccgtg tcatcctcat cgacaaggag ttcaacttcc tcggcacgga gggcaccaag     240
agcgatcagg gctgccgtcc cgacagcaac aagtgccctg gcaagggtgg ccaggatgcc     300
atcaaccagg ccaactggtg cgacaacggc aacgctggcg agggtgtctc ggccgtcacc     360
gtcaagtacg accaggctgc gctcaagggc atcgctgtca gagcaacaa gtccatcgtc      420
ggtgttggcg acaagggtgt cctcaagggc aagggcctca gcctgactgg tggcgttgag     480
aacgttatca tccagaacat ccacatcacc gacctgaacc ccgagtacat ctgggtggt      540
gatgccatca cgctcgctgg ttccgacaag gtctggatgc gtttcctgag agagcatccc     600
acatcatgct atatccttta ctatgctttc aacagtaaaa ctaacgcccg aaacgtcgat     660
catgtcaaaa tttctctcgt cggtcgccag atgatcgtta ccggctacga caaggccggt     720
agggtcacga tctccaactc cgagttcgac ggccagaccg actggtccgc ctcctgcaac     780
ggcgaacact actggaccgt cctcgtgtac ggtgccgacg accagatcac cttcgcaaac     840
aactacatgc acgacacctc gggccgttcg cccaagatcg tggtgccga cggcgctggc      900
atcaccttcc acgcggtcaa caacgtcttc cagaccaaca agggccataa cttcgacatc     960
ggctccggtg ccgaggtttt gctcgagggt aacaccttca cgagtgcaa ccagcccatc     1020
acctccaagt cggccaacga gggcggcgcc atcttcaaca cccctccgg ctccgagagc     1080
tcctgctcca gctacctcaa gcgcgcctgc caggccaaca ctctcaccag ctccggtgac     1140
ttcggcactt acaaggacac ctcggttctc gagggcttca cggcgccac ctccatctgg     1200
gaggccgtca cgctgagga ggctgctgcg tccgtcatcg ccaacgccgg tattggcaag     1260
ctccagggcg gtgctagcaa ctccactgcc aagttcaggc gcttccaatc ctag          1314
```

<210> SEQ ID NO 30
<211> LENGTH: 437
<212> TYPE: PRT
<213> ORGANISM: M. phaseolina

<400> SEQUENCE: 30

```
Met Val Asn Ile Ala Ala Val Cys Arg Ala Ala Phe Phe Leu Pro
1               5                   10                  15

Val Leu Ala Ala Ala Gln Ser Gly Val Val Gly Thr Pro Ser Gly Phe
            20                  25                  30

Ala Ala Gly Thr Thr Gly Gly Asp Ala Ala Ala Ala Pro Ser
        35                  40                  45

Asp Val Ala Glu Leu Ile Ser Trp Leu Glu Asp Glu Thr Pro Arg Val
    50                  55                  60

Ile Leu Ile Asp Lys Glu Phe Asn Phe Leu Gly Thr Glu Gly Thr Lys
65                  70                  75                  80

Ser Asp Gln Gly Cys Arg Pro Asp Ser Asn Lys Cys Pro Gly Lys Gly
                85                  90                  95

Gly Gln Asp Ala Ile Asn Gln Ala Asn Trp Cys Asp Asn Gly Asn Ala
            100                 105                 110

Gly Glu Gly Val Ser Ala Val Thr Val Lys Tyr Asp Gln Ala Ala Leu
        115                 120                 125
```

Lys Gly Ile Ala Val Lys Ser Asn Lys Ser Ile Val Gly Val Gly Asp
    130                 135                 140

Lys Gly Val Leu Lys Gly Lys Gly Leu Ser Leu Thr Gly Gly Val Glu
145                 150                 155                 160

Asn Val Ile Ile Gln Asn Ile His Ile Thr Asp Leu Asn Pro Glu Tyr
                165                 170                 175

Ile Trp Gly Gly Asp Ala Ile Thr Leu Ala Gly Ser Asp Lys Val Trp
            180                 185                 190

Met Arg Phe Leu Arg Glu His Pro Thr Ser Cys Tyr Ile Leu Tyr Tyr
        195                 200                 205

Ala Phe Asn Ser Lys Thr Asn Ala Arg Asn Val Asp His Val Lys Ile
    210                 215                 220

Ser Leu Val Gly Arg Gln Met Ile Val Thr Gly Tyr Asp Lys Ala Gly
225                 230                 235                 240

Arg Val Thr Ile Ser Asn Ser Glu Phe Asp Gly Gln Thr Asp Trp Ser
                245                 250                 255

Ala Ser Cys Asn Gly Glu His Tyr Trp Thr Val Leu Val Tyr Gly Ala
            260                 265                 270

Asp Asp Gln Ile Thr Phe Ala Asn Asn Tyr Met His Asp Thr Ser Gly
        275                 280                 285

Arg Ser Pro Lys Ile Gly Gly Ala Asp Gly Ala Gly Ile Thr Phe His
    290                 295                 300

Ala Val Asn Asn Val Phe Gln Thr Asn Lys Gly His Asn Phe Asp Ile
305                 310                 315                 320

Gly Ser Gly Ala Glu Val Leu Leu Glu Gly Asn Thr Phe Asn Glu Cys
                325                 330                 335

Asn Gln Pro Ile Thr Ser Lys Ser Ala Asn Glu Gly Gly Ala Ile Phe
            340                 345                 350

Asn Thr Pro Ser Gly Ser Glu Ser Ser Cys Ser Ser Tyr Leu Lys Arg
        355                 360                 365

Ala Cys Gln Ala Asn Thr Leu Thr Ser Ser Gly Asp Phe Gly Thr Tyr
    370                 375                 380

Lys Asp Thr Ser Val Leu Glu Gly Phe Asn Gly Ala Thr Ser Ile Trp
385                 390                 395                 400

Glu Ala Val Ser Ala Glu Glu Ala Ala Ser Val Ile Ala Asn Ala
                405                 410                 415

Gly Ile Gly Lys Leu Gln Gly Gly Ala Ser Asn Ser Thr Ala Lys Phe
            420                 425                 430

Arg Arg Phe Gln Ser
        435

<210> SEQ ID NO 31
<211> LENGTH: 1326
<212> TYPE: DNA
<213> ORGANISM: M. phaseolina

<400> SEQUENCE: 31
accaatcgtc acagatccgc tggacacgat gcagcgtgca catatagatc ggctccgcag      60
cgttaatgct gtcctccagc agcagcctca actttctctt cacctttctc ttcacctttc     120
tcttcaccac cagcccagcc caccctcacc atgaagtttc tttccacttt ggccctggcg     180
gccctcgcgc acctggcgtg cgccgtcccc atggccgaga gcgtgccccc gcggccacg      240 cccgtcggct acgcctcgca gaacggcggc gtgaccggcg gtcagggcgg caccaccacc     300

| | |
|---|---|
| accgtctcct cgctgcccga gatgacggct gcccttaaga aggggacac ggagaagaag | 360 |
| gtcgtctacg tcaagggcaa gatctccggc aaggcgaaga tctacgttgg ctcgaacaag | 420 |
| gtgcggcctc acccctcac tccatgacat ccgggtagct aacgcagcct gcagtccatc | 480 |
| ctcggcgttg actccagctc cggcctcgag gcatcggac tcctcgtccg tgacgccaag | 540 |
| aacgtcatca tccgcaacct ggccatctcc aaggtcgagg ccgacacggg cggcgacgcc | 600 |
| atcgccatcg acggctccac caacgtctgg gtcgaccact cgacctgtc cagcgacctg | 660 |
| gccgccgaca aggacttcta cgacggcctg ctcgacatct cccacggcgc cgactacgtc | 720 |
| accgtctcga acgtctactt ccacgaccac acaagaact cgctcgtcgg ccactccgac | 780 |
| tccaacgccg gcgaggacac gggcaagctg cacgtcacct acgccaacaa ctactggagc | 840 |
| aacgtcggct cgcgctgccc gctcgtgcgc ttcggcaccg tccacatcgt caacaactac | 900 |
| ttcgaggacg tctccgtctc cggcatcaac acccgcatgg gcgcccaggt cctcgtcgag | 960 |
| aacaacgtct tcaacaacgt cgtgcaggcc ctcgtctcga tcgactccaa ggagctcggc | 1020 |
| tacgccgtcg cgcgaggcaa cgactggggc acctccaaga acgaggcccc cgagggtacc | 1080 |
| cttaccaagg tgccttacac ctacaccgct gttgaagcga gcgcggtcaa ggctgctgtt | 1140 |
| gttggcagcg cgggcaacac cctctctggc ttgtaaacat ttgacctcga cgggttgctc | 1200 |
| gagagaagcc tatctacata gcctgtgttt acaagcaatt ctctgtagat attttttatac | 1260 |
| aatctctaat tgtaaatacg aaatcaaatc cgaattagtg aatgcttgc cttaagctct | 1320 |
| tcggag | 1326 |

<210> SEQ ID NO 32
<211> LENGTH: 972
<212> TYPE: DNA
<213> ORGANISM: M. phaseolina

<400> SEQUENCE: 32

| | |
|---|---|
| atgaagtttc tttccacttt ggccctggcg gccctcgcgc acctggcgtg cgccgtcccc | 60 |
| atggccgaga agcgtgcccc cgcggccacg cccgtcggct acgcctcgca gaacggcggc | 120 |
| gtgaccggcg gtcagggcgg caccaccacc accgtctcct cgctgcccga gatgacggct | 180 |
| gcccttaaga aggggacac ggagaagaag gtcgtctacg tcaagggcaa gatctccggc | 240 |
| aaggcgaaga tctacgttgg ctcgaacaag tccatcctcg gcgttgactc cagctccggc | 300 |
| ctcgagggca tcggactcct cgtccgtgac gccaagaacg tcatcatccg caacctggcc | 360 |
| atctccaagg tcgaggccga cacgggcggc gacgccatcg ccatcgacgg ctccaccaac | 420 |
| gtctgggtcg accactgcga cctgtccagc gacctggccg ccgacaagga cttctacgac | 480 |
| ggcctgctcg acatctccca cggcgccgac tacgtcaccg tctcgaacgt ctacttccac | 540 |
| gaccaccaca gaactcgct cgtcggccac tccgactcca acgccggcga ggacacgggc | 600 |
| aagctgcacg tcacctacgc caacaactac tggagcaacg tcggctcgcg ctgcccgctc | 660 |
| gtgcgcttcg gcaccgtcca catcgtcaac aactacttcg aggacgtctc cgtctccggc | 720 |
| atcaacaccc gcatgggcgc ccaggtcctc gtcgagaaca acgtcttcaa caacgtcgtg | 780 |
| caggccctcg tctcgatcga ctccaaggag ctcggctacg ccgtcgcgcg aggcaacgac | 840 |
| tggggcacct ccaagaacga ggcccccgag ggtacccta ccaaggtgcc ttacacctac | 900 |
| accgctgttg aagcgagcgc ggtcaaggct gctgttgttg gcagcgcggg caacaccctc | 960 |
| tctggcttgt aa | 972 |

<210> SEQ ID NO 33
<211> LENGTH: 323
<212> TYPE: PRT
<213> ORGANISM: M. phaseolina

<400> SEQUENCE: 33

```
Met Lys Phe Leu Ser Thr Leu Ala Leu Ala Leu Ala His Leu Ala
1               5                   10                  15

Cys Ala Val Pro Met Ala Glu Lys Arg Ala Pro Ala Thr Pro Val
            20                  25                  30

Gly Tyr Ala Ser Gln Asn Gly Val Thr Gly Gly Gln Gly Gly Thr
            35                  40                  45

Thr Thr Thr Val Ser Ser Leu Pro Glu Met Thr Ala Ala Leu Lys Lys
50                      55                      60

Gly Asp Thr Glu Lys Lys Val Val Tyr Val Lys Gly Lys Ile Ser Gly
65                  70                  75                  80

Lys Ala Lys Ile Tyr Val Gly Ser Asn Lys Ser Ile Leu Gly Val Asp
                85                  90                  95

Ser Ser Ser Gly Leu Glu Gly Ile Gly Leu Leu Val Arg Asp Ala Lys
            100                 105                 110

Asn Val Ile Ile Arg Asn Leu Ala Ile Ser Lys Val Glu Ala Asp Thr
            115                 120                 125

Gly Gly Asp Ala Ile Ala Ile Asp Gly Ser Thr Asn Val Trp Val Asp
130                 135                 140

His Cys Asp Leu Ser Ser Asp Leu Ala Ala Asp Lys Asp Phe Tyr Asp
145                 150                 155                 160

Gly Leu Leu Asp Ile Ser His Gly Ala Asp Tyr Val Thr Val Ser Asn
                165                 170                 175

Val Tyr Phe His Asp His His Lys Asn Ser Leu Val Gly His Ser Asp
            180                 185                 190

Ser Asn Ala Gly Glu Asp Thr Gly Lys Leu His Val Thr Tyr Ala Asn
            195                 200                 205

Asn Tyr Trp Ser Asn Val Gly Ser Arg Cys Pro Leu Val Arg Phe Gly
210                 215                 220

Thr Val His Ile Val Asn Asn Tyr Phe Glu Asp Val Ser Val Ser Gly
225                 230                 235                 240

Ile Asn Thr Arg Met Gly Ala Gln Val Leu Val Glu Asn Asn Val Phe
                245                 250                 255

Asn Asn Val Val Gln Ala Leu Val Ser Ile Asp Ser Lys Glu Leu Gly
            260                 265                 270

Tyr Ala Val Ala Arg Gly Asn Asp Trp Gly Thr Ser Lys Asn Glu Ala
            275                 280                 285

Pro Glu Gly Thr Leu Thr Lys Val Pro Tyr Thr Tyr Thr Ala Val Glu
290                 295                 300

Ala Ser Ala Val Lys Ala Ala Val Val Gly Ser Ala Gly Asn Thr Leu
305                 310                 315                 320

Ser Gly Leu
```

<210> SEQ ID NO 34
<211> LENGTH: 1320
<212> TYPE: DNA
<213> ORGANISM: M. phaseolina

<400> SEQUENCE: 34
tctccaagtt catcttcatc ttcagtcttt ctctattaaa cgcgttgact cgcgccattc     60

```
tttgacagcc atcagcctgc tgagcacgct tgaccacata ttccttccct tgaaagttcc    120
cgtttgctca acaacacttc caccgcaacc atgaaggcca ccaccctcgc tactttttgct   180 ctttccgccg tgagcgctct ggcagcgccc accaagacct tcgccaagcg tgccgccatc    240
actgacggcc ccgacgtcgg ctatgccacc ctgaacggtg gcaccactgg cggtgctggc    300
ggttccacca ccaccgtctc cagcctggcc cagttcaccg ctgccgccga ggctgatggc    360
gccgccgtca ttgtcgtctc cggcaacatc tctggcgccg ccaaggtccg cgtcggcagc    420
gacaagacca tcatcggcaa ggactccagc gccgtgctcg agggcgtcgg tctctacatc    480
aacaagcaga gaacgtcat cgtccgcaac ctgtccatca agaatgtgct tgcggagaat     540
ggtgacgcca tcggcatcca ggcttcccag aacgtctgga tcgaccactg cgacctgtcc    600
tcggaccgtg accacgacaa ggactactac gacggtctcc tcgacgtgac ccacgcctct    660
gactacatca ccctgtccaa caactacctc catgaccact ggaaggcctc gctcgtcggc    720
cactccgact ccaacggctc tgaggacaag ggccacttga ccgtcaccta ctaccagaac    780
cacttcgaga acctgaactc gcgtggtcct tcttccgct tcggcaccgg tcacattgta     840
tgttgcccac caacctgaca ccacagtaat gattctaacg gcaaatgcta ggtcaacaac    900
ctctacacca gcgtcagcga cggtatcaac gctcgccagg gcgcccagct ccttgttgag    960
ggcaacgtct tcactggcag caagaagccg ctgtacagca ccgatgccgg ctacgccgcc   1020
gtcaacgaca acgacttcgg cggcgctgag aacactgctg aggctggcac cctcactgcc   1080
tctgacctcg gctacaagta taccgctctg aagtcttccg aggtctctgc cgccgtctcc   1140
aagtcggctg cgccacgct cactttctaa acgaagtcgc gacgctctct cgttttggaa    1200
ctcgccgcaa tgcccgagcc agggttcgga tgcatggaag gaatgcattg tgatggatga   1260
agagcaacat acttttttgg ggggaaaaa gcacagggcg tgctacttt tcatgtacat      1320
```

<210> SEQ ID NO 35
<211> LENGTH: 966
<212> TYPE: DNA
<213> ORGANISM: M. phaseolina

<400> SEQUENCE: 35

```
atgaaggcca ccaccctcgc tactttttgct ctttccgccg tgagcgctct ggcagcgccc    60
accaagacct tcgccaagcg tgccgccatc actgacggcc ccgacgtcgg ctatgccacc   120
ctgaacggtg gcaccactgg cggtgctggc ggttccacca ccaccgtctc cagcctggcc   180
cagttcaccg ctgccgccga ggctgatggc gccgccgtca ttgtcgtctc cggcaacatc   240
tctggcgccg ccaaggtccg cgtcggcagc gacaagacca tcatcggcaa ggactccagc   300
gccgtgctcg agggcgtcgg tctctacatc aacaagcaga gaacgtcat cgtccgcaac    360 ctgtccatca agaatgtgct tgcggagaat ggtgacgcca tcggcatcca ggcttcccag   420
aacgtctgga tcgaccactg cgacctgtcc tcggaccgtg accacgacaa ggactactac   480
gacggtctcc tcgacgtgac ccacgcctct gactacatca ccctgtccaa caactacctc   540
catgaccact ggaaggcctc gctcgtcggc cactccgact ccaacggctc tgaggacaag   600
ggccacttga ccgtcaccta ctaccagaac cacttcgaga acctgaactc gcgtggtcct   660
tctttccgct tcggcaccgg tcacattgtc aacaacctct acaccagcgt cagcgacggt   720
atcaacgctc gccagggcgc ccagctcctt gttgagggca acgtcttcac tggcagcaag   780
aagccgctgt acagcaccga tgccggctac gccgccgtca acgacaacga cttcggcggc   840
gctgagaaca ctgctgaggc tggcaccctc actgcctctg acctcggcta caagtatacc   900
```

```
gctctgaagt cttccgaggt ctctgccgcc gtctccaagt cggctggcgc cacgctcact    960
ttctaa                                                               966
```

<210> SEQ ID NO 36
<211> LENGTH: 321
<212> TYPE: PRT
<213> ORGANISM: M. phaseolina

<400> SEQUENCE: 36

```
Met Lys Ala Thr Thr Leu Ala Thr Phe Ala Leu Ser Ala Val Ser Ala
1               5                   10                  15

Leu Ala Ala Pro Thr Lys Thr Phe Ala Lys Arg Ala Ala Ile Thr Asp
            20                  25                  30

Gly Pro Asp Val Gly Tyr Ala Thr Leu Asn Gly Gly Thr Thr Gly Gly
        35                  40                  45

Ala Gly Gly Ser Thr Thr Thr Val Ser Ser Leu Ala Gln Phe Thr Ala
    50                  55                  60

Ala Ala Glu Ala Asp Gly Ala Ala Val Ile Val Ser Gly Asn Ile
65                  70                  75                  80

Ser Gly Ala Ala Lys Val Arg Val Gly Ser Asp Lys Thr Ile Ile Gly
                85                  90                  95

Lys Asp Ser Ser Ala Val Leu Glu Gly Val Gly Leu Tyr Ile Asn Lys
            100                 105                 110

Gln Lys Asn Val Ile Val Arg Asn Leu Ser Ile Lys Asn Val Leu Ala
        115                 120                 125

Glu Asn Gly Asp Ala Ile Gly Ile Gln Ala Ser Gln Asn Val Trp Ile
    130                 135                 140

Asp His Cys Asp Leu Ser Ser Asp Arg Asp His Asp Lys Asp Tyr Tyr
145                 150                 155                 160

Asp Gly Leu Leu Asp Val Thr His Ala Ser Asp Tyr Ile Thr Leu Ser
                165                 170                 175

Asn Asn Tyr Leu His Asp His Trp Lys Ala Ser Leu Val Gly His Ser
            180                 185                 190

Asp Ser Asn Gly Ser Glu Asp Lys Gly His Leu Thr Val Thr Tyr Tyr
        195                 200                 205

Gln Asn His Phe Glu Asn Leu Asn Ser Arg Gly Pro Ser Phe Arg Phe
    210                 215                 220

Gly Thr Gly His Ile Val Asn Asn Leu Tyr Thr Ser Val Ser Asp Gly
225                 230                 235                 240

Ile Asn Ala Arg Gln Gly Ala Gln Leu Leu Val Glu Gly Asn Val Phe
                245                 250                 255

Thr Gly Ser Lys Lys Pro Leu Tyr Ser Thr Asp Ala Gly Tyr Ala Ala
            260                 265                 270

Val Asn Asp Asn Asp Phe Gly Gly Ala Glu Asn Thr Ala Glu Ala Gly
        275                 280                 285

Thr Leu Thr Ala Ser Asp Leu Gly Tyr Lys Tyr Thr Ala Leu Lys Ser
    290                 295                 300

Ser Glu Val Ser Ala Ala Val Ser Lys Ser Ala Gly Ala Thr Leu Thr
305                 310                 315                 320

Phe
```

<210> SEQ ID NO 37
<211> LENGTH: 1896
<212> TYPE: DNA

<213> ORGANISM: M. phaseolina

<400> SEQUENCE: 37

```
cagccaatac ggtggcctga acatactca tattcctata tccaattcca cccagaaaca      60
tatttacacg gcccgtccct tagcccaatt gaccccggaa gcgtctctct ttttcccta     120
cgctcgtttc ttttctccc tgtcatgctg atggcgtcct gtcttcccct ggccctagtg     180
gccttttctt cactttccta tgctcttcag ccctacagtg gcccggcgcc agaccttcct    240
gatcgtaagc cattcggctt cggtgccgcc gccacaggtg gcggtacccc cacgccgaac    300
aatacctacc tggtcgacaa catgcctgat ctgcggaccg ttctaaagat ggagactccc    360
cgcacagttt acgtgaaggg cgagatcaaa ggcaacgaaa tcaacgagac cacgaccggc    420
aattgccaat tctacattga cagcagcaac aactccaagt tcaactttac cctctacatc    480
cagagctaca acgagaccta catgggccag gttaaggctg cctccgaagc gggccagcta    540
ttcgacggac agaacgccac cgagctcctc aatctactcg gccgccagaa cgtgagcttc    600
catgtgcccg gaaaggtttc aaaataacag caacgctaac ccacctcgca gggctggcgc    660
ggccaagtgc aaaacgtgca aaagtcctac gaagccattg acgtggccag caaccttacg    720
cttatcggct gggactcgtc cgcgtacctg aatggcgtca atctcgggtt caactcgcgc    780
tccaacatca tcatgcgcaa cctgcgcatt tcgtcgccgc gtgactgctt cccgtcgccg    840
gaaacctacc ccagcagctg gaacgcgcgt tacgacgccg tgtccatggt gtcgacgacg    900
accgcgtggc tcgacggcaa catcttcgag gacgccccg tcgccgtcgc gcccgacgac    960
ttcgcgggcg ggtggaaggt cgaccggtac gacggcttgt tgacgccga ggacggcagc   1020
gacgacatca ccttctcgca caacatcgtc accaaccacc acaagagcct gctgtggggc   1080
ggcggcaaca aggaggcgga ccgcgacatc ggcaagatga agttcaccgt cttcggcaac   1140
cgcttcgtcg acagcttgtc gcgcaacccg ctgatgcgct cggcaccttt ctacatcgtc   1200
gccaacgtct tcgagaacta cgccgagcgc gcgccgctgt tcgaggacga cagcgtcgcc   1260
gcgagcgcgg ccgcctcgcg gctcgttcga cgcgcggaca atgccaccac ctacaggccg   1320
gacttccagt acaacatggg catctacaac gccagcaccg tgtacgtcgc ggcgaatgcg   1380
tttgtccaga cgggcaccta tgcggacgat tcgtcgcgcg tcttctcctt ctcggacctt   1440
gcgacgccgg gcctgcccgc gacgctgtgc tcgccggctg atggcgcgaa cgggacggcg   1500
tcggcgtcgt ccctgccgaa gagcgttttc aatggcaggc ctatcgacct tgcgaagaat   1560
gccaagaaca cgtgggcgta tttcctggag agcaagaatg aggacggcga ttcgccgag   1620
ggtgggttcg tgattggatg tgacgggctg gaggagcagg agacgccggt tgcgttttaag  1680
gatggtaacg aggtcgatgc atatgtgcgg aagaatgcag gcaggtagg gagggcgacg   1740
ccgtaggggt gcaagtggat gccaggctga tggttggtgg tggaatgttt gtggaaccgc   1800
gagcggatag acttggcggg aagtgcctcc tcttggcgga aggtatgcat gtacaatggg   1860
tcaacggtag agatctgcgg cttttccggc ggcggg                              1896
```

<210> SEQ ID NO 38
<211> LENGTH: 1536
<212> TYPE: DNA
<213> ORGANISM: M. phaseolina

<400> SEQUENCE: 38

```
atggcgtcct gtcttcccct ggccctagtg gccttttctt cactttccta tgctcttcag     60
ccctacagtg gcccggcgcc agaccttcct gatcgtaagc cattcggctt cggtgccgcc    120
```

```
gccacaggtg gcggtacccc cacgccgaac aatacctacc tggtcgacaa catgcctgat      180
ctgcggaccg ttctaaagat ggagactccc cgcacagttt acgtgaaggg cgagatcaaa      240
ggcaacgaaa tcaacgagac cacgaccggc aattgccaat tctacattga cagcagcaac      300
aactccaagt tcaactttac cctctacatc cagagctaca acgagaccta catgggccag      360
gttaaggctg cctccgaagc gggccagcta ttcgacggac agaacgccac cgagctcctc      420
aatctactcg gccgccagaa cggctggcgc ggccaagtgc aaaacgtgca aaagtcctac      480
gaagccattg acgtggccag caaccttacg cttatcggct gggactcgtc cgcgtacctg      540
aatggcgtca atctcgggtt caactcgcgc tccaacatca tcatgcgcaa cctgcgcatt      600
tcgtcgccgc gtgactgctt cccgtcgccg gaaacctacc ccagcagctg aacgcgcgt       660 tacgacgccg tgtccatggt gtcgacgacg accgcgtggc tcgacggcaa catcttcgag      720
gacggccccg tcgccgtcgc gcccgacgac ttcgcgggcg ggtggaaggt cgaccggtac      780
gacggcttgt ttgacgccga ggacggcagc gacgacatca ccttctcgca aacatcgtc       840 accaaccacc acaagagcct gctgtggggc ggcggcaaca aggaggcgga ccgcgacatc      900
ggcaagatga agttcaccgt cttcggcaac cgcttcgtcg acagcttgtc gcgcaacccg      960
ctgatgcgct tcggcacctt ctacatcgtc gccaacgtct tcgagaacta cgccgagcgc      1020
gcgccgctgt tcgaggacga cagcgtcgcc gcgagcgcgg ccgcctcgcg gctcgttcga      1080
cgcgcggaca atgccaccac ctacaggccg gacttccagt acaacatggg catctacaac      1140
gccagcaccg tgtacgtcgc ggcgaatgcg tttgtccaga cgggcaccta tgcggacgat      1200
tcgtcgcgcg tcttctcctt ctcggacctt gcgacgccgg gcctgccgc gacgctgtgc       1260 tcgccggctg atggcgcgaa cgggacggcg tcggcgtcgt ccctgccgaa gagcgttttc      1320
aatggcaggc ctatcgacct tgcgaagaat gccaagaaca cgtgggcgta tttcctggag      1380
agcaagaatg aggacggcga gttcgccgag ggtgggttcg tgattggatg tgacgggctg      1440
gaggagcagg agacgccggt tgcgtttaag gatggtaacg aggtcgatgc atatgtgcgg      1500
aagaatgcag ggcaggtagg gagggcgacg ccgtag                                1536
```

<210> SEQ ID NO 39
<211> LENGTH: 511
<212> TYPE: PRT
<213> ORGANISM: M. phaseolina

<400> SEQUENCE: 39

```
Met Ala Ser Cys Leu Pro Leu Ala Leu Val Ala Phe Ser Ser Leu Ser
1               5                   10                  15

Tyr Ala Leu Gln Pro Tyr Ser Gly Pro Ala Pro Asp Leu Pro Asp Arg
            20                  25                  30

Lys Pro Phe Gly Phe Gly Ala Ala Thr Gly Gly Thr Pro Thr
        35                  40                  45

Pro Asn Asn Thr Tyr Leu Val Asp Asn Met Pro Asp Leu Arg Thr Val
    50                  55                  60

Leu Lys Met Glu Thr Pro Arg Thr Val Tyr Val Lys Gly Glu Ile Lys
65                  70                  75                  80

Gly Asn Glu Ile Asn Glu Thr Thr Thr Gly Asn Cys Gln Phe Tyr Ile
                85                  90                  95

Asp Ser Ser Asn Asn Ser Lys Phe Asn Phe Thr Leu Tyr Ile Gln Ser
            100                 105                 110

Tyr Asn Glu Thr Tyr Met Gly Gln Val Lys Ala Ala Ser Glu Ala Gly
```

```
                    115                 120                 125
        Gln Leu Phe Asp Gly Gln Asn Ala Thr Glu Leu Leu Asn Leu Leu Gly
            130                 135                 140

Arg Gln Asn Gly Trp Arg Gly Gln Val Gln Asn Val Gln Lys Ser Tyr
        145                 150                 155                 160

Glu Ala Ile Asp Val Ala Ser Asn Leu Thr Leu Ile Gly Trp Asp Ser
                            165                 170                 175

Ser Ala Tyr Leu Asn Gly Val Asn Leu Gly Phe Asn Ser Arg Ser Asn
                        180                 185                 190

Ile Ile Met Arg Asn Leu Arg Ile Ser Ser Pro Arg Asp Cys Phe Pro
                    195                 200                 205

Ser Pro Glu Thr Tyr Pro Ser Ser Trp Asn Ala Arg Tyr Asp Ala Val
                    210                 215                 220

Ser Met Val Ser Thr Thr Thr Ala Trp Leu Asp Gly Asn Ile Phe Glu
        225                 230                 235                 240

Asp Gly Pro Val Ala Val Ala Pro Asp Phe Ala Gly Gly Trp Lys
                            245                 250                 255

Val Asp Arg Tyr Asp Gly Leu Phe Asp Ala Glu Asp Gly Ser Asp Asp
                        260                 265                 270

Ile Thr Phe Ser His Asn Ile Val Thr Asn His His Lys Ser Leu Leu
                    275                 280                 285

Trp Gly Gly Asn Lys Glu Ala Asp Arg Asp Ile Gly Lys Met Lys
        290                 295                 300

Phe Thr Val Phe Gly Asn Arg Phe Val Asp Ser Leu Ser Arg Asn Pro
        305                 310                 315                 320

Leu Met Arg Phe Gly Thr Phe Tyr Ile Val Ala Asn Val Phe Glu Asn
                            325                 330                 335

Tyr Ala Glu Arg Ala Pro Leu Phe Glu Asp Asp Ser Val Ala Ala Ser
                        340                 345                 350

Ala Ala Ala Ser Arg Leu Val Arg Arg Ala Asp Asn Ala Thr Thr Tyr
                    355                 360                 365

Arg Pro Asp Phe Gln Tyr Asn Met Gly Ile Tyr Asn Ala Ser Thr Val
                    370                 375                 380

Tyr Val Ala Ala Asn Ala Phe Val Gln Thr Gly Thr Tyr Ala Asp Asp
        385                 390                 395                 400

Ser Ser Arg Val Phe Ser Phe Ser Asp Leu Ala Thr Pro Gly Leu Pro
                            405                 410                 415

Ala Thr Leu Cys Ser Pro Ala Asp Gly Ala Asn Gly Thr Ala Ser Ala
                        420                 425                 430

Ser Ser Leu Pro Lys Ser Val Phe Asn Gly Arg Pro Ile Asp Leu Ala
                    435                 440                 445

Lys Asn Ala Lys Asn Thr Trp Ala Tyr Phe Leu Glu Ser Lys Asn Glu
                    450                 455                 460

Asp Gly Glu Phe Ala Glu Gly Phe Val Ile Gly Cys Asp Gly Leu
        465                 470                 475                 480

Glu Glu Gln Glu Thr Pro Val Ala Phe Lys Asp Gly Asn Glu Val Asp
                            485                 490                 495

Ala Tyr Val Arg Lys Asn Ala Gly Gln Val Gly Arg Ala Thr Pro
                        500                 505                 510

<210> SEQ ID NO 40
<211> LENGTH: 1798
<212> TYPE: DNA
<213> ORGANISM: M. phaseolina
```

<400> SEQUENCE: 40

```
cgggttttgg gaatatctcc gggcttcggt ggaccgtcct atccgtctga gcatgccaat      60
atgttttctt gcctttctgt ccgtatataa aatgccagtc aagaagaatt ctcgtgtttc     120
acacctttct tcatccgatc tcgcctcagt atgcgtgcat cagtctcaat tacggtctcg     180
ctactggcat ttgccctgag ggcgtgcgct gttggtgtgg ttgggagtcc ggagggattt     240
ggctccggga caacaggtgg aggtagtgcc acgccggttt atccttcgac cacgagcgaa     300
ttgcagtcct acttggaaga cgatgttgcc cgagttatcg tcctgaacaa ggagtatgca     360
accaaacaat tgtttaataa gcctaaaact gaccatgtcc aggttcaact tcaagggcac     420
caccaccact gcgacgggct gcagacccac atccaacact gccccggta atggtggcca     480
agatgcaatt aatgccaacg gttggttagt atctgctggt tgctctcatc tggttctttg     540
tgactaatgt tcaacgcagg tgcggaagtg ctccggcggt ctccgtgaag tacgacacgg     600
ccgctattac gcccataaat ctcggctcta acaagtctct tatcggcatt ggcacatctg     660
gtgtcatccg cggaaagggt ctccgtatcg tcagtaaaac taattcttgc tatcagttga     720
cgaagaaact tacagttgat gaaatctctt caggccaacg gagctaaaaa tgtcatcatc     780
caaaatattc atattaccga tctcaacccg cagtacatct ggggtggaga tgccattacc     840
ctggatggtg ctgatctggt ttgggtggac acgttaagg gacgtatact cccgaaccct     900
cgctcgagca ttattctgac cttgccaact acagatctct ctcatcggcc gccagatgtt     960
tgtcgcgggc tacggggcat ctaacagagt aactatcagc aacacggagt tcgacggctc    1020
aacctcctgg agcgcaactt gcgacgggca tgtacgtgcc gcctcccagc ccaccaccac    1080
ctccttttctt tcactggagt agcttagatg ctaatatgcc ttatcttttcc ttctagcact    1140
actggactat tttgcttttg ggctcaaacg acttgatcac aatgaaaggc aactatatcc    1200
accacaccag cggccgtgga cccaagatcg gaggcaacac cctgctccac gccgtaagtt    1260
ccgccccaca aacacccttg cctcaccaat cgcctgctga acatgctat ttccacaggt     1320
caataatgag tggtacgccg tttcgggcca cgccttcgac ctgggcgagt cgggcgccat    1380
ggccgttgcc gagggcaacg ttttccagaa cgtcgtcacg ccgctgcttt cgcccgtcga    1440
gggccgcatc ttcacggcgc ccagcactag cgccaacacc gcctgcgcga cctaccttgg    1500
ccgcaactgc gtcgtcaacg ccttcggcag cagcggcacc ttctccggaa ccgacaccag    1560
cttcttctcc aacttcaacg gcaagacgat cgcgagtgca gccgccgccg catacaagga    1620
ttcgacagcg ggtgtgggga agatttaagg gcggagcggg tggttttgca tttaggggct    1680
gtgatattgc gttggatgtt ggaatgaggt cagcaaaaga aaatctaaaa tcaacgatca    1740
tgaatgctgg ctggaaggaa attgtttgag aactacttgt gctttttttt tattactg     1798
```

<210> SEQ ID NO 41
<211> LENGTH: 1137
<212> TYPE: DNA
<213> ORGANISM: M. phaseolina

<400> SEQUENCE: 41

```
atgcgtgcat cagtctcaat tacggtctcg ctactggcat ttgccctgag ggcgtgcgct      60
gttggtgtgg ttgggagtcc ggagggattt ggctccggga caacaggtgg aggtagtgcc     120
acgccggttt atccttcgac cacgagcgaa ttgcagtcct acttggaaga cgatgttgcc     180
cgagttatcg tcctgaacaa ggagttcaac ttcaagggca ccaccaccac tgcgacgggc     240
```

```
tgcagaccca catccaacac ttgccccggt aatggtggcc aagatgcaat taatgccaac    300
ggttggtgcg gaagtgctcc ggcggtctcc gtgaagtacg acacggccgc tattacgccc    360
ataaatctcg gctctaacaa gtctcttatc ggcattggca catctggtgt catccgcgga    420
aagggtctcc gtatcttgat gaaatctctt caggccaacg gagctaaaaa tgtcatcatc    480
caaaatattc atattaccga tctcaacccg cagtacatct ggggtggaga tgccattacc    540
ctggatggtg ctgatctggt ttgggtggac cacatctctc tcatcggccg ccagatgttt    600
gtcgcgggct acggggcatc taacagagta actatcagca cacggagtt cgacggctca     660
acctcctgga gcgcaacttg cgacgggcat cactactgga ctattttgct tttgggctca    720
aacgacttga tcacaatgaa aggcaactat atccaccaca ccagcggccg tggacccaag    780
atcggaggca acaccctgct ccacgccgtc aataatgagt ggtacgccgt tcgggccac     840
gccttcgacc tgggcgagtc gggcgccatg gccgttgccg agggcaacgt tttccagaac    900
gtcgtcacgc cgctgctttc gcccgtcgag ggccgcatct tcacggcgcc cagcactagc    960
gccaacaccg cctgcgcgac ctaccttggc cgcaactgcg tcgtcaacgc cttcggcagc   1020
agcggcacct tctccggaac cgacaccagc ttcttctcca acttcaacgg caagacgatc   1080
gcgagtgcag ccgccgccgc atacaaggat tcgacagcgg gtgtggggaa gatttaa      1137
```

<210> SEQ ID NO 42
<211> LENGTH: 378
<212> TYPE: PRT
<213> ORGANISM: M. phaseolina

<400> SEQUENCE: 42

```
Met Arg Ala Ser Val Ser Ile Thr Val Ser Leu Leu Ala Phe Ala Leu
1               5                   10                  15

Arg Ala Cys Ala Val Gly Val Val Gly Ser Pro Glu Gly Phe Gly Ser
            20                  25                  30

Gly Thr Thr Gly Gly Gly Ser Ala Thr Pro Val Tyr Pro Ser Thr Thr
        35                  40                  45

Ser Glu Leu Gln Ser Tyr Leu Glu Asp Asp Val Ala Arg Val Ile Val
    50                  55                  60

Leu Asn Lys Glu Phe Asn Phe Lys Gly Thr Thr Thr Ala Thr Gly
65                  70                  75                  80

Cys Arg Pro Thr Ser Asn Thr Cys Pro Gly Asn Gly Gly Gln Asp Ala
                85                  90                  95

Ile Asn Ala Asn Gly Trp Cys Gly Ser Ala Pro Ala Val Ser Val Lys
            100                 105                 110

Tyr Asp Thr Ala Ala Ile Thr Pro Ile Asn Leu Gly Ser Asn Lys Ser
        115                 120                 125

Leu Ile Gly Ile Gly Thr Ser Gly Val Ile Arg Gly Lys Gly Leu Arg
    130                 135                 140

Ile Leu Met Lys Ser Leu Gln Ala Asn Gly Ala Lys Asn Val Ile Ile
145                 150                 155                 160

Gln Asn Ile His Ile Thr Asp Leu Asn Pro Gln Tyr Ile Trp Gly Gly
                165                 170                 175

Asp Ala Ile Thr Leu Asp Gly Ala Asp Leu Val Trp Val Asp His Ile
            180                 185                 190

Ser Leu Ile Gly Arg Gln Met Phe Val Ala Gly Tyr Gly Ala Ser Asn
        195                 200                 205

Arg Val Thr Ile Ser Asn Thr Glu Phe Asp Gly Ser Thr Ser Trp Ser
    210                 215                 220
```

```
Ala Thr Cys Asp Gly His His Tyr Trp Thr Ile Leu Leu Leu Gly Ser
225                 230                 235                 240

Asn Asp Leu Ile Thr Met Lys Gly Asn Tyr Ile His His Thr Ser Gly
            245                 250                 255

Arg Gly Pro Lys Ile Gly Gly Asn Thr Leu Leu His Ala Val Asn Asn
        260                 265                 270

Glu Trp Tyr Ala Val Ser Gly His Ala Phe Asp Leu Gly Glu Ser Gly
                275                 280                 285

Ala Met Ala Val Ala Glu Gly Asn Val Phe Gln Asn Val Val Thr Pro
        290                 295                 300

Leu Leu Ser Pro Val Glu Gly Arg Ile Phe Thr Ala Pro Ser Thr Ser
305                 310                 315                 320

Ala Asn Thr Ala Cys Ala Thr Tyr Leu Gly Arg Asn Cys Val Val Asn
                325                 330                 335

Ala Phe Gly Ser Ser Gly Thr Phe Ser Gly Thr Asp Thr Ser Phe Phe
            340                 345                 350

Ser Asn Phe Asn Gly Lys Thr Ile Ala Ser Ala Ala Ala Ala Ala Tyr
        355                 360                 365

Lys Asp Ser Thr Ala Gly Val Gly Lys Ile
    370                 375
```

<210> SEQ ID NO 43
<211> LENGTH: 1631
<212> TYPE: DNA
<213> ORGANISM: M. phaseolina

<400> SEQUENCE: 43

```
ggtggtggtc ttgcacctct tccggtccac tactcacatt aacccgttca atcgttccca      60
cacattcact tatattccaa ctctcacaca ttcgttctgt atcacgcaat caatcttttt     120
gtttttgttt tttgatctat tttagcaaac atgaagctca ctctcttgtc tattgttctc     180
gctcttgccc accagactcg ggccaccagg gttacgggcg ctgccgaagg cttcgccaaa     240
ggcgtcacag ggggtggctc tgctgcccct gtcaccccca aaaatattgt tgagctgacc     300
aaataccttg ccgacgctca gccccgtgtc atcatcttgg acaaggagta agtccgctat     360
cacgggaggg cttcaaccgc tctatctggg ggattttctc cagccgaacg aacgctgaca     420
tctatcttcc tcagattcaa cttcaagggc tcagagggaa ccgtcaagga gatgggctgc     480
cgtcctcgta ccaaatgctc cgagactggc ggtggccaag atgccatcaa ccacgctagc     540
tggtgcacaa acggcaacgc tggtgccggc tccaaagccg tttctgtcac ctatgataga     600
gcgggaaccc tcgccttaaa ggtaaactcc aacaaatcca ttgtcggtgt cggcaacaag     660
ggtgtcatcc gcggcaaggg tctccgtctc gccggcgcta agaacgtcat catccaaaac     720
atccacatta ccgagcttaa ccctcagtac atctggggcg gtgacggcat tcagatcgac     780
ggcgccgaca tggtctggat cgacaggtcc aagatctctc tcgtgggccg gcagatgctt     840
gtccttggca acggcgcgtc cggcagggtc tcggtcacca caacgaattc gacggctct     900
actagtatgc tgatctccat agccccttg atcaccaaac ggctaatcgc tctttccagg     960
ctggtcggct acctgtgacg gtcaccacta ctgggccctc tacttcaccg gttccaacga    1020
catggtcacg ttcaagggta actacatcca ccacttct ggccggagcc ccaagatcgg     1080
cggtaccacg ctcctccacg ctgtaagatc cccaatgatc cgtgtctcgt gactcgcgct    1140
gattccacgc ccaggtcaac aacgtctggt atgccaactc cggccacgct ttcgagatcc    1200
```

```
tcgcgcccaa gtcgaacgcc ctcatcgagg gcaacatctt ccagaacgtc gtccgaccca    1260
tgaaggccag cacgggcaag gtctttgctc cctcttcggt ccaggccgtc tgcaatcgcg    1320
ctcttggccg cgcttgccag gccaactctt tcggctcctc tggccccttg accggcaccg    1380
acagcagctt cctcggtctg ttcaagggca agaaccccgc tactgcttcc gccgccagcc    1440
ccgccatttc tggccgcgct ggtgtcggga agattgccta aatgctggct atgttctggg    1500
ttggacgctt gctgagcaag ctgtcttggc tggttgggtg catgcactca gttgataggc    1560
acaaccaaca atctctggac gtgttatctc acttgtctgg cactgagtgg gaatgattta    1620
tgacagtttt t                                                         1631
```

```
<210> SEQ ID NO 44
<211> LENGTH: 1137
<212> TYPE: DNA
<213> ORGANISM: M. phaseolina

<400> SEQUENCE: 44
```

```
atgaagctca ctctcttgtc tattgttctc gctcttgccc accagactcg ggccaccagg     60
gttacgggcg ctgccgaagg cttcgccaaa ggcgtcacag ggggtggctc tgctgcccct    120 gtcacccccca aaatattgt tgagctgacc aaataccttg ccgacgctca gccccgtgtc    180
atcatcttgg acaaggaatt caacttcaag ggctcagagg gaaccgtcaa ggagatgggc    240
tgccgtcctc gtaccaaatg ctccgagact ggcggtggcc aagatgccat caaccacgct    300
agctggtgca caaacggcaa cgctggtgcc ggctccaaag ccgtttctgt cacctatgat    360
agagcgggaa ccctcgcctt aaaggtaaac tccaacaaat ccattgtcgg tgtcggcaac    420
aagggtgtca tccgcggcaa gggtctccgt ctcgccggcg ctaagaacgt catcatccaa    480
aacatccaca ttaccgagct taaccctcag tacatctggg gcggtgacgg cattcagatc    540
gacggcgccg acatggtctg gatcgacagg tccaagatct ctctcgtggg ccggcagatg    600
cttgtccttg caacggcgc gtccggcagg gtctcggtca ccaacaacga attcgacggc    660
tctactagct ggtcggctac ctgtgacggt caccactact gggccctcta cttcaccggt    720
tccaacgaca tggtcacgtt caagggtaac tacatccacc acacttctgg ccggagcccc    780
aagatcggcg gtaccacgct cctccacgct gtcaacaacg tctggtatgc caactccggc    840
cacgctttcg agatcctcgc gcccaagtcg aacgccctca tcgagggcaa catcttccag    900
aacgtcgtcc gacccatgaa ggccagcacg ggcaaggtct ttgctccctc ttcggtccag    960
gccgtctgca atcgcgctct tggccgcgct tgccaggcca actctttcgg ctcctctggc   1020
cccttgaccg gcaccgacag cagcttcctc ggtctgttca agggcaagaa ccccgctact   1080
gcttccgccg ccagccccgc catttctggc cgcgctggtg tcgggaagat tgcctaa     1137
```

```
<210> SEQ ID NO 45
<211> LENGTH: 378
<212> TYPE: PRT
<213> ORGANISM: M. phaseolina

<400> SEQUENCE: 45
```

```
Met Lys Leu Thr Leu Leu Ser Ile Val Leu Ala Leu Ala His Gln Thr
1               5                   10                  15

Arg Ala Thr Arg Val Thr Gly Ala Ala Glu Gly Phe Ala Lys Gly Val
            20                  25                  30

Thr Gly Gly Gly Ser Ala Ala Pro Val Thr Pro Lys Asn Ile Val Glu
        35                  40                  45
```

```
Leu Thr Lys Tyr Leu Ala Asp Ala Gln Pro Arg Val Ile Ile Leu Asp
 50                  55                  60

Lys Glu Phe Asn Phe Lys Gly Ser Glu Gly Thr Val Lys Glu Met Gly
 65                  70                  75                  80

Cys Arg Pro Arg Thr Lys Cys Ser Glu Thr Gly Gly Gly Gln Asp Ala
                 85                  90                  95

Ile Asn His Ala Ser Trp Cys Thr Asn Gly Asn Ala Gly Ala Gly Ser
            100                 105                 110

Lys Ala Val Ser Val Thr Tyr Asp Arg Ala Gly Thr Leu Ala Leu Lys
        115                 120                 125

Val Asn Ser Asn Lys Ser Ile Val Gly Val Asn Lys Gly Val Ile
130                 135                 140

Arg Gly Lys Gly Leu Arg Leu Ala Gly Ala Lys Asn Val Ile Ile Gln
145                 150                 155                 160

Asn Ile His Ile Thr Glu Leu Asn Pro Gln Tyr Ile Trp Gly Gly Asp
                165                 170                 175

Gly Ile Gln Ile Asp Gly Ala Asp Met Val Trp Ile Asp Arg Ser Lys
            180                 185                 190

Ile Ser Leu Val Gly Arg Gln Met Leu Val Leu Gly Asn Gly Ala Ser
        195                 200                 205

Gly Arg Val Ser Val Thr Asn Asn Glu Phe Asp Gly Ser Thr Ser Trp
210                 215                 220

Ser Ala Thr Cys Asp Gly His His Tyr Trp Ala Leu Tyr Phe Thr Gly
225                 230                 235                 240

Ser Asn Asp Met Val Thr Phe Lys Gly Asn Tyr Ile His His Thr Ser
                245                 250                 255

Gly Arg Ser Pro Lys Ile Gly Gly Thr Thr Leu Leu His Ala Val Asn
            260                 265                 270

Asn Val Trp Tyr Ala Asn Ser Gly His Ala Phe Glu Ile Leu Ala Pro
        275                 280                 285

Lys Ser Asn Ala Leu Ile Glu Gly Asn Ile Phe Gln Asn Val Val Arg
290                 295                 300

Pro Met Lys Ala Ser Thr Gly Lys Val Phe Ala Pro Ser Ser Val Gln
305                 310                 315                 320

Ala Val Cys Asn Arg Ala Leu Gly Arg Ala Cys Gln Ala Asn Ser Phe
                325                 330                 335

Gly Ser Ser Gly Pro Leu Thr Gly Thr Asp Ser Ser Phe Leu Gly Leu
            340                 345                 350

Phe Lys Gly Lys Asn Pro Ala Thr Ala Ser Ala Ala Ser Pro Ala Ile
        355                 360                 365

Ser Gly Arg Ala Gly Val Gly Lys Ile Ala
370                 375
```

<210> SEQ ID NO 46
<211> LENGTH: 1573
<212> TYPE: DNA
<213> ORGANISM: M. phaseolina

<400> SEQUENCE: 46

```
cggatgccgt gcagctgtca aagtcatgat aaaagtcccc actcccaggt acataatgtg      60
atcggtagtt ctgcgctctc ctttccaacg gttgtccctt gagcttcccg tgccatggta     120
gccttttctt cccttacgtc tggcaatgcc atggcgtccc tcctgtctct atccgtcctt     180
tcagcttttc ttgcttcacc gacacttgca tacagtcgtg ctgaatgcca ggctccatct     240
```

| | | |
|---|---|---|
| gccgaccccc | tggcgggctg cgtacccgga acgctgctcg tcagtccaaa cagcaccgtg | 300 |
| acggctaaca | acagcacctc ctttacctct gtccaatcag ctatccttc cctcggcaac | 360 |
| accaccacac | ccgccaccat cctcattctt cccggcacct atgttgagca agtcaatatc | 420 |
| acccgcccgg | gaccagtgac gctcctcggg cagacttcat ccccgaacaa ttcctccacc | 480 |
| aacggcgtta | agatcctctg gcgtcaggcc actggcaact cggtcaacac cttcgacaac | 540 |
| gcctataccct | ctgtcctcac tgtcgcgccg accctcgaga gcagcctaac aggcagcggg | 600 |
| cccaccggat | acgccgtccc cgccggcacg cccttcggca acgaggactt ccgcgcatac | 660 |
| aacgtcgact | tcgtcaacga ctacgcgccc tactcggccg gcccggcact cgccattagc | 720 |
| atcagctacg | ccaacgcggg cttctacttc tgcggcttct acagctatca ggacaccgta | 780 |
| agtgtcatct | ccactcgtcc actacacgca acaaacaaac atgcatccga gaatcccttt | 840 |
| tccccaccaa | ctaacgccaa accgcaaggt ctacatcggc aagctcggca acgcctactt | 900 |
| ctacgactcc | atcatcgccg gccaaaccga cttcctctac ggcttcggca ccgcctggat | 960 |
| ccagtcatcg | cagctctctc tccgctcctg cggcggcggc atcaccgcct ggaagggcac | 1020 |
| caatacgtcc | ttccccaacg cctacggcgt ctacatccac gacagcgtcg tcgagaaggc | 1080 |
| caacgcctcg | ctctccatcg ccgggctctg cgccctcggc aggccctgga atgcgcagca | 1140 |
| tcgctccatc | ttcgcgaaca cgtggctcga tgacagcatc aagccgagcg ggtacatcat | 1200 |
| ctggggagc | acggatccga ggaccaacaa ttacacgttt atggcggagt atgaggactt | 1260 |
| tgggccgggt | tggaatgaga ccgggaggag ggcggcgaat attacgaagg tgttgacgga | 1320 |
| ggccgagtat | gagccgtatg acagtctgga aaggtgttc cagtatccgt tcagtggcga | 1380 |
| gttcgggaac | gtggggtgga tcgatgagag tccggaggct tgagccggtg gggatagtgt | 1440 |
| ggattgtggt | ggccagcggc gtagacgagg cggatctggt aagaactgcg tagcatgaat | 1500 |
| gaaattcgtt | tgtacatacg tctttatatc gagcagcgct tatgcaagtt aaatgacgcc | 1560 |
| gtatttgcat | gcg | 1573 |

<210> SEQ ID NO 47
<211> LENGTH: 1182
<212> TYPE: DNA
<213> ORGANISM: M. phaseolina

<400> SEQUENCE: 47

| | | |
|---|---|---|
| atggcgtccc | tcctgtctct atccgtcctt tcagcttttc ttgcttcacc gacacttgca | 60 |
| tacagtcgtg | ctgaatgcca ggctccatct gccgaccccc tggcgggctg cgtacccgga | 120 |
| acgctgctcg | tcagtccaaa cagcaccgtg acggctaaca acagcacctc ctttacctct | 180 |
| gtccaatcag | ctatccttc cctcggcaac accaccacac ccgccaccat cctcattctt | 240 |
| cccggcacct | atgttgagca agtcaatatc acccgcccgg gaccagtgac gctcctcggg | 300 |
| cagacttcat | ccccgaacaa ttcctccacc aacggcgtta agatcctctg gcgtcaggcc | 360 |
| actggcaact | cggtcaacac cttcgacaac gcctataccct ctgtcctcac tgtcgcgccg | 420 |
| accctcgaga | gcagcctaac aggcagcggg cccaccggat acgccgtccc cgccggcacg | 480 |
| cccttcggca | acgaggactt ccgcgcatac aacgtcgact tcgtcaacga ctacgcgccc | 540 |
| tactcggccg | gcccggcact cgccattagc atcagctacg ccaacgcggg cttctacttc | 600 |
| tgcggcttct | acagctatca ggacaccgta tacatcggca agctcggcaa cgcctacttc | 660 |
| tacgactcca | tcatcgccgg ccaaaccgac ttcctctacg gcttcggcac cgcctggatc | 720 |
| cagtcatcgc | agctctctct ccgctcctgc ggcggcggca tcaccgcctg gaagggcacc | 780 |

```
aatacgtcct tccccaacgc ctacggcgtc tacatccacg acagcgtcgt cgagaaggcc    840
aacgcctcgc tctccatcgc cgggctctgc gccctcggca ggccctggaa tgcgcagcat    900
cgctccatct tcgcgaacac gtggctcgat gacagcatca agccgagcgg gtacatcatc    960
tgggggagca cggatccgag gaccaacaat tacacgttta tggcggagta tgaggacttt   1020
gggccgggtt ggaatgagac cgggaggagg gcggcgaata ttacgaaggt gttgacggag   1080
gccgagtatg agccgtatga cagtctggag aaggtgttcc agtatccgtt cagtggcgag   1140
ttcgggaacg tggggtggat cgatgagagt ccggaggctt ga                     1182
```

<210> SEQ ID NO 48
<211> LENGTH: 393
<212> TYPE: PRT
<213> ORGANISM: M. phaseolina

<400> SEQUENCE: 48

```
Met Ala Ser Leu Leu Ser Leu Ser Val Leu Ser Ala Phe Leu Ala Ser
 1               5                  10                  15

Pro Thr Leu Ala Tyr Ser Arg Ala Glu Cys Gln Ala Pro Ser Ala Asp
            20                  25                  30

Pro Leu Ala Gly Cys Val Pro Gly Thr Leu Leu Val Ser Pro Asn Ser
        35                  40                  45

Thr Val Thr Ala Asn Asn Ser Thr Ser Phe Thr Ser Val Gln Ser Ala
    50                  55                  60

Ile Leu Ser Leu Gly Asn Thr Thr Thr Pro Ala Thr Ile Leu Ile Leu
65                  70                  75                  80

Pro Gly Thr Tyr Val Glu Gln Val Asn Ile Thr Arg Pro Gly Pro Val
                85                  90                  95

Thr Leu Leu Gly Gln Thr Ser Ser Pro Asn Asn Ser Ser Thr Asn Gly
            100                 105                 110

Val Lys Ile Leu Trp Arg Gln Ala Thr Gly Asn Ser Val Asn Thr Phe
        115                 120                 125

Asp Asn Ala Tyr Thr Ser Val Leu Thr Val Ala Pro Thr Leu Glu Ser
    130                 135                 140

Ser Leu Thr Gly Ser Gly Pro Thr Gly Tyr Ala Val Pro Ala Gly Thr
145                 150                 155                 160

Pro Phe Gly Asn Glu Asp Phe Arg Ala Tyr Asn Val Asp Phe Val Asn
                165                 170                 175

Asp Tyr Ala Pro Tyr Ser Ala Gly Pro Ala Leu Ala Ile Ser Ile Ser
            180                 185                 190

Tyr Ala Asn Ala Gly Phe Tyr Phe Cys Gly Phe Tyr Ser Tyr Gln Asp
        195                 200                 205

Thr Val Tyr Ile Gly Lys Leu Gly Asn Ala Tyr Phe Tyr Asp Ser Ile
    210                 215                 220

Ile Ala Gly Gln Thr Asp Phe Leu Tyr Gly Phe Gly Thr Ala Trp Ile
225                 230                 235                 240

Gln Ser Ser Gln Leu Ser Leu Arg Ser Cys Gly Gly Ile Thr Ala
                245                 250                 255

Trp Lys Gly Thr Asn Thr Ser Phe Pro Asn Ala Tyr Val Tyr Ile
            260                 265                 270

His Asp Ser Val Val Glu Lys Ala Asn Ala Ser Leu Ser Ile Ala Gly
        275                 280                 285

Leu Cys Ala Leu Gly Arg Pro Trp Asn Ala Gln His Arg Ser Ile Phe
    290                 295                 300
```

```
Ala Asn Thr Trp Leu Asp Asp Ser Ile Lys Pro Ser Gly Tyr Ile Ile
305                 310                 315                 320

Trp Gly Ser Thr Asp Pro Arg Thr Asn Asn Tyr Thr Phe Met Ala Glu
            325                 330                 335

Tyr Glu Asp Phe Gly Pro Gly Trp Asn Glu Thr Gly Arg Arg Ala Ala
        340                 345                 350

Asn Ile Thr Lys Val Leu Thr Glu Ala Glu Tyr Glu Pro Tyr Asp Ser
        355                 360                 365

Leu Glu Lys Val Phe Gln Tyr Pro Phe Ser Gly Glu Phe Gly Asn Val
    370                 375                 380

Gly Trp Ile Asp Glu Ser Pro Glu Ala
385                 390

<210> SEQ ID NO 49
<211> LENGTH: 1330
<212> TYPE: DNA
<213> ORGANISM: M. phaseolina

<400> SEQUENCE: 49
tcaggctcgt atgccttgtc cttcatttgc ttgcactcta gggctggcta agacctcctt      60
acttgaataa tgtatctctc tacgtccgcc tttatagtct gcctggcggc tccaaaaccc     120
ctgagcctca caacattcat tcgcttaacc atgcatagtt cttccatcct tttcagcctt     180
ttcggctccg cactcgctct gacatctcca ccgccaggag cgctgactgt tggaggctct     240
gagggaaaat tctccaccgt tcaagctgcg gttgacgctc tccagaacac cactgctcgg     300
caatccatat tcatctactc cggcacttac gaggagcagg tgtatatcgc caaacacaat     360
ggccccattt ccatttatgg acaagcctcg gatgacagct cataccacac caatactgtc     420
actctctctt tcggcctcag ccaggccttc aaccttagca acgacctcac ggccacccctc     480
cgcgctcact ctcccgattt caacttgtac aacgtgaatg tggagaacac ctacggcaaa     540
gggagccagg ccgtcgctgt ctcggcctac ggtaccgagc aggcatacta cggctgcaag     600
ctcacgggct tccaagacac cctcctcacc cagagaggca ggcactactt cgtaaacacc     660
tacattgaag gtaaggaggt cttttctcaag ctgcggaaag cgcggtctct gacggacatg     720
cacaggcgcc accgacttca tttttcggcca gtattccgcg gcctggtttg agaactgcga     780
cctgcgcgtc cccgcggcca agcagggatg ggtcaccgcg agcggccgca acacgaccaa     840
cgacggctgg tatgtcatca acggaggcag cgtgcaagcg gcacccggcc agaacgtaac     900
tgccggcgcg tacttcctgg gccggccgtg gcgcagcttc gcgcgcgccg tcttccagaa     960
cgtctacttg agcgaggtca tcaaccctgc gggctgggcc atctggtcca cgagcacgcc    1020
caacacgggc aacgtcacgt tcgcggagta caacaacacc ggacctggtg cttccaacgg    1080
gacgcgggcc agcttttcgc agcagctggc ggagccggtg acatcacgg aggtgctagg    1140
atcgaactac acactctgga ttgatcccaa gttcttgtga atagcaagcg ggtagaaagc    1200
cgcggtacga acgcctttgc cgtaattaga taatcccagg aagacggaga gaatgattat    1260
cttctcctct aatgcgccgt gggacgacgg atccgtgact gaatagtgag agcaaaagtg    1320
cgcctgcatg                                                           1330

<210> SEQ ID NO 50
<211> LENGTH: 975
<212> TYPE: DNA
<213> ORGANISM: M. phaseolina
```

```
<400> SEQUENCE: 50
atgcatagtt cttccatcct tttcagcctt ttcggctccg cactcgctct gacatctcca      60
ccgccaggag cgctgactgt tggaggctct gagggaaaat tctccaccgt tcaagctgcg     120
gttgacgctc tccagaacac cactgctcgg caatccatat tcatctactc cggcacttac     180
gaggagcagg tgtatatcgc caaacacaat ggccccattt ccatttatgg acaagcctcg     240
gatgacagct cataccacac caatactgtc actctctctt tcggcctcag ccaggccttc     300
aaccttagca acgacctcac ggccaccctc cgcgctcact ctcccgattt caacttgtac     360
aacgtgaatg tggagaacac ctacggcaaa gggagccagg ccgtcgctgt ctcggcctac     420
ggtaccgagc aggcatacta cggctgcaag ctcacgggct tccaagacac cctcctcacc     480
cagagaggca ggcactactt cgtaaacacc tacattgaag cgccaccgan cttcattttc     540
ggccagtatt ccgcggcctg gtttgagaac tgcgacctgc cgtccccgc ggccaagcag      600 ggatgggtca ccgcgagcgg ccgcaacacg accaacgacg gctggtatgt catcaacgga     660
ggcagcgtgc aagcggcacc cggccagaac gtaactgccg cgcgtacttc ctgggccgg      720 ccgtggcgca gcttcgcgcg cgccgtcttc cagaacgtct acttgagcga ggtcatcaac     780
cctgcgggct gggccatctg gtccacgagc acgcccaaca cgggcaacgt cacgttcgcg     840
gagtacaaca caccggacc tggtgcttcc aacgggacgc gggccagctt tcgcagcag       900 ctggcggagc cggtggacat cacggaggtg ctaggatcga actacacact ctggattgat     960
cccaagttct tgtga                                                      975

<210> SEQ ID NO 51
<211> LENGTH: 324
<212> TYPE: PRT
<213> ORGANISM: M. phaseolina

<400> SEQUENCE: 51

Met His Ser Ser Ser Ile Leu Phe Ser Leu Phe Gly Ser Ala Leu Ala
1               5                   10                  15

Leu Thr Ser Pro Pro Gly Ala Leu Thr Val Gly Gly Ser Glu Gly
                20                  25                  30

Lys Phe Ser Thr Val Gln Ala Ala Val Asp Ala Leu Gln Asn Thr Thr
            35                  40                  45

Ala Arg Gln Ser Ile Phe Ile Tyr Ser Gly Thr Tyr Glu Glu Gln Val
        50                  55                  60

Tyr Ile Ala Lys His Asn Gly Pro Ile Ser Ile Tyr Gly Gln Ala Ser
65                  70                  75                  80

Asp Asp Ser Ser Tyr His Thr Asn Thr Val Thr Leu Ser Phe Gly Leu
                85                  90                  95

Ser Gln Ala Phe Asn Leu Ser Asn Asp Leu Thr Ala Thr Leu Arg Ala
                100                 105                 110

His Ser Pro Asp Phe Asn Leu Tyr Asn Val Asn Val Glu Asn Thr Tyr
            115                 120                 125

Gly Lys Gly Ser Gln Ala Val Ala Val Ser Ala Tyr Gly Thr Glu Gln
        130                 135                 140

Ala Tyr Tyr Gly Cys Lys Leu Thr Gly Phe Gln Asp Thr Leu Leu Thr
145                 150                 155                 160

Gln Arg Gly Arg His Tyr Phe Val Asn Thr Tyr Ile Glu Gly Ala Thr
                165                 170                 175

Asp Phe Ile Phe Gly Gln Tyr Ser Ala Ala Trp Phe Glu Asn Cys Asp
            180                 185                 190
```

```
Leu Arg Val Pro Ala Ala Lys Gln Gly Trp Val Thr Ala Ser Gly Arg
        195                 200                 205

Asn Thr Thr Asn Asp Gly Trp Tyr Val Ile Asn Gly Gly Ser Val Gln
210                 215                 220

Ala Ala Pro Gly Gln Asn Val Thr Ala Gly Ala Tyr Phe Leu Gly Arg
225                 230                 235                 240

Pro Trp Arg Ser Phe Ala Arg Ala Val Phe Gln Asn Val Tyr Leu Ser
                245                 250                 255

Glu Val Ile Asn Pro Ala Gly Trp Ala Ile Trp Ser Thr Ser Thr Pro
                260                 265                 270

Asn Thr Gly Asn Val Thr Phe Ala Glu Tyr Asn Asn Thr Gly Pro Gly
            275                 280                 285

Ala Ser Asn Gly Thr Arg Ala Ser Phe Ser Gln Gln Leu Ala Glu Pro
290                 295                 300

Val Asp Ile Thr Glu Val Leu Gly Ser Asn Tyr Thr Leu Trp Ile Asp
305                 310                 315                 320

Pro Lys Phe Leu

<210> SEQ ID NO 52
<211> LENGTH: 7706
<212> TYPE: DNA
<213> ORGANISM: M. phaseolina

<400> SEQUENCE: 52
gctgcttctc tgagcggctc caagaacgcc ttttacaact gccaattcat ctccgccggc     60
gatttaggaa tatcctcgtc caccggtacc acgttcgtct acaattcgta catcgaagcg    120
cgttctaagc tcatctacaa tacgcctaac atgtacattt acggctcaac tctcacgcct    180
acggcgagca acgcactctt ggtttataac aagggcgtgt cttctggcac ggtggtgacc    240
accaactcca ccgttgtctt cgactcctgc accgtcactc cgaagccggg caccactgtg    300
accggtattt cccttgccgc agcgaacggt gttgggtcaa ttgtggtcta tagaaactcc    360
gtcctgccag gcttcattct cagcaccggt attcacgttg acgccaagac ccaggcagca    420
cagaacttct acgcgagtt cggtaacaca ggtgccggat cctactcttc caactccgcc    480
gcgagggcct cctacgtgaa gagcctgagc gtcgatcagc tttctcaatt ctccgttgat    540
caagtgttcg gcaccgcaaa cactaactgg atcgactctt cagtcatctc cctcgtccag    600
gattcggatg catctcaagc ggcaaggcg accacggcag gtgtggtgtc atacactact    660
acgtcttcct cttcaagtac tacaagctct gtactgtcga gcagcttggt cacccgcatcg    720
ggcagctccg tgtccacatc atcaagctcg gtgtcgtcta cgtcttcaac ctccgcctct    780
gccagtgacg cgccttcgct ttccagcagt gctgctctcg cttcatcagt acctggatct    840
tcctccaaca ctacagtgac caccagcggc acagcaagct caagctctgt cactggttcc    900
tcgttcgcac tgtccactag ctcgatctcc tccagcgtga gcactccggg ggacacagcg    960
agctccaccg ccgctgcgtc taattcgact tcgagttgcg ctcttccttc ctcagtgccc   1020
accactgctc gcgtcgtggg tccggctggg tcctgcgcca actacaccag catcgccgat   1080
gccgtcaaag acctttctac ggatcaatct aagacggaat atgtgtacat tctcgctggc   1140
acctataccg agcagatcat tttcagccgt gtaggtccca ccgtcttccg cggcgagaca   1200
tcaagcgagc tcgatcagtc cagcaacaaa gtgactatca agtcttctac tggtgtgccc   1260
tccagtagcg ggggatcttc cagtaccgcc ccgttccagg cgactcagta ctacagcaag   1320
```

| | |
|---|---|
| agtatcagtt tctataacat caatttcgag aacacctacg ctgcagctac gggttacaat | 1380 |
| gcggttgcat tgtccagcaa agctttgaag gcctattatt acaactgcgg gatcacttcc | 1440 |
| tctcaaggag ctctgctgct caacttcggc gcccacttct tctcgggctg caagattacc | 1500 |
| ggtaccaccg acatcgtctg gggccaaggt ggcgcttaca tctacaattc gaagatcgtt | 1560 |
| agcaccggaa ccacgactgg tcagtctctc tccgcacagt cgtaccagtc acaatacaat | 1620 |
| ccttcgcagt ttgtcttcga cacttgcgct ttcgtgccga acgacagcac cgtgccgaag | 1680 |
| gcgagcacgt acttgggccg cgactataca gcttcggcac gtgttgcggt gatcaactct | 1740 |
| tacctggacg ctcatattac tcctgttgga tggttgattg cgtccaagac tacgaacgtg | 1800 |
| acgtttgttg aggccagcaa ctccgggcct ggagcgtcga ccgcatctag agtttcccag | 1860 |
| attgtgaccg atacgtctgc ctacgccgcc aacaacgtgc tcggttctct ttcgatcgac | 1920 |
| accgccgctg ttgctcctgt tgctgccttc cccgacagcg tctacggtag tcctctttcc | 1980 |
| cccagctctt ctactgtctt ggccaactca acgacagcga cttccgtgtc tgcttcgaca | 2040 |
| tccagcactt ctgctgctgc aactgcggcc aacaccctca ttgtctcaac cacgcctgcc | 2100 |
| tctggcgaat acggcaacgt cacagcagcc atcgccgccc ttcccaacga tagcaaggag | 2160 |
| tacaccatct acatccgcgc cggcacctac caggagcagt tcaccattgt gcggaatggc | 2220 |
| aaggtcacac tgcgtggcga gacggcgttc cccaacgact tctcgcagaa ccaggtcacc | 2280 |
| atccagttct cctatggtgt tctcaccagc gctggccaga acgagttgac gcccgttatc | 2340 |
| aacgccaaga gaacgatgg ctccggcctc gcgttgtaca acatcaactt catcaacacg | 2400 |
| tacccgcaga cgaagaacac ggctgcgctt gcggctgact tctacggtac caatatggct | 2460 |
| gcctatggct gcaagttcgt cggctaccag gacaccctcc tcgccaacaa gggcacccaa | 2520 |
| gtcttttcca acagctacat tgaaggctct attgactata tctggggttt ctcgacggcc | 2580 |
| tacttccacc agtgctacat cgcatccaac acagctggtg gctacatttc tgccatgagc | 2640 |
| cgcgcttcgg cttcggctac tggaggttat gtctttgaca gctgctatgt cacctacacg | 2700 |
| agcacctacg gatcgacctt tggcaccagc tacctcggtc gcccgtactc gagctacagc | 2760 |
| atcgccgtct acatgaactc gttcattgac aagcacatta gccccgccgg ttgggctgtg | 2820 |
| tggcaaacga gtaacccgca gacggacaac gtcctgtttg gagagttcaa caacaccggc | 2880 |
| cccggaagct ggtccagctc tcgcgcgtct ttcgcgacga acttgaccga gtcccaggcg | 2940 |
| gatgcttaca agctgtctac ttggatcggc agcacgtcgt ggcttgacat ggatgcttac | 3000 |
| aactacgtgc cttcgtacga tatttccggc gcagctggtg catcaaccac gaccccctcg | 3060 |
| gcgtcagctt cctctaccac tgccacagcc actgccacct gggcgcatcc ctcgagtggt | 3120 |
| gctaccccac ctatcggtgc cgtcctggtg tccgttggag gctccgtcaa cgggtcatac | 3180 |
| agcaatctta ccgccgccct cgcgtctctg ccatcggata gctcgacaca ggtcatcttc | 3240 |
| atgtaccccg gaacctacaa cgagcagccc ccggccgtaa acaggccggg ccccatccag | 3300 |
| atcatcggtg ctcaagatgg caatccaggc cagagctaca agaccaataa agtcattctg | 3360 |
| acccagtctc gcggcttgtc ggtctctccg ttgccgaccg acactctga cgctgaaacc | 3420 |
| gcaacattct ccactaccag caacaaaatt gccatgtaca acatcgacat catcaactcc | 3480 |
| gataatcttg acggttcgct ttcctcttac gtgacgctgg ccggctcaat ttatggctcg | 3540 |
| cgcattgcgt tctatgggtg cagcttcatt ggctggcagg atacgctgtt gactggaagc | 3600 |
| accagtggct accagtacta cgaatcctgc tacattgatg gcgccatcga tttcatctgg | 3660 |
| ggctactcta aggcttactt caaaggctgc accatcggcg ccaaaaggca aagtcggcc | 3720 |

```
atcacggctc acagccgtgc ttcctccagc gcagtcggag gctacatctt cgaccagtgc    3780
ctgttcactg ctgcctcgtc tgcgacggtt gaccttacgc agtctgttta cctcggccgc    3840
ccttacagca agtacgccct cgtggttgtc aagaactcgt acctggacaa gacgatccag    3900
cctgctggtt ggaagatctg gtctgccacc gacccgcgta ccgactacgt taccttcgcc    3960
gagttcaaca actccggacc tggtaactgg gagaacaacg ccgcggcgcg taccgctttc    4020
ggctactgca ccctgttgac gtcggacacg tactccctat ctgccgtcat ggactcaccc    4080
tctgactgga ttgacatgac gtactgggac tcgatcacca caccgacagt ggccgctgtt    4140
gctacgggaa acaccactac ggcggtcaac ggtacttcgg tctatgatgg caccacccca    4200
cctgccggcg cattgattgt ctccaagacg gccattgagg gcgtgacgac gtacgatacc    4260
atccagagcg ctctgaatgc gctgcctact tcgagcagca agaccggcac catcttcatc    4320
taccccggtg tgtactcgga gcagcttgtg ctgagcaagt ctggtaccac cgtgttcatc    4380
ggctactcaa actccaccga cgattacctg cagaaccagg tgacgatcga cttcaacaag    4440
ggaatcgata cgcaagcaga tgcttccaac tctgacagcg ctactgtgta tgccacaggc    4500
aactacttcc aggcatacaa catcaacttc aagaactctt tcggcacaac cgaggactac    4560
gcctcgctcg gcttcggtgt caagtccagc aagtacgcat cgctgtatgg ctgccaggtc    4620
tggggcaatc aggactcgct actcatcaac ggctacttct tcgccttcaa ctcgctgatt    4680
gtcggtaaca tcgacatgat ctggggctcc ggcgcgggct atttcctcag ctcaaccatc    4740
tcacccaaca ccgacgacgt cagcctgacc gccagcaagc gcgcgaccaa cactacagct    4800
gccggttttg tcttcgacca gtgcaccgtt aagcccgccc ccggtaccgg ccccttcacc    4860
gagatcagcc tcggacgtcc gtggaacaac cttgcccgtg tcgcgtatat cgagacgtat    4920
ctcgattcca gcgttgaggc tgcaggctgg agccagtggt ccaagtccaa tccacagacc    4980
gaaggagtga cttttgccga gtacgggaac tatggaccgg gtgcaagcac ttcgggccgt    5040
gcgaaatttt ccacgcagct ctcggctgcc gatgccgccc agtttcagct cgccaacttc    5100
ttcgccgtca cctcctggat caacttcacg cggatcgatg tccaacccct cgtggccagc    5160
gaggttgttg ttccaacctc ggcggtcact tcgtctgtcc ttctctcttc cacccttagc    5220
actccgatct cgtcttcaac gcttatactg agcaccctct tcctcactaa agtcactacc    5280
gacaaggaga ctctcttcac aaccgtcact ggcgctgttc cgaccctcac ttcaacgcag    5340
actatcacgc tggacatggg tgccaccgtt accccgacc cagtgtacaa gaccagcacc    5400
gtgaagagta cgacaacgat cattgagacc gtatcgcagc ccgatgttac gcagacgtct    5460
actgtggtcg tcaccagcga tatcggaacc acaatcacac cggagccgag cacgatcacc    5520
actgtgctca agcagacgac tactgttttc gccacctcga ccaaggcgcc ccagacgatt    5580
actgagaaga gtaccattac ttcgacgagt ttggctaccc ggacgctcga tcccattacg    5640
tcaacactca gcctcggatc taccgtttat gtgaccagcg ttttcacccc gaaggccgcg    5700
cgggtcacct ctagtctaac catcactacg ggcactggcg gcacgtcaac taagacgacc    5760
aaagcaacca cgacttacgt cactgtcact tctgtgaaaa tgacaacgaa gaaatccaca    5820
acaaccctct cctgtgtgcc caccgacagt ctccaaaggc gctcgtaccc cttaggtccc    5880
cgcgccgccg gtgacagcgt caccacatcc accatttttct ccaccctcct cacctacgtc    5940
aagacctcta cagcaacctt agcccccggc tcgaccgcca cgaccttgt gtcgatcacc    6000
aagaccgtcg gctccaccac caccctcaag cccaccacca tcacggtctc cactgtctcc    6060
```

| atcgccacca | agtcctccac | cctcacccac | ccggcatcca | ccttcttcac | aaccgtaacc | 6120 |
| tcgaccaaac | tcaccggcaa | aaccacctcg | ctgaaagcct | caacactgac | ggtgacatcc | 6180 |
| acctcccttg | cagccacccg | cacctccgtc | accaccctct | ccgctgcggg | cgccgctaca | 6240 |
| acgacttctc | tcgccaccgt | gacgcggaaa | tcgacgataa | cgctccccgc | gagcaccgtc | 6300 |
| gtcaaaacat | cttcgcggga | cgccacgagc | agtgtagtca | tcacggcggc | ggcgagcacg | 6360 |
| agtacggtgt | ggaagacggc | cacgatcacg | ctggcaccga | gccagacagt | ggtgttgcag | 6420 |
| agcacagtcg | tcaaagaaac | gacggcaaag | gtaacaagca | cggttcttag | tacgataaca | 6480 |
| aagacggcga | aaggggcggc | ggcgtgtaca | gaggtataag | taaagattgg | aagagaagaa | 6540 |
| ggagggaat | agagttgaaa | ataaataaag | agaataaata | gtagcggggg | ttttatatat | 6600 |
| ttataatatt | ttaagtaact | agttacttaa | ttattaaatt | tcctaaaggc | cgaattctac | 6660 |
| acctgctcac | tgctgatgga | cgatacgggc | tgtgttccac | gatctatagt | cacatggaaa | 6720 |
| agcagaagtt | gcaaaattat | attatactta | cacgaaatat | ttcccggaaa | atcagacacc | 6780 |
| ttagtgtatt | acagttgtgc | caaggttcta | tctaagttga | aactccttta | tctactgtga | 6840 |
| gaaagagact | tgcatagact | taggtatatt | tcacgagaat | aacagcaatc | aacatatttg | 6900 |
| tagcagtaga | gcattgcttg | cacaggatag | gttcaattgc | ctttgaagtt | tctaagtcac | 6960 |
| tagagctgcc | tcgttcagtc | agagtcgttc | tttctggcgt | tcagcgaatg | actgctggca | 7020 |
| tccaaaatcg | agaatgaagt | gattccatat | gtgaggatgc | aatgcgacca | ttcaatcgaa | 7080 |
| cagcgcctcc | gcactcgcag | cctgagcgag | ttcccctctc | aatcgtgtgg | atataatccc | 7140 |
| ttgtcgactg | aatcaagtaa | ggggcataag | cctgagtagc | tctcttgtgt | ccagccacaa | 7200 |
| caatgtgcgg | gttcaaagcc | tcgatgcgat | caatagcatc | aagccgctcc | ctgcgtttgg | 7260 |
| ccggggcgtt | tgcctccccg | aaatgtggat | gacaatcgcc | gtagatgata | tcgccagaga | 7320 |
| caacgagacg | gacggaaggg | acgtggggga | agctggaaaa | ctcgttgtcg | gtgtgcccaa | 7380 |
| cttcaattcc | gtgccattta | tggccgttcg | acggagaact | cccccgacgc | tggaagcgcc | 7440 |
| ttgggcactg | gcttggcagt | atcgagctgg | ccggggaaca | tgccaggcca | gatgtgctcg | 7500 |
| caactcgtat | tgcatacggg | ataatacaac | gtgcacactc | ttggcgtgca | atataacact | 7560 |
| ttgcacactt | gcgtagcaaa | atacacacct | gttttactaa | gaaatacgat | cttttcttaa | 7620 |
| atatctctac | tacaacgcag | taatatataa | atagctaact | taaatataga | aatttagggt | 7680 |
| cttctttagg | attaggaggg | ttaggg | | | | 7706 |

<210> SEQ ID NO 53
<211> LENGTH: 5895
<212> TYPE: DNA
<213> ORGANISM: M. phaseolina

<400> SEQUENCE: 53

| atgtacattt | acggctcaac | tctcacgcct | acggcgagca | acgcactctt | ggtttataac | 60 |
| aagggcgtgt | cttctggcac | ggtggtgacc | accaactcca | ccgttgtctt | cgactcctgc | 120 |
| accgtcactc | cgaagccggg | caccactgtg | accggtattt | cccttgccgc | agcgaacggt | 180 |
| gttgggtcaa | ttgtggtcta | tagaaactcc | gtcctgccag | gcttcattct | cagcaccggt | 240 |
| attcacgttg | acgccaagac | ccaggcagca | cagaacttct | acggcgagtt | cggtaacaca | 300 |
| ggtgccggat | cctactcttc | caactccgcc | gcgagggcct | cctacgtgaa | gagcctgagc | 360 |
| gtcgatcagc | tttctcaatt | ctccgttgat | caagtgttcg | gcaccgcaaa | cactaactgg | 420 |
| atcgactctt | cagtcatctc | cctcgtccag | gattcggatg | catctcaagc | ggcaaaggcg | 480 |

```
accacggcag gtgtggtgtc atacactact acgtcttcct cttcaagtac tacaagctct      540
gtactgtcga gcagcttggt caccgcatcg ggcagctccg tgtccacatc atcaagctcg      600
gtgtcgtcta cgtcttcaac ctccgcctct gccagtgacg cgccttcgct ttccagcagt      660
gctgctctcg cttcatcagt acctggatct tcctccaaca ctacagtgac caccagcggc      720
acagcaagct caagtctgt cactggttcc tcgttcgcac tgtccactag ctcgatctcc       780
tccagcgtga gcactccggg ggacacagcg agctccaccg ccgctgcgtc taattcgact      840
tcgagttgcg ctcttccttc ctcagtgccc accactgctc gcgtcgtggg tccggctggg      900
tcctgcgcca actacaccag catcgccgat gccgtcaaag acctttctac ggatcaatct      960
aagacggaat atgtgtacat tctcgctggc acctataccg agcagatcat tttcagccgt     1020
gtaggtccca ccgtcttccg cggcgagaca tcaagcgagc tcgatcagtc cagcaacaaa     1080
gtgactatca agtcttctac tggtgtgccc tccagtagcg ggggatcttc cagtaccgcc     1140
ccgttccagg cgactcagta ctacagcaag agtatcagtt tctataacat caatttcgag     1200
aacacctacg ctgcagctac gggttacaat gcggttgcat tgtccagcaa agctttgaag     1260
gcctattatt acaactgcgg gatcacttcc tctcaaggag ctctgctgct caacttcggc     1320
gcccacttct tctcgggctg caagattacc ggtaccaccg acatcgtctg gggccaaggt     1380
ggcgcttaca tctacaattc gaagatcgtt agcaccggaa ccacgactgg tcagtctctc     1440
tccgcacagt cgtaccagtc acaatacaat ccttcgcagt ttgtcttcga cacttgcgct     1500
ttcgtgccga acgacagcac cgtgccgaag gcgagcacgt acttgggccg cgactataca     1560
gcttcggcac gtgttgcggt gatcaactct tacctggacg ctcatattac tcctgttgga     1620
tggttgattg cgtccaagac tacgaacgtg acgtttgttg aggccagcaa ctccgggcct     1680
ggagcgtcga ccgcatctag agtttcccag attgtgaccg atacgtctgc ctacgccgcc     1740
aacaacgtgc tcggttctct ttcgatcgac accgccgctg ttgctcctgt tgctgccttc     1800
cccgacagcg tctacggtag tcctctttcc cccagctctt ctactgtctt ggccaactca     1860
acgacagcga cttccgtgtc tgcttcgaca tccagcactt ctgctgctgc aactgcggcc     1920
aacaccctca ttgtctcaac cacgcctgcc tctggcgaat acggcaacgt cacagcagcc     1980
atcgccgccc ttcccaacga tagcaaggag tacaccatct acatccgcgc cggcacctac     2040
caggagcagt tcaccattgt gcggaatggc aaggtcacac tgcgtggcga cggcgttc       2100 cccaacgact ctctcgcagaa ccaggtcacc atccagttct cctatggtgt tctcaccagc     2160
gctggccaga acgagttgac gcccgttatc aacgccaaga agaacgatgg ctccggcctc     2220
gcgttgtaca acatcaactt catcaacacg tacccgcaga cgaagaacac ggctgcgctt     2280
gcggctgact tctacggtac caatatggct gcctatggct gcaagttcgt cggctaccag     2340 gacacccctcc tcgccaacaa gggcacccaa gtcttttcca acagctacat tgaaggctct     2400
attgactata tctgggttt ctcgacggcc tacttccacc agtgctacat cgcatccaac     2460
acagctggtg gctacatttc tgccatgagc cgcgcttcgg cttcggctac tggaggttat     2520
gtctttgaca gctgctatgt cacctacacg agcacctacg gatcgacctt tggcaccagc     2580
tacctcggtc gcccgtactc gagctacagc atcgccgtct acatgaactc gttcattgac     2640
aagcacatta gccccgccgg ttgggctgtg tggcaaacga gtaacccgca gacggacaac     2700
gtcctgtttg gagagttcaa caacaccggc cccggaagct ggtccagctc tcgcgcgtct     2760
ttcgcgacga acttgaccga gtcccaggcg gatgcttaca agctgtctac ttggatcggc     2820
```

```
agcacgtcgt ggcttgacat ggatgcttac aactacgtgc cttcgtacga tatttccggc    2880
gcagctggtg catcaaccac gaccccctcg gcgtcagctt cctctaccac tgccacagcc    2940
actgccacct gggcgcatcc ctcgagtggt gctaccccac ctatcggtgc cgtcctggtg    3000
tccgttggag gctccgtcaa cgggtcatac agcaatctta ccgccgccct cgcgtctctg    3060
ccatcggata gctcgacaca ggtcatcttc atgtaccccg gaacctacaa cgagcagccc    3120
ccggccgtaa acaggcccgg ccccatccag atcatcggtg ctcaagatgg caatccaggc    3180
cagagctaca agaccaataa agtcattctg acccagtctc gcggcttgtc ggtctctccg    3240
ttgccgaccg gacactctga cgctgaaacc gcaacattct ccactaccag caacaaaatt    3300
gccatgtaca acatcgacat catcaactcc gataatcttg acggttcgct ttcctcttac    3360
gtgacgctgg ccggctcaat ttatggctcg cgcattgcgt tctatgggtg cagcttcatt    3420
ggctggcagg atacgctgtt gactggaagc accagtggct accagtacta cgaatcctgc    3480
tacattgatg gcgccatcga tttcatctgg ggctactcta aggcttactt caaaggctgc    3540
accatcggcg ccaaaaggca aaagtcggcc atcacggctc acagccgtgc ttcctccagc    3600
gcagtcggag gctacatctt cgaccagtgc ctgttcactg ctgcctcgtc tgcgacggtt    3660
gaccttacgc agtctgttta cctcggccgc ccttacagca agtacgccct cgtggttgtc    3720
aagaactcgt acctggacaa gacgatccag cctgctggtt ggaagatctg gtctgccacc    3780
gacccgcgta ccgactacgt taccttcgcc gagttcaaca actccggacc tggtaactgg    3840
gagaacaacg ccgcggcgcg taccgctttc ggctactgca ccctgttgac gtcggacacg    3900
tactccctat ctgccgtcat ggactcaccc tctgactgga ttgacatgac gtactgggac    3960
tcgatcacca caccgacagt ggccgctgtt gctacgggaa acaccactac ggcggtcaac    4020
ggtacttcgg tctatgatgg caccacccca cctgccggcg cattgattgt ctccaagacg    4080
gccattgagg gcgtgacgac gtacgatacc atccagagcg ctctgaatgc gctgcctact    4140
tcgagcagca agaccggcac catcttcatc taccccggtg tgtactcgga gcagcttgtg    4200
ctgagcaagt ctggtaccac cgtgttcatc ggctactcaa actccaccga cgattacctg    4260
cagaaccagg tgacgatcga cttcaacaag ggaatcgata cgcaagcaga tgcttccaac    4320
tctgacagcg ctactgtgta tgccacaggc aactacttcc aggcatacaa catcaacttc    4380
aagaactctt tcggcacaac cgaggactac gcctcgctcg gcttcggtgt caagtccagc    4440
aagtacgcat cgctgtatgg ctgccaggtc tggggcaatc aggactcgct actcatcaac    4500
ggctacttct tcgccttcaa ctcgctgatt gtcggtaaca tcgacatgat ctggggctcc    4560
ggcgcgggct atttcctcag ctcaaccatc tcacccaaca ccgacgacgt cagcctgacc    4620
gccagcaagc gcgcgaccaa cactacagct gccggttttg tcttcgacca gtgcaccgtt    4680
aagcccgccc ccggtaccgg ccccttcacc gagatcagcc tcggacgtcc gtggaacaac    4740
cttgcccgtg tcgcgtatat cgagacgtat ctcgattcca gcgttgaggc tgcaggctgg    4800
agccagtggt ccaagtccaa tccacagacc gaaggagtga cttttgccga gtacgggaac    4860
tatggaccgg gtgcaagcac ttcgggccgt gcgaaatttt ccacgcagct ctcggctgcc    4920
gatgccgccc agtttcagct cgccaacttc ttcgccgtca cctcctggat caacttcacg    4980
cggatcgatg tccaacccct tcgtggccagc gaggttgttg ttccaacctc ggcggtcact    5040
tcgtctgtcc ttctctcttc cacccttagc actccgatct cgtcttcaac gcttatactg    5100
agcaccctct tcctcactaa agtcactacc gacaaggaga ctctcttcac aaccgtcact    5160
ggcgctgttc cgaccctcac ttcaacgcag actatcacgc tggacatggg tgccaccgtt    5220
```

```
acccccgacc cagtgtacaa gaccagcacc gtgaagagta cgacaacgat cattgagacc    5280
gtatcgcagc ccgatgttac gcagacgtct actgtggtcg tcaccagcga tatcggaacc    5340
acaatcacac cggagccgag cacgatcacc actgtgctca agcagacgac tactgttttc    5400
gccacctcga ccaaggcgcc ccagacgatt actgagaaga gtaccattac ttcgacgagt    5460
ttggctaccc ggacgctcga tcccattacg tcaacactca gcctcggatc taccgtttat    5520
gtgaccagcg ttttcacccc gaaggccgcg cgggtcacct ctagtctaac catcactacg    5580
ggcactggcg gcacgtcaac taagacgacc aaagcaacca cgacttacgt cactgtcact    5640
tctatgatat cgccagagac aacgagacgg acggaaggga cgtgggggaa gctggaaaac    5700
tcgttgtcgg tgtgcccaac ttcaattccg tgccatttat ggccgttcga cggagaactc    5760
ccccgacgct ggaagcgcct tgggcactgg cttggcagta tcgagctggc cggggaacat    5820
gccaggccag atgtgctcgc aactcgtatt gcatacggga taatacaacg tgcacactct    5880
tggcgtgcaa tataa                                                     5895

<210> SEQ ID NO 54
<211> LENGTH: 1964
<212> TYPE: PRT
<213> ORGANISM: M. phaseolina

<400> SEQUENCE: 54

Met Tyr Ile Tyr Gly Ser Thr Leu Thr Pro Thr Ala Ser Asn Ala Leu
1               5                   10                  15

Leu Val Tyr Asn Lys Gly Val Ser Ser Gly Thr Val Val Thr Thr Asn
            20                  25                  30

Ser Thr Val Val Phe Asp Ser Cys Thr Val Thr Pro Lys Pro Gly Thr
        35                  40                  45

Thr Val Thr Gly Ile Ser Leu Ala Ala Ala Asn Gly Val Gly Ser Ile
    50                  55                  60

Val Val Tyr Arg Asn Ser Val Leu Pro Gly Phe Ile Leu Ser Thr Gly
65                  70                  75                  80

Ile His Val Asp Ala Lys Thr Gln Ala Ala Gln Asn Phe Tyr Gly Glu
                85                  90                  95

Phe Gly Asn Thr Gly Ala Gly Ser Tyr Ser Ser Asn Ser Ala Ala Arg
            100                 105                 110

Ala Ser Tyr Val Lys Ser Leu Ser Val Asp Gln Leu Ser Gln Phe Ser
        115                 120                 125

Val Asp Gln Val Phe Gly Thr Ala Asn Thr Asn Trp Ile Asp Ser Ser
    130                 135                 140

Val Ile Ser Leu Val Gln Asp Ser Asp Ala Ser Gln Ala Ala Lys Ala
145                 150                 155                 160

Thr Thr Ala Gly Val Val Ser Tyr Thr Thr Thr Ser Ser Ser Ser Ser
                165                 170                 175

Thr Thr Ser Ser Val Leu Ser Ser Ser Leu Val Thr Ala Ser Gly Ser
            180                 185                 190

Ser Val Ser Thr Ser Ser Ser Val Ser Ser Thr Ser Ser Thr Ser
        195                 200                 205

Ala Ser Ala Ser Asp Ala Pro Ser Leu Ser Ser Ser Ala Ala Leu Ala
    210                 215                 220

Ser Ser Val Pro Gly Ser Ser Asn Thr Thr Val Thr Thr Ser Gly
225                 230                 235                 240

Thr Ala Ser Ser Ser Ser Val Thr Gly Ser Ser Phe Ala Leu Ser Thr
```

```
                245                 250                 255
Ser Ser Ile Ser Ser Ser Val Ser Thr Pro Gly Asp Thr Ala Ser Ser
            260                 265                 270

Thr Ala Ala Ala Ser Asn Ser Thr Ser Ser Cys Ala Leu Pro Ser Ser
            275                 280                 285

Val Pro Thr Thr Ala Arg Val Val Gly Pro Ala Gly Ser Cys Ala Asn
            290                 295                 300

Tyr Thr Ser Ile Ala Asp Ala Val Lys Asp Leu Ser Thr Asp Gln Ser
305                 310                 315                 320

Lys Thr Glu Tyr Val Tyr Ile Leu Ala Gly Thr Tyr Thr Glu Gln Ile
                325                 330                 335

Ile Phe Ser Arg Val Gly Pro Thr Val Phe Arg Gly Glu Thr Ser Ser
                340                 345                 350

Glu Leu Asp Gln Ser Ser Asn Lys Val Thr Ile Lys Ser Ser Thr Gly
                355                 360                 365

Val Pro Ser Ser Ser Gly Gly Ser Ser Ser Thr Ala Pro Phe Gln Ala
            370                 375                 380

Thr Gln Tyr Tyr Ser Lys Ser Ile Ser Phe Tyr Asn Ile Asn Phe Glu
385                 390                 395                 400

Asn Thr Tyr Ala Ala Thr Gly Tyr Asn Ala Val Ala Leu Ser Ser
                405                 410                 415

Lys Ala Leu Lys Ala Tyr Tyr Asn Cys Gly Ile Thr Ser Ser Gln
                420                 425                 430

Gly Ala Leu Leu Leu Asn Phe Gly Ala His Phe Phe Ser Gly Cys Lys
            435                 440                 445

Ile Thr Gly Thr Thr Asp Ile Val Trp Gly Gln Gly Gly Ala Tyr Ile
            450                 455                 460

Tyr Asn Ser Lys Ile Val Ser Thr Gly Thr Thr Thr Gly Gln Ser Leu
465                 470                 475                 480

Ser Ala Gln Ser Tyr Gln Ser Gln Tyr Asn Pro Ser Gln Phe Val Phe
                485                 490                 495

Asp Thr Cys Ala Phe Val Pro Asn Asp Ser Thr Val Pro Lys Ala Ser
            500                 505                 510

Thr Tyr Leu Gly Arg Asp Tyr Thr Ala Ser Ala Arg Val Ala Val Ile
            515                 520                 525

Asn Ser Tyr Leu Asp Ala His Ile Thr Pro Val Gly Trp Leu Ile Ala
            530                 535                 540

Ser Lys Thr Thr Asn Val Thr Phe Val Glu Ala Ser Asn Ser Gly Pro
545                 550                 555                 560

Gly Ala Ser Thr Ala Ser Arg Val Ser Gln Ile Val Thr Asp Thr Ser
                565                 570                 575

Ala Tyr Ala Ala Asn Asn Val Leu Gly Ser Leu Ser Ile Asp Thr Ala
            580                 585                 590

Ala Val Ala Pro Val Ala Ala Phe Pro Asp Ser Val Tyr Gly Ser Pro
            595                 600                 605

Leu Ser Pro Ser Ser Ser Thr Val Leu Ala Asn Ser Thr Thr Ala Thr
            610                 615                 620

Ser Val Ser Ala Ser Thr Ser Ser Thr Ser Ala Ala Thr Ala Ala
625                 630                 635                 640

Asn Thr Leu Ile Val Ser Thr Thr Pro Ala Ser Gly Glu Tyr Gly Asn
                645                 650                 655

Val Thr Ala Ala Ile Ala Ala Leu Pro Asn Asp Ser Lys Glu Tyr Thr
            660                 665                 670
```

```
Ile Tyr Ile Arg Ala Gly Thr Tyr Gln Glu Gln Phe Thr Ile Val Arg
        675                 680                 685

Asn Gly Lys Val Thr Leu Arg Gly Glu Thr Ala Phe Pro Asn Asp Phe
    690                 695                 700

Ser Gln Asn Gln Val Thr Ile Gln Phe Ser Tyr Gly Val Leu Thr Ser
705                 710                 715                 720

Ala Gly Gln Asn Glu Leu Thr Pro Val Ile Asn Ala Lys Lys Asn Asp
            725                 730                 735

Gly Ser Gly Leu Ala Leu Tyr Asn Ile Asn Phe Ile Asn Thr Tyr Pro
            740                 745                 750

Gln Thr Lys Asn Thr Ala Ala Leu Ala Ala Asp Phe Tyr Gly Thr Asn
            755                 760                 765

Met Ala Ala Tyr Gly Cys Lys Phe Val Gly Tyr Gln Asp Thr Leu Leu
            770                 775                 780

Ala Asn Lys Gly Thr Gln Val Phe Ser Asn Ser Tyr Ile Glu Gly Ser
785                 790                 795                 800

Ile Asp Tyr Ile Trp Gly Phe Ser Thr Ala Tyr Phe His Gln Cys Tyr
                805                 810                 815

Ile Ala Ser Asn Thr Ala Gly Gly Tyr Ile Ser Ala Met Ser Arg Ala
            820                 825                 830

Ser Ala Ser Ala Thr Gly Gly Tyr Val Phe Asp Ser Cys Tyr Val Thr
            835                 840                 845

Tyr Thr Ser Thr Tyr Gly Ser Thr Phe Gly Thr Ser Tyr Leu Gly Arg
        850                 855                 860

Pro Tyr Ser Ser Tyr Ser Ile Ala Val Tyr Met Asn Ser Phe Ile Asp
865                 870                 875                 880

Lys His Ile Ser Pro Ala Gly Trp Ala Val Trp Gln Thr Ser Asn Pro
                885                 890                 895

Gln Thr Asp Asn Val Leu Phe Gly Glu Phe Asn Asn Thr Gly Pro Gly
            900                 905                 910

Ser Trp Ser Ser Ser Arg Ala Ser Phe Ala Thr Asn Leu Thr Glu Ser
        915                 920                 925

Gln Ala Asp Ala Tyr Lys Leu Ser Thr Trp Ile Gly Ser Thr Ser Trp
            930                 935                 940

Leu Asp Met Asp Ala Tyr Asn Tyr Val Pro Ser Tyr Asp Ile Ser Gly
945                 950                 955                 960

Ala Ala Gly Ala Ser Thr Thr Pro Ser Ala Ser Ala Ser Ser Thr
            965                 970                 975

Thr Ala Thr Ala Thr Ala Thr Trp Ala His Pro Ser Ser Gly Ala Thr
            980                 985                 990

Pro Pro Ile Gly Ala Val Leu Val Ser Val Gly Gly Ser Val Asn Gly
        995                 1000                1005

Ser Tyr Ser Asn Leu Thr Ala Ala Leu Ala Ser Leu Pro Ser Asp
    1010                1015                1020

Ser Ser Thr Gln Val Ile Phe Met Tyr Pro Gly Thr Tyr Asn Glu
    1025                1030                1035

Gln Pro Pro Ala Val Asn Arg Pro Gly Pro Ile Gln Ile Ile Gly
    1040                1045                1050

Ala Gln Asp Gly Asn Pro Gly Gln Ser Tyr Lys Thr Asn Lys Val
    1055                1060                1065

Ile Leu Thr Gln Ser Arg Gly Leu Ser Val Ser Pro Leu Pro Thr
    1070                1075                1080
```

-continued

```
Gly His Ser Asp Ala Glu Thr Ala Phe Ser Thr Thr Ser Asn
1085                1090                1095

Lys Ile Ala Met Tyr Asn Ile Asp Ile Ile Asn Ser Asp Asn Leu
1100                1105                1110

Asp Gly Ser Leu Ser Ser Tyr Val Thr Leu Ala Gly Ser Ile Tyr
1115                1120                1125

Gly Ser Arg Ile Ala Phe Tyr Gly Cys Ser Phe Ile Gly Trp Gln
1130                1135                1140

Asp Thr Leu Leu Thr Gly Ser Thr Ser Gly Tyr Gln Tyr Tyr Glu
1145                1150                1155

Ser Cys Tyr Ile Asp Gly Ala Ile Asp Phe Ile Trp Gly Tyr Ser
1160                1165                1170

Lys Ala Tyr Phe Lys Gly Cys Thr Ile Gly Ala Lys Arg Gln Lys
1175                1180                1185

Ser Ala Ile Thr Ala His Ser Arg Ala Ser Ser Ala Val Gly
1190                1195                1200

Gly Tyr Ile Phe Asp Gln Cys Leu Phe Thr Ala Ala Ser Ser Ala
1205                1210                1215

Thr Val Asp Leu Thr Gln Ser Val Tyr Leu Gly Arg Pro Tyr Ser
1220                1225                1230

Lys Tyr Ala Leu Val Val Val Lys Asn Ser Tyr Leu Asp Lys Thr
1235                1240                1245

Ile Gln Pro Ala Gly Trp Lys Ile Trp Ser Ala Thr Asp Pro Arg
1250                1255                1260

Thr Asp Tyr Val Thr Phe Ala Glu Phe Asn Asn Ser Gly Pro Gly
1265                1270                1275

Asn Trp Glu Asn Asn Ala Ala Ala Arg Thr Ala Phe Gly Tyr Cys
1280                1285                1290

Thr Leu Leu Thr Ser Asp Thr Tyr Ser Leu Ser Ala Val Met Asp
1295                1300                1305

Ser Pro Ser Asp Trp Ile Asp Met Thr Tyr Trp Asp Ser Ile Thr
1310                1315                1320

Thr Pro Thr Val Ala Ala Val Ala Thr Gly Asn Thr Thr Thr Ala
1325                1330                1335

Val Asn Gly Thr Ser Val Tyr Asp Gly Thr Thr Pro Pro Ala Gly
1340                1345                1350

Ala Leu Ile Val Ser Lys Thr Ala Ile Glu Gly Val Thr Thr Tyr
1355                1360                1365

Asp Thr Ile Gln Ser Ala Leu Asn Ala Leu Pro Thr Ser Ser Ser
1370                1375                1380

Lys Thr Gly Thr Ile Phe Ile Tyr Pro Gly Val Tyr Ser Glu Gln
1385                1390                1395

Leu Val Leu Ser Lys Ser Gly Thr Thr Val Phe Ile Gly Tyr Ser
1400                1405                1410

Asn Ser Thr Asp Asp Tyr Leu Gln Asn Gln Val Thr Ile Asp Phe
1415                1420                1425

Asn Lys Gly Ile Asp Thr Gln Ala Asp Ala Ser Asn Ser Asp Ser
1430                1435                1440

Ala Thr Val Tyr Ala Thr Gly Asn Tyr Phe Gln Ala Tyr Asn Ile
1445                1450                1455

Asn Phe Lys Asn Ser Phe Gly Thr Thr Glu Asp Tyr Ala Ser Leu
1460                1465                1470

Gly Phe Gly Val Lys Ser Ser Lys Tyr Ala Ser Leu Tyr Gly Cys
```

```
            1475                1480                1485

Gln Val Trp Gly Asn Gln Asp Ser Leu Leu Ile Asn Gly Tyr Phe
    1490                1495                1500

Phe Ala Phe Asn Ser Leu Ile Val Gly Asn Ile Asp Met Ile Trp
    1505                1510                1515

Gly Ser Gly Ala Gly Tyr Phe Leu Ser Ser Thr Ile Ser Pro Asn
    1520                1525                1530

Thr Asp Asp Val Ser Leu Thr Ala Ser Lys Arg Ala Thr Asn Thr
    1535                1540                1545

Thr Ala Ala Gly Phe Val Phe Asp Gln Cys Thr Val Lys Pro Ala
    1550                1555                1560

Pro Gly Thr Gly Pro Phe Thr Glu Ile Ser Leu Gly Arg Pro Trp
    1565                1570                1575

Asn Asn Leu Ala Arg Val Ala Tyr Ile Glu Thr Tyr Leu Asp Ser
    1580                1585                1590

Ser Val Glu Ala Ala Gly Trp Ser Gln Trp Ser Lys Ser Asn Pro
    1595                1600                1605

Gln Thr Glu Gly Val Thr Phe Ala Glu Tyr Gly Asn Tyr Gly Pro
    1610                1615                1620

Gly Ala Ser Thr Ser Gly Arg Ala Lys Phe Ser Thr Gln Leu Ser
    1625                1630                1635

Ala Ala Asp Ala Ala Gln Phe Gln Leu Ala Asn Phe Phe Ala Val
    1640                1645                1650

Thr Ser Trp Ile Asn Phe Thr Arg Ile Asp Val Gln Pro Phe Val
    1655                1660                1665

Ala Ser Glu Val Val Val Pro Thr Ser Ala Val Thr Ser Ser Val
    1670                1675                1680

Leu Leu Ser Ser Thr Leu Ser Thr Pro Ile Ser Ser Ser Thr Leu
    1685                1690                1695

Ile Leu Ser Thr Leu Phe Leu Thr Lys Val Thr Thr Asp Lys Glu
    1700                1705                1710

Thr Leu Phe Thr Thr Val Thr Gly Ala Val Pro Thr Leu Thr Ser
    1715                1720                1725

Thr Gln Thr Ile Thr Leu Asp Met Gly Ala Thr Val Thr Pro Asp
    1730                1735                1740

Pro Val Tyr Lys Thr Ser Thr Val Lys Ser Thr Thr Ile Ile
    1745                1750                1755

Glu Thr Val Ser Gln Pro Asp Val Thr Gln Thr Ser Thr Val Val
    1760                1765                1770

Val Thr Ser Asp Ile Gly Thr Thr Ile Thr Pro Glu Pro Ser Thr
    1775                1780                1785

Ile Thr Thr Val Leu Lys Gln Thr Thr Thr Val Phe Ala Thr Ser
    1790                1795                1800

Thr Lys Ala Pro Gln Thr Ile Thr Glu Lys Ser Thr Ile Thr Ser
    1805                1810                1815

Thr Ser Leu Ala Thr Arg Thr Leu Asp Pro Ile Thr Ser Thr Leu
    1820                1825                1830

Ser Leu Gly Ser Thr Val Tyr Val Thr Ser Val Phe Thr Pro Lys
    1835                1840                1845

Ala Ala Arg Val Thr Ser Ser Leu Thr Ile Thr Thr Gly Thr Gly
    1850                1855                1860

Gly Thr Ser Thr Lys Thr Thr Lys Ala Thr Thr Thr Tyr Val Thr
    1865                1870                1875
```

| Val | Thr | Ser | Met | Ile | Ser | Pro | Glu | Thr | Thr | Arg | Arg | Thr | Glu | Gly |
| | 1880 | | | | 1885 | | | | | 1890 | | | | |

| Thr | Trp | Gly | Lys | Leu | Glu | Asn | Ser | Leu | Ser | Val | Cys | Pro | Thr | Ser |
| | 1895 | | | | 1900 | | | | 1905 | | | | | |

| Ile | Pro | Cys | His | Leu | Trp | Pro | Phe | Asp | Gly | Glu | Leu | Pro | Arg | Arg |
| | 1910 | | | | 1915 | | | | | 1920 | | | | |

| Trp | Lys | Arg | Leu | Gly | His | Trp | Leu | Gly | Ser | Ile | Glu | Leu | Ala | Gly |
| | 1925 | | | | 1930 | | | | | 1935 | | | | |

| Glu | His | Ala | Arg | Pro | Asp | Val | Leu | Ala | Thr | Arg | Ile | Ala | Tyr | Gly |
| | 1940 | | | | 1945 | | | | | 1950 | | | | |

| Ile | Ile | Gln | Arg | Ala | His | Ser | Trp | Arg | Ala | Ile |
| | 1955 | | | | | 1960 | | | | |

```
<210> SEQ ID NO 55
<211> LENGTH: 1281
<212> TYPE: DNA
<213> ORGANISM: M. phaseolina

<400> SEQUENCE: 55
caccggttgt tgatcattta caccctcagc gagcattccc ggccaggcgc ctcttgttga      60
acactgtcca gtccttcact cctctccttc cacccgctac ccggtctttt tccttttgcc     120
attccaattg cgtgaaccgt ccatcacagc atgcctcgcc tcgccagcct cctcgccctt     180
gcaagcccag tgcttgccct gacctcccct ccgtcaggcg ccctcaccgt cggctccagc     240
ggcaagtact cgaccatcca ggacgccgtc gacgcgctca gcaccagctc ctcgtcggcc     300
cagaccatct tcatctacca gggcacctac aaggaacaag tcgtgatccc gaagctatcg     360
ggcgccctca ccatctacgg ctactcgaag gatggatcat cgtacagcgg caacaccgtg     420
accatcagcg cgggcaagtc gcaggccgac ggcctctcca cgacggcac cgccacccte     480
gccgtccaca cgggcaacat caaggtctac aacatcaacg tcgccaacac gtacggctcc     540
ggctcgcagg ccgtcgcgct gtcggcctac gccagcggca ccacggcta ctacggcgtc     600
aagctcacgg gcttccaaga cacgctcctg gcgcaggagg gcaaacaagt ctacgccaac     660
tcgtacatcg agggcgcgac cgatttcatt ttcggccaga aggccgtcgc gtggtttgag     720
aactgcgacc tgcgcatcgc ctcggcctcg ctcggctacg tgacggccaa cggccgcgac     780
agcagctcca acccatccta ctacgtcatc aacaactcga ccgtcgccgc cgccgacggc     840
gccaccgtca gagcggcgg catctacctc ggccgcccct ggcgcaacta cgcccgcgtc     900
gtcttccagg agaccagcct gtccaacatc atcaacagcg ccggctgggt ccaatggggc     960
agcagcgacc cacgcaccga caatgtcaac ttcgccgagt acaaaaactc gggcgccggc    1020
gcctctacca gcgccgtgc tagctttcc aagcagttga gcagcccgt cagcatctcg      1080
gaagtcttgg gcagcaacta cgccgactgg atcgacacca gctacttcta aacgcgtgag    1140
gcttcgctaa tgtcggttgg atcggatgga ggcgggatgt agcatgcaag gaaccggcag    1200
gactgtttta acttctaat gtggatattt ttgtctctcg gacaaatata aaataagct      1260
ttctggagtg acttttgatg a                                              1281

<210> SEQ ID NO 56
<211> LENGTH: 981
<212> TYPE: DNA
<213> ORGANISM: M. phaseolina

<400> SEQUENCE: 56
```

```
atgcctcgcc tcgccagcct cctcgccctt gcaagcccag tgcttgccct gacctcccct      60
ccgtcaggcg ccctcaccgt cggctccagc ggcaagtact cgaccatcca ggacgccgtc     120
gacgcgctca gcaccagctc ctcgtcggcc cagaccatct tcatctacca gggcacctac     180
aaggaacaag tcgtgatccc gaagctatcg ggcgccctca ccatctacgg ctactcgaag     240
gatggatcat cgtacagcgg caacaccgtg accatcagcg cgggcaagtc gcaggccgac     300
ggcctctcca cgacggcac cgccaccctc gccgtccaca cgggcaacat caaggtctac      360
aacatcaacg tcgccaacac cgtacggctcc ggctcgcagg ccgtcgcgct gtcggcctac    420
gccagcggca accacggcta ctacggcgtc aagctcacgg gcttccaaga cacgctcctg     480
gcgcaggagg gcaaacaagt ctacgccaac tcgtacatcg agggcgcgac cgatttcatt     540
ttcggccaga aggccgtcgc gtggtttgag aactgcgacc tgcgcatcgc ctcggcctcg     600
ctcggctacg tgacggccaa cggccgcgac agcagctcca acccatccta ctacgtcatc     660
aacaactcga ccgtcgccgc cgccgacggc gccaccgtca agagcggcgg catctacctc     720
ggccgcccct ggcgcaacta cgcccgcgtc gtcttccagg agaccagcct gtccaacatc     780
atcaacagcg ccggctgggt ccaatggggc agcagcgacc cacgcaccga caatgtcaac     840
ttcgccgagt acaaaaactc gggcgccggc gcctctacca gcggccgtgc tagctttttcc    900
aagcagttga gcagccccgt cagcatctcg gaagtcttgg gcagcaacta cgccgactgg     960
atcgacacca gctacttcta a                                              981
```

<210> SEQ ID NO 57
<211> LENGTH: 326
<212> TYPE: PRT
<213> ORGANISM: M. phaseolina

<400> SEQUENCE: 57

```
Met Pro Arg Leu Ala Ser Leu Leu Ala Leu Ala Ser Pro Val Leu Ala
1               5                  10                  15

Leu Thr Ser Pro Pro Ser Gly Ala Leu Thr Val Gly Ser Ser Gly Lys
            20                  25                  30

Tyr Ser Thr Ile Gln Asp Ala Val Asp Ala Leu Ser Thr Ser Ser Ser
        35                  40                  45

Ser Ala Gln Thr Ile Phe Ile Tyr Gln Gly Thr Tyr Lys Glu Gln Val
    50                  55                  60

Val Ile Pro Lys Leu Ser Gly Ala Leu Thr Ile Tyr Gly Tyr Ser Lys
65                  70                  75                  80

Asp Gly Ser Ser Tyr Ser Gly Asn Thr Val Thr Ile Ser Ala Gly Lys
                85                  90                  95

Ser Gln Ala Asp Gly Leu Ser Asn Asp Gly Thr Ala Thr Leu Ala Val
            100                 105                 110

His Thr Gly Asn Ile Lys Val Tyr Asn Ile Asn Val Ala Asn Thr Tyr
        115                 120                 125

Gly Ser Gly Ser Gln Ala Val Ala Leu Ser Ala Tyr Ala Ser Gly Asn
    130                 135                 140

His Gly Tyr Tyr Gly Val Lys Leu Thr Gly Phe Gln Asp Thr Leu Leu
145                 150                 155                 160

Ala Gln Glu Gly Lys Gln Val Tyr Ala Asn Ser Tyr Ile Glu Gly Ala
                165                 170                 175

Thr Asp Phe Ile Phe Gly Gln Lys Ala Val Ala Trp Phe Glu Asn Cys
            180                 185                 190

Asp Leu Arg Ile Ala Ser Ala Ser Leu Gly Tyr Val Thr Ala Asn Gly
```

```
              195                 200                 205
Arg Asp Ser Ser Ser Asn Pro Ser Tyr Tyr Val Ile Asn Asn Ser Thr
    210                 215                 220

Val Ala Ala Ala Asp Gly Ala Thr Val Lys Ser Gly Gly Ile Tyr Leu
225                 230                 235                 240

Gly Arg Pro Trp Arg Asn Tyr Ala Arg Val Val Phe Gln Glu Thr Ser
                245                 250                 255

Leu Ser Asn Ile Ile Asn Ser Ala Gly Trp Val Gln Trp Gly Ser Ser
                260                 265                 270

Asp Pro Arg Thr Asp Asn Val Asn Phe Ala Glu Tyr Lys Asn Ser Gly
            275                 280                 285

Ala Gly Ala Ser Thr Ser Gly Arg Ala Ser Phe Ser Lys Gln Leu Ser
        290                 295                 300

Ser Pro Val Ser Ile Ser Glu Val Leu Gly Ser Asn Tyr Ala Asp Trp
305                 310                 315                 320

Ile Asp Thr Ser Tyr Phe
                325

<210> SEQ ID NO 58
<211> LENGTH: 1943
<212> TYPE: DNA
<213> ORGANISM: M. phaseolina

<400> SEQUENCE: 58
ctatatttcc attttgggga acgtacgcgt acgccttctg tggggcccct tactcccgga        60
ggattgctgc gggacttgga gaatgtataa agtacagcaa tcgagttgtc tgcgagctag       120
agcgttctcc aggcagtgtc taaacgtttc atgatgttgt ctaacgtcat cgtcggcctt       180
ctagctgccg cctatggaaa gcctgtgctg cagcgtttg ggctcacaga caatggcgac        240
agttacacca ttgatgctgg ctccaccaat ccctggtaa tcactgtcga cagttccaac       300
tgcgacatca cctctttcgt ctaccggagc cagaaatacc agtatgcctc gaaaggatcc       360
cacattagct caggccttgg ctcggctgat gtgacggcag agactattga tggtaaagcc       420
tgaagactgt gatgcaactt cccatccgct gaccacccgc agatgtaatc aaggtcactt       480
gcacaaccga cacactgatc cactactatg tcgtcaaatc cggagagagc aacgtctaca       540
tggctacgta cacttcagct gagccttcag tgggagagct cgctacatc gcacgacttg        600
atccttcgct gcttccatat gagtacccct tcggcgacgt ctccaccacc gccgacagca       660
cttcgacagt ggaaggttct gacgtcttca tcgtcgacgg agagactcgc agcaaattct       720
actccagcca gcgcttcatc gacgacgacg tccactgcgt ctacagcgac gacgtccacg       780
cgtgcatgct gatgccccag tacgagacct cgtccggcgg ccgttccac cgagacatca       840
acaccaacaa cgccggcgac tcgaccaacc tgtactggta catgaacagc ggacacgtgc       900
agaccgaggc cttccggatg ggcctccacg ggcctacgc cctcacgtgg tcgcgctctg        960
gcgtgcccag tctcagcggc ctcgacttct ccttcatggc ggacctcgac ctggaaggct      1020
acgtcgccga cagcgggcgc ggcaccgtct cgggcacagc atccggcgtc tccagcgact      1080
atgaggtcgt ggtgcactgg tacaacgacg acgcgcagta ctggacgtac gcctcttcgt      1140
ccggcgcctt cacgtcgccc gccatgaagc cggggaccta ccatggcc ctgtaccaga       1200
ccgaactcaa agtggccacg tcctcggtga cggtcaaggc cggatcggcc accagcgcca      1260
acatcgccag cacctggagc tccaatacca cgctcttcca gatcggcgac tgggacgggc      1320
agccgaccgg cttcctcaac gcggccagcc agctgcgcat gcacccgtcc gactcgcgca      1380
```

```
tggccgactg gggccccgtc acctacaccg tcggctcgtc ctccgacagc tccgtcccga    1440
tggcgctgtt caaggacgtc aacgacccgc tgaccatcag cttcacgctg gcgtcttcgc    1500
aggccagcgg cgcggcgacg ctgcgcgtcg gcaccacgct gtcgttcgcg ggcgggcggc    1560
cgagcgtcac cgtcaacgac tacagcgact ccgccgccgc gccgaccaag atcgactccc    1620
ggggcgtgac gcgcggcgcg tatcgcgggt acggcgagat ctacgacttc gagctgccgg    1680
acgggacgct gtcgacgagc aatacgatca ccatttcggt gatttcgggg agcagtgggg    1740
cggatttcct ggagccgaat tttgtgagtt ctcgcattcc tcttggccac tagcatgttt    1800
gagaggaatg tgacgctgac ggtgtgacag atccttgatg ctattgagct gtggagatag    1860
ggttgatagg tctgcggacg tgttgtggat ggtttcgcgg gtctgggatc ttgattggtt    1920
gttgggatgg tatgcagcaa aga                                             1943

<210> SEQ ID NO 59
<211> LENGTH: 1593
<212> TYPE: DNA
<213> ORGANISM: M. phaseolina

<400> SEQUENCE: 59
atgatgttgt ctaacgtcat cgtcggcctt ctagctgccg cctatggaaa gcctgtgctg      60
gcagcgtttg ggctcacaga caatggcgac agttacacca ttgatgctgg ctccaccaat     120
cccctggtaa tcactgtcga cagttccaac tgcgacatca cctctttcgt ctaccggagc     180
cagaaatacc agtatgcctc gaaaggatcc cacattagct caggccttgg ctcggctgat     240
gtgacggcag agactattga tgatgtaatc aaggtcactt gcacaaccga cacactgatc     300
cactactatg tcgtcaaatc cggagagagc aacgtctaca tggctacgta cacttcagct     360
gagccttcag tgggagagct gcgctacatc gcacgacttg atccttcgct gcttccatat     420 gagtaccccct tcggcgacgt ctccaccacc gccgacagca cttcgacagt ggaaggttct     480
gacgtcttca tcgtcgacgg agagactcgc agcaaattct actccagcca gcgcttcatc     540
gacgacgacg tccactgcgt ctacagcgac gacgtccacg cgtgcatgct gatgccccag     600
tacgagacct cgtccggcgg gccgttccac cgagacatca acaccaacaa cgccggcgac     660
tcgaccaacc tgtactggta catgaacagc ggacacgtgc agaccgaggc cttccggatg     720
ggcctccacg ggccctacgc cctcacgtgg tcgcgctctg gcgtgcccag tctcagcggc     780
ctcgacttct ccttcatggc ggacctcgac ctggaaggct acgtcgccga cagcgggcgc     840
ggcaccgtct cgggcacagc atccggcgtc tccagcgact atgaggtcgt ggtgcactgg     900
tacaacgacg acgcgcagta ctggacgtac gcctcttcgt ccggcgcctt cacgtcgccc     960
gccatgaagc cggggaccta caccatggcc ctgtaccaga ccgaactcaa gtggccacg    1020 tcctcggtga cggtcaaggc cggatcggcc accagcgcca acatcgccag cacctggagc    1080
tccaatacca cgctcttcca gatcggcgac tgggacgggc agccgaccgg cttcctcaac    1140
gcggccagcc agctgcgcat gcacccgtcc gactcgcgca tggccgactg gggccccgtc    1200
acctacaccg tcggctcgtc ctccgacagc tccgtcccga tggcgctgtt caaggacgtc    1260
aacgacccgc tgaccatcag cttcacgctg gcgtcttcgc aggccagcgg cgcggcgacg    1320
ctgcgcgtcg gcaccacgct gtcgttcgcg ggcgggcggc cgagcgtcac cgtcaacgac    1380
tacagcgact ccgccgccgc gccgaccaag atcgactccc ggggcgtgac gcgcggcgcg    1440
tatcgcgggt acggcgagat ctacgacttc gagctgccgg acgggacgct gtcgacgagc    1500
```

```
aatacgatca ccatttcggt gatttcgggg agcagtgggg cggatttcct ggagccgaat    1560
tttgtgagtt ctcgcattcc tcttggccac tag                                 1593
```

<210> SEQ ID NO 60
<211> LENGTH: 530
<212> TYPE: PRT
<213> ORGANISM: M. phaseolina

<400> SEQUENCE: 60

```
Met Met Leu Ser Asn Val Ile Val Gly Leu Leu Ala Ala Ala Tyr Gly
1               5                   10                  15

Lys Pro Val Leu Ala Ala Phe Gly Leu Thr Asp Asn Gly Asp Ser Tyr
            20                  25                  30

Thr Ile Asp Ala Gly Ser Thr Asn Pro Leu Val Ile Thr Val Asp Ser
        35                  40                  45

Ser Asn Cys Asp Ile Thr Ser Phe Val Tyr Arg Ser Gln Lys Tyr Gln
    50                  55                  60

Tyr Ala Ser Lys Gly Ser His Ile Ser Ser Gly Leu Gly Ser Ala Asp
65                  70                  75                  80

Val Thr Ala Glu Thr Ile Asp Asp Val Ile Lys Val Thr Cys Thr Thr
                85                  90                  95

Asp Thr Leu Ile His Tyr Tyr Val Val Lys Ser Gly Glu Ser Asn Val
            100                 105                 110

Tyr Met Ala Thr Tyr Thr Ser Ala Glu Pro Ser Val Gly Glu Leu Arg
        115                 120                 125

Tyr Ile Ala Arg Leu Asp Pro Ser Leu Leu Pro Tyr Glu Tyr Pro Phe
    130                 135                 140

Gly Asp Val Ser Thr Thr Ala Asp Ser Thr Ser Thr Val Glu Gly Ser
145                 150                 155                 160

Asp Val Phe Ile Val Asp Gly Glu Thr Arg Ser Lys Phe Tyr Ser Ser
                165                 170                 175

Gln Arg Phe Ile Asp Asp Val His Cys Val Tyr Ser Asp Asp Val
            180                 185                 190

His Ala Cys Met Leu Met Pro Gln Tyr Glu Thr Ser Ser Gly Gly Pro
        195                 200                 205

Phe His Arg Asp Ile Asn Thr Asn Asn Ala Gly Asp Ser Thr Asn Leu
    210                 215                 220

Tyr Trp Tyr Met Asn Ser Gly His Val Gln Thr Glu Ala Phe Arg Met
225                 230                 235                 240

Gly Leu His Gly Pro Tyr Ala Leu Thr Trp Ser Arg Ser Gly Val Pro
                245                 250                 255

Ser Leu Ser Gly Leu Asp Phe Ser Phe Met Ala Asp Leu Asp Leu Glu
            260                 265                 270

Gly Tyr Val Ala Asp Ser Gly Arg Gly Thr Val Ser Gly Thr Ala Ser
        275                 280                 285

Gly Val Ser Ser Asp Tyr Glu Val Val His Trp Tyr Asn Asp Asp
    290                 295                 300

Ala Gln Tyr Trp Thr Tyr Ala Ser Ser Ser Gly Ala Phe Thr Ser Pro
305                 310                 315                 320

Ala Met Lys Pro Gly Thr Tyr Thr Met Ala Leu Tyr Gln Thr Glu Leu
                325                 330                 335

Lys Val Ala Thr Ser Ser Val Thr Val Lys Ala Gly Ser Ala Thr Ser
            340                 345                 350

Ala Asn Ile Ala Ser Thr Trp Ser Ser Asn Thr Thr Leu Phe Gln Ile
```

Gly Asp Trp Asp Gly Gln Pro Thr Gly Phe Leu Asn Ala Ala Ser Gln
            355                 360                 365
370                     375                 380

Leu Arg Met His Pro Ser Asp Ser Arg Met Ala Asp Trp Gly Pro Val
385                     390                 395                 400

Thr Tyr Thr Val Gly Ser Ser Asp Ser Val Pro Met Ala Leu
                    405                 410                 415

Phe Lys Asp Val Asn Asp Pro Leu Thr Ile Ser Phe Thr Leu Ala Ser
                420                 425                 430

Ser Gln Ala Ser Gly Ala Ala Thr Leu Arg Val Gly Thr Thr Leu Ser
                435                 440                 445

Phe Ala Gly Gly Arg Pro Ser Val Thr Val Asn Asp Tyr Ser Asp Ser
        450                 455                 460

Ala Ala Ala Pro Thr Lys Ile Asp Ser Arg Gly Val Thr Arg Gly Ala
465                 470                 475                 480

Tyr Arg Gly Tyr Gly Glu Ile Tyr Asp Phe Glu Leu Pro Asp Gly Thr
                    485                 490                 495

Leu Ser Thr Ser Asn Thr Ile Thr Ile Ser Val Ile Ser Gly Ser Ser
                500                 505                 510

Gly Ala Asp Phe Leu Glu Pro Asn Phe Val Ser Ser Arg Ile Pro Leu
            515                 520                 525

Gly His
    530

<210> SEQ ID NO 61
<211> LENGTH: 2009
<212> TYPE: DNA
<213> ORGANISM: M. phaseolina

<400> SEQUENCE: 61
tcgctgatcg tcttggatat gcgcctggca gtgcattcgc gccggggact acaaaagcag     60
gggacgcatg ccacaacaga attggctttt cttgtcactg cacttcctgc cgctccaagt    120
ccccccctcg cgtttgaggg aaccgccaca atggctctct tgctctgtt tctgacccttt    180 atctctcttt tcgcaccgtc ggtgctggcc gcctttggag tgactacatc ctcttccagc    240
tatgttgtcg atgccggctc atccaacccc ttcgttgtta ccatttcgcg cagcagttgc    300
gacattacct cgatcaagta ccgtggagag gaattccagt actccggcaa gggttcgcac    360
atctcgtccg gccttggatc tgcgaccgta acgtcagaga tcgtcagcag tgagcgtctc    420
ttgcaacccg tcatacgccc ctcaggctaa caatcgacag gcacttatgc caagatcacc    480
tgcacggctg gcagcttgac ccattacatt attgtcaagt ccggagagag ctctttgtac    540
atgggcactt acttcactga ggagccctcg attggtgaag cccgtttcat cgctcgcttg    600
gacccggcca agctccctct cgaataccc tacggcactg cctccactac tgctgggagc    660
agcagcaccg tcgagggatc cgacgtcttt gttgtgaatg ccagacccg cagcaagttc    720 tactctagcc aacgtttcat cgacgacaag gtgcagtgcg tgtaccgcga tgatgatgct    780
gtccacgctt gcatgatctt gcagcctctc tcctacgagg gatccagcgg cggtcccttc    840
ttcagggaca tcaacaccaa caacgccggt gactcgacca acctgtactt ctacatgaac    900
tccaaccatg ctcagactga gagttaccgt atgggcttcc acggcccgta ccagttgcag    960
ttcagccgct ctggtattcc caacagcttt gacgcttcgt tcttcgccga cctcaagctc   1020
tccggctacg ttgctgagtc tgctcgtggc tacgtcaagg gtactgcttc tggagttggt   1080

| | |
|---|---|
| agctcttacc agaaagtcct tcattggtac aacagcaacg cgcagtactg ggtctatgcc | 1140 |
| tcgtctaacg gtgcctttac ttctcctgcc atgaagcctg gcacctacac ccaggtcctc | 1200 |
| taccaggacg aactcaaggt tgccaccgac tcggtcactg tctctgctgg atcgacggtc | 1260 |
| accaagaaca ttgcatctac cttctctttc ccttcgacca tctggacaat tggcgactgg | 1320 |
| gacggccagc cattcggctt ccgcaacgcc gacaagatcg agcgcatgca cccgtccgac | 1380 |
| agccgcatga gcagctgggg gccgttgacc tacacggtcg gctccagcgc actgactgac | 1440 |
| gttcccatgg cgctcttcaa gggcgtcaac acgcctttca ccatcaagtt cacgctctcc | 1500 |
| tcgtcgcaga caggtgcggc ggtcctccgg atcggcacga ctctggcctt cgccagcggc | 1560 |
| aggccgcagc ccaagatcaa cagctacagc ccttcggcgc cggcggcacc gacgaagatc | 1620 |
| gattcgcgcg cgtcacacg tggcacttac cgcggtttgg gtgagatcta cccttcgac | 1680 |
| attcccgcgg gcactctcgt gagtggctcg aacacgatca ccatcgactg catctcggga | 1740 |
| agctcgggcg acacctacct gtctcccaac tttgtaagtt tcgctctgca tacctccgcc | 1800 |
| atgcgccgtg ctaacgcaag aaacagatcc ttgacgccat tgacctgtac ctcaagtgag | 1860 |
| cgagggtcag gagaagggtg ctagctgagg ttcgcttctg taaataagtt tacgtcctac | 1920 |
| attgaacata cattttggct ttgattgccg gtctgcatta ctcgtcaata cgaagcttcg | 1980 |
| cgagcgcgca gctccaccga atgcgtggc | 2009 |

```
<210> SEQ ID NO 62
<211> LENGTH: 1605
<212> TYPE: DNA
<213> ORGANISM: M. phaseolina

<400> SEQUENCE: 62
```

| | |
|---|---|
| atggctctct tgctctgtt tctgacctttt atctctcttt tcgcaccgtc ggtgctggcc | 60 |
| gcctttggag tgactacatc ctcttccagc tatgttgtcg atgccggctc atccaacccc | 120 |
| ttcgttgtta ccatttcgcg cagcagttgc gacattacct cgatcaagta ccgtggagag | 180 |
| gaattccagt actccggcaa gggttcgcac atctcgtccg gccttggatc tgcgaccgta | 240 |
| acgtcagaga tcgtcagcag cacttatgcc aagatcacct gcacggctgg cagcttgacc | 300 |
| cattacatta ttgtcaagtc cggagagagc tctttgtaca tgggcactta cttcactgag | 360 |
| gagccctcga ttggtgaagc ccgtttcatc gctcgcttgg acccggccaa gctccctctc | 420 |
| gaataccct acggcactgc ctccactact gctgggagca gcagcaccgt cgagggatcc | 480 |
| gacgtcttg ttgtgaatgg ccagacccgc agcaagttct actctagcca acgtttcatc | 540 |
| gacgacaagg tgcagtgcgt gtaccgcgat gatgatgctg tccacgcttg catgatcttg | 600 |
| cagcctctct cctacgaggg atccagcggc ggtcccttct tcaggacat caacaccaac | 660 |
| aacgccggtg actcgaccaa cctgtacttc tacatgaact ccaaccatgc tcagactgag | 720 |
| agttaccgta tgggcttcca cggcccgtac cagttgcagt tcagccgctc tggtattccc | 780 |
| aacagctttg acgcttcgtt cttcgccgac ctcaagctct ccggctacgt tgctgagtct | 840 |
| gctcgtggct acgtcaaggg tactgcttct ggagttggta gctcttacca gaaagtcctt | 900 |
| cattggtaca acagcaacgc gcagtactgg gtctatgcct cgtctaacgg tgcctttact | 960 |
| tctcctgcca tgaagcctgg cacctacacc caggtcctct accaggacga actcaaggtt | 1020 |
| gccaccgact cggtcactgt ctctgctgga tcgacggtca ccaagaacat tgcatctacc | 1080 |
| ttctctttcc cttcgaccat ctggacaatt ggcgactggg acggccagcc attcggcttc | 1140 |
| cgcaacgccg acaagatcga gcgcatgcac ccgtccgaca gccgcatgag cagctggggg | 1200 |

-continued

```
ccgttgacct acacggtcgg ctccagcgca ctgactgacg ttcccatggc gctcttcaag    1260
ggcgtcaaca cgcctttcac catcaagttc acgctctcct cgtcgcagac aggtgcggcg    1320
gtcctccgga tcggcacgac tctggccttc gccagcggca ggccgcagcc caagatcaac    1380
agctacagcc cttcggcgcc ggcggcaccg acgaagatcg attcgcgcgg cgtcacacgt    1440
ggcacttacc gcggtttggg tgagatctac accttcgaca ttcccgcggg cactctcgtg    1500
agtggctcga acacgatcac catcgactgc atctcgggaa gctcgggcga cacctacctg    1560
tctcccaact ttatccttga cgccattgac ctgtacctca agtga                    1605
```

<210> SEQ ID NO 63
<211> LENGTH: 534
<212> TYPE: PRT
<213> ORGANISM: M. phaseolina

<400> SEQUENCE: 63

```
Met Ala Leu Phe Ala Leu Phe Leu Thr Phe Ile Ser Leu Phe Ala Pro
1               5                   10                  15

Ser Val Leu Ala Ala Phe Gly Val Thr Thr Ser Ser Ser Tyr Val
                20                  25                  30

Val Asp Ala Gly Ser Ser Asn Pro Phe Val Val Thr Ile Ser Arg Ser
            35                  40                  45

Ser Cys Asp Ile Thr Ser Ile Lys Tyr Arg Gly Glu Glu Phe Gln Tyr
        50                  55                  60

Ser Gly Lys Gly Ser His Ile Ser Ser Gly Leu Gly Ser Ala Thr Val
65                  70                  75                  80

Thr Ser Glu Ile Val Ser Ser Thr Tyr Ala Lys Ile Thr Cys Thr Ala
                85                  90                  95

Gly Ser Leu Thr His Tyr Ile Ile Val Lys Ser Gly Glu Ser Ser Leu
            100                 105                 110

Tyr Met Gly Thr Tyr Phe Thr Glu Glu Pro Ser Ile Gly Glu Ala Arg
        115                 120                 125

Phe Ile Ala Arg Leu Asp Pro Ala Lys Leu Pro Leu Glu Tyr Pro Tyr
    130                 135                 140

Gly Thr Ala Ser Thr Thr Ala Gly Ser Ser Ser Thr Val Glu Gly Ser
145                 150                 155                 160

Asp Val Phe Val Val Asn Gly Gln Thr Arg Ser Lys Phe Tyr Ser Ser
                165                 170                 175

Gln Arg Phe Ile Asp Asp Lys Val Gln Cys Val Tyr Arg Asp Asp Asp
            180                 185                 190

Ala Val His Ala Cys Met Ile Leu Gln Pro Leu Ser Tyr Glu Gly Ser
        195                 200                 205

Ser Gly Gly Pro Phe Phe Arg Asp Ile Asn Thr Asn Asn Ala Gly Asp
    210                 215                 220

Ser Thr Asn Leu Tyr Phe Tyr Met Asn Ser Asn His Ala Gln Thr Glu
225                 230                 235                 240

Ser Tyr Arg Met Gly Phe His Gly Pro Tyr Gln Leu Gln Phe Ser Arg
                245                 250                 255

Ser Gly Ile Pro Asn Ser Phe Ala Ser Phe Phe Ala Asp Leu Lys
            260                 265                 270

Leu Ser Gly Tyr Val Ala Glu Ser Ala Arg Gly Tyr Val Lys Gly Thr
        275                 280                 285

Ala Ser Gly Val Gly Ser Ser Tyr Gln Lys Val Leu His Trp Tyr Asn
    290                 295                 300
```

-continued

Ser Asn Ala Gln Tyr Trp Val Tyr Ala Ser Ser Asn Gly Ala Phe Thr
305                 310                 315                 320

Ser Pro Ala Met Lys Pro Gly Thr Tyr Thr Gln Val Leu Tyr Gln Asp
            325                 330                 335

Glu Leu Lys Val Ala Thr Asp Ser Val Thr Val Ser Ala Gly Ser Thr
        340                 345                 350

Val Thr Lys Asn Ile Ala Ser Thr Phe Ser Phe Pro Ser Thr Ile Trp
    355                 360                 365

Thr Ile Gly Asp Trp Asp Gly Gln Pro Phe Gly Phe Arg Asn Ala Asp
370                 375                 380

Lys Ile Glu Arg Met His Pro Ser Asp Ser Arg Met Ser Ser Trp Gly
385                 390                 395                 400

Pro Leu Thr Tyr Thr Val Gly Ser Ser Ala Leu Thr Asp Val Pro Met
                405                 410                 415

Ala Leu Phe Lys Gly Val Asn Thr Pro Phe Thr Ile Lys Phe Thr Leu
            420                 425                 430

Ser Ser Ser Gln Thr Gly Ala Ala Val Leu Arg Ile Gly Thr Thr Leu
        435                 440                 445

Ala Phe Ala Ser Gly Arg Pro Gln Pro Lys Ile Asn Ser Tyr Ser Pro
    450                 455                 460

Ser Ala Pro Ala Ala Pro Thr Lys Ile Asp Ser Arg Gly Val Thr Arg
465                 470                 475                 480

Gly Thr Tyr Arg Gly Leu Gly Glu Ile Tyr Thr Phe Asp Ile Pro Ala
                485                 490                 495

Gly Thr Leu Val Ser Gly Ser Asn Thr Ile Thr Ile Asp Cys Ile Ser
            500                 505                 510

Gly Ser Ser Gly Asp Thr Tyr Leu Ser Pro Asn Phe Ile Leu Asp Ala
        515                 520                 525

Ile Asp Leu Tyr Leu Lys
    530

<210> SEQ ID NO 64
<211> LENGTH: 21
<212> TYPE: DNA
<213> ORGANISM: Artificial Sequence
<220> FEATURE:
<223> OTHER INFORMATION: Synthetic primer

<400> SEQUENCE: 64
tcatcaccga cccacaatcg c                                    21

<210> SEQ ID NO 65
<211> LENGTH: 20
<212> TYPE: DNA
<213> ORGANISM: Artificial Sequence
<220> FEATURE:
<223> OTHER INFORMATION: Synthetic primer

<400> SEQUENCE: 65
cttagcaagc gggagccgtc                                      20

<210> SEQ ID NO 66
<211> LENGTH: 20
<212> TYPE: DNA
<213> ORGANISM: Artificial Sequence
<220> FEATURE:
<223> OTHER INFORMATION: synthetic primer

<400> SEQUENCE: 66
cagacaacgg cgtcgacagt                                              20

<210> SEQ ID NO 67
<211> LENGTH: 20
<212> TYPE: DNA
<213> ORGANISM: Artificial Sequence
<220> FEATURE:
<223> OTHER INFORMATION: Synthetic primer

<400> SEQUENCE: 67
acggaccaca tccaacgcga                                              20

<210> SEQ ID NO 68
<211> LENGTH: 20
<212> TYPE: DNA
<213> ORGANISM: Artificial Sequence
<220> FEATURE:
<223> OTHER INFORMATION: Synthetic primer

<400> SEQUENCE: 68
atgccctggt accctgcccc                                              20

<210> SEQ ID NO 69
<211> LENGTH: 20
<212> TYPE: DNA
<213> ORGANISM: Artificial Sequence
<220> FEATURE:
<223> OTHER INFORMATION: Synthetic primer

<400> SEQUENCE: 69
gaaaggtccc gggctcacgc                                              20

<210> SEQ ID NO 70
<211> LENGTH: 23
<212> TYPE: DNA
<213> ORGANISM: Artificial Sequence
<220> FEATURE:
<223> OTHER INFORMATION: Synthetic primer

<400> SEQUENCE: 70
ccgctcctct gtgcgttgtt gaa                                          23

<210> SEQ ID NO 71
<211> LENGTH: 22
<212> TYPE: DNA
<213> ORGANISM: Artificial Sequence
<220> FEATURE:
<223> OTHER INFORMATION: Synthetic primer

<400> SEQUENCE: 71
acagcgatag agccgcaaca cg                                           22

<210> SEQ ID NO 72
<211> LENGTH: 24
<212> TYPE: DNA
<213> ORGANISM: Artificial Sequence
<220> FEATURE:
<223> OTHER INFORMATION: Synthetic primer

<400> SEQUENCE: 72
tttcctcacc accacttccc ctct                                         24

<210> SEQ ID NO 73
<211> LENGTH: 20
<212> TYPE: DNA

```
<213> ORGANISM: Artificial Sequence
<220> FEATURE:
<223> OTHER INFORMATION: Synthetic primer

<400> SEQUENCE: 73
cgaaagccag cccaagcgac                                                    20

<210> SEQ ID NO 74
<211> LENGTH: 21
<212> TYPE: DNA
<213> ORGANISM: Artificial Sequence
<220> FEATURE:
<223> OTHER INFORMATION: Synthetic primer

<400> SEQUENCE: 74
ggcaagcatc ctctctccgg c                                                  21

<210> SEQ ID NO 75
<211> LENGTH: 21
<212> TYPE: DNA
<213> ORGANISM: Artificial Sequence
<220> FEATURE:
<223> OTHER INFORMATION: Synthetic primer

<400> SEQUENCE: 75
cctgaggccc atcgtccgag t                                                  21

<210> SEQ ID NO 76
<211> LENGTH: 23
<212> TYPE: DNA
<213> ORGANISM: Artificial Sequence
<220> FEATURE:
<223> OTHER INFORMATION: Synthetic primer

<400> SEQUENCE: 76
tccctgcctc tccatcctac cct                                                23

<210> SEQ ID NO 77
<211> LENGTH: 20
<212> TYPE: DNA
<213> ORGANISM: Artificial Sequence
<220> FEATURE:
<223> OTHER INFORMATION: Synthetic primer

<400> SEQUENCE: 77
ccaaccgtgt ggccgtcgaa                                                    20

<210> SEQ ID NO 78
<211> LENGTH: 23
<212> TYPE: DNA
<213> ORGANISM: Artificial Sequence
<220> FEATURE:
<223> OTHER INFORMATION: Synthetic primer

<400> SEQUENCE: 78
acatgcagtt caagtacgcc gct                                                23

<210> SEQ ID NO 79
<211> LENGTH: 20
<212> TYPE: DNA
<213> ORGANISM: Artificial Sequence
<220> FEATURE:
<223> OTHER INFORMATION: Synthetic primer

<400> SEQUENCE: 79
gcaggggccc acacctcttg                                                    20
```

```
<210> SEQ ID NO 80
<211> LENGTH: 23
<212> TYPE: DNA
<213> ORGANISM: Artificial Sequence
<220> FEATURE:
<223> OTHER INFORMATION: Synthetic primer

<400> SEQUENCE: 80
tccaaggcag agcctccgaa aca                                            23

<210> SEQ ID NO 81
<211> LENGTH: 21
<212> TYPE: DNA
<213> ORGANISM: Artificial Sequence
<220> FEATURE:
<223> OTHER INFORMATION: Synthetic primer

<400> SEQUENCE: 81
gctccctgcg ggcgtgtttt a                                              21

<210> SEQ ID NO 82
<211> LENGTH: 22
<212> TYPE: DNA
<213> ORGANISM: Artificial Sequence
<220> FEATURE:
<223> OTHER INFORMATION: Synthetic primer

<400> SEQUENCE: 82
acagacccca tcacatccgc ca                                             22

<210> SEQ ID NO 83
<211> LENGTH: 24
<212> TYPE: DNA
<213> ORGANISM: Artificial Sequence
<220> FEATURE:
<223> OTHER INFORMATION: Synthetic primer

<400> SEQUENCE: 83
ttgcattgag ccctcttggg ctgt                                           24

<210> SEQ ID NO 84
<211> LENGTH: 21
<212> TYPE: DNA
<213> ORGANISM: Artificial Sequence
<220> FEATURE:
<223> OTHER INFORMATION: Synthetic primer

<400> SEQUENCE: 84
ctgtcctcca gcagcagcct c                                              21

<210> SEQ ID NO 85
<211> LENGTH: 21
<212> TYPE: DNA
<213> ORGANISM: Artificial Sequence
<220> FEATURE:
<223> OTHER INFORMATION: Synthetic primer

<400> SEQUENCE: 85
cgagcaaccc gtcgaggtca a                                              21

<210> SEQ ID NO 86
<211> LENGTH: 21
<212> TYPE: DNA
<213> ORGANISM: Artificial Sequence
<220> FEATURE:
```

<223> OTHER INFORMATION: Synthetic primer

<400> SEQUENCE: 86
catgaaggcc accaccctcg c                                    21

<210> SEQ ID NO 87
<211> LENGTH: 20
<212> TYPE: DNA
<213> ORGANISM: Artificial Sequence
<220> FEATURE:
<223> OTHER INFORMATION: Synthetic primer

<400> SEQUENCE: 87
ccgaaccctg gctcgggcat                                      20

<210> SEQ ID NO 88
<211> LENGTH: 21
<212> TYPE: DNA
<213> ORGANISM: Artificial Sequence
<220> FEATURE:
<223> OTHER INFORMATION: Synthetic primer

<400> SEQUENCE: 88 accccacgc cgaacaatac c                                     21

<210> SEQ ID NO 89
<211> LENGTH: 21
<212> TYPE: DNA
<213> ORGANISM: Artificial Sequence
<220> FEATURE:
<223> OTHER INFORMATION: Synthetic primer

<400> SEQUENCE: 89
ccgccaagtc tatccgctcg c                                    21

<210> SEQ ID NO 90
<211> LENGTH: 21
<212> TYPE: DNA
<213> ORGANISM: Artificial Sequence
<220> FEATURE:
<223> OTHER INFORMATION: Synthetic primer

<400> SEQUENCE: 90
ggcttcggtg gaccgtccta t                                    21

<210> SEQ ID NO 91
<211> LENGTH: 20
<212> TYPE: DNA
<213> ORGANISM: Artificial Sequence
<220> FEATURE:
<223> OTHER INFORMATION: Synthetic primer

<400> SEQUENCE: 91
ccacccgctc cgcccttaaa                                      20

<210> SEQ ID NO 92
<211> LENGTH: 20
<212> TYPE: DNA
<213> ORGANISM: Artificial Sequence
<220> FEATURE:
<223> OTHER INFORMATION: Synthetic primer

<400> SEQUENCE: 92
aggagatggg ctgccgtcct                                      20

```
<210> SEQ ID NO 93
<211> LENGTH: 21
<212> TYPE: DNA
<213> ORGANISM: Artificial Sequence
<220> FEATURE:
<223> OTHER INFORMATION: Synthetic primer

<400> SEQUENCE: 93
gctcagcaag cgtccaaccc a                                             21

<210> SEQ ID NO 94
<211> LENGTH: 21
<212> TYPE: DNA
<213> ORGANISM: Artificial Sequence
<220> FEATURE:
<223> OTHER INFORMATION: Synthetic primer

<400> SEQUENCE: 94
tcccgtgcca tggtagcctt t                                             21

<210> SEQ ID NO 95
<211> LENGTH: 20
<212> TYPE: DNA
<213> ORGANISM: Artificial Sequence
<220> FEATURE:
<223> OTHER INFORMATION: Synthetic primer

<400> SEQUENCE: 95
gctggccacc acaatccaca                                               20

<210> SEQ ID NO 96
<211> LENGTH: 21
<212> TYPE: DNA
<213> ORGANISM: Artificial Sequence
<220> FEATURE:
<223> OTHER INFORMATION: Synthetic primer

<400> SEQUENCE: 96
tggcctcttg atcaggctcg t                                             21

<210> SEQ ID NO 97
<211> LENGTH: 20
<212> TYPE: DNA
<213> ORGANISM: Artificial Sequence
<220> FEATURE:
<223> OTHER INFORMATION: Synthetic primer

<400> SEQUENCE: 97
gcggtgaccc atccctgctt                                               20

<210> SEQ ID NO 98
<211> LENGTH: 20
<212> TYPE: DNA
<213> ORGANISM: Artificial Sequence
<220> FEATURE:
<223> OTHER INFORMATION: Synthetic primer

<400> SEQUENCE: 98
tcgtccaccg gtaccacgtt                                               20

<210> SEQ ID NO 99
<211> LENGTH: 23
<212> TYPE: DNA
<213> ORGANISM: Artificial Sequence
<220> FEATURE:
<223> OTHER INFORMATION: Synthetic primer
```

<400> SEQUENCE: 99
tgctacgcaa gtgtgcaaag tgt                                                    23

<210> SEQ ID NO 100
<211> LENGTH: 21
<212> TYPE: DNA
<213> ORGANISM: Artificial Sequence
<220> FEATURE:
<223> OTHER INFORMATION: Synthetic primer

<400> SEQUENCE: 100
atcacagcat gcctcgcctc g                                                      21

<210> SEQ ID NO 101
<211> LENGTH: 22
<212> TYPE: DNA
<213> ORGANISM: Artificial Sequence
<220> FEATURE:
<223> OTHER INFORMATION: Synthetic primer

<400> SEQUENCE: 101
cagtcctgcc ggttccttgc at                                                     22

<210> SEQ ID NO 102
<211> LENGTH: 21
<212> TYPE: DNA
<213> ORGANISM: Artificial Sequence
<220> FEATURE:
<223> OTHER INFORMATION: Synthetic primer

<400> SEQUENCE: 102
cggaggattg ctgcgggact t                                                      21

<210> SEQ ID NO 103
<211> LENGTH: 22
<212> TYPE: DNA
<213> ORGANISM: Artificial Sequence
<220> FEATURE:
<223> OTHER INFORMATION: Synthetic primer

<400> SEQUENCE: 103
ccgcgaaacc atccacaaca cg                                                     22

<210> SEQ ID NO 104
<211> LENGTH: 20
<212> TYPE: DNA
<213> ORGANISM: Artificial Sequence
<220> FEATURE:
<223> OTHER INFORMATION: Synthetic primer

<400> SEQUENCE: 104
acgggccaag gtgccagaac                                                        20

<210> SEQ ID NO 105
<211> LENGTH: 22
<212> TYPE: DNA
<213> ORGANISM: Artificial Sequence
<220> FEATURE:
<223> OTHER INFORMATION: Synthetic primer

<400> SEQUENCE: 105 caccctctc ctgaccctcg ct                                                      22